(12) United States Patent
Califorrniaa

(10) Patent No.: US 8,292,798 B2
(45) Date of Patent: Oct. 23, 2012

(54) INCUBATOR FOR BABIES BEFORE IMPLANTATION

(76) Inventor: Eurica Califorrniaa, Haleiwa, HI (US)

( * ) Notice: Subject to any disclaimer, the term of this patent is extended or adjusted under 35 U.S.C. 154(b) by 1559 days.

(21) Appl. No.: 11/549,972

(22) Filed: Oct. 16, 2006

(65) Prior Publication Data
US 2008/0097143 A1    Apr. 24, 2008

Related U.S. Application Data

(63) Continuation-in-part of application No. 10/908,861, filed on May 30, 2005, now Pat. No. 7,121,998.

(60) Provisional application No. 60/577,958, filed on Jun. 8, 2004.

(51) Int. Cl.
*A61D 7/00* (2006.01)

(52) U.S. Cl. ............................. 600/33; 600/22

(58) Field of Classification Search .............. 600/33–35, 600/21–22; 128/897–898; 435/7.2, 29, 366, 435/373, 374, 325, 288.4, 288.5, 297.5, 305.2, 435/305.3
See application file for complete search history.

(56) References Cited

U.S. PATENT DOCUMENTS

| | | | |
|---|---|---|---|
| 2,062,468 A | 12/1936 | Matz | |
| 2,802,918 A | 8/1957 | Boyle | |
| 3,249,724 A | 5/1966 | Hurvitz | |
| 3,582,590 A | 6/1971 | Eubank | |
| 3,588,408 A | 6/1971 | Beausoleil et al. | |
| 3,955,059 A | 5/1976 | Graf | |
| 3,986,384 A | 10/1976 | Giorgi | |
| 4,371,753 A | 2/1983 | Graf | |
| 4,450,472 A | 5/1984 | Tuckerman et al. | |
| 4,549,814 A | 10/1985 | Creel et al. | |
| 4,569,575 A | 2/1986 | Le Pesant et al. | |
| 4,574,000 A | 3/1986 | Hunter | |
| 4,579,461 A | 4/1986 | Rudolph | |
| 4,636,785 A | 1/1987 | Le Pesant | |
| 4,696,902 A * | 9/1987 | Bisconte | 435/286.2 |
| 4,750,474 A | 6/1988 | Dukhan et al. | |
| 4,863,423 A | 9/1989 | Wallace | |
| 4,880,314 A | 11/1989 | Kienitz | |
| 5,051,736 A | 9/1991 | Bennett et al. | |
| 5,119,467 A | 6/1992 | Barsky et al. | |
| 5,142,441 A | 8/1992 | Seibold et al. | |
| 5,296,375 A | 3/1994 | Kricka et al. | |
| 5,324,937 A | 6/1994 | Chen et al. | |
| 5,427,946 A | 6/1995 | Kricka et al. | |
| 5,659,330 A | 8/1997 | Sheridon | |
| 5,690,429 A | 11/1997 | Ng | |
| 5,744,366 A | 4/1998 | Kricka et al. | |
| 6,010,448 A | 1/2000 | Thompson | |
| 6,100,541 A | 8/2000 | Nagle et al. | |

(Continued)

OTHER PUBLICATIONS

Califorrniaa, "Thermoregulation of Human Embryos and Hatchlings in a Prenidial Incubator using Infrared Microthermography", Trends in Reproductive Biology, vol. 1, pp. 63-67, 2005.

(Continued)

*Primary Examiner* — John Lacyk

(57) ABSTRACT

The invention relates to an incubator for babies. It is of special value for the treatment of premature infants as an intensive care unit at any time during life from creation to implantation. A cradle is sided with ports to enable fluidic ventilation. Advantageously the incubator includes an optical path for imaging the patient via a clear bottom and open top. The incubator is provided with easy access and various accessories required for an intensive care unit.

20 Claims, 53 Drawing Sheets

U.S. PATENT DOCUMENTS

| | | | |
|---|---|---|---|
| 6,165,165 | A | 12/2000 | Cecchi et al. |
| 6,193,647 | B1 | 2/2001 | Beebe et al. |
| 6,369,954 | B1 | 4/2002 | Berge et al. |
| 6,448,069 | B1 | 9/2002 | Cecchi et al. |
| 6,488,872 | B1 | 12/2002 | Beebe et al. |
| 6,527,752 | B1 | 3/2003 | Bosley et al. |
| 6,610,005 | B1 | 8/2003 | Tao |
| 6,648,506 | B2 | 11/2003 | McGrath et al. |
| 6,673,008 | B1 | 1/2004 | Thompson et al. |
| 6,694,175 | B1 | 2/2004 | Califorrniaa |
| 6,695,765 | B1 | 2/2004 | Beebe et al. |
| 6,758,806 | B2 | 7/2004 | Kamrava et al. |
| 6,891,679 | B2 | 5/2005 | Atarashi et al. |
| 6,891,682 | B2 | 5/2005 | Aizenberg et al. |
| 6,911,132 | B2 | 6/2005 | Pamula et al. |
| 6,958,132 | B2 | 10/2005 | Chiou et al. |
| 6,960,437 | B2 | 11/2005 | Enzelberger et al. |
| 7,002,737 | B1 | 2/2006 | Akiyama et al. |
| 7,005,593 | B2 | 2/2006 | Gasparyan et al. |
| 7,015,031 | B2 * | 3/2006 | Cecchi et al. ............. 435/288.7 |
| 7,027,683 | B2 | 4/2006 | O'Connor et al. |
| 7,111,635 | B2 | 9/2006 | Beebe et al. |
| 7,121,998 | B1 | 10/2006 | Califorrniaa |
| 7,126,903 | B2 | 10/2006 | Feenstra et al. |
| 7,163,612 | B2 | 1/2007 | Sterling et al. |
| 7,170,832 | B2 | 1/2007 | Tukker et al. |

OTHER PUBLICATIONS

Califorrniaa E, "Micro ICU Project", (with section on "Micro Systems Technology" edited by C.-J. Kim), Embassy of the Juridic State of Nature, Rev. Aug. 29, 1998.

Shaikh et al., "A Modular Microfluidic Architecture for Integrated Biochemical Analysis," Proceedings of the National Academy of Sciences of the United States of America, vol. 102, No. 28, pp. 9745-9750, Jul. 2005.

Lin et al., "Microfluidic Devices on Polymer Substrates for Bioanalytical Applications," In 3rd International Conference on Microreaction Technology; Microreaction Technology: Industrial Prospects, IMRET 3, Apr. 18-21, 1999 (Frankfurt, Germany), New York, NY: Springer, pp. 451-460, 2000.

Heidemann et al., "Open-Dish Incubator for Live Cell Imaging with an Inverted Microscope," BioTechniques, vol. 35, No. 4, pp. 708-716, Oct. 2003.

Goodrich et al., "Enzymatically Amplified Surface Plasmon Resonance Imaging Method Using RNase H and RNA Microarrays for the Ultrasensitive Detection of Nucleic Acids," Analytical Chemistry, vol. 76, No. 21, pp. 6173-6178, Nov. 2004.

Burns et al., "Microfabricated structures for integrated DNA analysis," Proceedings of the National Academy of Sciences of the United States of America, vol. 93, No. 11, pp. 5556-5561, May 1996.

Pollack et al., "Electrowetting-Based Actuation of Liquid Droplets for Microfluidic Applications", Applied Physics Letters, vol. 77, No. 11, pp. 1725-1726, Sep. 2000.

Rosario et al., "Lotus Effect Amplifies Light-Induced Contact Angle Switching," Journal of Physical Chemistry B, vol. 1108, No. 34, pp. 12640-12642, 2004.

Chiou et al., "Optical Actuation of Microfluidics Based on Opto-Electrowetting," Technical Digest, Solid-State Sensor, Actuator and Microsystems Workshop, Hilton Head Island, SC, pp. 269-272, Jun. 2002.

Calhoun et al., "Paramagnetic Particles and Mixing in Micro-Scale Flows," Lab on a Chip, vol. 6, No. 2, pp. 247-257, Feb. 2006.

Zeng et al., "Principles of Droplet Electrohydrodynamics for Lab-on-a-Chip," Lab on a Chip, vol. 4, No. 4, pp. 265-277, Apr. 2004.

Pamula et al., "Cooling of Integrated Circuits using Droplet-Based Microfluidics," Proceedings of the Association for Computing Machinery Great Lakes Symposium on VLSI, pp. 84-87, 2003.

Eytan et al., "A Glance Into the Uterus During in Vitro Simulation of Embryo Transfer," Human Reproduction, vol. 19, No. 3, pp. 562-569, Mar. 2004.

Ok et al., "Pneumatically Driven Microcage for Micro-Objects in Biological Liquid," MEMS '99: Twelfth IEEE International Conference on Micro Electro Mechanical Systems, Technical Digest, Orlando, FL, pp. 459-463, 1999.

Wang et al., "Dual-Axis Confocal Microscope for High-Resolution in Vivo Imaging," Optical Letters, vol. 28, No. 6, pp. 414-416, Mar. 2003.

Warner Instruments, Inc., "OW Series Objective Warmers," Rev. Jan. 27, 2004.

Philips Research Press Release, "Philips' Fluid Lenses Bring Things into Focus," Mar. 3, 2004.

Robinson, "Common Misconceptions Relating to Infrared Inspection Ports," Global Maintenance Technologies (Chelmsford, United Kingdom), Rev. 2006.

Jacob, "Thermographic Imaging Essential to Avoid Thermal Calamities," Evaluation Engineering, Aug. 1996.

Malchoff et al., "A Novel Noninvasive Blood Glucose Monitor," Diabetes Care, vol. 25, No. 12, pp. 2268-2275, Dec. 2002.

Cone, Jr. History of the Care and Feeding of the Premature Infant. Boston: Little, Brown, pp. 21-22, 1985.

Berge et al., "Variable Focal Lens Controlled by an External Voltage: An Application of Electrowetting," The European Physical Journal E, vol. 3, pp. 159-163, 2000.

Kuiper et al., "Variable-Focus Liquid Lens for Miniature Cameras," Applied Physics Letters, vol. 85, No. 7, pp. 1128-1130, Aug. 2004.

Hendricks et al, "Through a Lens Sharply," IEEE Spectrum, pp. 32-36, Dec. 2004.

Kricka et al., "Micromachined Glass-Glass Microchips for in Vitro Fertilization," Clinical Chemistry, vol. 41, No. 9, pp. 1358-1359, 1995.

Ren et al., "Dynamics of Electro-Wetting Droplet Transport," Sensors and Actuators B, vol. 87, pp. 201-206, 2002.

Gu et al., "Computerized Microfluidic Cell Culture using Elastomeric Channels and Braille Displays," Proceedings of the National Academy of Sciences of the United States of America, vol. 101, No. 45, 15861-15866, Nov. 2004.

AutoMate Scientific, "Petri Profusion Chamber," Sales Brochure, 2004.

Gesellschaft fir Silizium-Mikrosysteme mbH, "MicCell: Versatile Perfusion System for the Microscope," Sales Brochure, 2006.

Ho et al., "Mini Chamber System for Long-Term Maintenance and Observation of Cultured Cells", BioTechniques, vol. 38, No. 2, pp. 267-273, Feb. 2005.

Petronis et al., "Transparent Polymeric Cell Culture Chip with Integrated Temperature Control and Uniform Media Perfusion," BioTechniques, vol. 40, No. 3, pp. 368-376, Mar. 2006.

Song et al., "Computer-Controlled Microcirculatory Support System for Endothelial Cell Culture and Shearing," Analytical Chemistry, vol. 77, No. 13, pp. 3993-3999, 2005.

* cited by examiner

Source: Eytan et al., Human Reproduction, vol. 19, no. 3, pp. 562-9, March 2004.

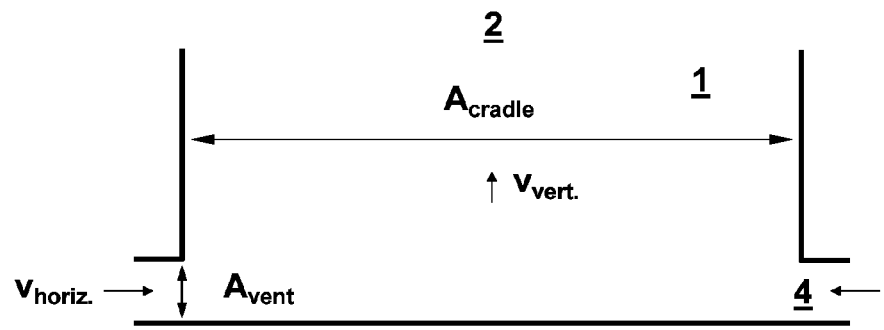
FIG. 15
$$v_{vert} A_{cradle} = \sum v_{horiz} A_{vent}$$
FIG. 16
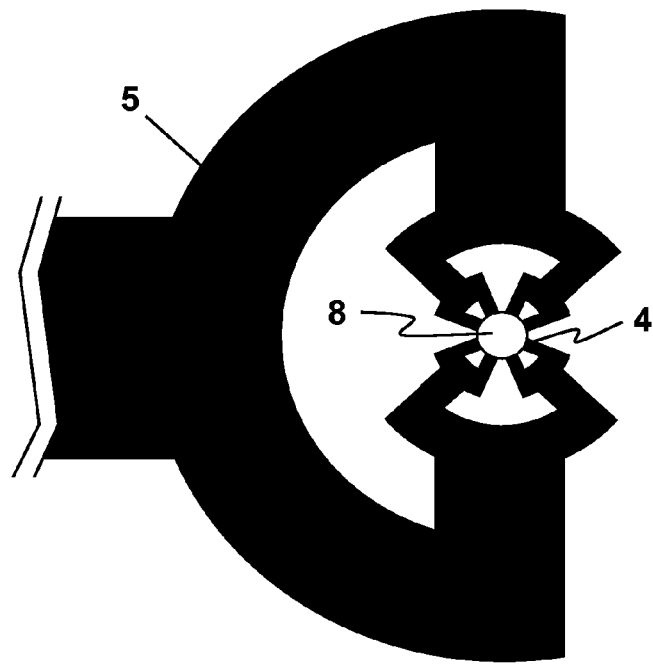
FIG. 17

(Califorrniaa, US 6,694,175)

Middle layer/top face

Middle layer/bottom face

Bottom layer/top face

Convex-concave/meniscus

Biconcave    Plano-concave

Biconvex    Plano-convex

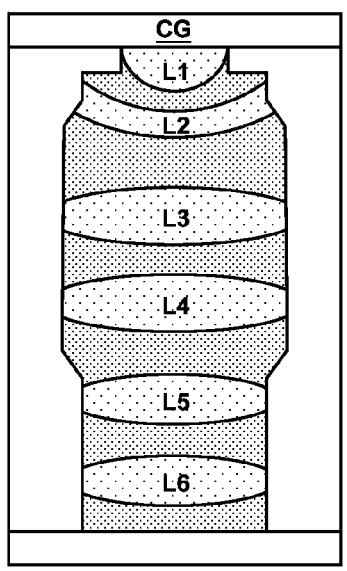
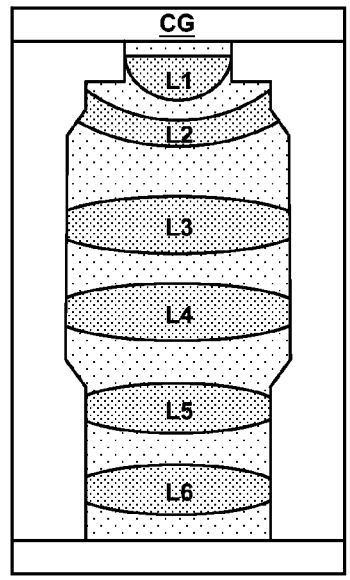
FIG. 38A  FIG. 38B
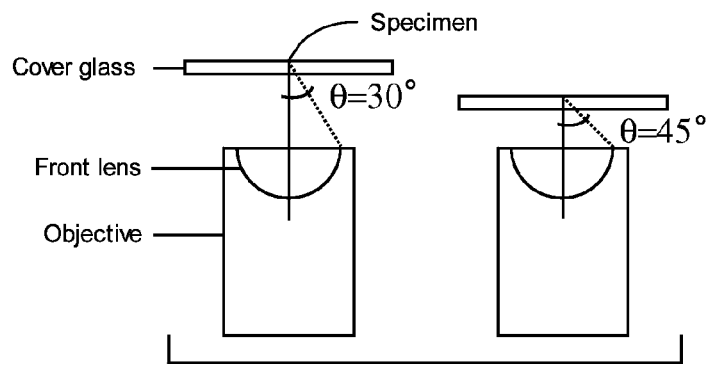
FIG. 39
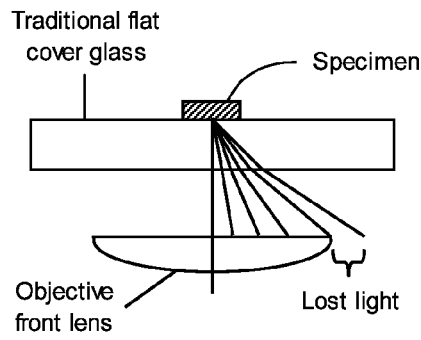
FIG. 40
(Prior Art)
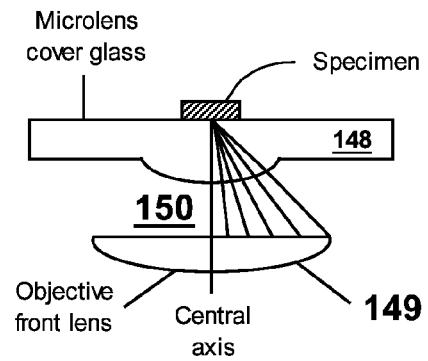
FIG. 41

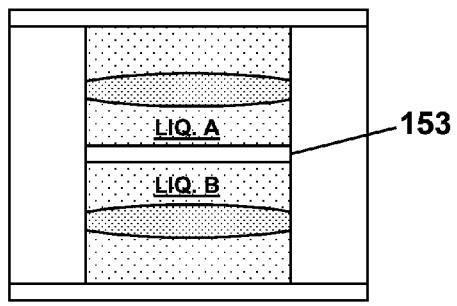
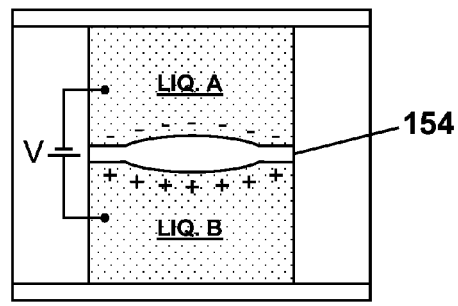
FIG. 45  FIG. 46
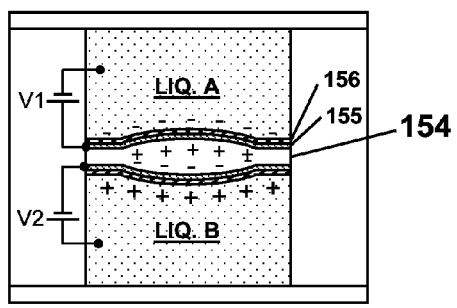
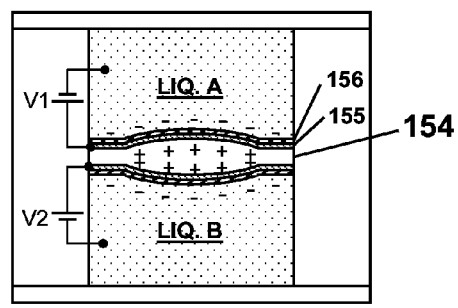
FIG. 47A  FIG. 47B

Early Embryo

Late Embryo

Human Baby Hatching

Empty Egg Capsule

Hatchling

"Prenidial Life"

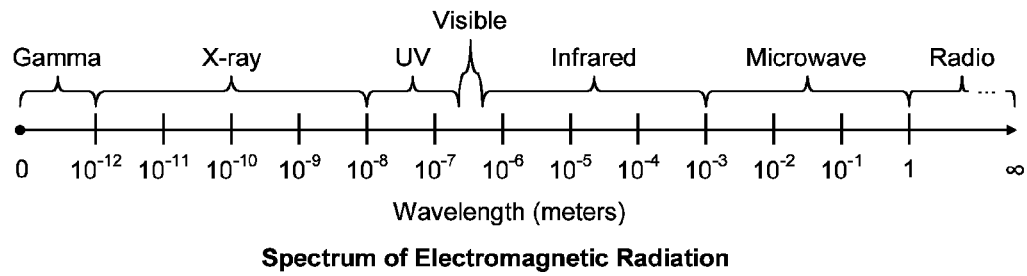

FIG. 49

Visible Spectrum

380-420 nm — wavelength of violet light
420-440 nm — wavelength of indigo light
440-500 nm — wavelength of blue light
500-520 nm — wavelength of cyan light
520-565 nm — wavelength of green light
565-590 nm — wavelength of yellow light
590-625 nm — wavelength of orange light
625-740 nm — wavelength of red light Source: http://en.wikipedia.org/wiki/1_E-7_m

FIG. 50A

Infrared (IR) Spectrum

0.75-1.4 microns — wavelength of near infrared (NIR)
1.4-3 microns — wavelength of short wavelength IR (SWIR)
3-8 microns — wavelength of mid wavelength IR (MWIR)
8-15 microns — wavelength of long wavelength IR (LWIR)
15-1,000 microns — wavelength of far infrared (FIR)

Source: http://en.wikipedia.org/wiki/Infrared

FIG. 50B

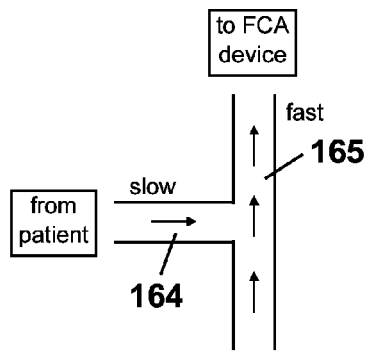
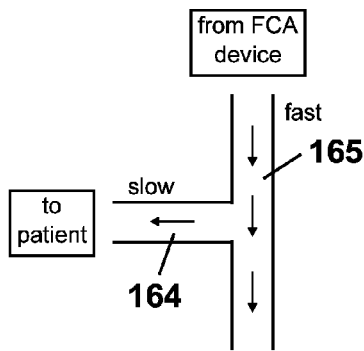
FIG. 61A  FIG. 61B
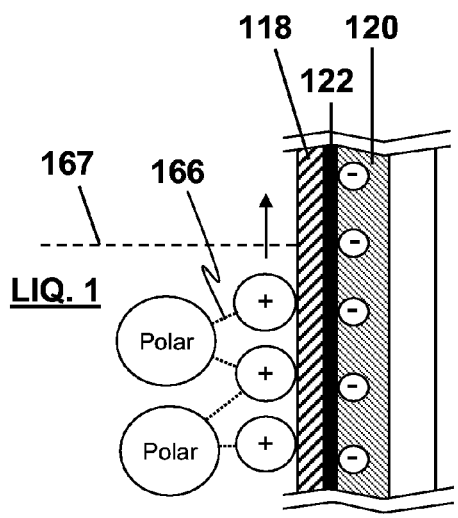
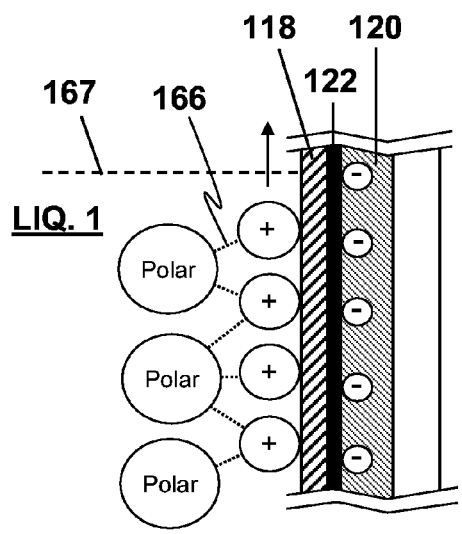
FIG. 62A  FIG. 62B Source: Pollack et al., Appl. Phys. Lett., Vol. 77, No. 11, pp. 1725-26, September 2000.

(Dielectric) Electrowetting Principle of Digital Microfluidics

Source: Chiou et al., IEEE Solid-State Sensor, Actuator and Microsystems Workshop, Hilton Head Island, South Carolina, June 2-6, 2002, pp. 269-72.

(Dielectric) Opto-Electrowetting Principle of Digital Microfludics

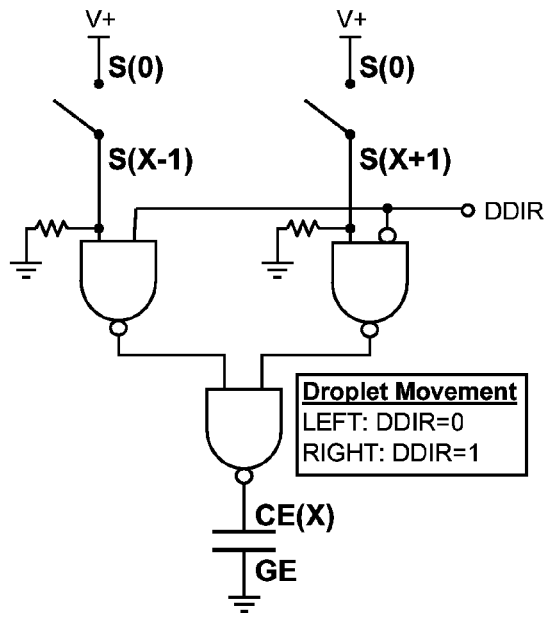
FIG. 67A
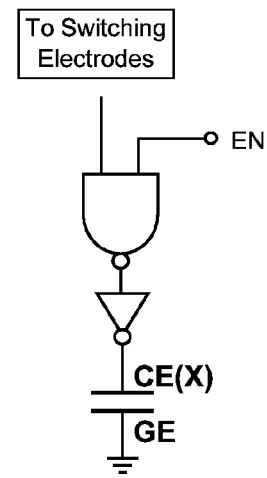
FIG. 67B
$CE_X = OR[AND[S_{X-1}, DDIR], AND[S_{X+1}, NOT[DDIR]]]$
FIG. 67C
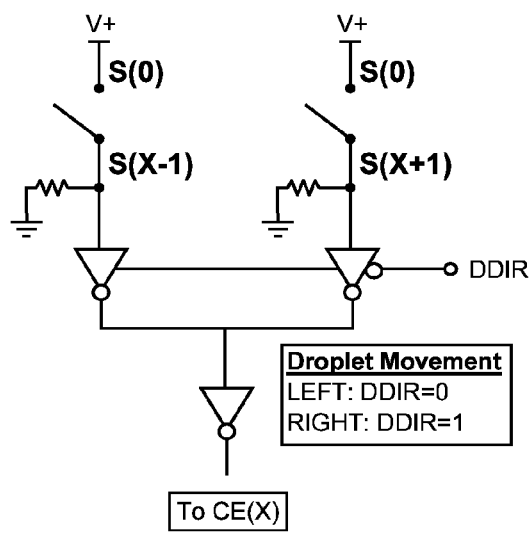
FIG. 67D
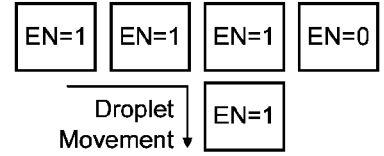
FIG. 67E
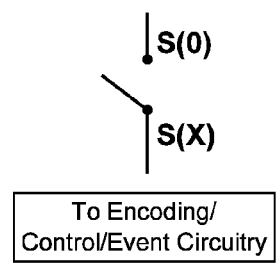
FIG. 67F

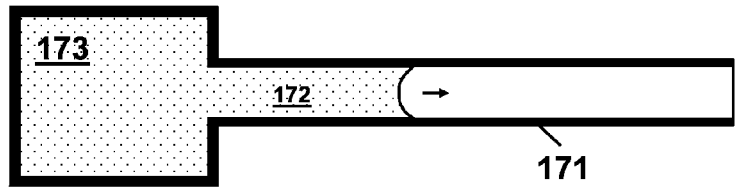
FIG. 68
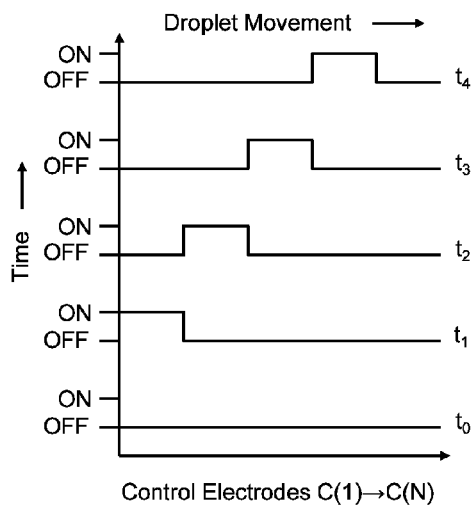
FIG. 69A
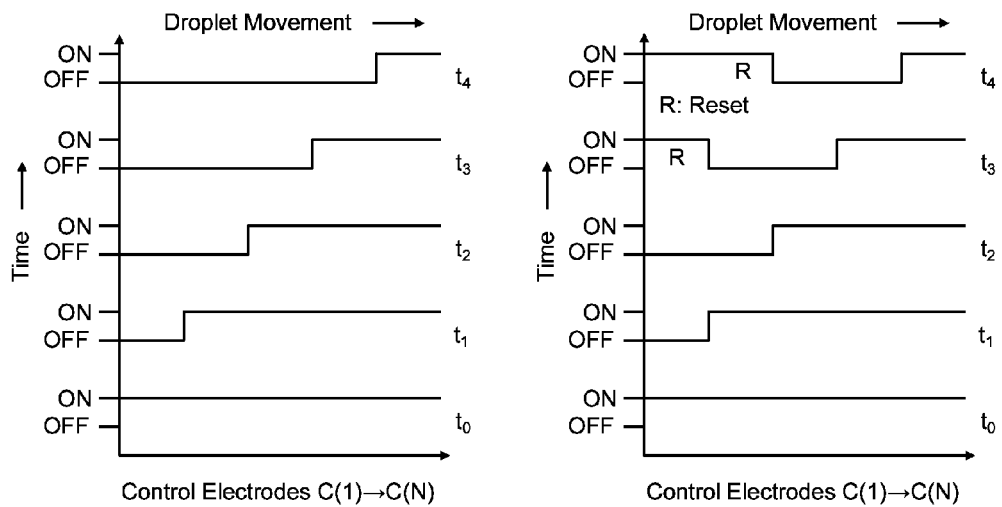
FIG. 69B
FIG. 69C

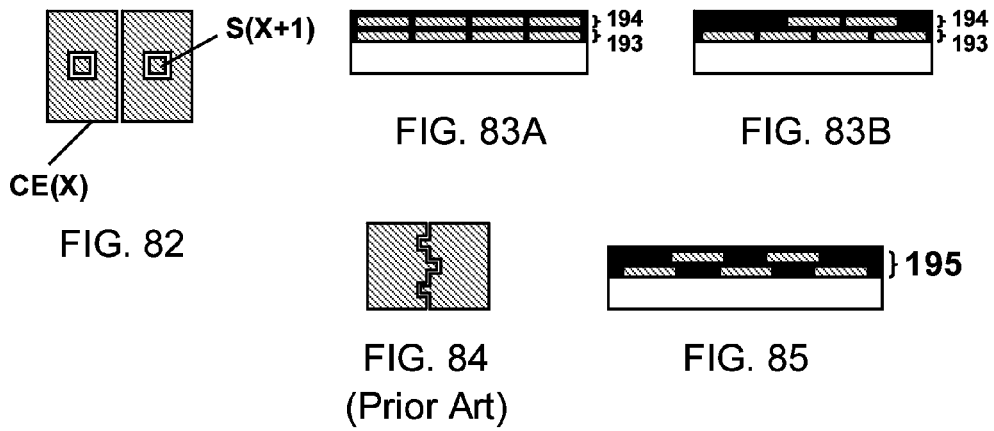
FIG. 82
FIG. 83A
FIG. 83B
FIG. 84
(Prior Art)
FIG. 85
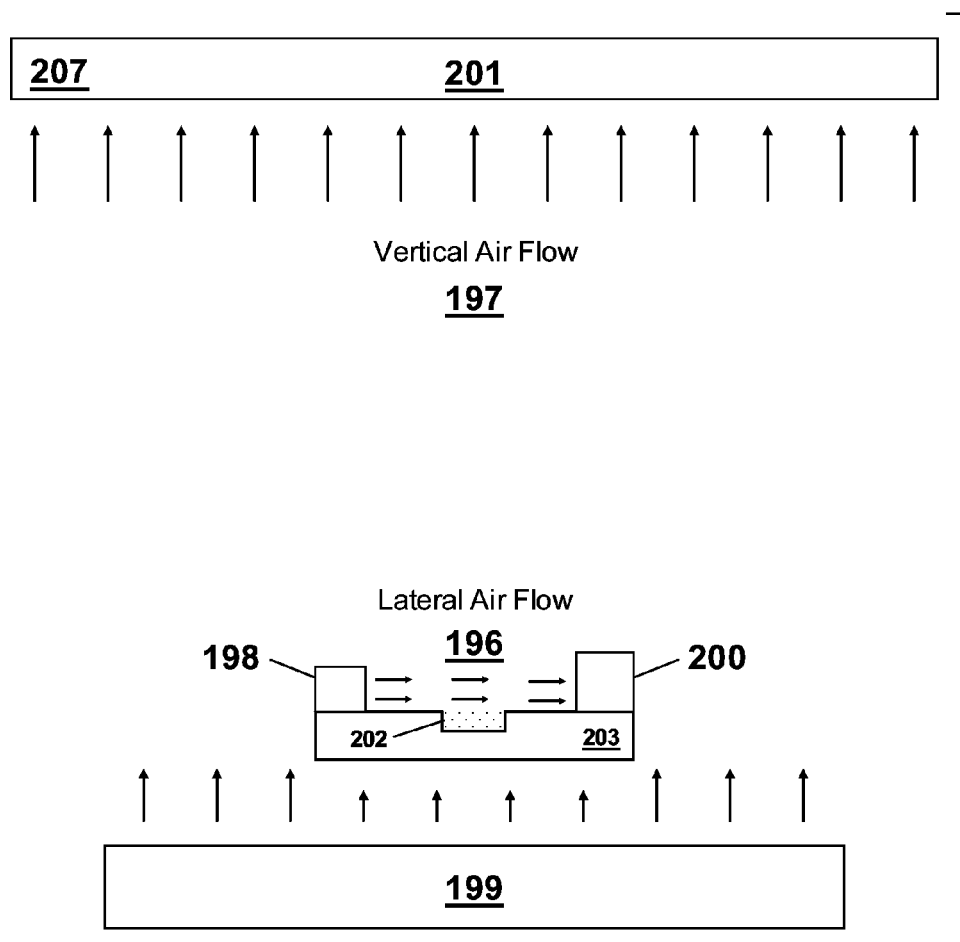
FIG. 86

(Cecchi et al, US 6,448,069)

(Matz, US 2,062,468)

(Le Pesant et al, US 4,569,575)

INCUBATOR FOR BABIES BEFORE IMPLANTATION

CROSS-REFERENCE TO RELATED APPLICATIONS

This application is a continuation-in-part of U.S. application Ser. No. 10/908,861, filed May 30, 2005, now U.S. Pat. No. 7,121,998, which claims the benefit of U.S. Provisional Application No. 60/577,958, filed Jun. 8, 2004.

BACKGROUND OF THE INVENTION

1. Field of the Invention

My invention relates to infant incubators.

The purpose of this teaching is to add new matter to the parent application.

My invention relates to a vented microcradle for use in an incubator system specifically designed to maintain a premature infant in a controlled care environment from creation to implantation. The incubator system is thus an engineered environment specifically designed for the care of human embryos and hatchlings.

A human infant is properly termed an embryo only from creation until hatching, and then from hatching until implantation he or she is termed a hatchling. Hatching is a milestone of human development in which the embryo makes a hole in the shell of the human egg and then escapes in an extrusive behavior. Hatching is a prerequisite to implantation. Incorrect definitions of the term embryo have persisted due to ignorance of the human hatching event.

Nidation is another word for implantation. A human infant is termed a prenid (PRE-nid) from creation to implantation. The word prenid is derived by shortening of pre-nidation, which means pre-implantation, and prenidial (pre-NID-e-al) is the adjectival form. The term prenid is convenient because it encompasses both human embryos and hatchlings. According to this etymology, the uterine cavity is the nest (Latin nidus, from which the term nidation is derived) and the settlement the infant makes in the nest at implantation time is called the nidia (compare Latin colonus, colonia). Hence, prenidal (pre-NIGH-dal) would mean before the infant has entered the uterine cavity, whereas prenidial means before the infant has actually implanted.

Prenidial gestation refers to a maternal, bodily provision for prenidial development as well as to prenidial developmental needs in general, whereas prenidial incubation refers to an engineered provision for development outside the maternal body in a manner analogous to natural gestation. Whether due to preterm delivery or external creation, outside the maternal body prenids are premature infants because it is premature for them to be outside the maternal body on their own.

Sophisticated incubator systems for premature infants prior to implantation are termed prenidial incubators. Prenidial incubators are analogous to neonatal incubators, except they relate to patient care for prenids instead of for neonates.

My invention relates to a vented microcradle for a prenidial incubator, more specifically a side-vented microcradle for a prenidial incubator.

2. Prior Art

Historically and to the present, medicine has had trouble understanding the principles of thermoregulation needed to care for infants in incubators. Time and again practitioners have made the basic mistake of confusing a patient's temperature with the ambient temperature of the environment inside the incubator. To finally be clear on this, it is incorrect to measure the quantity corresponding to the temperature inside an incubator and to interpret it as data corresponding to the variable of the patient's own temperature! Instead, the patient's temperature must be monitored distinctly in contrast to the temperature of the patient's environment.

Another key ingredient for incubator competence is ventilation. A stagnant environment is not healthy and so a circulation of the environment is necessary. Though similar in principle, neonates and prenids differ in their ventilation requirements because neonates live in a gas/vapor phase environment whereas prenids live in a liquid phase environment. Prenids transfer all metabolic resources and wastes via an incubation medium in which they are submerged. Prenids require gentle fluidic ventilation, which means the incubation medium must be circulated around the infant to remove wastes and to refresh metabolic resources, but gently enough so that beneficial substances produced by the infant are not stripped away. Fluidic ventilation is provided in the fallopian tube by cilia and small muscular contractions that urge fluid to-and-fro past the infant.

My teaching in U.S. Pat. No. 6,694,175 introduces the competent manner of thermoregulation for infants in a prenidial incubator. My teaching in the parent application introduces the competent manner of ventilation for infants in a prenidial incubator. These teachings are incorporated here by way of reference. These teachings combine to establish prenidial incubation as a competent discipline for the care of infants prior to implantation. A thorough understanding of these teachings is prerequisite to the present disclosure. Thorough understanding of the discussions presented in papers found in the file wrappers of the corresponding applications, with particular emphasis on discussions of the prior art, is strongly recommended.

Following upon the parent disclosure, this disclosure adds variety and complexity to the medical science of prenidial ventilation. In addition, because the medical and scientific communities continue to struggle helplessly with even the most basic concepts, the principles of prenidial thermoregulation are reviewed.

Genifection (JEN-ih-feck-shun) is the crime of using assisted reproductive technologies to create human embryos in an environment where they are unlikely to be cared for with full responsibility as individual patients, beloved family members, and equal members of society. The word is coined using Latin roots, by combining geni—(one's kind) with—fection (the making of, by artful means). Genifection is a terrible crime against humanity.

At present practitioners of in vitro fertilization rely heavily on genifection to compensate for their extremely poor success in incubating human embryos and hatchlings. Unable to reduce the tragic mortality rates that result from their poorly skilled incubation and transfer methods, practitioners of in vitro fertilization typically create a plurality of embryos so that the product of their numbers despite low survival rates will sometimes result in at least one survivor for the sake of entrepreneurial success. In other words, such practitioners use genifection to compensate commercially for their extremely poor medical and scientific practices.

In other cases, though comparatively less common, human embryos have been created in the lab with only their harm in mind, e.g., for experiments in stem cell research.

Please join me in putting an end to these dehumanizing crimes of genifection.

3. Statement of the Necessity

For a neonatal incubator, the cradle portion of the incubator must allow for easy access to a patient while at the same time affording proper thermoregulation and ventilation at all times. A well-designed prenidial incubator should offer the same advantages.

It may also be desirable to visualize an infant in a prenidial incubator from below as well as from above. A variety of vented microcradle is needed to satisfy this objective.

What is needed is a side-vented microcradle for a prenidial incubator, more specifically a side-vented microcradle with a clear bottom and an open top.

4. Note

A number of cited references were found after filing the original specification. These are discussed in several papers available in the electronic file wrapper of this application having the document description "Information Disclosure Statement Letter". These are available online at the U.S. Patent and Trademark Office website using the public Patent Application Information Retrieval system (Public PAIR). Engineers should consider these papers along with the associated references. Note that the non-patent literature cited is also available in the file wrapper under "NPL Documents".

Of particular note, Matz (U.S. Pat. No. 2,062,468), Le Pesant et al (U.S. Pat. No. 4,569,575), and Tuckerman et al (U.S. Pat. No. 4,450,472) provide teachings in their respective arts that pre-date prior art references cited in the original specification.

Referring to FIG. 105, Matz teaches a variable focus liquid lens; in contrast, teachings such as those of Berge et al (U.S. Pat. No. 6,369,954) and Feenstra et al (U.S. Pat. No. 7,126,903) provide relatively modern examples of renewed interest in this art.

Referring to FIG. 106, Le Pesant et al teach a digital microfluidic system, and refer to an even earlier example of this art; in contrast, teachings such as that of Pamula et al (U.S. Pat. No. 6,911,132) provide relatively modern examples of renewed interest in this art.

Tuckerman et al teach a use of microfluidics to cool integrated circuits.

Also of particular note, Petronis et al describe a microfluidic cell culture chip employing substantially planar layers laminated together. However, they do not employ an open-top microcradle design. (Petronis et al, "Transparent Polymeric Cell Culture Chip with Integrated Temperature Control and Uniform Media Perfusion," BioTechniques, vol. 40, no. 3, pp. 368-76, March 2006.) Noted is the abstract and FIG. 1, p. 369.

Kricka et al (U.S. Pat. No. 5,296,375) teach a device made of micromachined glass layers comprising separate wells for holding sperm and egg separated by a swim-up channel for sperm. They employ pumps or capillarity to fill channels and wells and means such as a pump or syringe to expel a fertilized egg. (column 3, lines 51-64) They do not teach or fairly suggest fluidic ventilation of an embryo or hatchling.

BRIEF SUMMARY OF THE INVENTION

My invention satisfies the above-stated needs.

The invention comprises a microfabricated cradle ("microcradle") forming an enclosure for the care of a premature infant during preimplantation development with a clear bottom and an open top and having one or more side vents for fluid entry/exit to provide a circulation of fluid within the cradle via a system of microfluidic channels and related devices. The invention is therefore a side-vented microcradle with a clear bottom and an open top.

The microcradle along with its related systems and devices are collectively referred to as an incubator, more specifically a prenidial incubator; similarly, a medical care environment provided by the incubator for infant care is called the incubator environment. The purpose of the incubator is to sustain the life of a premature infant during life before implantation.

The invention further comprises a fluidic circuit assembly (FCA), which is necessary for the practice of elaborate embodiments, a temperature bath to maintain an ambient temperature for the incubator, machine-readable indicia or markings, and a specialized catheter to transfer a patient to/from the incubator.

The invention incorporates and is compatible with various modifications of my teaching in U.S. Pat. No. 6,694,175 to achieve proper thermoregulation of the patient. The invention may also incorporate additional technologies to achieve increasing sophistication.

The invention forms a central structure in an incubator for the care of premature infants during life at any time prior to implantation.

The invention finds use whenever an infant requires incubation outside the maternal body during life before implantation.

BRIEF DESCRIPTION OF THE SEVERAL VIEWS OF THE DRAWING

FIG. 15 is a side cross-sectional view of a side-vented microcradle.

FIG. 16 is a mathematical formula relying on notation used in FIG. 15.

FIGS. 17-18 are exemplary mask patterns used in etching microfluidic channels and vias for a side-vented microcradle.

FIGS. 38A-B are side cross-sectional views of variable focus liquid lens objectives according to the invention.

FIG. 39 is a side cross-sectional view of a prior art microscopy setup illustrating, in view of FIG. 20C, a relationship between working distance and numerical aperture.

FIG. 40 is a side cross-sectional view of a prior art microscopy setup illustrating a problem of lost light when employing a flat cover glass.

FIG. 41 is a side cross-sectional view of a microscopy setup employing a microlens cover glass according to the invention.

FIG. 45 is a side cross-sectional view of a variable focus liquid lens objective according to the invention.

FIG. 46 is a side cross-sectional view of a liquid lens with variable optical properties according to the invention.

FIGS. 47A-B are side cross-sectional views of a liquid lens with variable optical properties according to the invention.

FIG. 49 is a graph of the electromagnetic spectrum.

FIGS. 50A-B list data on the electromagnetic spectrum.

FIGS. 61A-B are simplified top cross-sectional views of microfluidic systems for exchanging parcels of fluid between slow and fast moving channels so as to speed fluid transit and delivery between a patient and a fluidic circuit assembly device.

FIGS. 62A-B are side cross-sectional views of ions and polar molecules gathered near a sidewall electrode to illustrate a theory of capacitive spreading.

FIGS. 67A-B, D are schematic views of electronic circuits for self-scooting circuitry according to the invention.

FIG. 67C is a formula for an electronic circuit for self-scooting circuitry according to the invention.

FIG. 67E is a top orthogonal view of control electrodes being enabled and disabled according to the invention so as to route droplet movement at a fork.

FIG. 67F is a schematic view of a droplet switch being employed according to the invention to enable other circuitry.

FIG. 68 is a top orthogonal view of a liquid flowing continuously from a reservoir according to the action of electrowetting.

FIGS. 69A-C are timing diagrams for self-scooting circuitry according to the invention, showing different alternatives for turning control electrodes on and off over time.

FIG. 82 is a top orthogonal view of an electrode arrangement for self-scooting circuitry according to the invention.

FIGS. 83A-B are side cross-sectional views of electrode arrangements for self-scooting circuitry according to the invention.

FIG. 84 is a top orthogonal view of a prior art interdigitated electrode arrangement.

FIG. 85 is a side cross-sectional view of an electrode arrangement for self-scooting circuitry according to the invention.

FIG. 86 is a side cross-sectional view of a combination lateral and vertical airflow system according to the invention.

FIG. 106 is a side cross-sectional view of a prior art digital microfluidic system.

DETAILED DESCRIPTION OF THE INVENTION

Figure 1:
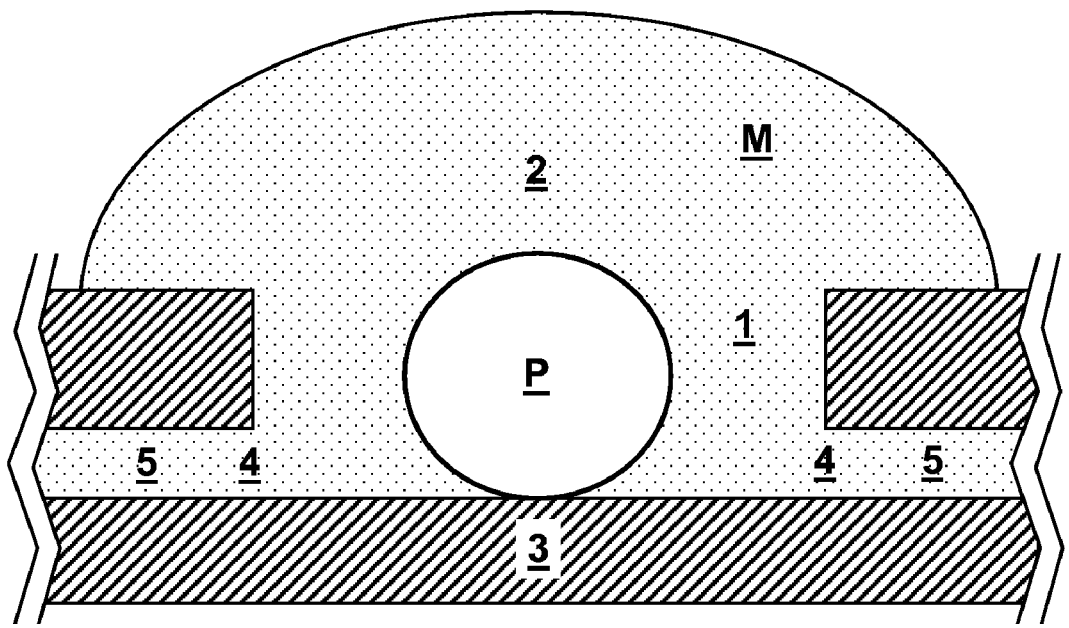
FIG. 1 is a side cross-sectional view of a side-vented microcradle.

Analogous to a cradle for neonatal care, a vented microcradle forms a central structure in an incubator environment for the care of infants before implantation. As with the cradle of a neonatal incubator, key ingredients of the vented microcradle are easy access to a patient combined with proper thermoregulation and ventilation at all times. Disclosed is a side-vented embodiment of a microcradle with a clear bottom and an open top.

The invention relies on integrated microfabrication technology (IMT) for its manufacture. IMT is a broad, interdisciplinary field employing diverse arts to make small size systems and devices. IMT technology includes submillimeter, micrometer (micron), submicron, and nanometer technologies, and often incorporates these with larger scale technologies. In the world of micromanufacturing, IMT designs offer important benefits such as intimate integration with electronic circuitry and the ability to manufacture arrays of designs on a single substrate. Although many other IMT arts are also implicated by the invention, microfluidic technology and glass microfabrication technology are especially relevant. Microfluidic technology relates to fluid flow on a microscopic scale and includes a number of rapidly evolving specialty areas such as micropump and microvalve technology. Using IMT technologies for prenidial incubation enables infants to be precisely handled and cared for in a way that is tailored to their microscopic size and gentle fluidic requirements during life before implantation.

1. Preferred Embodiment

My invention is a side-vented microcradle with a clear bottom and an open top for the purpose of prenidial infant care in an incubator setting. According to the preferred embodiment shown in FIG. 1, the side-vented microcradle has the following minimum features: a cradle 1 for cradling a prenidial patient P, the cradle 1 having an open top 2, a clear bottom 3, and one or more side vents 4 to allow for an entry/exit of a fluid medium M into/out of the cradle 1 via microfluidic channels 5. The fluid is a liquid incubation medium M in which the patient P is submerged. In operation, fluid exiting the side vents 4 is translated into a vertical direction so as to ventilate the patient P inside the cradle 1. Similarly, fluid inside the cradle 1 may be withdrawn through the side vents 4 so as to ventilate the prenid P. Accordingly, fluid M may be made to flow over the prenid's body P in an upward, downward, or to-and-fro direction. Using microfluidics, including means to urge fluid to flow (such as means of a micropump), fluid M is urged via the microfluidic channels 5 through the side vents 4 so as to cause fluid M to circulate gently over the prenid's body P for the purpose of fluidic ventilation.

The open-top design offers a number of distinct advantages over the prior art. Unlike the art of Hunter (U.S. Pat. No. 4,574,000), Beebe et al (U.S. Pat. No. 6,193,647), and Thompson et al (U.S. Pat. No. 6,673,008), as well as what has been disclosed by Campbell et al (US published application 2002/0068358), using my invention the patient is easy to access in a direct fashion, fluidic ventilation does not need to be interrupted while the patient is being accessed, and the patient is exposed to an ambient pressure above the microcradle rather than to a pressure used to urge fluid to flow.

As will appreciated by those skilled in microfluidics and other arts in the field of integrated microfabrication technology (IMT), numerous variations of the FIG. 1 embodiment are easy and cost-effective to manufacture.

2. Example of Manufacture

A side-vented microcradle is preferably made of glass. Here a minimal embodiment is described to give a basic manufacturing example. Referring to FIGS. 1 & 2A-D, the clear bottom 3 of the microcradle is formed by the bottom of a clear petri dish 6 made of glass. A desired pattern of microfluidic channels 5 is etched on one side of a glass sheet 7 that in this example is 100 microns thick. A hole 8 that in this example is 500 microns in diameter is etched through the glass sheet 7. This hole 8 forms the walls 9 of the cradle 1. A second hole 10 is made through the glass sheet 7 to form a via (through-hole) in fluidic communication with the microfluidic channels 5. The glass sheet 7 is directly bonded (preferably without adhesive) to the bottom of the petri dish 6 with the pattern of microfluidic channels 5 facing the petri dish 6. A microfluidic connector 11 is bonded on top of the glass sheet 7 over the second hole 10 by melting a fine strand of glass where the edges of the connector 11 meet the glass sheet 7. A fluid supply line 12 is connected to the microfluidic connector 11, said line 12 being further connected in series to a flow meter 13, micropump 14, and fluid reservoir 15. The flow meter 13 may be omitted if the micropump 14 is self-metered or another means of monitoring flow is provided.

To achieve operation the petri dish 6 is partially filled with a fluid incubation medium M and the microfluidic system comprising the reservoir 15, micropump 14, flow meter 13, and microfluidic channels 5 is primed with the same fluid; the micropump 14, which is preferably reversible, is operated as desired with the aid of flow rate indications. Movement of fluid in the to-and-fro direction, with net movement in one direction, is preferred. For example, the net movement may occur in the downward direction, meaning with fluid flowing out of the microcradle through the side vents 4. In this simplistic example, the fluid filling the petri dish 6 provides a reservoir of fresh medium M for the patient; a to-and-fro movement helps to maintain endogenously produced substances around the patient's body; at the same time, a net downward movement removes wastes and draws upon fresh fluid medium M from above the patient P. The to-and-fro movement may be likened to the beating of cilia in the fallopian tube. It is contemplated that in order to maintain a gentle state of fluid flow the rate of flow past the patient P should generally not exceed an upperbound of 1 to 10 microns per second. The side vents 4, which are ventilation ports located on the sidewalls 9 of the microcradle, are formed where the microfluidic channels 5 meet the hole 8 forming the cradle walls 9; at the point where the microfluidic channels 5 meet the hole 8 forming the cradle walls 9, the channels are 20 microns high and 150 microns wide in this example. Correspondence between a rate of fluid flow through the side vents 4 and a desired flow rate past the patient P can be determined by calculation. More detail on this topic is given under "Design Considerations" below. An embryo P with an eggshell 140 microns in outer diameter will stick out a ways above the 100 micron height of the cradle walls 9 in this example; however, in general the cradle walls can be made to any desired height.

Figure 3:
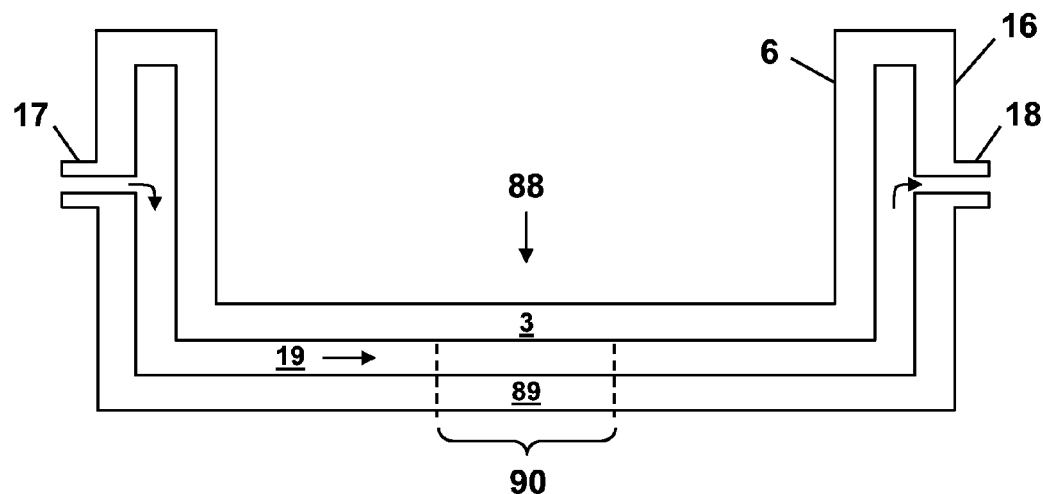
FIG. 3 is a side cross-sectional view of a petri dish formed into a double-walled vessel with an inlet and outlet for a running fluid.
Figure 4:
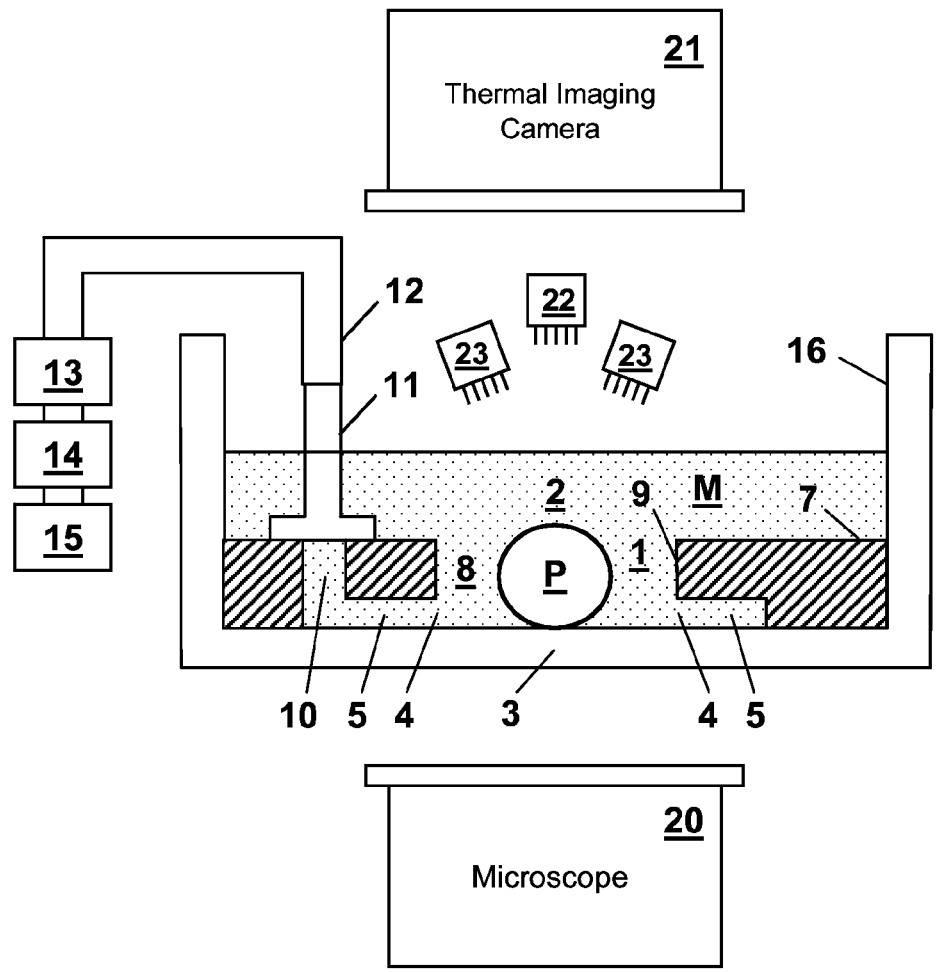
FIG. 4 is a side cross-sectional view of a side-vented microcradle, and is most descriptive of the invention.

Referring to FIG. 3, the petri dish 6 is preferably formed into a double-walled vessel 16 with an inlet 17 and outlet 18 for a running fluid 19. The fluid serves as a precisely controlled temperature bath to maintain ambient temperature for the incubator environment. Referring to FIG. 4, a microscope 20 may be positioned below to visualize the patient P and a thermal imaging camera 21 according to U.S. Pat. No. 6,694,175 may be placed above to monitor the temperature of the patient P. A lamp 22 used with the microscope for lighting should not produce infrared radiation at a level that will overheat the patient P; if necessary, a surface half-mirrored with gold or other filter for infrared radiation may be used. According to U.S. Pat. No. 6,694,175, infrared heat lamps 23 may be focused on the patient P from any location (here shown above) to provide warmth. More detail on the topic of positioning a thermal imaging camera and infrared heat lamps is given under "Design Considerations" below, particularly in reference to an absorption of infrared radiation by an aqueous medium. If necessary, the lamps 23 may be shuttered each moment a thermal image is taken so that their signature does not interfere. The incubator is kept in a clean room environment and a laminar flow hood provides additional protection from contaminants. Humidity, air temperature, air composition, and air pressure are maintained in the flow region of the hood.

As a notable feature, when no sources of impurity are introduced by the manufacturing process, the patient will only be exposed to the glass of the incubator, which is inert. Thus, this particular manufacturing example results in an ultrapure incubator environment for the patient. Impurities associated with the manufacture of devices located down the line 12, e.g., the micropump 14, will not reach the patient if they are not made to flow up the line 12 and into the microcradle where the patient P rests. A net downward flow (draining fluid out of the microcradle) offers this advantage. The ultrapure environment eliminates a need for clinical studies on the effect of patient exposure to manufacturing impurities, e.g., from adhesives. This explains why the direct bonding of glass to glass with no adhesive is preferred.

Microchannels can be etched in glass using a variety of microfabrication technologies, including laser etching, powder blasting, DRIE (deep reactive ion etching), HF (hydrofluoric) etching, or ion-beam etching. Precision Microfab, LLC (Arnold, Md.) is able to laser etch microchannels in a glass substrate. Micronit Microfluidics, BV (Enschede, The Netherlands) offers direct glass to glass bonding with no adhesive.

Other manufacturing processes and substrates can also be used in making the invention, e.g., polymer molding techniques can be used with a polystyrene substrate. Yet, compared to glass, polymer designs will typically present added design challenges, particularly in relation to hydrophobicity. This topic is discussed under "Design Considerations" below.

The above-described embodiment will be shipped clean and sterile and will typically be disposable (or kept by the patient's family as a memento) after a single use.

Numerous variations of the invention are possible, including highly elaborate ones.

3. Fluidic Circuit Assembly (FCA)

The preferred embodiment not only satisfies the basis for a complete prenidial incubator system that combines easy access to a patient along with proper thermoregulation and fluidic ventilation at all times, but it is also simple enough that it can be manufactured in a way that results in an ultrapure environment for the patient such that chemical and other forms of exposure (e.g., to electrical energy) are avoided. However, despite the inherent advantages of simplicity, it is contemplated that elaborate embodiments of the invention may also be desirable, particularly as science advances.

To satisfy this possibility, my invention further comprises a fluidic circuit assembly (FCA). The FCA is not a distinct invention because it forms an integral part of the practice of elaborate embodiments of the invention; in fact, the preferred embodiment may be taken to incorporate a simplistic version of the FCA. In order to manufacture highly elaborate embodiments of the invention, it is necessary to employ an elaborate routing of microfluidic channels in intimate combination with a microcradle and any number of sophisticated devices. My invention satisfies this routing and integration requirement by employing an FCA.

A vented microcradle is an essential component of an FCA according to the invention. Compared to the prior art, what is distinct about the FCA of the claimed invention is that is integrated with a vented microcradle for the care of a prenidial infant.

By analogy, accomplishing an elaborate routing of microfluidic channels is like a similar challenge solved in the field of electronics using a printed circuit board (PCB), except in this case vias and traces are replaced by vias and channels. The channels and vias are formed in layers of "board" that are laminated together. The result is a fluidic circuit board, or FCB. A variety of small-sized devices can be directly mounted to an FCB to form a fluidic circuit (board) assembly (FCA) in a manner similar to mounting devices on a PCB to form a printed circuit (board) assembly (PCA). Furthermore, a PCB/PCA may be included in an FCA to enable integrated electronic control and monitoring of a microfluidic system. Devices can be added or replaced by mounting them to the FCB at any time. This eliminates the need to rely on a single monolithic device, thus helping to speed development time, to linearize the relationship between cost and complexity, and to improve versatility and customization down the road.

The term "FCB" may also be used to mean an "FCA" in the same way that the term "PCB" is often used to mean a "PCA". That is to say, an FCB may refer not only to a plain FCB but also to an FCB populated with components, or more specifically an FCA.

An FCA is a type of integrated microfabrication technology (IMT) and can accommodate other IMT technologies (i.e., submillimeter, micrometer (micron), submicron, and nanometer technologies). In addition to being able to support a large variety of small-sized components (e.g., microfluidic components, microelectronic components, microsensors, micro-electro-mechanical (MEMS) devices, labs-on-a-chip, etc.) the FCA can also accommodate intimate combination with various large scale devices (e.g., a microscope, thermal imaging camera, spectroscopy devices, chemical analysis equipment, etc.). According to the invention, the FCA may also include machine-readable indicia or markings as well as a temperature bath to maintain ambient temperature for the incubator environment and various FCB components.

Figure 5:
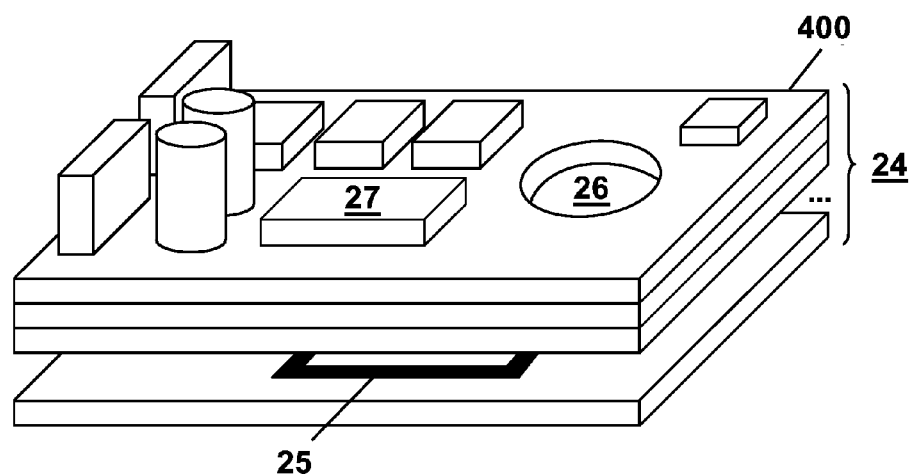
FIG. 5 is an exploded perspective view of a fluidic circuit board having a side-vented microcradle.

Referring to FIG. 5, a generalized embodiment of an FCA 400 according to the invention comprises a plurality of wafer or board layers 24 (e.g., made of glass) laminated together (e.g., using direct bonding of glass to glass without adhesive). The FCA 400 includes the following minimum features: a network of microfluidic channels 25 patterned in board layers 24 to serve the cradle 26 of a vented microcradle with fluid. Microfluidic channels and vias patterned in an FCB may connect or serve any number of devices or components 27. The FIG. 1 embodiment incorporates a simplistic FCA involving two board or wafer layers, the layers being formed by the glass petri dish 6 and the glass sheet 7, which are laminated together using direct bonding without adhesive; microfluidic channels 5 and via 10 are patterned in one of the board layers (glass sheet 7) to serve the cradle 1 of the vented microcradle with fluid. In general, note that vented microcradles (and, hence, an FCA, which incorporates a vented microcradle) are easily distinguished from prior art enclosures for prenidial infants because they specifically combine a cradle 1 having an open top 2 with a microfluidic circulator system. A vented flooring according to the parent teaching may also be incorporated within the scope of an FCA.

Figure 6A:
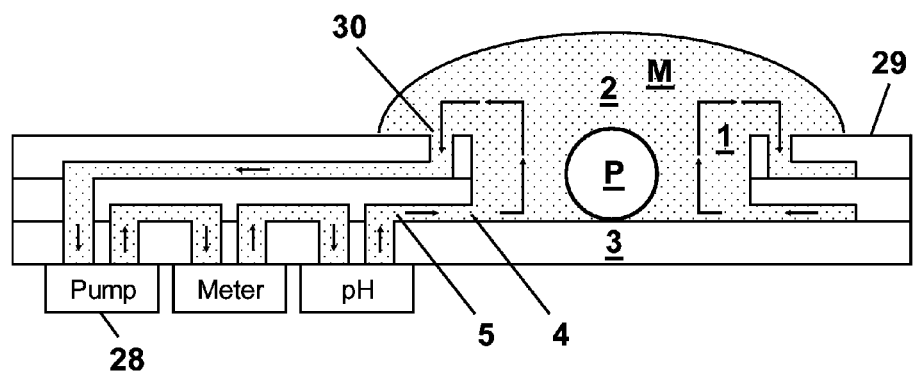
FIGS. 6A-D are side cross-sectional views of side-vented microcradles.
Figure 6B:
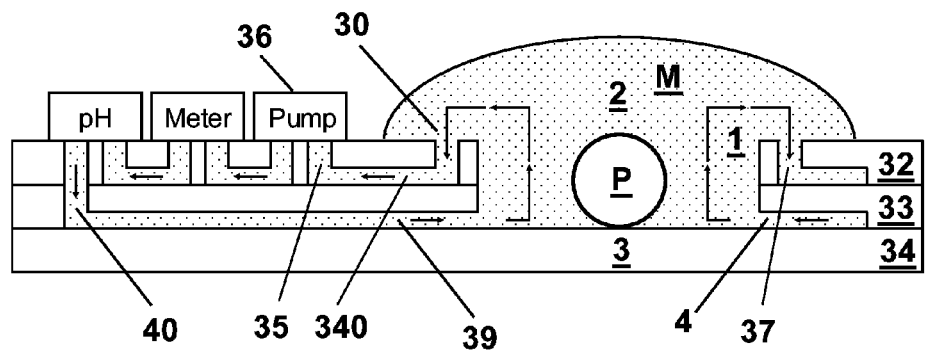
Figure 6C:
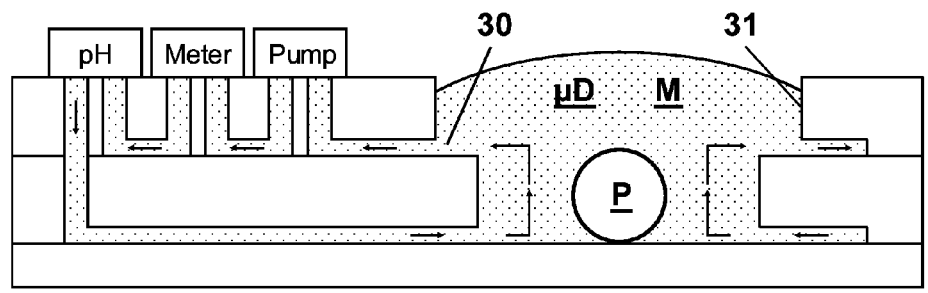
Figure 6D:
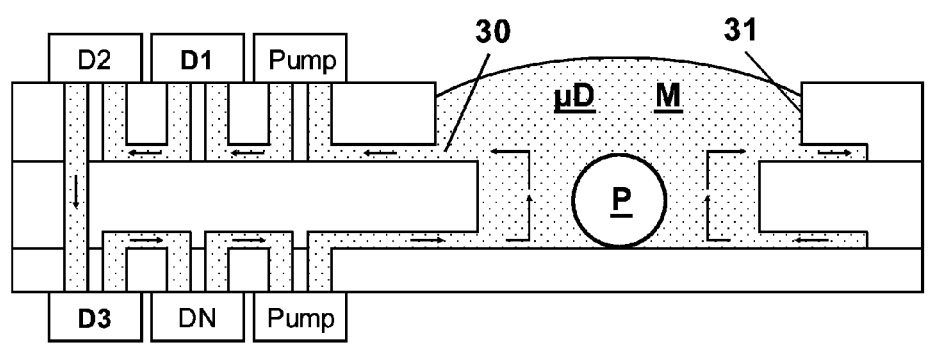

FIGS. 6A-D illustrate embodiments of a side-vented microcradle employing FCAs of modest complexity limited to three board layers. Referring to FIG. 6A, a micropump 28 mounted to the bottom of an FCB 29 causes a fluid incubation medium M to be urged through a network of microfluidic channels 5 so as to fluidically ventilate a patient P inside the side-vented microcradle 1. Various devices (e.g., a flow meter, pH meter, etc.) can be mounted to the FCB. Note that in contrast to the FIG. 2D embodiment, the embodiments shown in FIGS. 6A-6D enable a return path for fluid by adding additional ventilation ports 30 for this purpose. In FIGS. 6A-B the additional ports operate vertically whereas in FIGS. 6C-D they operate horizontally. In FIGS. 6C-D the uppermost board layer provides a retaining wall 31 for a microdrop μD under which the patient P is submerged. FIG. 6D illustrates a mounting of devices D to both top and bottom sides of an FCB. Although fluid M is shown by arrows to be circulated in one direction, it is understood that to-and-fro or reversible circulation can be accomplished with an appropriate pumping scheme. In FIG. 6D, dual or opposing pumps are provided.

Figure 7A:
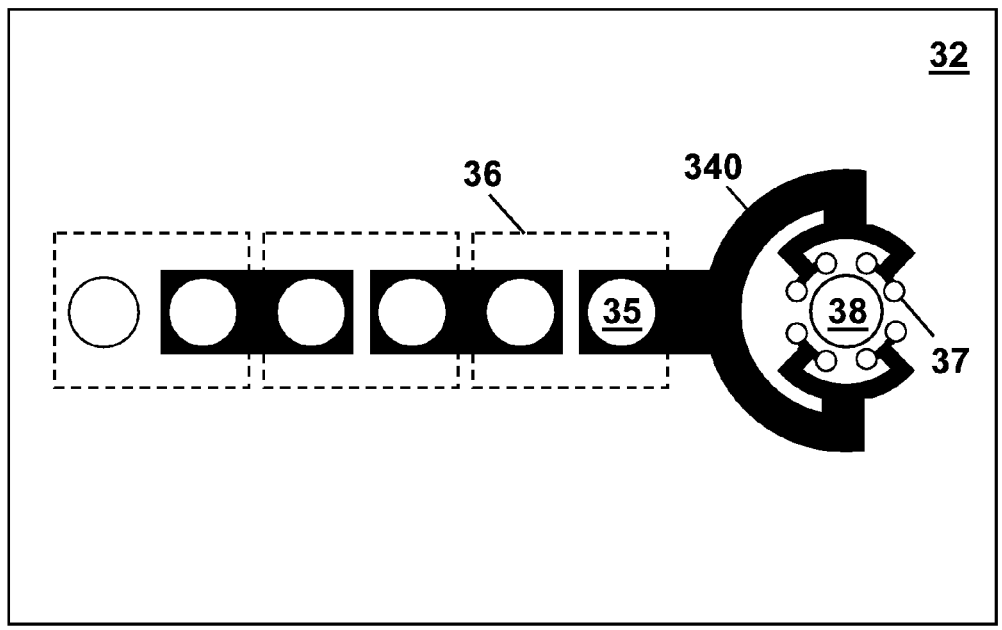
FIGS. 7A-B are bottom orthogonal views of glass sheets having microfluidic channels and vias etched in them for a side-vented microcradle.
Figure 7B:
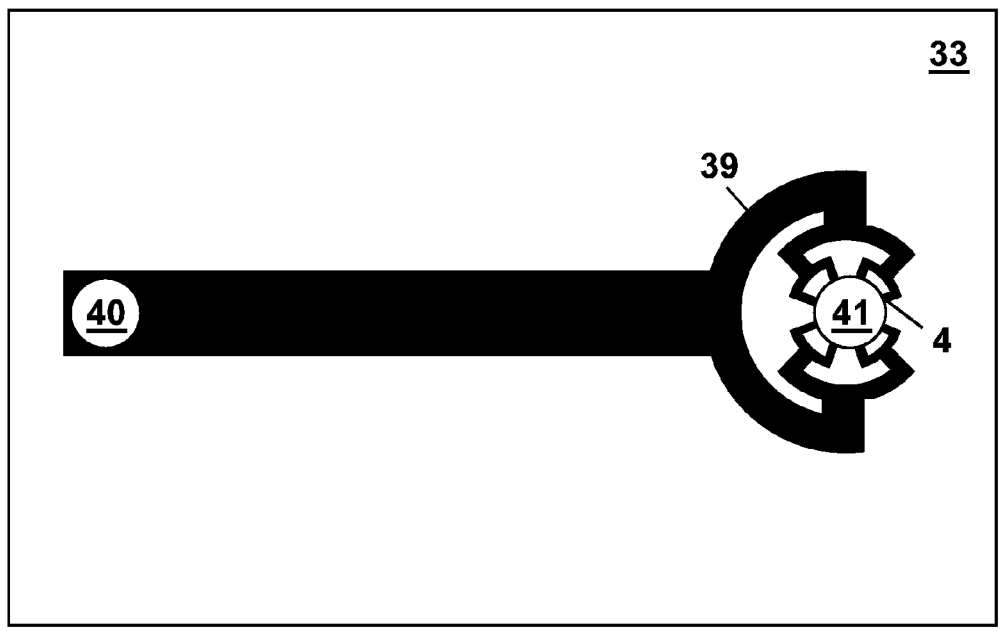

FIGS. 7A-B show an easy method of making the FIG. 6B embodiment using glass sheets for the board layers 32-34. Referring to FIG. 7A, microfluidic channels 340 are etched on the bottom side of the topmost layer 32; vias are etched through the layer 32, including vias 35 for fluidic communication with devices 36 mounted on top (shown in outline), vias 37 for ventilation ports 30, and a via 38 forming the top half of the cradle walls of the microcradle 1. Referring to FIG. 7B, microfluidic channels 39 are etched on the bottom side of the middle layer 33; vias are etched through the layer 33, including a via 40 for fluidic communication with a device mounted on top of the FCB and a via 41 forming the bottom half of the cradle walls of the microcradle 1. The bottommost layer 34 does not require micromachining.

Figure 8:
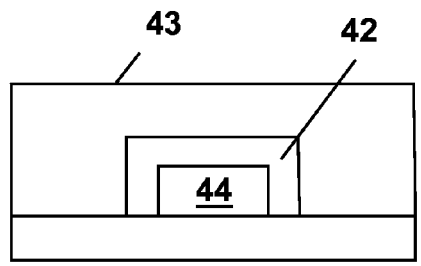
FIG. 8 is a side cross-sectional view of a chamber etched in a layer to support a device inside a fluidic circuit board according to the invention.

FCBs allow for versatile placement of component devices. Devices can be mounted on the top, sides, or bottom, or even inside the FCB. The FCB can also support devices that are placed above a microcradle or that reach into the microcradle. Referring to FIG. 8, a chamber 42 can be etched in a layer 43 to support a device 44 inside the FCB. Devices can also be placed in microchannels or in the microcradle itself.

Figure 9A:
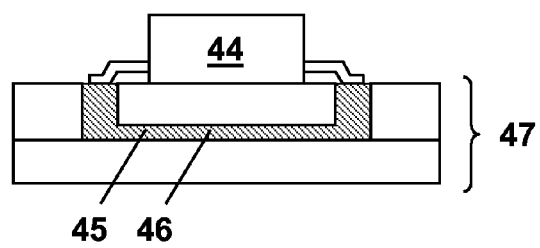
FIGS. 9A-C, E are side cross-sectional views of sections of a fluidic circuit board according to the invention.
Figure 9B:
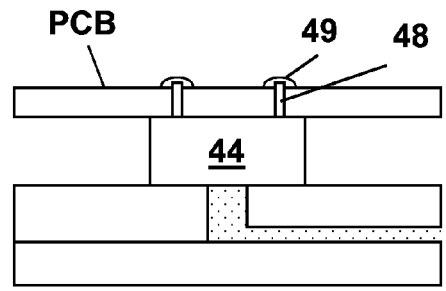
Figure 9D:
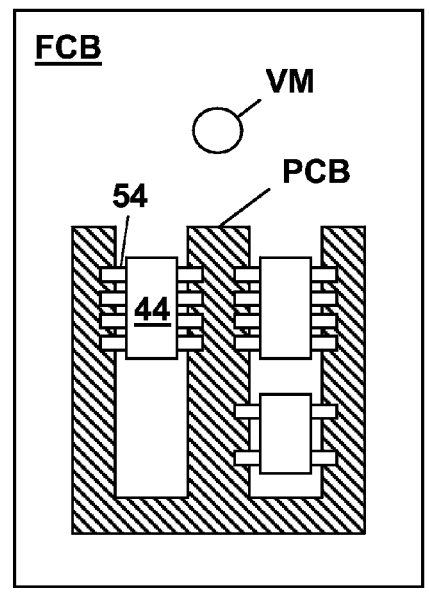
FIG. 9D is a top orthogonal view of a fluidic circuit board having a side-vented microcradle.
Figure 9C:
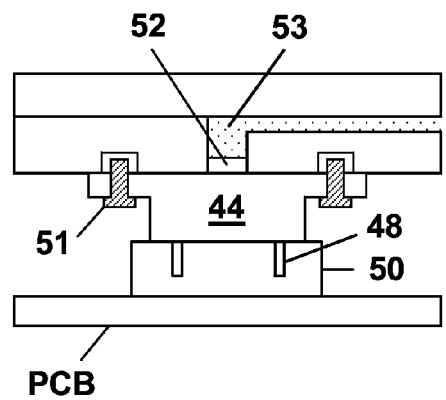
Figure 9E:
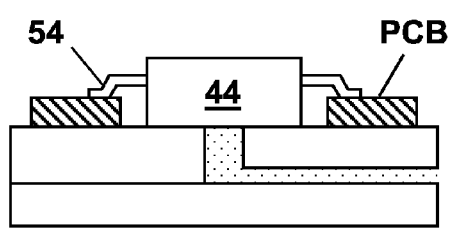

FCBs also allow for versatile placement of electrical connections. Conductive traces and vias can be directly patterned on the board layers of an FCB in a manner analogous to PCB manufacture. Referring to FIG. 9A, since raised traces between layers would interfere with lamination, channels 45 can be etched in a board layer and traces 46 can then be deposited in the channels so that the layers 47 will make flush contact with each other. Referring to FIG. 9B, component leads 48 of a device 44 mounted to an FCB are inserted through holes in a PCB in the manner of through-hole construction and attached with metal solder 49. FCBs will generally be used only once for health reasons; yet it may still be desirable to recover some of the components on an FCA for repeated use. Referring to FIG. 9C, component leads 48 are inserted into a solderless connector 50 for easy removal; a removable anchoring means 51 (e.g., a screw or snap-in connector) can be used to mechanically fix a component device 44 to the FCB; a sealing means 52 can be used to seal a fluidic connection between the component device 44 and a microfluidic via 53 in the FCB. Referring to FIG. 9D, a PCB can be mounted to an FCB and component devices 44 can be mounted using surface-mount construction such that component leads 54 are soldered to pads on the PCB; a vented microcradle VM is shown in this figure; FIG. 9E shows a cross-sectional view of this surface-mount arrangement. A PCB may be recessed into an FCB board layer by etching into the layer. Insulation can be added for electrical isolation.

Devices requiring electrical support can be powered by a power supply located on or off of an FCB. Power can also be communicated wirelessly; for example, photoelectrical energy can be used to power a device embedded beneath transparent layers.

Some devices may require pneumatic support. Microfluidic channels can support both liquid and gaseous fluid flow. A network of gaseous microfluidic channels with a system of automated valve manifolds can be employed to connect a plurality of pneumatically-driven devices on an FCB. A similar arrangement can be used with liquids to communicate hydraulic power to devices. Gaseous channels can be used for other purposes as well (e.g., to serve chemical processes on a lab-on-a-chip, to maintain pH in a fluidic reservoir employing a $CO_2$ buffering system, etc.).

Optical fibers (fiber optics) along with lenses may be routed or embedded inside an FCB or in devices supported by the FCB. Fiber optics may be employed for visualization, data transfer, and illumination.

Figure 10:
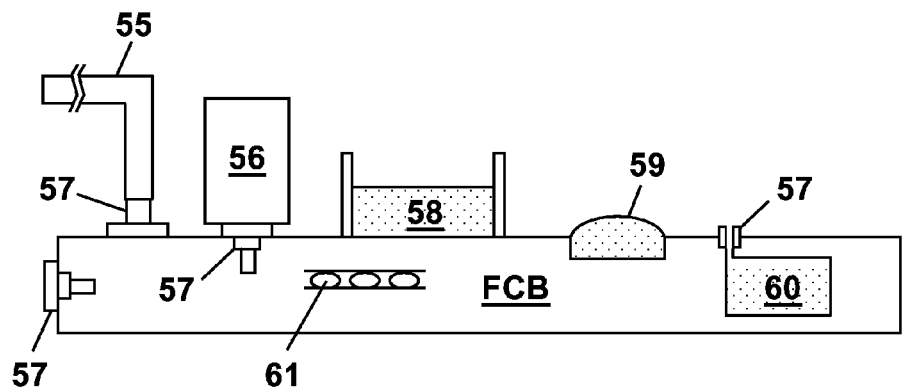
FIG. 10 is a side cross-sectional view of a fluidic circuit board according to the invention.

An FCA may include reservoirs for fluid, e.g., for sequential media, to condition the fluid incubation medium, to serve chemical processes on a lab-on-a-chip, etc. Referring to FIG. 10, the FCB may support fluid supply lines 55 and fluid microcontainers 56, including pressurized lines and microcontainers for gas or liquid; the FCB may include various types of male and female connectors 57 for fluid supply lines 55, microcontainers 56, and for filling or emptying reservoirs; the FCB may support wells 58 and microdrops 59 for liquid; the FCB may include embedded reservoirs 60 for fluid. Microcradles and even microchannels themselves also provide reservoirs for fluid in an FCB. Droplets 61 may be stored for digital microfluidics.

To connect an FCA externally, in addition to fluid supply line connectors, the FCA may also support connectors (or ports) for electrical lines and optical fibers. The FCA may also support wireless communication using both electronic and optical (e.g., infrared) signals. The FCA may also support mechanical connections for guide wires or other mechanisms to actuate devices mechanically. FCAs support a variety of interconnects.

For operation in a fixed position, an FCA is mechanically fixed or locked securely into position, preferably using a removable means, for example, a screw-down or clamping means, or alternatively a slotted, seated, or cartridge-type means, including any needed connectors or alignment guides. An FCB socket connection such as a PC-slot type electrical connection or a solderless-type electrical connection may double as a means of mechanically fixing the FCB into position; various other connections (e.g., fluid line connections) may also serve this purpose; connections may be modified to better serve this purpose. A retaining clip, lock, or other means may be employed to prevent accidental loosening of the FCA.

Sensors and alarms may be employed to indicate whether the FCB is fixed properly into position and to detect various conditions such as whether connections are properly made. In general, an FCA may support plug-and-play technology such that the FCA is recognized as a device by a computer running relevant software. The software can then be used to report various alarm or status conditions associated with the FCA device as detected by sensors.

In addition to including fluid ports for ventilation, a vented microcradle may also include fluid ports along with related microfluidic systems to satisfy a variety of other purposes as well, e.g., for dosing medications, dispensing, flushing/filling, hygiene, therapy, conditioning, analysis, transport, etc. Fluid ports may be reserved for dedicated purposes (e.g., ventilation only) or for dual or selectable purposes (e.g., ventilation and medicine delivery). Fluid ports may include various features (e.g., nozzles, a particular pattern or orientation, large sizing to speed fluid exchange, shutters or valves to prevent backflow or undesired mixing, etc.) to complement their function. Similar diversity may be achieved with respect to fluid ports situated elsewhere on an FCA, e.g., at the site of a reservoir, lab-on-a-chip, etc.

The variety of analysis purposes satisfied by microfluidic systems has been increasing; examples include compound screening and profiling, diagnostics and point-of-care (POC) testing, chemical analysis, proteomics, etc. Point-of-care testing means testing in proximity to a patient as opposed to sending a sample away to a lab for testing.

FCAs can support digital (discrete droplet) microfluidics as well as analog (continuous flow) microfluidics.

FCAs can support programmable microfluidic networks, including programmable valve arrays. FCBs can support removable covers to seal microfluidic vias and channels at places where optional or alternate components can later be added or removed as desired.

FCAs can be populated with a great variety of components and can be integrated with a great variety of larger scale equipment.

To give only a small sample of the possible variety, FCA components may include microfluidic, electronic (e.g., electrical, microelectronic, and computing), magnetic, chemical, biochemical, physical, mechanical, physiological, electrophysiological, biological, medical, radiological, optical (e.g., fiber optic, photoelectronic, and optoelectronic), and acoustical devices and sensors; lighting and illumination devices (for both visible and invisible, e.g., infrared, spectra); microsurgical, hygienic, and therapeutic devices; labs-on-a-chip, micro total analysis systems (μTAS), and micro-electro-mechanical (MEMS) devices; nanotechnology (e.g., coatings to make surfaces slipperier); fluid conditioning devices (e.g., for chemical and thermal conditioning of fluid) and various environmental maintenance devices; patient conditioning devices (e.g., devices to apply coatings or treatments to a patient's body or eggshell); micromanipulators and instrument positioning devices; and patient handling or transfer devices. Basic microfluidic devices include pumps, valves, mixers, filters, injection nozzles, and dosing devices. Notable sensors include sensors (and alarms) for pH, osmolarity, biochemicals or biochemical markers, temperature, heat output (microcalorimetry), pressure, internal pressure (e.g., a tonometer to measure hydrostatic pressure inside the egg), humidity, fluid reservoir levels, gas or liquid flow, biohazards (e.g., pathogens, toxins, teratogens), chemicals, biochemicals, light, electricity, magnetism, viscosity, biological signals, electrophysiology data, and data on patient growth or health status. Additionally, new devices are constantly being developed.

To again give a brief example of the possible variety, FCAs may be integrated with relatively large scale equipment such as equipment for optical coherence tomography, nuclear magnetic resonance and magnetic resonance imaging (MRI), thermal imaging, microscopy, spectroscopy, mass spectrometry, electrophoresis, chromatography, fluorescence, electrochemical detection, chemical analysis, sonography, micromanipulation and instrument positioning, automation, computing, recording, communication, etc.

FCA designs are compatible with modular microfluidic architectures, which in turn may also be adapted to accommodate vented microcradle designs. Referring to FIG. 5, an active component of a fluidic breadboard (FBB) may be treated as a component device 27 with respect to an FCB containing a passive component designed for the FBB. According to the FBB concept proposed by workers at the University of Illinois at Urbana-Champaign and Northwestern University, the FBB is conceptually and physically split up into two halves: one containing all of the active components, and the other containing all of the passive components. The active components include micro valves, pumps, mixers, sensors, heaters, and other elements that manipulate or sense fluids on the FBB. The passive components consist of microfluidic channel networks. (Shaikh et al, "A Modular Microfluidic Architecture for Integrated Biochemical Analysis," Proceedings of the National Academy of Sciences of the United States of America, vol. 102, no. 28, pp. 9745-50, July 2005.) In general, FCB/FCA designs are more versatile than FBB designs because according to the FCA concept active components may be integrated discretely instead of as a single, monolithic breadboard component. Also, FCA designs can accommodate a plurality of FBB designs. Thus, the FCA is both breadboard and motherboard for a vented microcradle, in the fluidic sense, to use a computer analogy.

Various modular microfluidic architectures are taught by Neukermans (U.S. Pat. No. 6,068,751), Kennedy (U.S. Pat. Nos. 6,086,740; 6,488,895), O'Connor et al (U.S. Pat. Nos. 6,536,477; 6,729,352; 6,827,095; 6,919,046), Bergh et al (U.S. Pat. Nos. 6,737,026; 6,749,814; 6,890,493), Karp et al (U.S. Pat. Nos. 6,814,938; 6,880,576), Pamula et al (U.S. Pat. No. 6,911,132), and Zhou et al (U.S. Pat. No. 7,011,793). Zhou et al ('793) also teach a microfluidic breadboard.

In terms of its design architecture, an FCA according to the present invention may be construed as a specialized type of microfluidic motherboard employing a vented microcradle for prenidial infant care. Microfluidic motherboards are known in the prior art. For example, workers at the Pacific Northwest National Laboratory employ a microfluidic motherboard for bioanalytical applications comprising a polymer substrate containing a microchannel network and outlet fittings, along with various surface-mountable component devices (e.g., plug-in reservoirs, micropumps, microvalves, and sensors) populated on top of the substrate, and also including fluidic connection to external equipment such as a mass spectrometer. (Lin et al, "Microfluidic Devices on Polymer Substrates for Bioanalytical Applications," In 3rd International Conference on Microreaction Technology; Microreaction Technology: Industrial Prospects, IMRET 3, Apr. 18-21, 1999 (Frankfurt, Germany), New York, N.Y.: Springer, pp. 451-60, 2000.) But unlike the present invention, prior art architectures do not include or serve a vented microcradle for infant care.

As a side note, regarding a macroscopic fluid system, Laakaniemi et al (U.S. Pat. Nos. 4,110,140; 4,188,977) teach a fluid system circuit board.

Those skilled in the art of microfabrication, and particularly microfluidics, will appreciate that a vented microcradle employing an FCA according to the invention can be practiced in a great variety of configurations along with numerous relevant technologies.

4. Temperature Bath

According to my teaching in U.S. Pat. No. 6,694,175, a patient's temperature must be monitored distinctly from the ambient temperature of the incubator environment, e.g., using a thermal imaging camera. In keeping with that teaching and that of the parent application, the invention accommodates and further provides a number of controls to regulate patient temperature in response to patient temperature readings. For in order to provide competent thermoregulation, the patient's temperature will need to be adjusted (e.g., due to activity or metabolism) based on patient temperature readings.

My present invention provides a temperature bath to maintain ambient temperature for the incubator environment. The extent to which a temperature bath is needed depends on a variety of factors. For example, if thermal perturbations of the incubator environment are small and infrequent then an air system in ambient contact with the incubator may provide sufficient thermal transfer by itself. However, a liquid system flowing over the incubator will provide much more thermal transfer than an ambient air system by itself, and so a liquid bath will buffer the incubator environment against larger perturbations in temperature.

The ambient temperature to which the patient is exposed regards the temperature of the fluid incubation medium bathing the patient in the microcradle. Alterations of the ambient temperature can be made in a variety of ways. The parent application teaches mixing media of fixed hot and cold temperatures to obtain a desired temperature or by heating or cooling the medium directly. The properly heated medium is then entered into the microcradle environment to provide the right ambient temperature. However, it is also desirable for a wider area of the environment to be at the proper ambient temperature, and not only the fluid medium that bathes the patient in the immediate sense.

A temperature bath according to the invention provides a means to regulate the ambient temperature throughout an FCA as a whole. The temperature bath employs a running fluid at a given temperature that circulates in thermal contact with the FCA to establish the ambient temperature. The running fluid may be pumped or fed by gravity. A pumping means may be located on or off of the FCA. The temperature of the running fluid is set by a thermal reservoir (thermostatic bath/circulator), by mixing (merging) fluids of different temperatures, or by heating or cooling the fluid directly.

The running fluid can be water or another liquid or even gas. Preferred qualities of the running fluid include being non-hazardous and having low flow resistance, high thermal conductivity, and high specific heat capacity. For a given substance, increasing the rate of flow of the running fluid will increase thermal transfer. Adjusting the temperature of the running fluid will enable the ambient temperature of the incubator environment to be set.

A desired temperature of the running fluid can be set and adjusted using any variety of means. For example, heating or cooling the running fluid to obtain a desired temperature may be achieved by means of heating and cooling devices located on or off of the FCA. Also, a thermostatic bath/circulator provides a stable reservoir for fluid at a precisely set temperature. Lauda Dr. R. Wobser GMBH & Co. KG (Lauda-Königshofen, Germany) makes thermostatic baths including a circulator pump, with bath temperatures controlled to ±0.01 Celsius degrees. Hart Scientific, Inc. (American Fork, Utah) makes ultrastable thermostatic baths, with bath temperatures controlled to ±0.001 Celsius degrees. The temperature of a stream of fluid from a set-temperature reservoir can also be adjusted by means of heating and cooling devices to obtain a desired temperature. However, according to the invention, and as further described below, it is most preferable to mix streams of fluid from two or more reservoirs at different set temperatures to obtain a running fluid at a desired temperature.

As used herein, thermal pull-up and pull-down times refer to an amount of time taken to respectively raise or lower ambient temperature to a desired temperature. Slow pull-up/down times create a large lag time (i.e., pull-up/down time) between detection of a need to change ambient temperature and completion of a response that establishes a new ambient temperature. As Heidemann et al explain, "[C]ontrol performance is limited by the lag time between detection and response." (p. 708) Consequently, short pull-up/down times are needed to control changes in ambient temperature as rapidly as possible.

Microscope stage warmers employing a resistive heating element are well known in the art of live cell microscopy. For example, Heidemann et al employ a temperature-controlled aluminum ring in thermal contact with a petri dish to provide a microscope stage warmer for a cell culture; the aluminum ring is heated by thermal contact with resistive heating elements. (Heidemann et al, "Open-Dish Incubator for Live Cell Imaging with an Inverted Microscope," BioTechniques, vol. 35, no. 4, pp. 708-716, October 2003). However, in absence of a cooling means (e.g., a thermoelectric cooler), resistive microscope stage warmers have relatively slow pull-down times, being limited by heat dissipation into the environment. Consequently, such microscope stage warmers do not enable a fine, rapid control of ambient temperature. Another problem is that infrared radiation emitted by a resistive device in close proximity to a patient may be undesirable in a prenidial incubator without shielding; similarly, an electronic means of heating/cooling placed in close proximity to the patient may introduce electrical effects that are problematic for the patient or for sensing equipment.

Barsky et al (U.S. Pat. No. 5,119,467) teach a transparent film radiant heat source for use with incubators comprising an optically transparent coating of indium tin oxide applied to the incubator walls. The coating is electrically conductive and serves as a resistive heating element. In the art of in vivo microscopy the bottom of an observation dish is sometimes coated with indium tin oxide to provide a heating source.

It is also well known to circulate a temperature bath around dishes placed in a container to maintain a certain temperature with respect to fluid inside the dish (incubation medium). In this regard, Okolab (Naples, Italy) employs a Lauda temperature bath/circulator to pump a running fluid at a preset temperature around petri dishes in a container so as to provide a fluidic microscope stage warmer. However, this approach is limited in its ability to provide a rapid change in ambient temperature (the temperature of the bath bathing the petri dishes) because the temperature bath/circulator (thermostatic reservoir) holds a volume of fluid and it will take a substantial amount of time for the bath to establish a new bath temperature that is equilibrated throughout the bath volume. This problem increases with the degree of temperature precision desired since the change in bath temperature must be slow in order to avoid overshooting the desired temperature.

Another possible limitation of this approach is found when the running fluid is allowed to circulate freely around the dishes; this limits the rate of flow because too great a flow rate might cause splashing of the freely flowing fluid. However, high flow rates may be desirable because they enable greater thermal transfer rates. Another problem is that a freely flowing fluid may take random paths as it circulates, making it harder to predict thermal transfer; in turn, this may result in an uneven temperature distribution. In contrast, housing the running fluid in channels or some kind of jacketing system would permit higher flow rates; also, controlling the path taken by the fluid would make it easier to predict and control thermal transfer.

Water jacketing systems find diverse uses. Of particular relevance, workers at the University of California, Irvine employ a water jacketing system to provide a microfluidic flow cell with a constant-temperature bath. (Goodrich et al, "Enzymatically Amplified Surface Plasmon Resonance Imaging Method Using RNase H and RNA Microarrays for the Ultrasensitive Detection of Nucleic Acids," Analytical Chemistry, vol. 76, no. 21, pp. 6173-8, November 2004.)

Enzelberger et al (U.S. Pat. No. 6,960,437) teach a temperature-controlled (glass) bed, such that a temperature bath flows inside the bed to maintain a desired temperature for a microfluidic chip placed on top and in thermal contact with the bed. They employ first and second temperature baths at different temperatures; initially, fluid flows from the first temperature bath through a first inlet into the bed, but then when the temperature of the bed is to be changed during a temperature cycle, fluid from the second temperature bath (at the next temperature in the cycle) is flowed into a second inlet, and the flow of fluid from the first temperature bath is stopped. As fluid at the second temperature is flowed via the second inlet into the bed, fluid continues to flow out of the bed via an outlet. (column 28, line 37 to column 29, line 5)

Enzelberger et al solve a different problem than solved by the invention. According to their art, two discrete temperatures (e.g., 60 degrees Celsius and 97 degrees Celsius) are required to promote different stages of a chemical reaction, such as a nucleic acid amplification process. In contrast, according to the present invention, fine, rapid control is needed over a continuous range of temperatures. For human infant care in a prenidial incubator, the applicable temperature range is centered about a temperature substantially near 37 degrees Celsius.

There are a number of reasons why control is needed over a continuous range of ambient temperatures in a prenidial incubator. For example, a patient may require a range of ambient temperatures over the course of incubation; for example, if the patient's temperature is taken and is too high, the ambient temperature may need to be lowered. In another type of example, sometimes it may also be necessary to relax (or perturb) a thermal condition in order to detect a condition of the patient; for example, as is known to be the case in neonatal incubation, exercising thermal controls may mask a patient's condition; however, by relaxing a thermal condition and monitoring the patient's progress to a new body temperature, valuable information can be gained about patient status and the influence of incubation parameters.

A temperature bath according to the invention overcomes the limitations of the prior art and satisfies these needs by providing a continuous temperature range with fast pull-up/down times and a fine control of ambient temperature. According to the invention, a desired temperature for a running fluid is established by mixing fluid from a plurality of temperature baths using any combination of valves and mixers, either by calculation or preferably with the aid of feedback controls from a temperature-detecting means. In principle, this is similar to mixing hot and cold water using a kitchen faucet to provide a desired temperature. To control ambient temperature, the running fluid can be made to flow at the desired temperature through channels in an FCA, or through a water jacket surrounding the FCA, or through a bed in thermal contact with the FCA.

The temperature bath may be implemented in a variety of ways. One way is to employ three thermostatic baths, consisting of a neutral bath and hot and cold baths. The temperature of the neutral bath is set substantially near 37 degrees Celsius. The other two thermostatic baths are set to maximum (hot bath) and minimum (cold bath) temperatures. These maximum and minimum temperatures determine a range of ambient temperatures provided by the temperature bath. To achieve a temperature warmer than the neutral temperature, a stream of fluid from the neutral thermostatic bath is mixed with a stream of fluid from the hot thermostatic bath to obtain a running fluid at the desired temperature. To achieve a temperature lower than the neutral temperature, a stream of fluid from the neutral thermostatic bath is mixed with a stream of fluid from the cold thermostatic bath. Another way is to eliminate the neutral bath and mix streams of fluid from the hot and cold baths directly together.

Streams may be mixed in analog or digital fashion. In digital fashion, a selectable number of (nominally identical) streams at one temperature are mixed with a selectable number of (nominally identical) streams at another temperature by selecting a number of valves to open or close discretely. In analog fashion, streams are mixed by selecting a number of valves to open or close and controlling the proportion of their opening; the opening proportion may be varied digitally or continuously depending on the valve and its means of actuation. A difference between analog versus digital mixing of streams is that digital mixing requires valves that simply open or close, whereas analog mixing requires adjustable valves. As an alternative to mixing streams of fluid from a plurality of thermostatic baths, a stream of fluid from the neutral bath may be heated or cooled as it flows past heating and cooling devices to provide a running fluid at a desired temperature.

As opposed to a stream, a running fluid may also be circulated in the form of droplets according to the art of digital microfluidics. Digital microfluidics is an emerging branch of microfluidics employing a variety of techniques to manipulate droplets of liquid as opposed to streams. For example, creating a difference in wettability between leading and trailing edges of a droplet and a surface will cause the droplet to move. Any combination of an electrical, optical, mechanical, magnetic, physical, or chemical means to create such a difference can be exploited to cause a droplet to move; the difference in wettability is measured as a difference in surface contact angle between the leading and trailing edges of the droplet. Known techniques of this sort include electrowetting, opto-electrowetting, and optical wetting. In general, with regard to the temperature bath application of the present invention, there is concern about heating the running fluid as a byproduct of fluid manipulation; an extreme example is provided by a digital microfluidic technique relying on thermocapillarity in the form of a thermocapillary pump, which involves a differential heating of leading versus trailing portions of a droplet within a microchannel. (Burns et al, "Microfabricated structures for integrated DNA analysis," Proceedings of the National Academy of Sciences of the United States of America, vol. 93, no. 11, pp. 5556-61, May 1996; Pollack et al, "Electrowetting-Based Actuation of Liquid Droplets for Microfluidic Applications", Applied Physics Letters, vol. 77, no. 11, pp. 1725-6, September 2000; Rosario et al, "Lotus Effect Amplifies Light-Induced Contact Angle Switching," Journal of Physical Chemistry B, vol. 1108, no. 34, pp. 12640-2, 2004; Chiou et al, "Optical Actuation of Microfluidics Based on Opto-Electrowetting," Technical Digest, Solid-State Sensor, Actuator and Microsystems Workshop, Hilton Head Island, S.C., pp. 269-72, June 2002.) In contrast to wettability techniques, a technique being explored by researchers at the Optical Trapping Group, University of St. Andrews uses optical tweezers to manipulate very fine droplets using a focused laser beam (optical trapping). Fluid movement can also be created by means of manipulating particles or beads in a fluid that are subject to forces produced by various means (e.g., optical tweezers, magnetism, non-uniform electric fields, etc.), or by subjecting the droplet itself to such forces (e.g., dielectrophoresis). (Calhoun et al, "Paramagnetic Particles and Mixing in Micro-Scale Flows," Lab on a Chip, vol. 6, no. 2, pp. 247-57, February 2006; Zeng et al, "Principles of Droplet Electrohydrodynamics for Lab-on-a-Chip," Lab on a Chip, vol. 4, no. 4, pp. 265-77, April 2004.)

Digital microfluidics enables operations to be performed using digital controls, often at high speeds, such as transporting droplets, dispensing droplets from a fluid stream or reservoir, splitting or cutting droplets, merging or mixing droplets, reacting droplets, analyzing droplets, and so on. Of note, circulation of fluid in discrete form (droplets) using digital microfluidics has been found to enable much higher flow rates than circulation of fluid in continuous form using stream-based microfluidics. High circulation rates aid thermal transfer. Droplets can be combined to form a stream or they can be stored to form a reservoir. Droplets at a desired temperature may be dispensed from a stream or reservoir bearing fluid at the desired temperature or by heating or cooling the droplets to obtain a desired temperature using a heating and cooling means; droplets from different temperature sources (i.e., neutral, hot, or cold sources) may be merged to create droplets at a desired temperature. Droplets at the desired temperature can be circulated in the form of a running fluid such that a desired ambient temperature results from thermal transfer between the droplets and the FCB/FCA or related devices, with assurances and feedback controls provided using a temperature-detecting means.

The mixing (merging) of fluid streams (or droplets) at different temperatures to obtain a running fluid at a desired temperature is preferably aided by means (e.g., valves and pumps, or, in the case of digital microfluidics, digital controls) controlled by feedback from a temperature-detecting means. An exemplary temperature-detecting means may include rapid-response thermistors or a thermal imaging system. Feedback from the thermal imaging system or other temperature-detecting means can be used to assess and control the impact of the temperature bath provided by the running fluid on ambient temperature. The thermal imaging system preferably includes a microscope lens for infrared microthermography and may be the same system used to detect the patient's body temperature.

Feedback controls enabled by a temperature-detecting means may include, for example, opening or closing valves to admit fluids of specific temperatures to specific areas or devices on an FCA (e.g., to provide added cooling to an area that is found to be overheated); controlling a merging of fluids at different temperatures to achieve a desired temperature; moderating a pump to increase a rate of fluid flow to provide added thermal transfer; turning on a microheater to raise temperature or turning on a microcooler to lower temperature; commencing a reaction on a lab-on-a-chip when proper temperature is achieved; etc. By using a layer material that is transparent to infrared radiation, a thermal imaging system can detect temperatures throughout the FCA. In general, the thermal imaging system can also be used to check temperatures indicated by other temperature-taking means associated with the FCA (e.g., thermocouples, thermistors, pyroelectric sensors, thermopiles, and any other devices exhibiting temperature-dependent electrical effects, and also nematic/thermochromic liquid crystal microthermography) to improve and verify their accuracy.

Calculations may also be used to predict and control a result of merging fluids in terms of a resulting temperature achieved.

Assuming latent heats are not involved, then in general when two volumes $V_1$ and $V_2$ of the same fluid substance are mixed, the resulting temperature T is given by the formula $T=(V_1T_1+V_2T_2)/(V_1+V_2)$, where $T_1$ and $T_2$ are the original temperatures. This formula can be converted to terms of relative proportion as $T=(p_1T_1+T_2)/(p_1+1)=(T_1+p_2T_2)/(p_2+1)$, where $p_1=V_1/V_2$ and $p_2=V_2/V_1$. This reduces to $T=(T_1+T_2)/2$ when the proportions are equal. Correction for a variation in specific heat capacity with temperature will seldom be necessary over a narrow range of temperatures centered about ambient temperature.

Correction will be necessary when a means of manipulating fluid volumes contributes heat. For example, if n droplets at $T_1$ are mixed with one droplet at $T_2$, then the predicted temperature is $T=(nT_1+T_2)/(n+1)$. However, if the process of manipulating the droplets adds heat, then the final temperature will be higher.

A temperature bath according to the invention, including separate ones, can be routed to devices on an FCA or to regions in an FCB having diverse thermal requirements, or even to external devices or equipment. In this way, ambient temperatures may be accurately maintained in a prenidial incubator by means of a temperature bath according to the invention.

The prior art is crowded with efforts to ensure a general cooling of electronic circuits by means of a circulating fluid, with increasing emphasis being placed on a use of microfluidics. However, the present invention solves a more specific problem. Namely, the present invention is concerned with establishing a specific ambient temperature. Nevertheless, of particular note is the teaching of Siebold et al (U.S. Pat. No. 5,142,441) for a circuit board containing an internal network of microchannels for a running fluid to provide a cooling of devices placed thereon.

Other examples noted along these lines include the teaching of Daikoku et al (U.S. Pat. No. 6,351,384) for a device and method for cooling multi-chip modules; Jun et al (U.S. Pat. No. 6,582,987) for a method of fabricating a microchannel array structure embedded in a silicon substrate; Zeighami et al (U.S. Pat. No. 7,002,801) for a method of cooling a semiconductor die using a microchannel thermosyphon; Nelson et al (U.S. Pat. No. 6,529,377) for an integrated cooling system in the form of a fluid-bearing tape; and, Goodson et al (U.S. Pat. No. 6,991,024) for an electroosmotic microchannel cooling system. Also of note, workers at Duke University employ digital microfluidics (electrowetting-based techniques) to cool microelectronic circuits (Pamula et al, "Cooling of Integrated Circuits using Droplet-Based Microfluidics," Proc. of the Association for Computing Machinery Great Lakes Symposium on VLSI, pp. 84-7, 2003.)

Those skilled in the art of regulating the temperatures of microfabricated devices will appreciate that an ambient temperature for a vented microcradle can be accurately monitored and maintained using a diversity of means.

5. Machine-Readable Indicia

Bennett et al (U.S. Pat. No. 5,051,736) teach a method of determining a location of an instrument over a glass surface of a computer screen by means of machine-readable etchings. At the time of their teaching a means to produce such etchings was not readily available. However, today ion-beam etching provides a cost-effective means for producing extremely fine etchings with remarkable detail. But the prior art does not teach or fairly suggest a use of machine-readable indicia or markings produced by ion-beam etching to aid in the automated control or positioning of instruments with respect to an incubator for premature infants or the patient contained therein. Cecchi et al (U.S. Pat. No. 6,448,069) teach a use of indicia to identify members of a community of embryos in a compartmentalized structure. But because indicia are typically imprinted at the time of manufacture, a problem with the art of Cecchi et al is that the means of identification is limited. To overcome this limitation, the invention provides a means to superimpose text and images on a display with the aid of a computer and software in reference to indicia etched into the incubator in a machine-readable format at the time of manufacture. The display can take the form of a hospital monitor for doctors and nurses to look at.

According to the invention, machine-readable indicia etched into a prenidial incubator at the time of manufacture (e.g., on the surface an FCB layer) can be read into the computer and linked to information stored in a data structure, for example, a patient's name or his or her uniquely assigned hospital identification number (Patient ID); in turn, for example, the information (e.g., the patient's name) can then be superimposed onto the display for the benefit of health care personnel. For example, the patient's image, obtained by microscopy and captured by means of a digital (e.g., CCD) camera, can be displayed in a visual field on the monitor along with superimposed information such as the Patient ID. Thus, by means of machine-readable indicia, the invention enables personal and relatively unlimited information about a patient to be displayed on a monitor and continuously updated in a user-friendly format.

Other exemplary uses of machine-readable indicia or markings are also achievable; for example, data concerning the model of incubator manufactured can be etched onto a surface of the incubator and read into a computer to tell the computer what software to run or what parameters to include when running the software. Similarly, rather than having to struggle with space and size limitations to imprint indicia that are humanly meaningful on the surface of a prenidial incubator, e.g., to identify Medication Port 1, a machine-readable description can be etched onto the surface and a humanly meaningful translation can be superimposed on a visual display (monitor) by aid of a computer. Icons and other user-friendly symbols (e.g., clickable symbols) can be shown on a display to indicate regions in a visual field where machine-readable indicia are embedded. Various information can be hidden or displayed according to user preferences or in keeping with systematic events. An optical means is preferred for reading the indicia or markings by computer.

According to the invention, with the aid of machine-readable indicia or markings etched onto a surface of a prenidial incubator, an instrument (e.g., a catheter or micropipette used in transferring a prenid) may be positioned by a computer-controlled machine over an incubator enclosure surrounding the infant (e.g., for the purpose of transfer). Additional controls, both manual and computer-assisted, may also be implemented in this scheme, e.g., with the additional aid of visualizing the infant optically under the microscope. For example, micromanipulation and microsurgery may be implemented in this scheme. In general, a grid or other framework of machine-readable markings can be etched onto a surface of a prenidial incubator along with appropriate machine-readable indicia to enable automated control and positioning of instruments for patient care and incubator maintenance.

According to the invention, artistic symbols, e.g., aesthetic or religious symbols, can be etched onto a visible surface of a prenidial incubator for the benefit and comfort of viewers. For example, koala bears may be etched onto the surface of the flooring of the incubator and matching bears may be printed on garments worn by nurses. Similarly, a dove might be etched in cases where parents plan to have their child baptized in the incubator. An alternative to visible etching provided by the invention is to simply have such symbols superimposed on a display for the benefit of viewers.

According to the invention, incubator units can be shipped with bar code labels that match model and serial numbers imprinted on the incubator at the time of manufacture. Other manufacturing data can also be included, e.g., for quality control purposes. Such data can be imprinted on the incubator in a machine-readable format using ion-beam etching so that a computer can verify the correct correspondence, for example, to make sure that the incubator being used is of the proper type and that a mix-up has not occurred.

Graduated markings (e.g., to indicate lengths, areas, degrees, etc.) may be etched onto an incubator surface with units of measure indexed in machine-readable form. Such graduations may be used to help measure the patient's body size (morphometric) parameters, to help guide or position instruments, and so on. Markings may also be used to produce diffraction gratings or patterns and other optical effects. For example, a diffraction pattern can be used in the alignment or focusing of optical equipment.

Ion-beam etching in a glass substrate is preferred for imprinting the machine-readable indicia or markings. However, other etching means or substrates may also be used.

Machine-readable indicia or markings may be etched anywhere on an FCA according to the invention. Binary encoding of indicia or markings is preferred.

6. Transfer Catheter

FCB/FCA designs according to the invention are so versatile that they can even assume instrumental forms, including the form of a catheter, cannula, aspiration needle, endoscope, laparoscope, or other instrument. A transfer catheter is an embodiment of the invention in a catheter form. The transfer catheter is used to transfer an infant from an incubator to the maternal body or, conversely, from the maternal body to an incubator.

Prenidial transfer means the transfer of embryos or hatchlings. In the prior art, hatchlings are seldom transferred because the prior art has had no success in incubating prenids to the hatchling stage, and so prenids are typically transferred to the maternal body at the embryo stage (i.e., before hatching). With respect to the maternal body, prenidial transfers may take place transcervically with placement in the uterine cavity or in a fallopian tube accessed via the uterine cavity; prenidial transfer may also occur laparoscopically. In a typical scenario, after a period of external incubation, transfer to the maternal body will take place transcervically, with the infant being placed in the uterine cavity ready for implantation.

Figure 11:
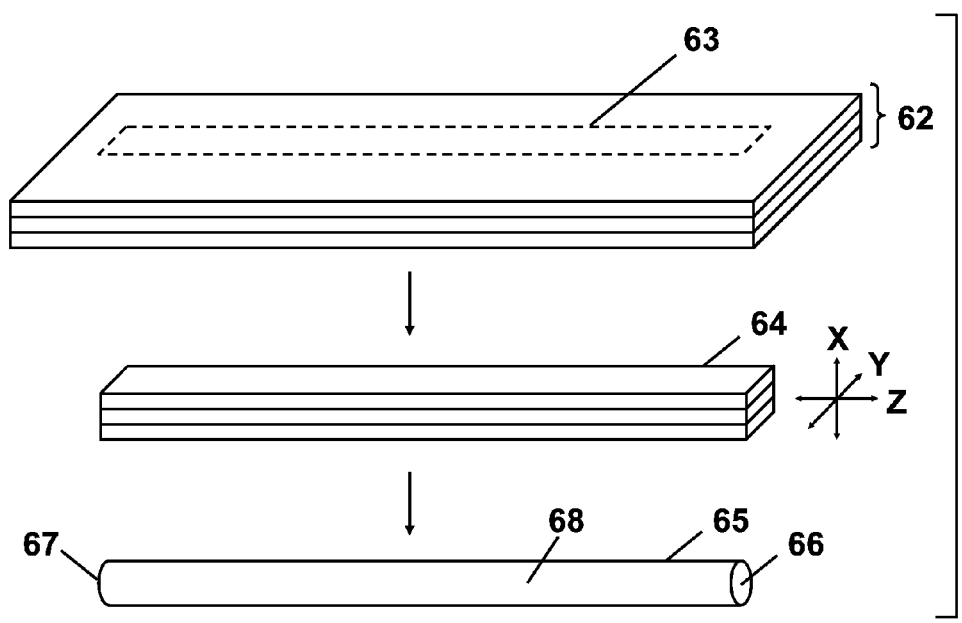
FIG. 11 is a perspective view showing steps in the manufacture of a transfer catheter formed by a fluidic circuit board according to the invention.

Referring to FIG. 11, to produce a transfer catheter according to the invention, an FCB design is created in layers 62. Typically, the FCB is cut 63 to trim away excess board material, and the cut FCB 64 is shaped by any combination of forming, machining, and polishing to produce a rounded catheter body 65. Microfabrication steps are generally included in producing the transfer catheter. The transfer catheter may include FCA devices/features located in/on the catheter body 65 and may be combined with external equipment.

Referring to FIG. 11, a Z-axis travels the catheter lengthwise, an X-axis is perpendicular to the laminated layers 62, and a Y-axis is parallel to the laminated layers 62. The prior art relies on extrusion to create a catheter body, resulting in isotropic flexibility in the X-Y plane. By employing laminated layers 62 to create the catheter body, the present invention is distinct from the prior art because it provides for anisotropic flexibility, such that the catheter is less flexible in the Y direction than in the X direction. (In FCA designs, a Z-axis is defined perpendicular to layers forming an X-Y plane; but an exception occurs with respect to transfer catheters, in which case axes are defined in view of compatibility with anatomical standards.)

The prior art generally teaches that a soft catheter is desirable to protect the tissues of the mother's reproductive tract, but that the softness makes transcervical insertion difficult. The prior art faces compromise in this regard, generally employing either a harder catheter or a stiff sheath to aid in insertion. But the present invention offers an exceptional advantage in that a slight twisting motion will effectively stiffen the catheter. Specifically, the catheter, when bowed in the X direction due to flexion caused by resistance to insertion, will tend to align along the Z-axis when twisted, so as to reduce the bowing, because the twisting rotates the more inflexible ZY-plane into a plane formerly occupied by the ZX-plane. Thus, with some art and tactile sensitivity on the part of an operator, using a slight twisting motion under tension, including a back and forth twisting motion, the catheter according to the invention can be made to serve the purpose of greater stiffness during insertion while retaining a greater softness overall.

Durometer measures the hardness of a material in terms of its resistance to permanent indentation and is used to compare polymers, elastomers, and rubbers. High durometer generally equates to stiffness and low durometer to flexibility. Cecchi et al (U.S. Pat. No. 6,165,165) teach an embryo transfer catheter produced by extruding mixtures of resins which have different durometers, and varying the percentage of the resins in the mixture along the length of the catheter; consequently, the catheter has a varying stiffness from the distal end to an opposite proximal end, the distal end being softer and the proximal end being more rigid; the result is a catheter that is non-abrasive at its distal end, and resistant to wobble at its proximal end. The present invention relies on a layer method, rather than an extrusion method along the lines of Cecchi et al. According to the present invention, layers 62 can be provided that vary in durometer along the length of the Z-axis according to various polymer techniques; layers 62 of different durometer can also be interlocked or laced to provide different stiffness qualities along the Z-axis; also, stiffening structures can be embedded in the layers 62.

The maternal body provides an infant incubator. And so in some sense transfer implies transit from one incubator to another. This is also the case when transfer is made between two manufactured incubators. In the past, prenidial transfer has presented a discontinuity of incubation, because transfer catheters of the prior art do not qualify as incubators in themselves. Thus, an object of sophisticated transfer is to provide for a continuity of incubation.

In satisfaction of this object, the present invention enables an instrument of transfer, such as a catheter, to serve as an incubator in its own right. Those skilled in the art of microfabrication will appreciate that this object can be accomplished with any desired level of sophistication based on the FCB/FCA concept. Such instruments may embody not only an incubator according to the invention but also other features as well, as are needed according to an overall function of the instrument (e.g., microsurgical tools to operate on the maternal body, MEMS-actuated covers, valves, or shields to keep cervical mucus out, lights and fiber optics to visualize the maternal body or surroundings, etc.). Such instruments may also be practiced in combined form (e.g., a cannula can be designed by fabricating a channel (lumen) along the Z-axis of an FCB that is large enough to accommodate a catheter).

Those skilled in the art of medical engineering will appreciate that modifications of the FCB/FCA concept can be analogously applied to a variety of arts, e.g., oocyte aspiration, so as to relieve a number of limitations previously encountered.

A transfer catheter according to the invention may be construed as a transfer incubator combined with an instrument to effectuate transfer (e.g., the catheter body 65), which may be combined with a number of auxiliary instruments. In other words, the transfer catheter may be construed as an instrument of transfer containing a transfer incubator. To achieve full sophistication, the transfer catheter preferably includes a number of desirable incubator features such as a vented microcradle and a temperature bath or heating and cooling devices to maintain ambient temperature for the patient to avoid thermal shock. A means of taking the patient's temperature according to my teaching in U.S. Pat. No. 6,694,175 is also desirable, such as the exemplary means described below for use in a transfer catheter.

Successful transfer to the maternal body is needed for patient survival after incubation in a prenidial incubator. A problem with prior art transfer methods involves an amount of air and liquid fluid expelled from the catheter into the uterus during transfer. Although a general consensus is that a volume of fluid transferred should be kept to a minimum so as to avoid flushing the patient from the uterus or displacing the patient from a preferred site, a dilemma arises because a larger volume is also desirable to flush a patient who may otherwise stick to a wall of the catheter. Another problem is that the patient may be drawn out of the uterine cavity or displaced from a preferred site when the catheter is extracted.

Figure 12:
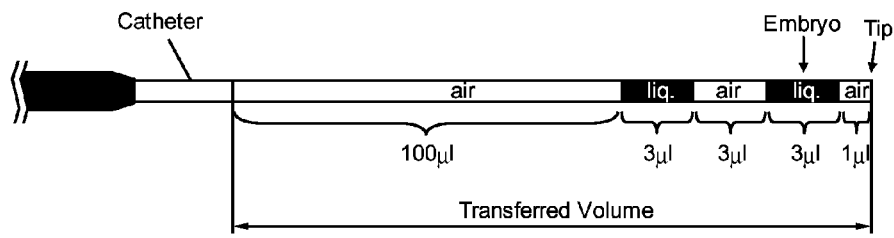
FIG. 12 is a side cross-sectional view of a prior art transfer catheter.

Using a transparent model of the human uterus, workers at Tel-Aviv Sourasky Medical Center and Tel-Aviv University made simulated catheter transfers to study different catheter loading arrangements. Regarding background on the problem, in a 2004 paper they report: "The technical protocol of embryo transfer (ET) has not been changed since it was first introduced three decades ago. Typically, the catheter is positioned within the uterine cavity with its tip 5-15 mm proximal to the fundus, whereupon its load is carefully injected and the catheter is then extracted. [ . . . ] Mechanical factors, such as uterine contractions, catheter type, the method of loading the catheter, the placement of the catheter tip and physician skills, have been proposed to explain some of the disparity between the embryonic development and pregnancy rates." (p. 562, citations omitted.) FIG. 12 shows one of their typical catheter loading arrangements. One of the conclusions of their study is particularly interesting: "The viscosity of the transferred liquid should be as close as possible to that of the uterine fluid in order to avoid transport of embryos towards the cervix." (p. 562) (Eytan et al, "A Glance Into the Uterus During In Vitro Simulation of Embryo Transfer," Human Reproduction, vol. 19, no. 3, pp. 562-9, March 2004.)

Figure 13:
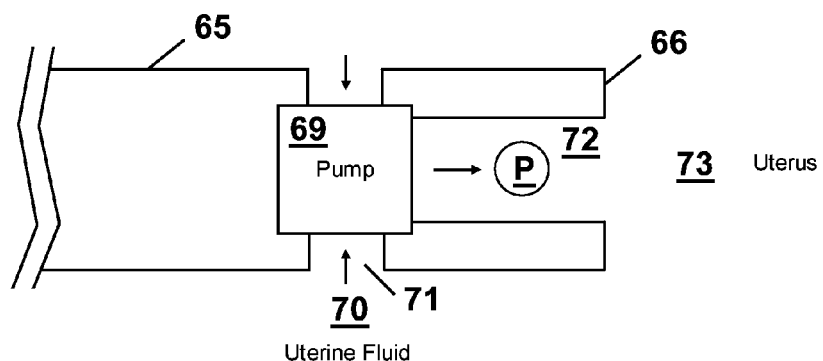
FIG. 13 is a side cross-sectional view of a transfer catheter having a side-vented microcradle.

Given such concerns, those skilled in the arts of microfluidics and microfabrication will appreciate that a transfer catheter according to the invention presents unique alternatives to the traditional transfer protocol. For example, how could a transfer catheter be provided that enables an embryo or hatchling to be flushed from a catheter into the uterus with an unlimited volume of fluid, without increasing an amount fluid in the uterus itself, and while employing a fluid with the same viscosity as uterine fluid? Referring to FIG. 13, an embodiment of a transfer catheter according to invention offers a solution to this problem. A micropump 69 fabricated inside the distal end 66 of a transfer catheter 65 according to the invention circulates uterine fluid 70, such that the fluid 70 passes in via inlets 71 and out via a vented microcradle 72, so as to cause a prenid P to transit out of the microcradle (transfer incubator) 72 and into the uterine cavity 73 to effectuate transfer. The micropump 69 may preferably be a peristaltic pump with pneumatic actuation. The pump 69 may be reversible to assist in loading the patient P into the transfer incubator 72. Because the fluid 70 being circulated is that contained by the uterine cavity 73 itself, then unlike the prior art, any amount or volume of fluid 70 may be circulated (e.g., for the purpose of flushing the patient out of the catheter) without increasing the volume of fluid in the uterus; moreover, the fluid being circulated has the same viscosity as the uterine fluid 70 itself. Additionally, a circulation may be made to continue as the catheter 65 is being extracted, to prevent the prenid P from being drawn out or displaced by a movement of the catheter 65. Thus, the present invention provides a means to overcome the prior art limitations.

Those skilled in the arts of microfluidics and microfabrication will also appreciate that a transfer catheter according to the invention presents other unique alternatives to the traditional transfer protocol as well. For example, according to the FCB/FCA concept of the invention, an instrument of transfer may be equipped with a mechanical means such as a microgripper or other microdevice to mechanically move a patient from the instrument into a desired release location or position. As is well-known in the art of microfabrication, microgrippers and related microfabricated devices (e.g., a microcage) are able to manipulate small bodies and can be adapted to patient handling at the small size of prenidial infants. (Ok et al, "Pneumatically Driven Microcage for Micro-Objects in Biological Liquid," MEMS '99: Twelfth IEEE International Conference on Micro Electro Mechanical Systems. Technical Digest. Orlando, Fla., pp. 459-63, 1999.) In addition, microsurgical tools can be included, including with the aid of visualization aids, to prepare a reception in the maternal body for the patient and also to deposit the patient with the aid of a securing agent or structure.

Those skilled in the arts of microfluidics and microfabrication will also appreciate that a transfer catheter according to the invention presents an exceptional means of refinement even within the context of traditional transfer protocols. For example, the invention enables gaseous and liquid fluid samples to be urged through a catheter with greater control. In the prior art, a syringe-catheter complex is employed to urge fluids. However, according to the present invention, a micropump may be used instead. In such a case, there is no need for a syringe as with the prior art. With no need of a bothersome syringe, referring to FIG. 14, the proximal end of the catheter 65, which is handled by the operator, may conclude with a housing 74 provided to cover internal devices and to allow for convenient handling by the operator.

Figure 14:
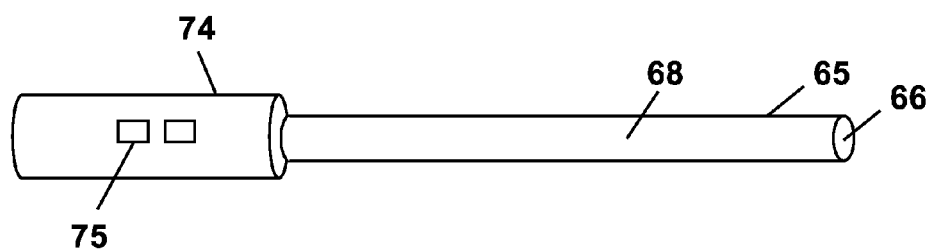
FIG. 14 is a perspective view of a transfer catheter according to the invention.

Referring to FIG. 14, means of wireless communication may also be included to establish communication between a catheter's devices and external equipment, whereby one or more functions of the catheter can be monitored and controlled. Controls and indicators 75 may also be provided on the transfer catheter 65 itself.

Although constraints will apply, thanks to the versatility of FCB/FCA designs a transfer catheter according to the invention can include many of the features generally available to prenidial incubator design. However, certain features will still be peculiar to the needs of transfer (e.g., articulating wires to flex the catheter, or echogenic structures such as ridges to locate the catheter in the uterus under ultrasound). To give an extreme example of versatility, a transfer catheter may even contain an incubator sophisticated enough to serve as a stand-alone incubator in its own right when docked with a support system. However, in general it is contemplated that the transfer catheter will serve as an incubator only part-time (i.e., during transfer).

Referring to FIG. 11, the FCB design for the catheter is preferably created in polymer layers 62. However, a semiconductor, polysilicon, polydimethylsiloxane (PDMS), or other substrate for the microfabrication of active and passive components may also be employed as one or more of the layers 62, and a surface 68 of the catheter 65 may be coated with a protective layer if necessary. The FCB generally includes a network of microfluidic channels and vias and provision for a vented microcradle; however, a single lumen may suffice for delivery of a prenidial infant. Optical fibers and lenses, articulating wires and anchors, electrical contacts, and sensors and devices may be embedded inside the FCB. Relatively large channels (lumens) may also be included for delivery of substances and other purposes. To provide for clearer ultrasonic guidance, the catheter may include echogenic structures to disperse ultrasonic waves according to the art. The distal end 66 of the catheter wherein the vented microcradle is located may be formed to a desired shape. The proximal end 67 may be connected to external equipment, including fluid lines, and electrical, mechanical, and optical equipment. Articulating wires routed and anchored inside the catheter may cause the catheter to flex to a desired shape and angle, and these wires may be actuated externally (e.g., via articulating levers) or internally (e.g., via micromechanical actuation). The catheter may also be sheathed in a laparoscopic device or other housing. Components may be populated on the FCB surface at the proximal end 67, which does not necessarily need to be rounded like the distal end 66.

The transfer catheter may be molded or formed into a fixed bent shape. As an alternative to articulating wires, MEMS-actuated devices may cause the catheter to flex. The catheter should have markings or an orientation structure at the proximal end 67 to define X-Y axes and a top, bottom, and sides to help guide the operator. The catheter may also have sensors to sense orientation. A microcradle may be housed at the tip or on the sides at the distal end 66. A proximal portion of the catheter may have graduated markings to enable a depth of insertion to be measured by the operator. A microcradle array may be housed by the catheter in cases where fraternal twins are being transferred and individual transfer incubators are preferred. A stream of fluid may be directed along a surface of a sidewall of the microcradle to help prevent the patient from sticking to the wall; coatings, structures, and mechanical means may also be used for this purpose.

The portion of the catheter at the distal end 66 where the infant is housed is preferably made of a translucent material to aid in microscopic examination, e.g., to verify that transfer has taken place. However, optical fibers provided for illumination and visualization may also be used for this purpose. Optical fibers contained by the FCB may be used to visualize the infant and tissues of the maternal body. Fiber optics may also be employed in conjunction with the FCB to visualize instrument activities. Patient temperature can be detected via an optical fiber by maintaining a temperature sensor in an optical field of view, such that the temperature of the patient (along with other bodies as well) can be determined by reference. The sensor provides a reference point within the field of view. Employing a calibration reference in a radiometer's field of view is discussed further under "Design Considerations" below.

FCB designs can be made of diverse materials. For example, surgical metal layers can be laminated in high vacuum after cleaning with hydrogen ion or they can be bonded anodically. Those skilled in the art of microfabrication, with particular emphasis on microfluidics, will appreciate that employing laminated FCB layers according to the invention offers greater versatility, functionality, and miniaturization in a transfer catheter design than the prior art, which relies on extrusion rather than lamination to form a catheter body and related lumens. As with FCA designs in general, a transfer catheter according to the invention can be operated using diverse external equipment as an aid to operation.

The prior art does not teach or fairly suggest a transfer catheter manufactured from laminated layers. Nevertheless, the following prior art references are of additional note. Wallace (U.S. Pat. No. 4,863,423) teaches a catheter and cannula assembly, such that when "an obstruction or tortuous path is encountered in the cervical canal . . . the catheter may be gently rotated within the cannula to assist its advance" (column 2, lines 49-52); he also teaches graduated markings on a proximal portion of the catheter and cannula to enable an operator to measure insertion depth. Tao (U.S. Pat. No. 6,610,005) teaches a catheter system utilizing a protective catheter sleeve for introducing a catheter into the uterus without mucus contamination of an inner catheter. Bosley et al (U.S. Pat. No. 6,527,752) teach a transfer catheter that includes ultrasonically reflective components or features to enhance its visibility under transabdominal or transvaginal ultrasound guidance. Thompson (U.S. Pat. No. 6,010,448) teaches a transfer catheter having a lumen to deliver adhesive to aid implantation and fiber optics to aid site selection. Bacich (U.S. Pat. No. 5,472,419) teaches a transfer catheter employing a special shape of a distal opening for transfer transcervically through the uterus into a fallopian tube or transcervically into the uterus. Kamrava et al (U.S. Pat. Nos. 6,758,806; 7,033,314) teach articulating wires coupled to anchors (dumb bells) to provide for articulation of a distal portion of a hysteroscope using an articulating lever; they also teach a hysteroscope having fiber optics to aid in visualization and illumination of the uterus.

7. Design Considerations

Referring to FIG. 1, fluid flowing out through a ventilation port 4 is translated from a horizontal direction into a vertical direction so as to flow past the patient P and out of the open top 2 of the side-vented microcradle 1. Correspondence between the rate of fluid flow through the side vents 4 and a desired flow rate past the patient P can be determined by calculation. In general, the cross-sectional area of a vertical cross-section of the microcradle 1 ($A_{cradle}$) times the rate of flow in the vertical direction ($v_{vert}$) equals a sum over all ventilation ports of a cross-sectional area of the ventilation port ($A_{vent}$) times the rate of flow out of the ventilation port ($v_{horiz}$). Here, the rate (or velocity) of fluid flow is measured in units of distance per unit time. See FIGS. 15-16. However, in operation, in the equation of FIG. 16, the cross-sectional area of the microcradle 1 ($A_{cradle}$) will actually be replaced by an effective cross-sectional area, which may change along the vertical direction. The effective cross-sectional area will take into account an amount of space taken up by the patient and any objects made present inside the microcradle 1. If all ventilation ports have the same cross-sectional area and rate of flow, then a ratio of vertical and horizontal velocities will observe a constant proportion, determined by the cross-sectional area of the microcradle ($A_{cradle}$) and the net cross-sectional area presented by a sum of all ventilation ports ($A_{ports}$), such that $v_{vert}/v_{horiz} = A_{ports}/A_{cradle}$.

Flow through the ventilation ports 4 may observe a directional pattern so as to cause any number of desired flow effects in the microcradle (e.g., vortex flow). Flow out of a ventilation port may also be deflected to cause a desired effect (e.g., deflection in an upward direction upon exit may be caused by a structure impeding a path of flow). In this way, a desired circulation can be achieved and problems like having areas of stagnation can be avoided.

Figure 2A:
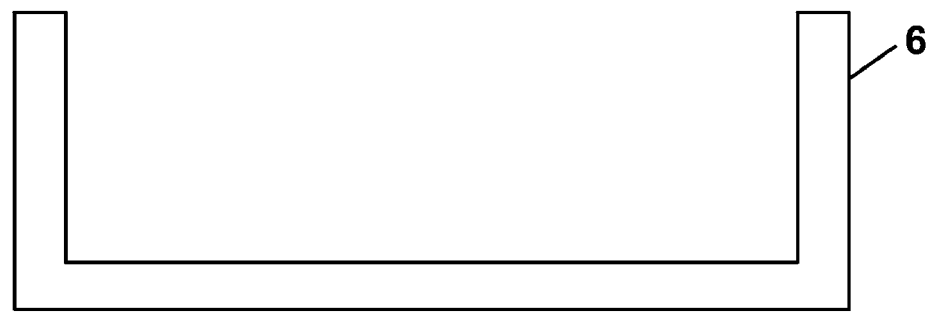
FIG. 2A is a side cross-sectional view of a glass petri dish.
Figure 2B:
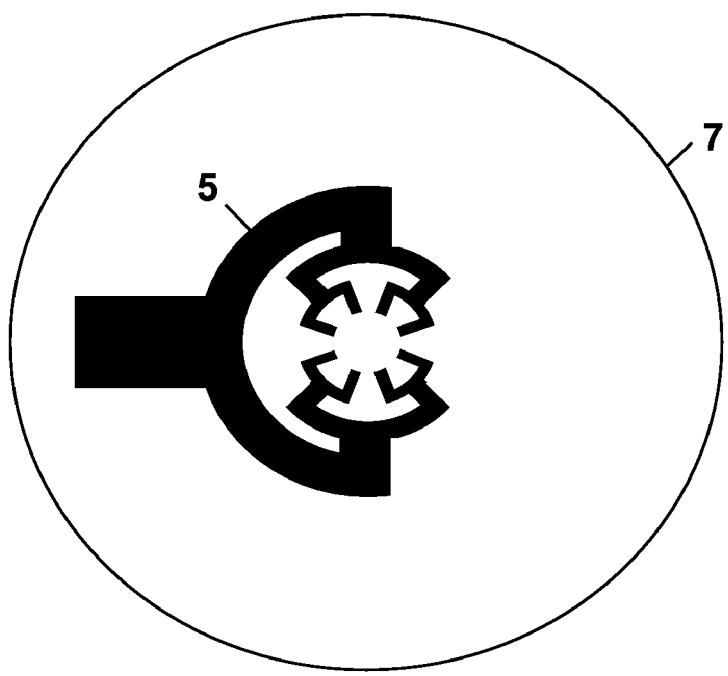
FIGS. 2B-C are bottom orthogonal views of a glass sheet having microfluidic channels and vias etched in it for a side-vented microcradle.
Figure 2C:
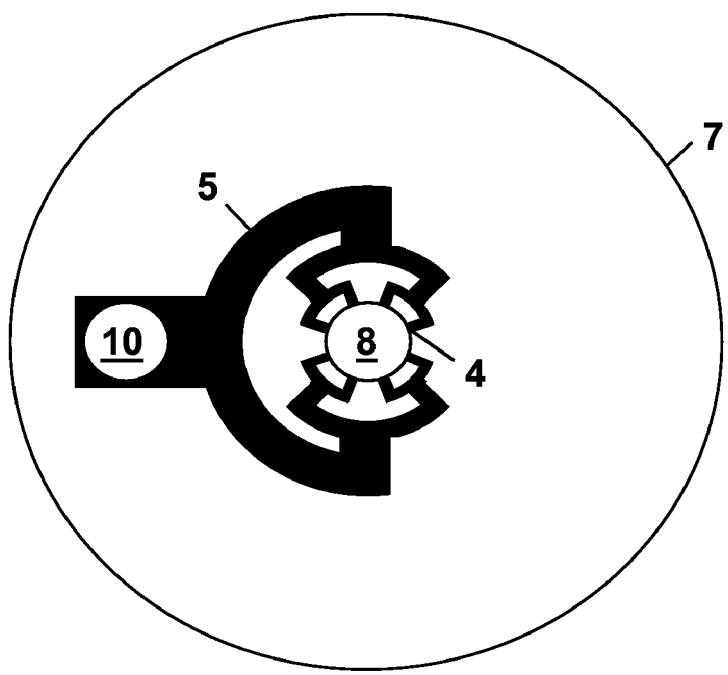
Figure 2D:
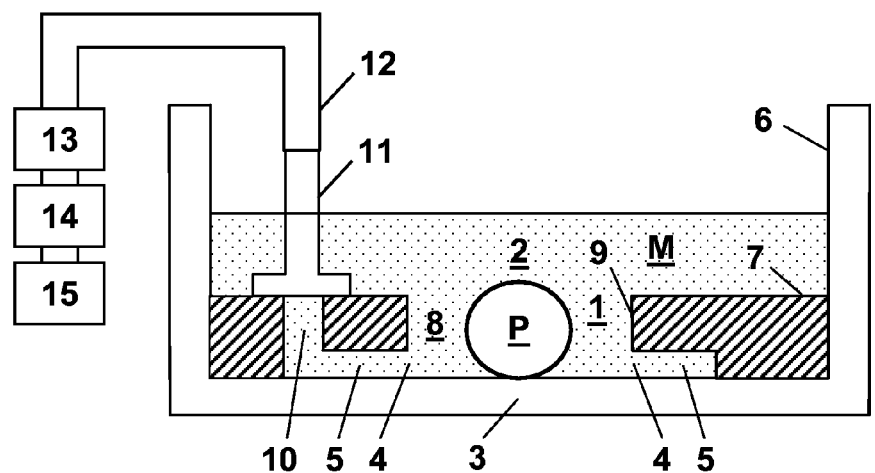
FIG. 2D is a side cross-sectional view of a side-vented microcradle.
Figure 18:
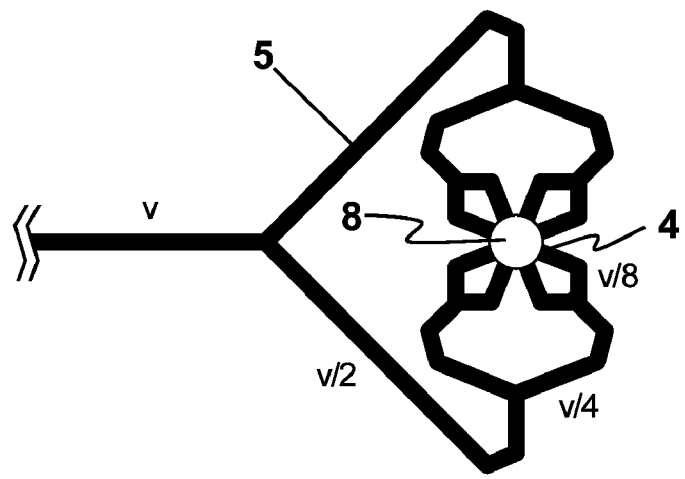

Drawn in this case more closely to a true relative proportion of features, FIG. 17 shows an exemplary mask pattern for the microfluidic channels 5 of a side-vented microcradle along the lines of FIG. 2C. The FIG. 17 design is based on a three-stage multiplexer (multi-splitter). A multiplexer design such as this ensures that a path length of fluid traveling to each ventilation port 4 is the same and that flow is balanced among the paths. This design employs constant-velocity stages, such that a net sum of the cross-sectional areas of the channels in each stage is conserved by starting with a wide channel (the $0^{th}$ stage) and then narrowing channels for each stage in succession (stages 1-3); alternatively, successive stages can be etched at different depths to conserve net cross-sectional area and, hence, a constant rate (velocity) of fluid flow. In another example, FIG. 18 shows a design which, like the FIG. 17 design, ensures a constant path length for fluid traveling to each of the ventilation ports 4. But unlike the FIG. 17 design, this design employs non-constant velocity stages; because the microchannels 5 maintain the same cross-sectional area, velocity (v) in the channels decreases as the channels are split successively into more channels.

Figure 19:
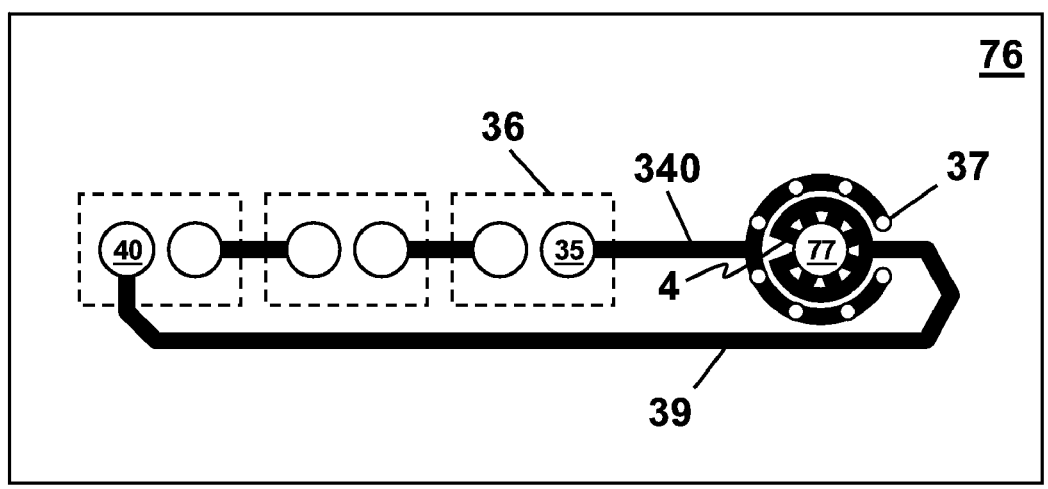
FIG. 19 is a bottom orthogonal view of a glass sheet having microfluidic channels and vias etched in it for a side-vented microcradle.

In general, it is desirable to conserve path length among ventilation ports because this ensures fluid will arrive at each of the ports at the same time. However, FIG. 19 shows a design in which path length is not conserved. This design serves as a substitute for the FIG. 6B embodiment, such that only two glass layers are required instead of three. In this case, microchannels and vias are etched in a top layer 76 and then bonded to a bottom layer; referring to FIG. 6B and FIGS. 7A-B for comparison, the top layer 76 of the FIG. 19 embodiment replaces top and middle layers (32, 33) in the FIG. 6B embodiment. A via 77 forms the walls of the vented microcradle 1 that were formed together by vias 38, 41 in FIGS. 7A-B.

Referring to FIG. 19, devices 36 can be mounted underneath the bottom layer by etching vias (35, 40) in the bottom layer rather than in the top layer 76; similarly, devices can be mounted on the surface of both top and bottom layers. Devices 36 can be arranged, for example, in a geometry that reduces the path length of channels (e.g., in a circumference around the microcradle) or, for example, in a manner that leaves a greater distance between a device 36 and the patient. Non-limiting design considerations such as these illustrate versatility.

The fluid incubation medium is an aqueous physiologic solution. Water is attracted to a hydrophilic surface and 'repelled' by a hydrophobic surface. Glass is hydrophilic and so water will automatically fill channels and vias etched in glass based on capillarity. In contrast, many polymers are hydrophobic or not as wettable as glass, and so filling channels and vias with an aqueous solution introduces a number of design considerations; otherwise, channels and vias may not fill, resulting in device malfunction.

Whether a material is hydrophobic or hydrophilic is not so important once channels and vias have actually been filled. As McNeely et al (U.S. Pat. No. 6,296,020) explain, "[O]nce water has been introduced into the [capillary] tube the flow rates of the water are dependent more on pressure gradients and friction and less on whether the material is hydrophobic or hydrophilic." Yet getting fluid to fill channels and vias having non-wettable surfaces can be problematic. One approach is simply to alter the surface of a polymer to make it hydrophilic after channels and vias have been formed; coatings, UV exposure, and oxygen plasma exposure are commonly employed. But these methods may introduce unwanted chemical considerations; also, a shelf life is introduced in cases where given treatments deteriorate over time.

Another approach, which may also include altering the wettability of specific regions with treatments or coatings, is to engineer channels to ensure a balanced urging of fluid, including through split (or forked) channels, without having to pipette forked branches individually. Without engineering of this sort, often what happens is that one half of a forked branch will fill with water and the other will not, since the polymer channels are hydrophobic. But with proper engineering fluid urged through a given channel can be made to fill tributaries equally. Similar considerations apply to combining and mixing fluid streams.

Examples of such engineering considerations include teachings commonly assigned to BioMicro Systems, Inc. (Salt Lake City, Utah), including the teachings of McNeely et al (U.S. Pat. Nos. 6,296,020; 6,591,852; 6,601,613; 6,615,856) and Lei et al (U.S. Pat. No. 6,637,463); the teachings of Jeon et al (U.S. Pat. Nos. 6,705,357; 6,883,559); as well as teachings commonly assigned to Nanostream, Inc. (Pasadena, Calif.), including the teachings of Pezzuto et al (U.S. Pat. No. 6,418,968; 6,748,978), Dantsker et al (U.S. Pat. No. 6,499,499), O'Connor et al (U.S. Pat. Nos. 6,755,211; 6,919,046; 6,981,522), and Karp et al (U.S. Pat. Nos. 6,845,787; 6,877,892; 6,890,093; 6,935,772). McNeely et al ('020) also teach a use of air escape channels to facilitate complicated fluid processing.

Also of particular note, Bhullar et al (U.S. Pat. No. 6,451,264) teach a fluid flow control in curved capillary channels; Fuhr et al (U.S. Pat. No. 6,727,451) and Karp et al (U.S. Pat. No. 6,880,576) teach a microfluidic control of microparticles (e.g., solid catalyst media) suspended in channels; Griffiths et al (U.S. Pat. No. 6,733,730) teach a method and apparatus for reducing sample dispersion in turns and junctions of microchannel systems; Weigl et al (U.S. Pat. No. 6,743,399) teach a pumpless microfluidic device that is entirely driven by a readily available force, such as gravity, capillary action, absorption in porous materials, chemically induced pressures or vacuums (e.g., by a reaction of water with a drying agent), or by vacuum and pressure generated by simple manual action, rather than by an external fluidic driver requiring a separate power source having moving parts; Ismagilov et al (U.S. Pat. No. 6,843,262) teach fluidic switches and methods for controlling flow in fluidic systems; Lim et al (U.S. Pat. No. 6,866,067) teach a micro channel unit having a shape designed to reduce a pressure drop when fluid passes through a connecting channel portion; Gilbert et al (U.S. Pat. No. 6,883,957) teach an on chip dilution system; and, Kim et al (U.S. Pat. No. 6,901,963) teach a microfluidic device for controlling a flow time of fluid.

As the above references make clear, the available body of knowledge to assist in making design considerations is growing rapidly in the arts of microfluidics and microfabrication. By keeping up-to-date in the art, one of ordinary skill will be able to make obvious modifications to the present invention on a continuing basis. Also, many inventive technologies will be devised over time to complement and improve the practice of the invention. The science of the invention is highly interdisciplinary and draws on many fields, and not only in the "micro" dimension, but also in larger and smaller dimensions as well.

Turning to the subject of visualizing the patient, Campbell et al (US published application 2002/0068358) disclose a window with an accessory lens for visualizing an embryo contained in a microfabricated chamber. Thompson et al (U.S. Pat. No. 6,673,008) teach windows along with means of fiber optics for visualizing an embryo in a chamber.

Workers at Stanford Medical School's Network for Translational Research in Optical Imaging are developing a MEMS-based dual-axes confocal microscope. (Wang et al, "Dual-Axis Confocal Microscope for High-Resolution In Vivo Imaging," Optical Letters, vol. 28, no. 6, pp. 414-6, March 2003.) Small in size, MEMS-based microscopes such as this could be developed for introduction like a probe into the fluid incubation medium of a prenidial incubator to visualize the patient. As opposed to a probe-type MEMS-based microscope, a MEMS-based microscope might also be designed for physical integration with the prenidial incubator itself, as a structural part of the microcradle or inside or in close proximity to it.

A vented microcradle employing a vented flooring according to the parent application offers a number of advantages. But a notable limitation overcome by the present invention is an incompatibility with a number of important microscopy techniques. However, if such techniques were replaced by a MEMS-based technology, the limitation would vanish. Essentially, the problem is that the vented flooring may interfere with an optical path needed for a number of techniques. These techniques minimally require a clear view from below the patient, as is required by an inverted microscope, or more generally a clear optical path in a vertical direction from above and below the patient. A MEMS-based solution would obviate this requirement by enabling an optical path to be established laterally or with a probe. However, in absence of a MEMS-based solution, a side-vented microcradle with a clear bottom and an open top offers the advantage of fluidic ventilation combined with a clear vertical path for optics.

Figure 20A:
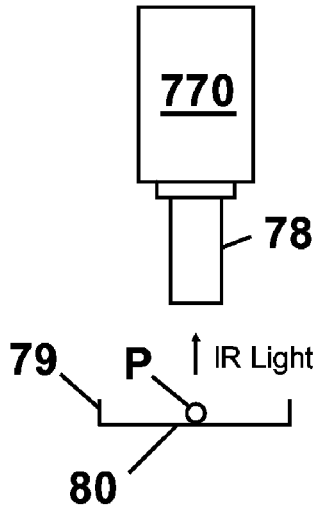
FIG. 20A is a side cross-sectional view of a temperature-detecting infrared camera attached to a microscope lens to detect the body temperature of a patient inside a prenidial incubator according to U.S. Pat. No. 6,694,175.
Figure 20B:
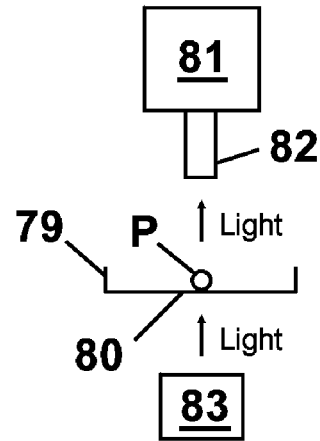
FIG. 20B is a side cross-sectional view of a prior art set up for ordinary microscopy of a prenid in an incubator.

Referring to FIG. 20A, a temperature-detecting infrared camera 770 (e.g., a quantum well infrared photodetector (QWIP) camera) is attached from above to a microscope lens 78 for purposes of infrared microthermography to detect the body temperature of a patient P inside a prenidial incubator 79 (U.S. Pat. No. 6,694,175). In this case, it does not matter if the floor 80 of the incubator is opaque because the infrared radiation being detected is emitted light. The same arrangement can be achieved with focus from underneath provided that the flooring 80 does not block or distort the infrared radiation. Referring to FIG. 20B, a microscope 81 is positioned with its objective (lens) 82 over the patient P. In this case, light from a light source 83 beneath the flooring 80 will provide illumination for many ordinary viewing purposes provided the flooring 80 is transparent enough. Light shining from above may also provide illumination; the illumination can be enhanced if the flooring 80 or other structures (e.g., walls) are mirrored or reflective.

If the flooring 80 has a pattern of vents according to the parent teaching, then making the vented flooring 80 out of a material with a refractive index more closely matched to that of the physiologic solution (incubation medium) filling the vents will help to reduce a distortion of light passing through the vented flooring 80; digital corrections for distortions can also be made by computer. Techniques like these may make it possible to clearly view the patient P even through the vented flooring from below (i.e., using an inverted microscope).

Referring to FIG. 20B, some microscope techniques require light with special qualities, and so filters, polarizers, compensators, and other optical means (not shown) may be placed in the optical path. Consequently, even when viewed from above, a vented flooring 80 may still detract from a desired quality of light by causing distortions of light quality. These distortions may be reduced to some extent either by making digital corrections or by controlling properties of the vented flooring 80, such as refractive index, diffraction, birefringence, grill pattern, and so on. Nonetheless, full compatibility with a number of today's high end microscopy techniques will generally require a clear, undistorted optical path as provided by a side-vented microcradle with a clear bottom and an open top according to the present invention.

Accordingly, when certain high end microscopy techniques are necessary, and assuming an optical MEMS implementation is not available, then a side-vented microcradle with a clear bottom and an open top according to the invention will likely provide the best choice. However, a number of such techniques introduce strict design requirements. Those skilled in the arts of engineering and microscopy will appreciate a need to observe a number of design considerations in this regard.

Figure 20C:
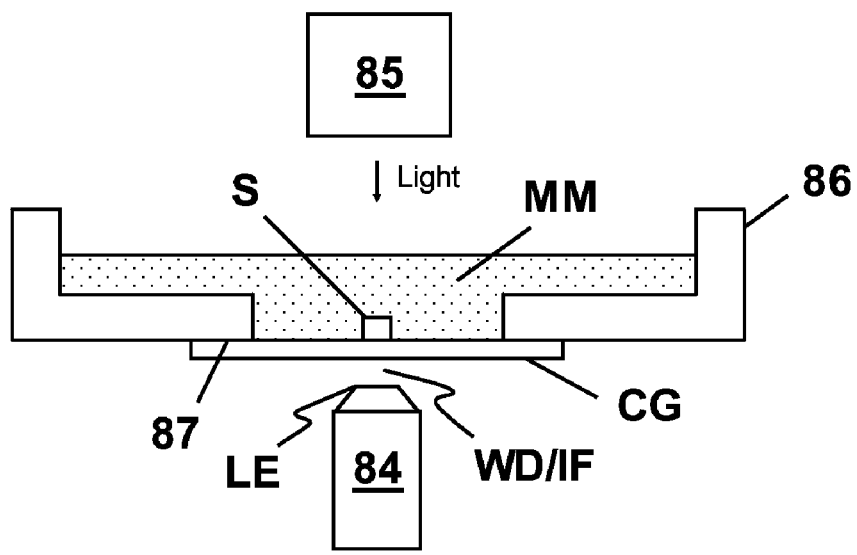
FIG. 20C is a side cross-sectional view of a prior art setup for high resolution microscopy of a specimen in a petri dish using an inverted microscope having a high numerical aperture objective lens.

FIG. 20C illustrates a familiar setup for high resolution microscopy using an inverted microscope having a high numerical aperture objective lens 84. Light from a light source passes through a condenser 85 to illuminate a biological specimen S in a petri dish 86. The specimen S may be covered with various mounting media, but for in vivo microscopy applications the medium is a physiologic solution MM. Typically, the specimen S rests or is plated on a coverslip (cover glass) CG that has been affixed using adhesive 87 over a hole in the bottom of the petri dish 86. A working distance WD for an objective lens 84 is defined as the distance between the objective front lens element LE and the bottom of the cover glass CG above.

High numerical aperture objective lenses 84 are designed with a particular immersion fluid IF in mind. The importance of the immersion fluid IF is its refractive index. The immersion fluid fills the working distance WD space, meaning the space between the objective front lens element LE and the bottom of the cover glass CG above. Air (dry immersion), water, and oil are the most common immersion fluids IF; glycerol/water mixtures are also used. Dry immersion objectives offer large working distances up to ~2 mm, whereas oil immersion objectives and water immersion objectives generally rely on relatively short working distances, for example, on the order of 220 microns (0.22 mm).

According to theory, best optical performance is achieved when the mounting medium MM, specimen S, cover glass CG, immersion fluid IF, and the objective front lens element LE all have the same refractive index; however, if imaging is limited to a focal plane immediately adjacent to the cover glass CG, e.g., to a surface region of cells making direct contact with the cover glass CG, then only the refractive indices of the cover glass CG, immersion fluid IF, and objective front lens element LE are important. With present technology, objective lenses 84 are made of glass having a refractive index of 1.515; consequently, oil immersion objectives offer the highest numerical aperture (a measure of resolving power) because some oils have the same refractive index. However, cellular matter has an index of refraction ranging from about 1.33 to 1.39 and a physiologic solution has a refractive index of about 1.33. Thus, when imaging beyond a focal plane immediately adjacent to the cover glass CG, some refractive index mismatch is inevitable. As a consequence, with present technology, water immersion objectives allow for imaging of the highest resolution through cells or aqueous to a depth of 200 microns past the cover glass CG; in contrast, oil immersion objectives offer higher resolution for imaging limited to a focal plane strictly adjacent to the cover glass CG, such that focus through an aqueous layer is avoided. In general, high resolution microscopy techniques can be particularly sensitive to a thickness and index of refraction of the cover glass CG. The thickness of the cover glass CG may nominally be 170 microns with an index of refraction of 1.515; other values are possible. The objective 84 may also include a correction collar to compensate for cover glasses with non-ideal values. Cover glasses may also be selected based on other properties such as transmission to certain wavelengths of light, polarization, birefringence, florescence, and so on. See Nikon's MicroscopyU website (www.microscopyu.com) for an in-depth discussion.

Referring to FIG. 1, the present invention generally enables high resolution microscopy using an inverted microscope by specifically employing a layer for the clear bottom 3 of a vented microcradle having desirable optical properties such as thickness, refractive index, and so on. Using FIG. 6B as an example, to enable high resolution microscopy in conjunction with an embodiment of the invention by employing an inverted microscope with a high numerical aperture objective, such as a Nikon (Melville, N.Y.) 60× plan apochromat correction water immersion objective featuring a 1.2 numerical aperture and a 220 micron working distance, the bottom layer 34 is preferably a cover glass having a thickness of 170 microns and a refractive index of 1.515. Other modifications of the invention to enable high resolution microscopy will be appreciated by one skilled in the art.

Micronit Microfluidics, BV (Enschede, The Netherlands) offers a microfluidic chip having a 145 micron thick cover glass bottom to enable viewing by means of confocal microscopy inside a microchannel etched in the bottom of an adjacent upper layer.

Referring to FIGS. 3-4, an embodiment of a temperature bath according to the invention employing a double-walled vessel 16 would generally not be suitable for use with high resolution microscopy if, as shown in FIG. 3, an optical path 88 though the clear bottom 3 encounters the running fluid 19 and an additional layer of glass 89. In other words, as shown in FIG. 4, even though the clear bottom 3 remains "clear", in general it will not be optically suitable for meeting the strict requirements of a number of high resolution microscopy techniques. Thus, to ensure optimum compatibility with such techniques, it is preferable to route the running fluid 19 around a clear area (forming an optical window) 90 in a line-of-sight with the optical path 88. Though maintaining laminar flow in the clear area 90 may improve clarity, for optimum compatibility the running fluid 19 must be routed around the optical path 88.

Figure 21A:
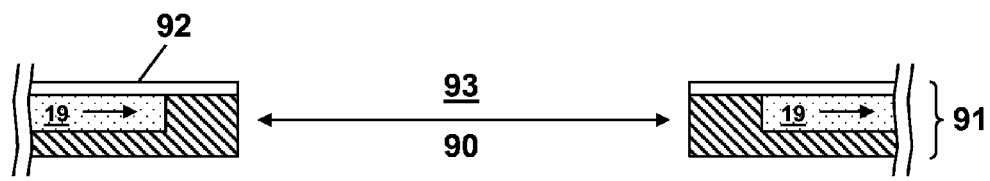
FIG. 21A is a side cross-sectional view of a temperature-controlled bed according to the invention.
Figure 21B:
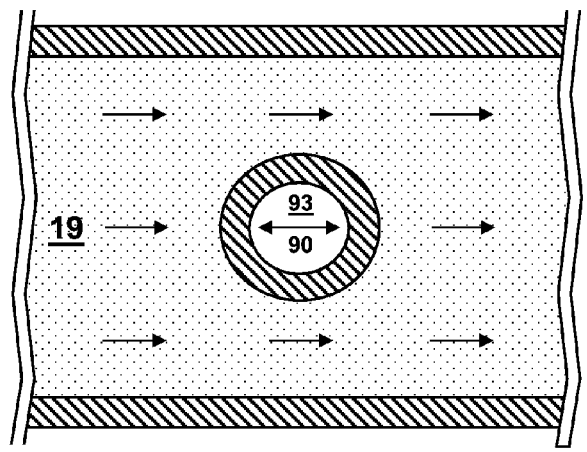
FIG. 21B is a top cross-sectional view of the bed shown in FIG. 21A.

Referring to FIGS. 21A-B, a variety of temperature bath according to the invention is provided in the form of a temperature-controlled (glass) bed 91, which preferably takes the form of a microscope stage, such that the temperature bath flows inside the bed in the form of a running fluid 19 to maintain an ambient temperature for an FCA (not shown) that rests in thermal contact with a top layer 92 of the bed 91. The thermal contact may be aided by means of a heat sink compound thinly applied to the top layer 92 or by means of pressing and holding the FCA against the top layer 92. Though not shown, it is understood in practice that a clear bottom of a vented microcradle contained by the FCA is positioned over an open area 93 in the bed 91 to provide a clear area 90 for an optical path for microscopy. The temperature-controlled bed 91 according to the invention is distinct from the temperature-controlled bed of Enzelberger et al because it provides for a continuous range of temperatures (as opposed to two temperatures) and an opening 93 to ensure an area 90 for a clear optical path for microscopy.

Figure 22:
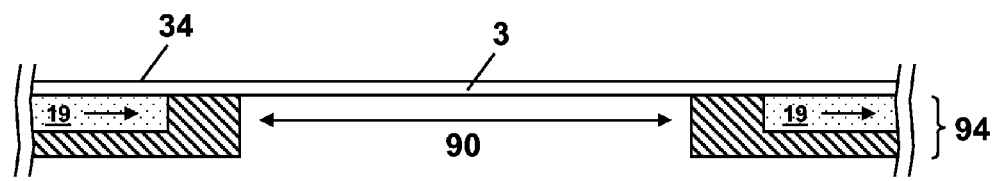
FIG. 22 is a side cross-sectional view of a temperature-controlled bed according to the invention incorporating a fluidic circuit board assembly layer.

Alternatively, referring to FIG. 22, which is likened to FIG. 21A, an FCA layer providing a clear bottom 3 for a vented microcradle (e.g., the bottom layer 34 of the FIG. 6B embodiment) can replace the top layer 92 of the temperature-controlled bed shown in FIG. 21A to directly bond the FCA to a bed-like temperature bath 94. In FIG. 22, upper layers of the FCA (e.g., layers 32-33 in the FIG. 6B embodiment) are not shown.

In general, microfluidic channels and vias can be routed within an FCA with any degree of complexity. This includes routing a running fluid for a temperature bath through an FCA in such a way as to leave an area for a clear optical path for microscopic viewing into a vented microcradle contained by the FCA. In the art of electronics, traces and vias can be routed on a PCB with the aid of auto-routing software programs. Analogous skills applied to FCA channels and vias will be appreciated by those skilled in the art of microfluidics. To give a non-limiting example, referring to FIG. 23, a running fluid 19 is routed through an FCA in such a way that a clear area 90 is left to provide for a clear optical path for microscopy. This example is similar to the FIG. 6C embodiment.

Figure 24A:
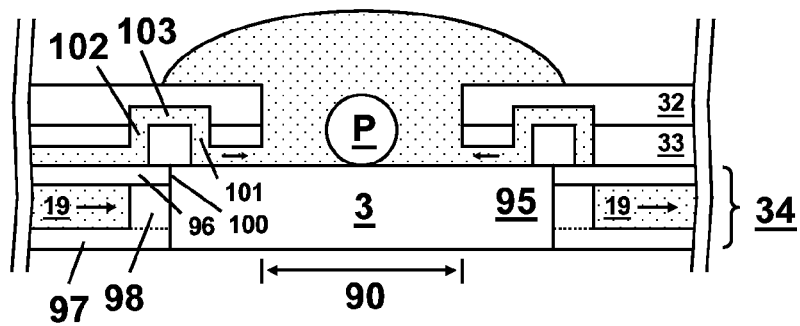
FIG. 24A is a side cross-sectional view of a side-vented microcradle taken along a line 99 with respect to FIGS. 24B-C.
Figure 24B:
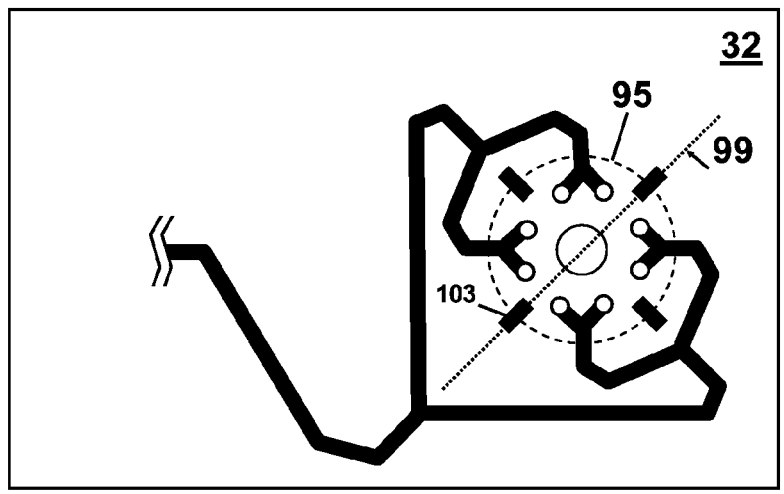
FIGS. 24B-C are bottom orthogonal views of glass sheets having microfluidic channels and vias etched in them for the side-vented microcradle shown in FIG. 24A.
Figure 24C:
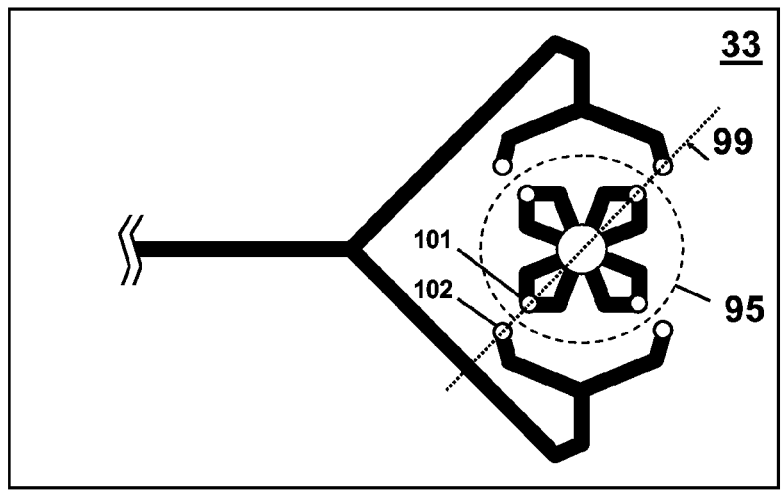

For exemplary purposes, FIGS. 24A-C depict a variation of the embodiment shown in FIGS. 6B & 7A-B. Referring to FIG. 24A, note that a cover glass portion 95 of the bottom layer 34 may be pieced in instead of being continuous. A design consideration being explored in this example is that with present technology it is possible to directly bond two or possibly three layers of glass without adhesive; however, for microfluidic designs it remains challenging to directly bond more than three glass layers. Therefore, as long as this limitation persists, it is desirable to limit to three or less the number of FCA layers that are fluidically contiguous with a vented microcradle, since such layers need to be bonded without adhesive in order to help assure an ultrapure environment for patient care. In this sense, what fluidically contiguous means is that if the layers were to employ an adhesive instead of being directly bonded, then the adhesive might leak through a seam or boundary into fluid that a patient will be exposed to in the vented microcradle. However, non-fluidically contiguous layers (or regions) do not present this problem, and so adhesive may be used to bond layers without compromising the purity of the care environment. Thus, it may be desirable to piece in a layer for a fluidically contiguous region so that adhesive can be used to bond added layers in a non-contiguous region.

For example, referring to FIG. 24A, layer regions 95 (e.g., the cover glass) and 96 can be directly bonded to layer 33, whereas layers 96 and 97, including an optional intermediary layer 98, can be bonded to each other with adhesive. FIG. 24A is a side cross-sectional view taken along a line 99 with respect to FIGS. 24B-C. Note that channels must be routed to prevent a leakage of fluid along a vertical seam 100 where a pieced-in layer 95 meets an adjacent layer 96. In this example, vias 101-102 route a channel 103 from a lower layer 33 up into an upper layer 32 and then back down to avoid the seam 100. In general channels and vias bearing potentially contaminated fluid (e.g., contaminated with adhesive residues) can be routed anywhere in an FCA provided that the channels and vias are not contiguous with seams or boundaries that might permit contamination of the care environment.

Figure 25:
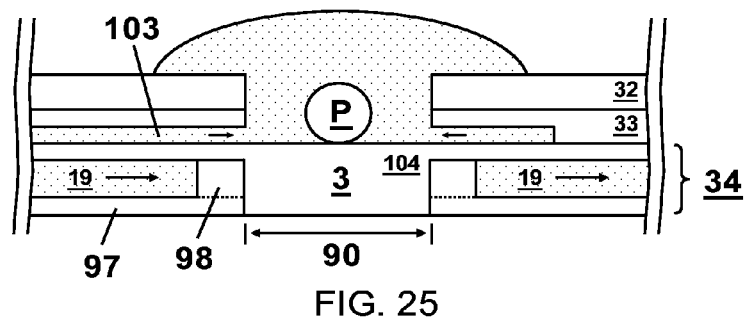
FIGS. 25-26 are side cross-sectional views of side-vented microcradles.

Referring to FIG. 25 in comparison with FIG. 24A, routing of a microfluidic channel 103 into an upper layer and back down again to avoid a seam would not be necessary if a bottom layer 104 were continuous (though of non-uniform thickness) rather than being pieced-in, so that in effect layer regions 95 and 96 (having different thicknesses) were formed by a single piece of glass. This approach would enable other layers (e.g., 97-98) to be added on with adhesive without contaminating the care environment, while also providing a flat bottom for a FCA. However, direct bonding of a glass layer 104 of non-uniform thickness as shown in FIG. 25 might be too challenging to perform with present technology due to a risk of cracking the glass. Yet etching could be performed after direct bonding of a layer of uniform thickness, resulting in a layer 104 of non-uniform thickness as shown in FIG. 25. But if a flat bottom for the FCA is not necessary, then something along the lines of FIG. 22 might be preferable.

Figure 26:
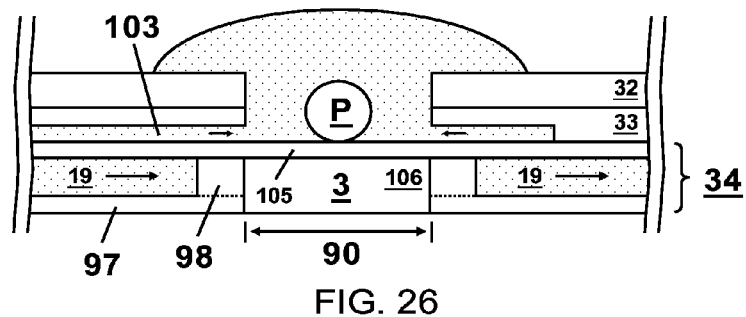

Referring to FIG. 26, which is similar to FIG. 25, another option is to directly bond layers 32-33, 105 to each other without any adhesive first and to then bond an additional layer 106 with adhesive to layer 105. For example, glass layers 105-106 may nominally be 30 and 140 microns thick respectively and have a refractive index of 1.515. Accordingly, the bottom layer 34 will total 170 microns in thickness and have a refractive index of 1.515 in the clear area 90 provided for an optical path, as is desirable for high resolution microscopy techniques. Great flexibility is afforded by this approach, as discussed further below. For example, layers 97 and 105 could both be continuous and an additional layer could serve as a spacer in between.

Figure 27:
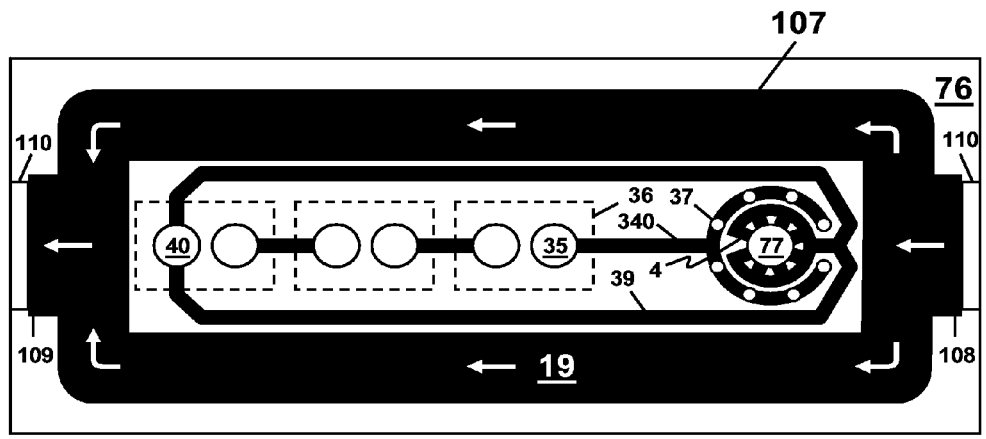
FIG. 27 is a bottom orthogonal view of a glass sheet having microfluidic channels and vias etched in it for a side-vented microcradle.

Although routing of any complexity can be accomplished according to the art, it is not necessarily a complex matter to include routing for such optimal features as a running fluid for a temperature bath that is compatible with high resolution microscopy. For example, referring to FIG. 27, which is a version of the FIG. 19 embodiment employing bilateral symmetry and a temperature bath, which in turn is a two-layer version of the FIG. 6B embodiment, a channel pattern 107 is etched in the upper 76 of two glass layers to provide for a running fluid 19 that proceeds from an inlet 108 to an outlet 109 to establish a temperature bath. Vias 110 may be etched in the upper layer 76 to aid in making fluidic contact with fluid supply line connectors (not shown) at respective inlet and outlet ends. To meet with standard requirements for high resolution microscopy, the bottom layer is preferably 170 microns thick, with a refractive index of 1.515. The two glass layers are directly bonded without adhesive. The channel pattern 107 may be varied to accommodate other types of fluid supply line connectors; also, additional features (e.g., holes, notches, etc.) can be made in one or more of the glass layers to aid in establishing such connections. The channel pattern 107 for the running fluid 19 can also be etched in the bottom glass layer instead, or both layers can be etched to enable a greater rate of flow for the running fluid 19 by providing a deeper channel.

In general, optimal patterns for routing fluids in an FCA can be determined according to the art with the aid of fluorescent dyes (to observe mixing and flow), optical doppler tomography (to detect flow velocity), infrared microthermography (to determine temperature distribution), and other techniques (e.g., to measure volume, etc.); and so, the pattern examples described in this disclosure are intended for interpretation as enabling examples, but not as limiting examples, as will be appreciated by one skilled in the art.

Referring to FIG. 20C, it has been noted in the field of in vivo microscopy that when wet immersion objectives are used (e.g., oil or water), the microscope objective 84 will serve as a heat sink (or source) unless it is at the same temperature as the physiologic medium MM. This effect results in a loss of temperature control. Warner Instruments, Inc. (Hamden, Conn.) notes that "it has been observed that the solution temperature directly above an immersion objective can change as much as 10° C. for a 37° C. solution perfusing at 5 ml/min in an apparatus maintained at ambient [room] temperature [~21-23° C.]." (Warner Instruments, Inc., "OW Series Objective Warmers," Rev. Jan. 27, 2004, p. 4). This effect would be especially disastrous in the case of a prenidial incubator because according to the traditional setup for high resolution microscopy using a wet immersion objective the objective 84 would have to be placed directly underneath the patient resting in the microcradle. In general, prior artisans in the field of in vivo microscopy have responded to the heat sink problem either by warming the microscope in a cage incubator or by heating the objective 84 by a temperature-controlled resistive means.

Okolab (Naples, Italy) employs a cage incubator for in vivo microscopy enclosing both the specimen and substantially enclosing the microscope. An exclusive reliance on this approach is inadequate because temperature will fluctuate when the cage is opened. Warner Instruments, Inc. employs a temperature-controlled resistive heating collar (the OW-37 Objective Warmer) that heats an objective 84 indirectly by warming air very close to the objective. Warner Instruments, Inc. claims that indirect warming of this sort is less stressful for the objective 84 than a resistive means that warms by direct contact with the objective. A general problem with employing a resistive means is that it may interfere with highly sensitive electrical or magnetic equipment used to investigate physiological signals; also, temperature pulldown times are relatively slow with this type of means because cooling relies on dissipation; but perhaps the most important and overlooked problem is that infrared radiation from a resistive heating element placed in close proximity to a prenidial infant may warm or overheat the patient in the incubator. Of added concern, a specific problem with heating air to warm the objective 84 is that the heated air may rise to heat the cover glass CG by an undesirable amount.

When needed to eliminate a potential heat sink or source, a temperature bath according to the invention is generally preferred to maintain a desired temperature of equipment such as a microscope objective placed in thermal contact with an FCA. To circulate a running fluid, the objective may be surrounded by a water jacket, coils, or the like. Objective heater designs employing a copper tubing water jacket are known in the art of live cell imaging. But preferably the temperature bath may be integrally routed within a structure of the objective, particularly if the objective is fabricated using a technology compatible with microfluidics, such as a layer-based technology. Microfabricated objectives of this sort are discussed further below under this sub-section on "Design Considerations", including objectives forming part of an FCA. Unlike a resistive means that cycles on and off to produce a desired temperature, the temperature bath does not subject the objective to a thermal cycle since the temperature bath is generally constant; in contrast, a resistive heating element is usually hotter than a desired ambient temperature when turned on, and must therefore be cycled on and off; thus, the temperature bath avoids subjecting the objective to the stress of thermal cycling without relying on warmed air. If the temperature needs to be changed the temperature bath enables fast pull-up/down times; the change can also be produced gradually; also, there is no electronic or magnetic signature, and there is no resistive heating element to generate infrared radiation in close proximity to the infant. The temperature bath should circulate in such a manner (e.g., in a downward direction away from the patient) that a gradient of heat transfer moves away from the patient care region.

In general, note that a degree of isolation between the patient care environment and the surroundings may still be desirable even despite being able to employ means to equilibrate temperatures. For example, popular manufacturers of high resolution microscopy equipment suggest operating environments within a range of 20-30 degrees Celsius and a humidity of 60% or less. This is outside the range of 37 degrees Celsius and 95-100% humidity for prenidial incubation. Another problem is radiant heat transfer. In the art of neonatal incubation, double-walled incubators are employed to reduce radiant heat transfer between the infant and the surroundings. For example, the Air-Shields® Isolette® C2000e infant incubator sold by Drager Medical AG & Co. KG (Lübeck, Germany) employs a double-wall construction.

Figure 28:
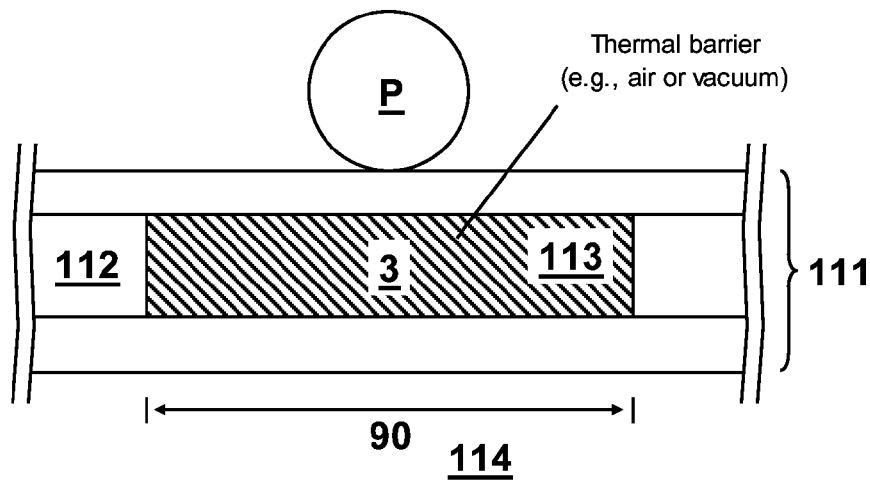
FIG. 28 is a side cross-sectional view of a section of a side-vented microcradle.

Referring to FIG. 28, the bottom of a microcradle may be formed by a composite layer 111 comprising any number of layers. In this example, an intermediary layer 112 provides a thermal barrier or void 113 to isolate the patient P from the surrounding environment 114 in the manner of a double-walled incubator bottom. For example, the thermal barrier or void 113 may comprise an air or vacuum chamber. An objective lens may be designed to accommodate specific parameters associated with the design of the composite layer 111. For example, the thermal barrier or void 113 may be of a certain depth. Additional thermal barriers or voids may be formed by various techniques between or alongside channels or devices, around the sides of a vented microcradle, or elsewhere in an FCA. Such techniques may include the use of etching to create a void or the use of stencil layers, layer spacers, or thermally insulating layers or regions to produce thermal barriers or voids. Coatings, surface finishes, and materials with relevant properties may also be used to regulate an emission and absorption of thermal radiation. In general, FCA's may also include structures and devices to conduct, dissipate, or distribute heat from devices that warrant it (e.g., away from an integrated circuit chip).

A number of teachings in the field of microfluidics commonly assigned to Nanostream, Inc. teach use of a stencil layer comprising channel boundaries cut in a pattern entirely through the layer to provide lateral boundaries for fluid movement when sandwiched between top and bottom layers, e.g., the teachings of Pezzuto et al (U.S. Pat. No. 6,418,968) and O'Connor et al (U.S. Pat. No. 6,481,453). The prior art of microfluidics does not teach or fairly suggest a substantially planar stencil layer to provide a thermally insulating layer in the form of a thermal barrier or void when sandwiched between top and bottom layers; the prior art also does not teach or fairly suggest a thermal barrier or void etched in one or more layers to provide thermal insulation. Stencil patterns are limited to open paths because separate cutouts will result for each closed path. However, various cutouts may be bonded to a layer, including in combination with a stencil, to achieve a desired pattern in a substantially planar layer including closed paths.

Microoptics is a rapidly evolving technology in microfabrication and it would be highly desirable to have available an optical MEMS implementation to replace bulky, large-scale microscopy and infrared microthermography for use with a vented microcradle. MEMS optics may include such exemplary features as light sources, filters (e.g., a circular polarizer, interference filter, or tunable filter), condensers, compensators (e.g., a universal liquid crystal compensator or Pockels cell), mirrors, microlenses and microlens arrays, objectives, adaptive optics, diffractive optics, means of focusing, means of microscopic instrument control (e.g., device positioning), means of signal detection (e.g., photodiodes or microbolometers), means of data communication, microinterferometry, microspectroscopy, microrefractometry, and more. But, generally speaking, a number of challenges still need to be overcome to develop optical MEMS implementations that on are on par with their large-scale counterparts. Also, integration of an optical MEMS device with a vented microcradle inside the fluid incubation medium brings with it additional challenges such as compatibility and device cooling.

An optical MEMS implementation enabling a lateral optical path (side-to-side within the microcradle) for both microscopy (for visualization) and infrared microthermography (for patient temperature detection) would be ideal. It would also relax the need for an optically clear bottom for the vented microcradle. However, in absence of such an implementation, a compromise route to optical MEMS would be to integrate MEMS optics with the clear bottom itself.

Figure 29A:
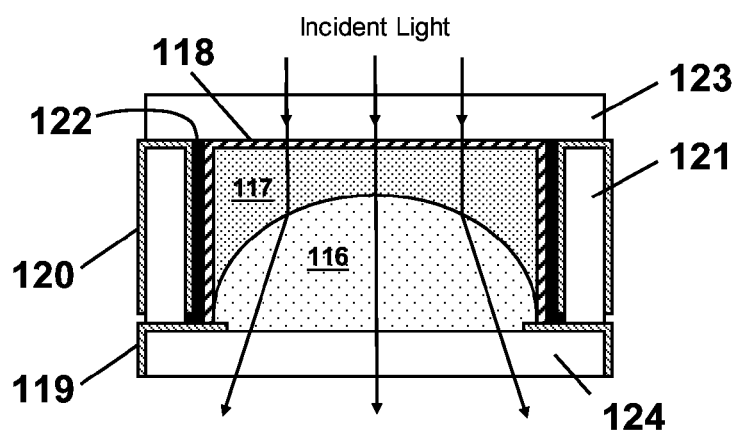
FIGS. 29A-B are side cross-sectional views of a prior art variable focus liquid lens.
Figure 29B:
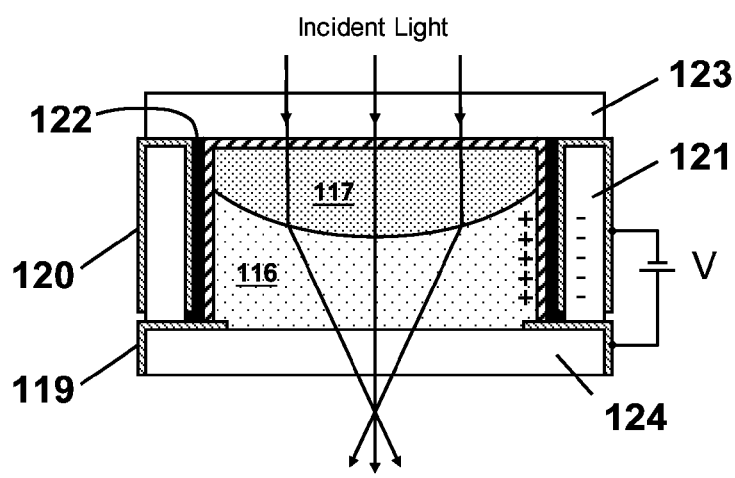

To give an example for illustration, Koninklijke Philips Electronics Nev. (Amsterdam, the Netherlands) makes an electrically focusable liquid lens (brand name FluidFocus) suitable for MEMS optics applications. Referring to FIG. 29A, a conducting aqueous solution 116 forms a convex meniscus with respect to a non-conducting, immiscible, and hydrophobic liquid 117 having a different index of refraction to form a lens; the aqueous 116 takes on a convex shape in simple contact with a hydrophobic coating 118. Referring to FIG. 29B, when a voltage difference is applied between respective bottom and sidewall electrodes 119-120 a static charge builds up, creating an attraction between cations in the aqueous and neighboring electrons residing on an outer surface of the sidewall electrode 120 where it covers the inside of a glass wall 121; this attraction compensates in a pseudo-hydrophilic sense for the otherwise hydrophobic coating 118; the attraction causes the aqueous to form a concave lens shape. An insulator 122 separates electrodes 119-120. Bottom electrode 119 makes electrical contact with the conducting solution 116 whereas sidewall electrode 120 is insulated. Notably, a capacitive relationship is formed between cations in the conducting solution 116 and electrons residing on the surface of the side electrode 120; it is a polar attraction of the aqueous for these cations that causes the sidewall surface to be wetted. The lens shape and, hence, focus varies with applied voltage; an applied voltage does not need to be maintained to maintain the lens shape because the charges are maintained by capacitance.

Kohashi et al (U.S. Pat. No. 4,030,813) teach a control element having a liquid layer attainable to a geometrically uneven state in response to an electrical signal, with function as an electrically controllable optical lens. Berge et al (U.S. Pat. No. 6,369,954) teach a lens with variable focus comprising a liquid lens (also known as a tunable liquid microlens) having a lens shape controlled by electrowetting. Berge et al licensee Varioptic, Inc. (Lyon, France) is the leading manufacturer of focusable liquid lenses. Modifications of the liquid lens concept are known, e.g., the FluidFocus lens. For simplicity of comparison with respect to various new modifications presented below, a discussion has been given above of the Philips version (FluidFocus) because the FluidFocus lens employs straight sidewalls as opposed to sloped sidewalls employed by Varioptic lenses (e.g. ARTIC lenses), the latter being a little more complicated to manufacture. The Philips FluidFocus lens is disclosed in the published application of Feenstra et al (US 2005/0113912). A comparable Varioptic lens is disclosed in the published application of Berge et al (US 2006/0126190).

New modifications of the liquid lens concept are needed to improve compatibility of the lens with the present invention. For example, Phillips makes a FluidFocus lens having a diameter of 3 mm. However, lenses of substantially smaller diameter (e.g., 0.25-1 mm) will likely work better with the present invention. But to achieve operability in a smaller diameter lens it becomes necessary to increase capacitance between the polar (hydrophilic) conducting solution 116 and the sidewall electrode 120, otherwise the lens will not change shape or undesirably large voltages will be required to produce the change. Thus, one object of modification is to promote increased capacitance. Various options can satisfy this object to varying degrees. For example, the hydrophobic coating 118 can double as an insulator 122 to strengthen capacitance by minimizing a distance between charges by eliminating an added thickness; moreover, a composition of matter to achieve this goal with as thin a coating as possible would be preferred. Another option is to employ an insulator 122 with a high dielectric constant to promote capacitance. For the same reason, all else being equal, a hydrophobic coating 118 with a higher dielectric constant will promote more capacitance than one with a lower one. An effect on capacitance of tradeoff between a coating's thickness (i.e., charge separation distance) and the magnitude of its dielectric constant is understood in view of capacitor physics.

In the drawing, note that although insulator coatings 122 and hydrophobic coatings 118 are being drawn and labeled separately to emphasize their distinct physical functions, it is understood that in practice they may be one and the same coating. It will also be appreciated by one skilled in the art that a hydrophobic coating may be applied wherever hydrophobic interaction is undesirable, and similarly that a hydrophilic coating may be applied to promote hydrophilic interaction; thus, an omission of such a coating in a part of the drawing does not imply that such a coating would not be of use in specific circumstances.

An approach to liquid lens design employing laminated planar layers is preferred for use with the present invention because layer-based designs enable seamless integration with FCA designs. Philips and Varioptic employ laminated glass or plastic layers. For example, a FluidFocus lens 3 mm in diameter and 2.2 mm in length employs an annular member for the glass sidewall 121 with glass end caps 123-124 to form a cylindrical lens for use in a digital camera. (Philips Research Press Release, "Philips' fluid lenses bring things into focus," Mar. 3, 2004.) However, the prior art does not employ microfluidics to fill the lenses. Instead, the prior art pairs together one drop each of oil and aqueous and sandwiches them between layers. A published application for a "prop Centering Device" by Berge (US 2005/0002113) underscores the complexity of this process. As taught by the present invention, a microfluidic approach to filling the lens with liquid is needed for a very small diameter lens (e.g., 0.35 mm) and simplifies the filling of larger lenses as well.

Figure 30A:
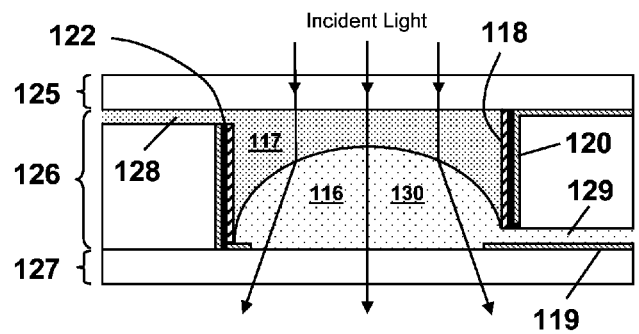
FIGS. 30A-B are side cross-sectional views of a variable focus liquid lens according to the invention.
Figure 30B:
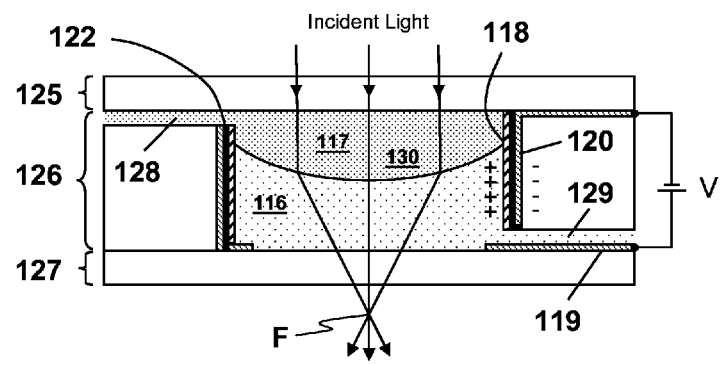
Figure 31A:
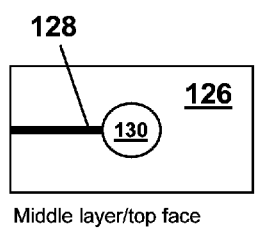
FIGS. 31A-B are respective top and bottom orthogonal views of a glass sheet having microfluidic channels and a via etched in it for the liquid lens shown in FIGS. 30A-B.
Figure 31B:
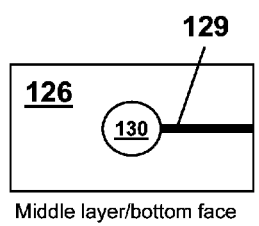
Figure 31C:
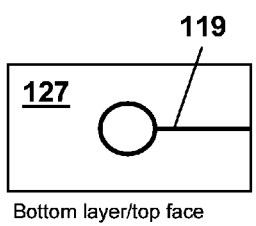
FIG. 31C is a top orthogonal view of a glass sheet having a conductive trace deposited on it to form an electrode for the liquid lens shown in FIGS. 30A-B.

FIGS. 30A-B show an exemplary small diameter liquid lens according to the invention employing a layer-based approach compatible with an FCA; referring to FIG. 31A, a microfluidic channel 128 is etched in the top face of a middle glass layer 126 and a via is etched through the middle layer 126 to form a microfluidic lens chamber 130; referring to FIG. 31B, another microfluidic channel 129 is etched in the bottom face of the middle glass layer 126; though not shown in FIGS. 31A-B, and as best seen in FIGS. 30A-B, the sidewalls of the microfluidic lens chamber 130 are 1) coated with a conductor of electricity to form a sidewall electrode (cylindrical capacitor plate) 120, 2) coated with an electrical insulator 122, and 3) coated with a hydrophobic substance 118; the insulator coating 122 and hydrophobic substance 118 may preferably be one and the same coating; the coatings may be accomplished using conformal chemical vapor deposition; a conductive trace is routed to connect the cylindrical capacitor plate 120 to a point of electrical contact; referring to FIG. 31C, a conductive trace 119 is deposited on the top face of a bottom glass layer 127 to form a bottom electrode 119.

The three glass layers 125-127 are bonded together, e.g., with adhesive. As best seen in FIGS. 30A-B, the microfluidic channels 128-129 establish fluidic communication with the microfluidic lens chamber 130. To form a liquid lens, the microfluidic lens chamber 130 is first filled with a non-conducting, immiscible, and hydrophobic liquid 117 (e.g., an oil) via the microfluidic channels 128-129 and then a conducting, hydrophilic liquid 116 (e.g., an aqueous solution) is urged into the chamber 130 via the bottom microfluidic channel 129; alternatively, the chamber 130 is first filled with the aqueous solution 116 and then the oil 117 is entered into the chamber 130 via the top channel 128. The water 116 and oil 117 touch each other so there is no gap in between and the meniscus between them forms a lens, the two liquids having different refractive indexes. An exact filling of the lens chamber 130 to form a lens is preferably accomplished using a visualization means. The visualization means may include a microscope placed under the lens chamber 130 or a photodiode array placed under the lens chamber 130. A test pattern or specimen may be placed above the lens chamber 130 so that the progress of filling the lens chamber 130 can be monitored in terms of an image visualized and a degree of focus obtained. As shown in FIG. 30B, the liquid lens is shaped by changing a DC voltage applied between the sidewall electrode 120 and the bottom electrode 119. The sidewall electrode 120 (insulated) is preferably given a negative charge and the bottom electrode 119 (in contact with the conducting solution) is given a positive charge, or vice versa. Focusing operations, e.g., shaping the lens by applying different voltages, or raising or lowering the meniscus 131 between liquids (described below), may aid in monitoring the liquid lens filling process.

Figure 32:
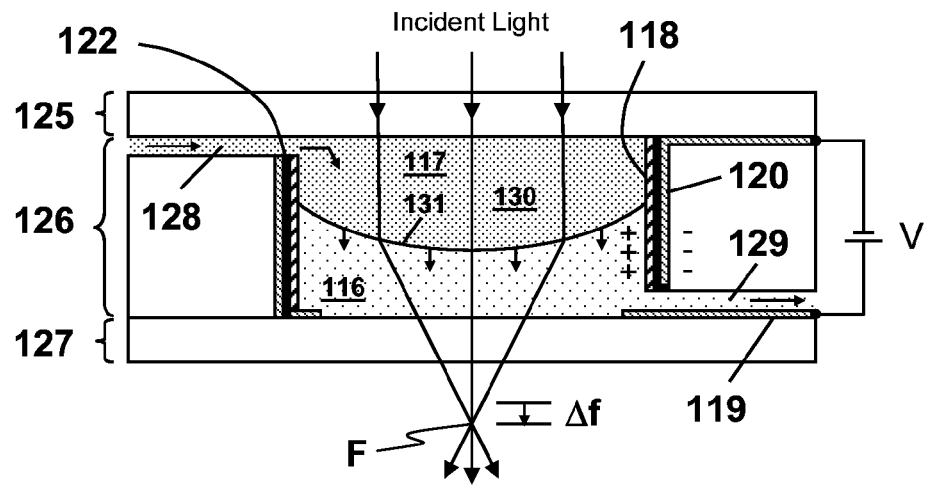
FIG. 32 is a side cross-sectional view of a variable focus liquid lens according to the invention.

Referring to FIG. 32 in view of FIG. 30B, in addition to being able to form a very small diameter liquid lens, another distinct advantage of employing microfluidics to fill the lens chamber 130 of a liquid lens is that a meniscus 131 between liquids may be lowered or raised hydraulically to change a focal distance f between a lens and its focal point F by an incremental amount AC FIG. 32 shows oil 117 being urged into the lens chamber 130 via the top microfluidic channel 128 to increase the focal distance by an amount AC Conversely, the aqueous 116 can be urged into the lens chamber 130 via the bottom microfluidic channel 129 to reduce the focal distance by an incremental amount. In other words, the lens focus can be controlled not only by changing the lens shape by applying different voltages but also by moving the lens hydraulically within the lens chamber 130 by means of microfluidics.

Referring to FIG. 32, the middle layer 126 forming the lens chamber 130 can be made of any thickness, thus enabling the meniscus 131 (liquid lens) to be moved up and down over any desirable range of distances. Because microfluidics can handle extremely small volumes of fluid and, hence, very small values for AC hydraulic focus of a liquid lens according to the invention enables an extremely fine focus, as will be appreciated by those skilled in the arts of hydraulics and microfluidics. A hydraulically focusable liquid lens may also be combined with another lens to provide zoom lens capability. In contrast, Varioptic relies exclusively on a reshaping of fixed liquid lenses to provide a relatively limited 'zoom' focus.

Figure 33A:
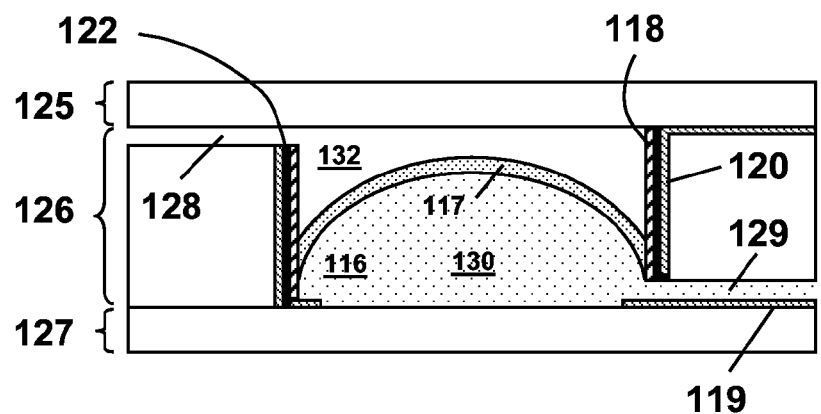
FIGS. 33A-B are side cross-sectional views of a variable focus liquid lens according to the invention.
Figure 33B:
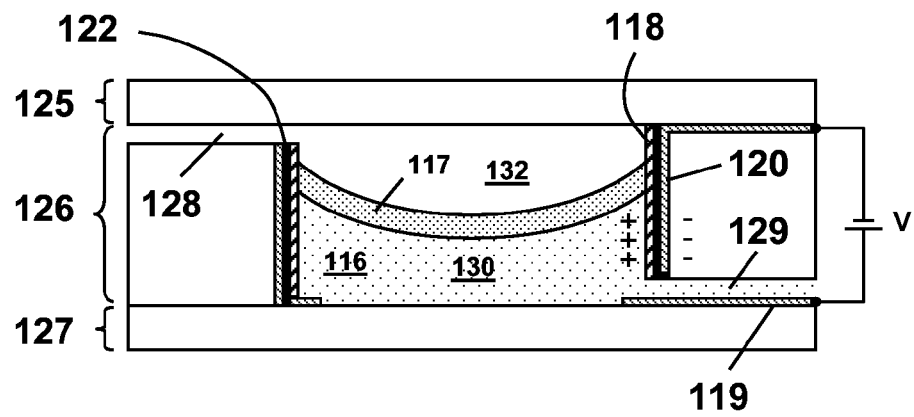

Referring to FIGS. 33A-B, the aqueous solution 116 may be coated with a thin layer of oil 117 to form a meniscus lens, with air 132 on the other side of the meniscus. The shape of the meniscus lens may be changed by electrowetting. (Note that a meniscus forms a lens even apart from an electrowetting means.) Employing air 132 or other gas affords a degree of thermal isolation within the lens chamber. Note that if both sides of the oil meniscus contain the same aqueous solution (as opposed to placing air 132 on one side and aqueous 116 on the other) then the oil (non-conducting) layer 117 forming the meniscus will lie flat. Of analytical interest, deviations from flatness can be attributed to differences in conducting solutions placed on either side of the meniscus formed by the non-conducting layer 117, such differences being detected as changes in focus caused by a curvature of the meniscus as a function of voltage.

The simple meniscus lens shown in FIGS. 33A-B has a few limitations. For example, a pressure of the air 132 must be maintained to shape the meniscus by electrowetting, otherwise the aqueous 116 will move upward based on capillary action. But because the air 132 is highly compressible, then even if the upper microfluidic channel 128 is valved shut, there can still be some movement. Valving the lower microfluidic channel 129 shut will eliminate net movement of the aqueous 116. In general, if channels such as microfluidic channels 128-129 are not closed off or, more to the point, if a pressure opposing flow is not maintained, then electrowetting forces will create a pumping effect based on capillarity. In other words, though not shown in the drawing, a means to resist undesirable flow is understood. Another limitation of this simple meniscus lens, as will be appreciated by one skilled in the art of optics, is that the respective shapes or radii of the convex and concave sides of the lens cannot be independently controlled by electrowetting.

Figure 34A:
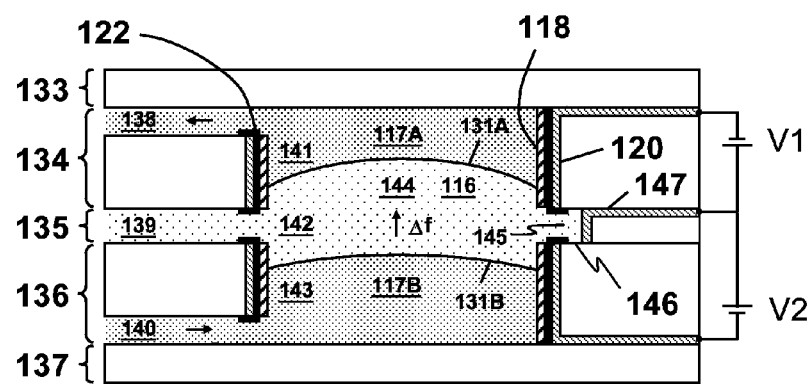
FIG. 34A is a side cross-sectional view of a variable focus liquid lens according to the invention.
Figure 34B:
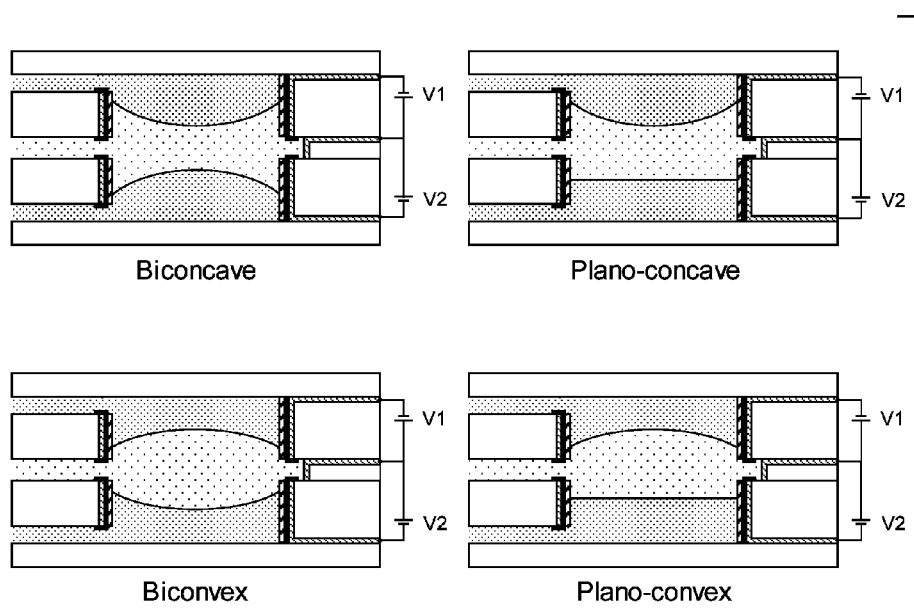
FIG. 34B is a side cross-sectional view of a number of lens shapes achievable by the liquid lens shown in FIG. 34A.
Figure 35:
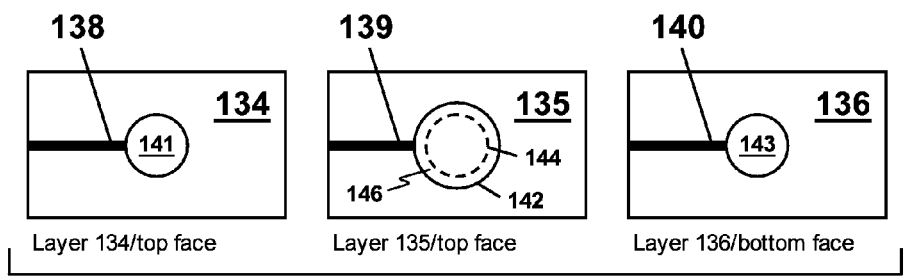
FIG. 35 shows designated top and bottom orthogonal views of glass sheets having microfluidic channels and vias etched in them for the liquid lens shown in FIGS. 34A-B.

FIGS. 34A-B show a more advanced liquid lens capable of assuming the six basic lens shapes: convex-concave, meniscus, biconcave, plano-concave, biconvex, and plano-convex. This versatile lens can easily be manufactured in a simplistic embodiment employing five glass layers 133-137. It may be noted in general that only layers in line with an optical path need to be optically clear (e.g., top and bottom layers) and that the remaining layers can be of another material that is not necessarily clear. Referring to FIGS. 34A and 35, microfluidic channels 138-140 and vias 141-143 are etched in respective layers 134-136; the vias 141-143 combine to form an internal lens housing 144 (lens chamber). If desired to limit layer thickness, the channel 139 of the middle layer 135 may be etched all the way through. Upper 134 and lower 136 layers forming the internal lens housing 144 are identically manufactured except their top and bottom faces are oppositely oriented. The via 142 of the middle layer 135 is preferably etched wider than the circumference of the internal lens housing 144 so as to provide a recess 145 to help seat a lens formed by a hydrophilic, conducting liquid 116 (e.g., an aqueous solution); the via 142 may also be crenulated to increase surface area to promote hydrophilic interaction; a region 146 of upper 134 and lower 136 layers is preferably hydrophilic to aid in seating the aqueous 116. Insulated sidewall electrodes covered by a hydrophobic coating are formed on the sidewalls of the upper 141 and lower 143 vias by depositing a conductor of electricity 120, insulator 122, and hydrophobic coating 118. An uninsulated sidewall electrode 147 is formed on the sidewall of the middle via 142 by depositing a conductor of electricity 120. Though not shown in FIG. 35, and as best seen in FIG. 34A, electrical traces are routed from the sidewall electrodes to a point of electrical contact. The upper and lower portions of the internal lens housing 144 are filled with non-conducting, immiscible, and hydrophobic liquids 117A-B (e.g., oils) and the middle portion is filled with a hydrophilic, conducting liquid 116. In other words, the non-conducting liquids 117A-B do not necessarily need to be the same. For example, as will be appreciated by one skilled in the art of optics, the non-conducting liquids 117A-B may exhibit different refractive index dispersion. In operation, the shapes of upper and lower menisci 131A-B are independently controlled by applying DC voltages between electrodes; as shown in FIGS. 34A-B, a voltage potential V1 applied to upper and middle electrodes controls the upper meniscus shape 131A and a voltage potential V2 applied to lower and middle electrodes controls the lower meniscus shape 131B; V1 and V2 observe the same polarity with respect to the middle electrode. As shown in FIG. 34A, fluid may be urged through top and bottom microfluidic channels 138, 140 to provide fine changes in lens focus AC Fluid may also be urged via the middle microfluidic channel 139 to change the thickness of the aqueous layer 116 forming the lens.

Figure 36:
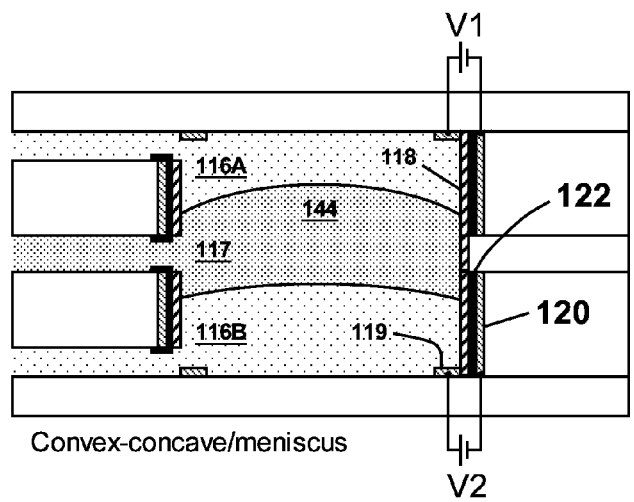
FIG. 36 shows a side cross-sectional view of a variable focus liquid lens according to the invention.
Figures 37A, 37B:
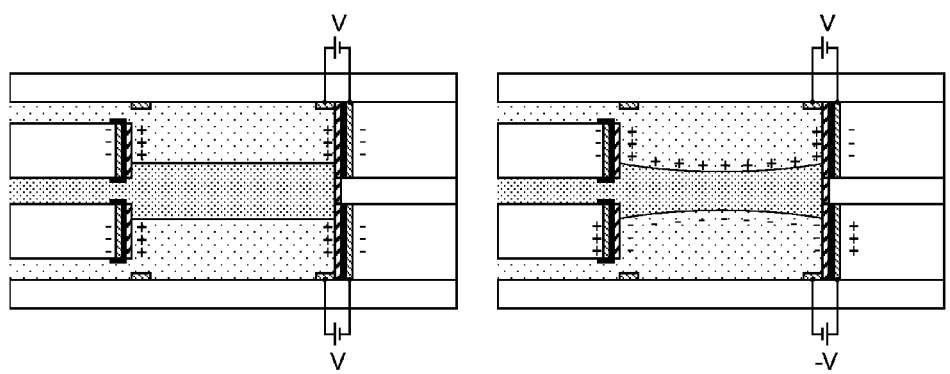
FIGS. 37A-B are side cross-sectional views of lens shapes achievable by the liquid lens shown in FIG. 36 according to alterations of electrical polarity.

Similarly, FIG. 36 shows a liquid lens paralleling the same design and operation as the embodiment shown in FIGS. 34A-B, except the conducting and non-conducting liquid layers are reversed. Note that the routing of electrical contacts has been simplified to facilitate the drawing. In effect, the FIG. 36 embodiment joins two units of the embodiment shown in FIGS. 30A-B head-to-head and forms a single lens chamber 144. Like the FIGS. 34A-B embodiment, this lens is capable of assuming all of the basic lens shapes. However, as illustrated in FIGS. 37A-B, an operational difference needs to be pointed out. In FIG. 37A, conducting liquids 116A-B are exposed to a DC voltage of the same polarity using a potential difference that for illustrative purposes causes respective menisci to lie flat. But then, referring to FIG. 37B, when the polarity is reversed on one of the liquids, in this case conducting liquid 116B, a "meniscus capacitor" is formed by a build up of charges of opposite polarity on either side of the non-conducting liquid 117, thereby resulting in a biconcave lens shape. It is contemplated that this sort of meniscus capacitor will enable a number of analytical advancements, including a study of an effect of ion concentration and ion species on refractive index and refractive index dispersion; additionally, properties of the conducting 116A-B and non-conducting 117 solutions can also be investigated analytically by detecting changes in focus caused by changes in the curvature of the menisci as a function of voltage.

Referring to FIGS. 38A-B, any number of liquid lenses L1, L2, . . . , LN may be combined to form an objective lens. The objective may be separate from a cover glass or, as shown, the cover glass CG may form the top layer of the objective. In some cases, as shown in FIG. 38B, if the front lens is not formed by an aqueous solution then it may be desirable to place a liquid layer with the same refractive index as the aqueous solution between the front lens L1 and the cover glass CG to account for refractive index requirements.

In the prior art, a limitation arises because in some cases it is desirable to focus at some depth into an aqueous medium but in other cases it is desirable to focus on cells plated on the surface of the cover glass CG. According to the art of high resolution microscopy, this would entail having to switch between water immersion and oil immersion objectives. But switching immersion fluids would be particularly complicated and problematic with in vivo microscopy because the switching process would involve contact, e.g., to remove water or oil, which in turn would have thermal implications for the in vivo environment. The present invention is able to solve this problem with a microfluidic approach. In general, in some cases it may be desirable to exchange a liquid in a liquid lens objective via microfluidics, e.g., to employ a liquid with a different index of refraction; for example, to image coculture cells plated on the surface of the floor of a vented microcradle (the floor of the microcradle forming the cover glass CG of the objective), it may be desirable to employ a liquid immediately under the cover glass CG having the same index of refraction as the cover glass CG, e.g., an oil with a refractive index of 1.515; in contrast, to focus at some distance past the cover glass CG into the aqueous solution or patient's body, it may be desirable to employ a liquid immediately under the cover glass CG having an index of refraction similar to the aqueous solution or the tissues of the body, e.g., a refractive index between 1.33 and 1.39.

Referring to FIGS. 20C and 39, according to theory in microscopy, numerical aperture, which is a measure of an objective's light gathering ability and resolution power, is limited by the formula $n \cdot \sin(\theta)$ where n is the refractive index of an immersion fluid between the cover glass and the objective front lens and $\theta$ is one-half the angular aperture. The value of $\theta$ and, hence, numerical aperture increases as the working distance WD decreases. Referring to FIGS. 38A-B, a liquid lens objective according to the invention enables an extremely small working distance by incorporating the cover glass CG with the objective itself; all else being equal, this serves to benefit an increase in numerical aperture.

But it should also be noted that the formula for numerical aperture assumes a flat cover glass, as shown in FIG. 40. However, referring to FIG. 41, a microlens cover glass can be used to improve numerical aperture and/or reduce the dependency of numerical aperture on the refractive index of the immersion fluid between the objective front lens and the cover glass. A microlens cover glass is not practical with prior art objectives because it would be very difficult to align the microlens along the central axis of the objective if the objective lens and cover glass are separate, as is the case with traditional microscopy. This problem is overcome by integrating the cover glass CG with the objective, as shown in FIGS. 38A-B. Notably, however, an alignment means, e.g., using automation combined with machine-readable indicia of alignment, would also make it possible to use a microlens cover glass even without such integration.

Lenses of a layer-based objective according to the invention do not need to be exclusively liquid lenses, for an objective may also be constructed in layers using any combination of microfabricated microlenses as well. For example, referring to FIG. 41, a layer-based objective may include a microlens cover glass 148 and a microlens front lens 149, and the space between the front lens 149 and cover glass 148 may be filled with air 150 to provide a thermal barrier. When focusing on a point on the surface of the cover glass, use of the plano-convex microlens cover glass 148 compensates for a loss in numerical aperture that would otherwise occur with an oil immersion objective when substituting air as the immersion medium.

Those skilled in the art of microscopy will appreciate that a microlens cover glass may employ any variety of lens shapes depending on such factors as the design of the objective (and particularly the front lens), the refractive indices and refractive index dispersions involved, and whether focus is aimed at the surface of the cover glass or past the cover glass into tissues or through a medium; for example, a biconcave or positive meniscus microlens cover glass may be followed by a biconvex objective front lens.

Figure 42:
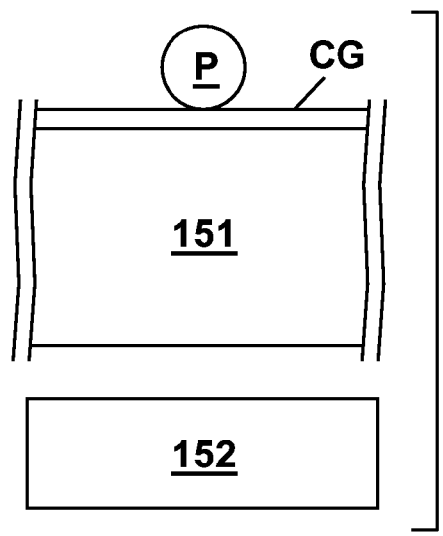
FIG. 42 is a side cross-sectional view of a section of a side-vented microcradle with optical equipment separate from its fluidic circuit assembly placed underneath.

Referring to FIG. 42, a patient P is resting on the floor layer of a side-vented microcradle with a clear "cover glass" bottom CG. The cover glass CG may be a microlens cover glass. A microlens may be directly formed in the floor layer or microlens layers may be laminated to the top and/or bottom of the floor layer. Additional FCA layers 151 may contain any combination of exemplary features of an MEMS optical system, including but not limited to thermal barriers, temperature baths, microlenses, liquid lenses, traditional lenses, prisms, beamsplitters, polarizers, filters, mirrors, and image receptors (e.g., a CCD, CMOS, or microbolometer).

Figure 43:
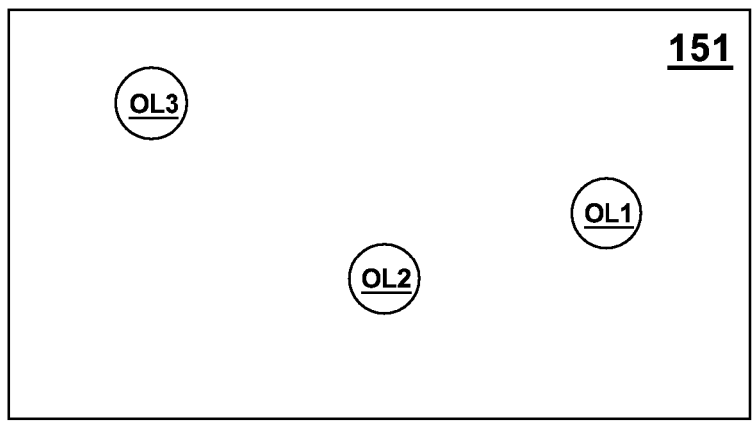
FIG. 43 is a top orthogonal view of an array of optical devices in a layer of a fluidic circuit assembly according to the invention.
Figure 44:
FIG. 44 is a top orthogonal view of an array of variable focus liquid lens objectives according to the invention.

Additionally, or alternatively, optical equipment 152 separate from the FCA may also be placed underneath the FCA of a vented microcradle. Compared to traditional optical systems, a particular advantage of a layer-based system employing microfabrication technology is that it can be readily practiced in array form. Referring to FIGS. 5 and 43, a layer-based optical system may be practiced in array form in the context of FCA layers 151, so that optical devices (e.g., objective lenses OL1-OL3) may be focused not only on the vented microcradle but also on various other FCA devices as well. Referring to FIG. 44, optical devices 152 placed underneath (or above) the FCA may also be practiced in array form so that individual devices (e.g., objective lenses OL1-OL3) can be selectably moved into position mechanically.

From an optical perspective, referring to FIG. 30A for example, the lens formed in this case may be thought of as a lens doublet, given that the top 117 and bottom 116 lenses may have different refractive index dispersion properties. Similarly, referring to FIG. 34A for example, the lens formed in this case may be thought of as a lens triplet, given that the top 117A, middle 116, and bottom 117B lenses may have different refractive index dispersion properties. Referring to FIGS. 38A-B, liquids with various optical properties, such as refractive index dispersion, may be employed according to the art, for example, to correct the objective for chromatic aberration. Cargille-Sacher Laboratories, Inc. (Cedar Grove, N.J.) specializes in optical liquids (and gels) of desirable properties. Other substances, e.g., proteins, may also find interest.

To make a highly corrected immersion objective, such as a plan apochromat objective, opticians must take into account the refractive index and Abbe's number of each lens element comprising the objective. The Abbe's number is a measure of refractive index dispersion. Referring to FIG. 45, in order to allow for more flexibility in choosing liquids with specific optical properties, a region in a liquid objective that would otherwise be occupied by a single liquid may be partitioned with a transparent layer 153 so that two liquids with different optical properties (LIQ. A and LIQ. B) can occupy opposite sides of the partition.

Referring to FIG. 46, and to compare with FIG. 37B, ionic charges may be placed on both sides of a microlens 154 using a voltage potential V applied to liquids on opposite sides of the microlens 154. At the surface of the microlens, this can affect optical properties related to ion species type and concentration, such as refractive index and reflectance. Ion concentration and ion species type can be varied in LIQ. A and LIQ. B as desired, as can voltage potential V. However, charge amounts on respective surfaces of the microlens will be equal and opposite, and capacitance between the charges (and, hence, local ion concentrations) will depend on the thickness of the microlens, which is not uniform, and the dielectric constant of the microlens material, e.g., glass. Referring to FIGS. 47A-B, a more versatile arrangement is obtained by separately coating each side of the microlens 154 with a conductor of electricity 155 covered by an electrical insulator 156 to form separate capacitors with respect to ions in the neighboring liquids. Like the electrical insulator 156, the conductor of electricity 155 (e.g., indium tin oxide) must also be transparent. By applying voltages V1 and V2, ionic charges on either side of the microlens can be independently controlled. In general it may also be noted that a microlens may be coated with any variety of optical coatings.

FIGS. 48A-E depict human anatomy at different stages of prenidial life, that is to say, during life before implantation.

Figure 48A:
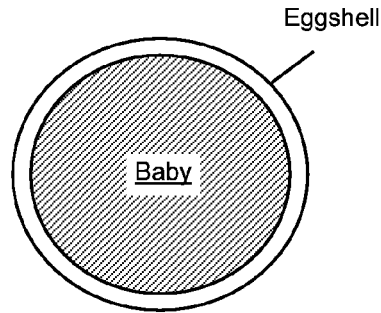
FIGS. 48A-E are side cross-sectional views of a human infant and his or her egg capsule during different stages of prenidial life.
Figure 48B:
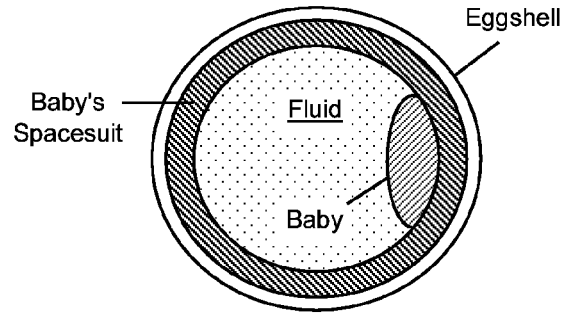

Referring to FIG. 48A, a baby is conceived within an egg; three small polar bodies are not shown. At this point the baby's body incorporates a cell having a cell size much larger than usual. This is the early embryo stage. The cell size will be reduced by successive divisions. The first few cell divisions proceed linearly in a serial fashion (1, 2, 3, . . . , 8) rather than exponentially in a parallel fashion (1, 2, 4, 8) as was once mistakenly presumed. A mulberry-shaped cluster of cells (the "morula") will develop. Before leaving the protection of the shell-covered egg capsule, the baby must first grow a protective spacesuit. Referring to FIG. 48B, by the late embryo stage, the baby is surrounded by a spacesuit filled with fluid. The baby is attached to the inside wall of the spacesuit. From the time when the baby first starts to build a spacesuit until after birth when the umbilical cord is cut, the baby's whole body consists of a "baby" part and a spacesuit part. The spacesuit portion of the anatomy is called the peripheral body and the astronaut or baby portion is called the formal body. The entire body is called the conceptus, which is another name for the baby during gestation. In later development the spacesuit includes an umbilical cord and a plug to plug the spacesuit into the maternal body. At hatching time, the spacesuit only consists of a covering. The covering takes the form of a spherical layer of relatively large cells and is filled with fluid, in contrast to the smaller cells of the baby's formal body. No cord or plug is formed until after implantation begins.

Figure 48C:
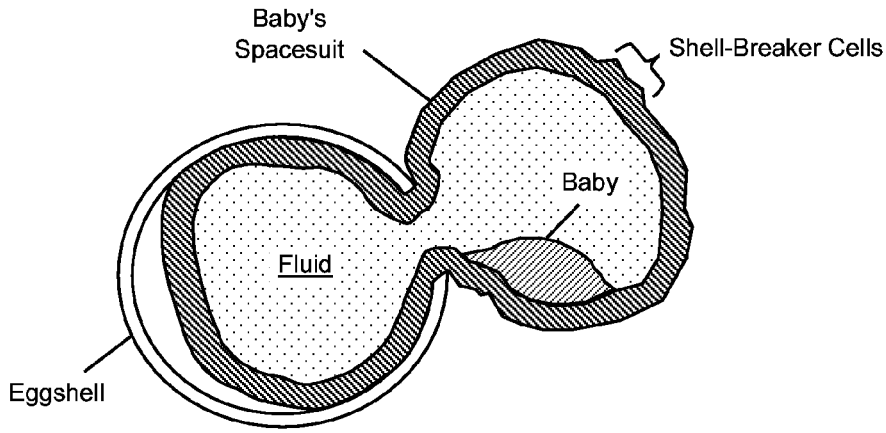
Figure 48D:
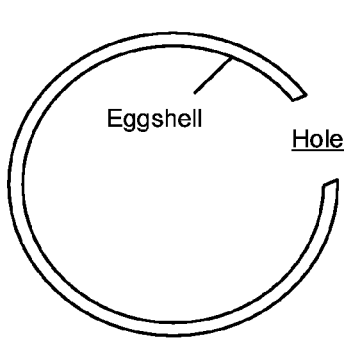
Figure 48E:
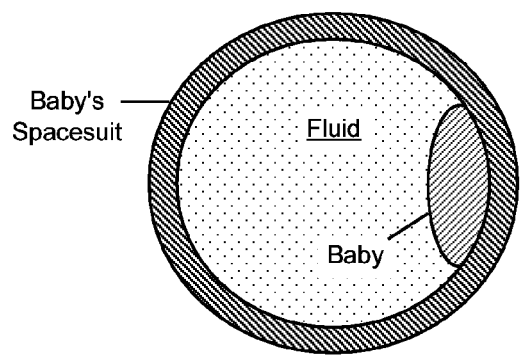

Referring to FIG. 48C, a baby uses specialized shell-breaker cells on the covering of his or her spacesuit to make a hole in the shell of the egg, and then he or she exits the egg through the hole in an extrusive behavior involving movement. The baby relies on brain power in the form of molecular computing inside cells to implement this intelligent behavior, and the basis for locomotion is contained in the form of chemical contractions exerted on the cytoskeleton within cells, as is all muscular movement. Human babies hatch from their eggs about 5-6 days after fertilization. Referring to FIGS. 48D-E, after hatching the baby leaves the empty egg capsule behind and is now free to approach the lining of the maternal uterus and implant. The baby's formal body is protected from exposure outside the egg capsule thanks to the protective spacesuit the baby put on before leaving the egg capsule.

The significance of implantation is simply that this is when the baby attaches his or her spacesuit to the mother ship, so to speak, like an astronaut would. Referring to FIG. 48E, note in particular that the tissues of the baby's spacesuit are bare because there is no more shell surrounding the baby's body. The reason for the baby's protective spacesuit is that without it the tissues of the formal body (the "baby" part) would be exposed inside the mother.

According to the process of implantation, a plug formed by chorionic villi on the outside of the spacesuit (at the far end of the umbilical cord) attaches the baby's spacesuit (and, hence, the baby) to the mother's body for the remainder of gestation. The baby exits the spacesuit after the covering (the birth sac) breaks. The spacesuit will be discarded after birth when the umbilical cord is cut. Then the astronaut goes home in a car seat from the hospital.

It took doctors a long time to realize this. They used to think the birth sac and umbilical cord were a part of the mother's body, not the baby's. Another problem preventing their grasp of the significance of implantation was that they thought an egg simply attached to the maternal body. They did not realize the baby has to hatch first! Accordingly, they did not realize that the field they called comparative placentation is really the subject of gestational spacesuits and their manner of attachment. Notably, different species exhibit different types of gestational spacesuits, which also form different types of attachments to the mother.

One skilled in the art of MEMS will appreciate that thermistors may be placed in contact with an embryo by means of a MEMS-based device or probe to monitor patient temperature. An array of thermistors may be placed around the embryo to monitor thermal gradients. A contact means of temperature monitoring other than a thermistor, e.g., a thermocouple, may also be employed. Unlike embryos, who are covered by the shells of their eggs, the body tissues of hatchlings are directly exposed. For this reason, a contact means presents an added complication when monitoring the temperatures of hatchlings.

Attention is therefore turned to the subject of non-contact temperature measurement.

Referring to FIG. 49, the spectrum of electromagnetic radiation is divided into gamma ray, X-ray, UV (ultraviolet), visible, infrared, microwave, and radio wave spectral regions, in order of increasing wavelength, decreasing frequency, and decreasing photonic energy. Referring to FIGS. 49-50A, a visible spectrum defines a region of the electromagnetic spectrum to which the human eye is sensitive. The wavelength of light in the visible region ranges from 400 to 700 nanometers for most eyes, but some people's eyes are sensitive to wavelengths as low as 380 nm or as high as 780 nm. FIG. 50A divides the visible region by color response for the human eye. Referring to FIGS. 49 & 50B, infrared light extends from the longest wavelength of visible light (red light), at approximately 700 to 750 nanometers, all the way to the shortest microwaves at 1000 microns. FIG. 50B divides the infrared region using an accepted scheme, though a number of other schemes are also known and may rely on similar terms.

Radiometry is the general science of detecting and measuring electromagnetic radiation as it is emitted and reflected by physical bodies. The term radiometer refers broadly to any means of detecting and measuring electromagnetic radiation. Bodies naturally emit a broad spectrum of electromagnetic radiation as a function of their temperature, with a shift towards radiation at higher frequencies (shorter wavelengths) with increasing temperature. In simple terms, the temperature dependence of this phenomenon enables the temperature of a body to be measured in a non-contact way by means of a radiometer.

In this disclosure, emissive flux means an energy amount of radiation emitted over a given surface area per unit time (dimensions: Watts per meter squared). Elsewhere, emissive flux may be known as radiant emittance or radiant flux per unit area.

A number of design considerations need to be factored in when using a radiometer for the non-contact temperature monitoring of a human embryo or hatchling. First of all, the emissive flux of the patient's body will be greater at certain wavelengths than at others. Second, media between the patient's body and the radiometer will generally absorb radiation more strongly at certain wavelengths compared to others. Third of all, the sensitivity of the radiometer to radiation may vary according to wavelength depending on the radiometer's physics.

Figure 51:
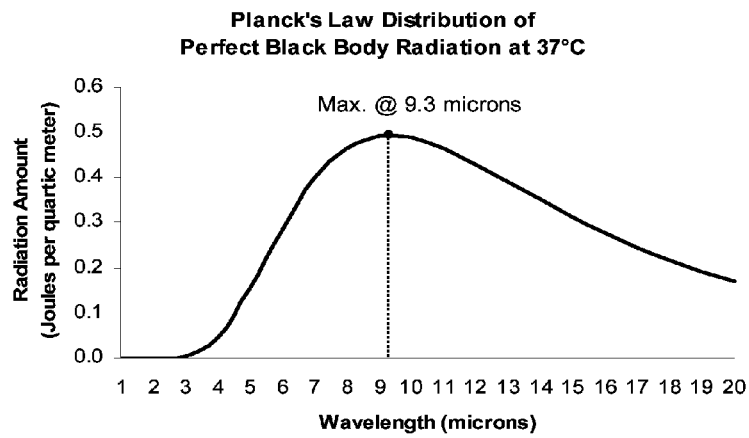
FIG. 51 is a graph of a Planck's law distribution.

Referring to FIG. 51, a Planck's law distribution of perfect black body radiation describes radiation amount as a function of wavelength for a perfect black body at 37 degrees Celsius. According to Wien's displacement law, a maximum radiation amount is emitted at a wavelength of 9.3 microns for a perfect black body radiating at 37 degrees Celsius.

Without considering absorption by intervening media, such as by the patient's incubation medium, and without considering the physics of the radiometer, a radiometer that is sensitive to wavelengths near 9.3 microns, assuming this is where emissive flux is highest at 37 degrees Celsius, would seem to provide the best alternative. For example, a QWIP infrared camera is sensitive to radiation in the 8-9.2 micron range. To compare, an indium antimonide (InSb) infrared camera is sensitive in the 3-5.5 micron range, an area of the perfect black body distribution curve at 37 degrees Celsius where emissive flux is significantly lower at given wavelengths. "This [comparison] can be misleading," however, "because QWIPs have much lower quantum efficiency (ability to turn photons into charge) than InSb detectors," says Ross Overstreet, a senior scientific engineer at FLIR Systems, Inc (Wilsonview, Oreg.). This example helps illustrate why the physics of the radiometer (e.g., quantum efficiency, noise) must be considered.

Figure 52A:
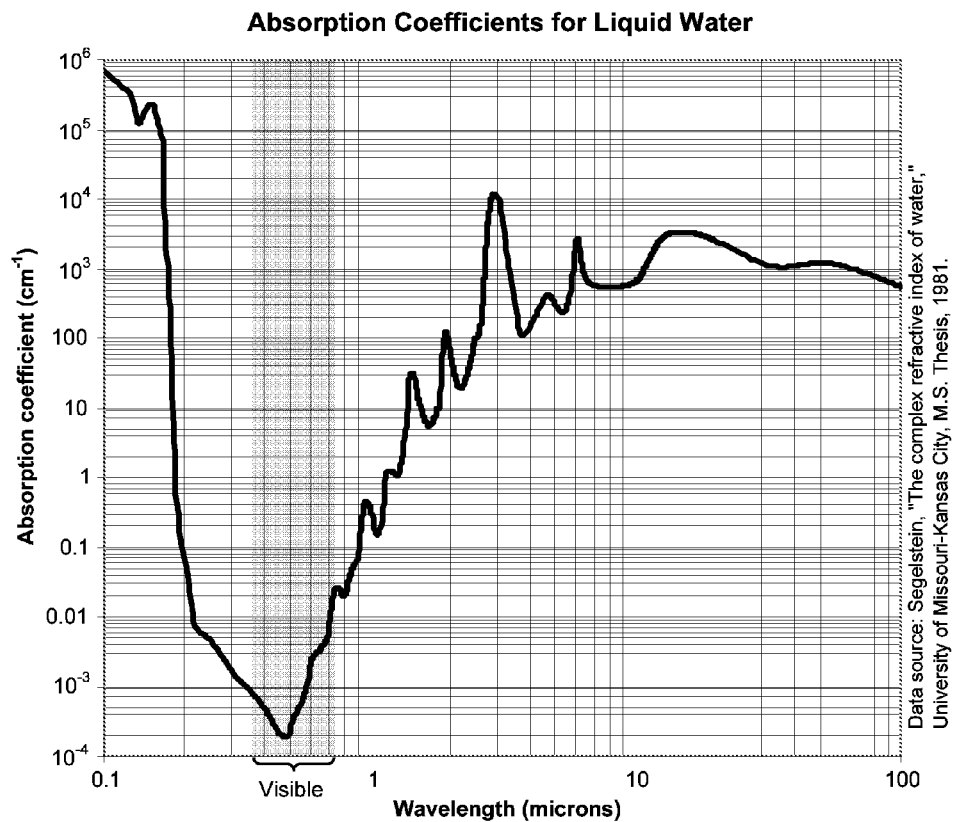
FIGS. 52A-B are graphs of electromagnetic absorption by water.
Figure 52B:
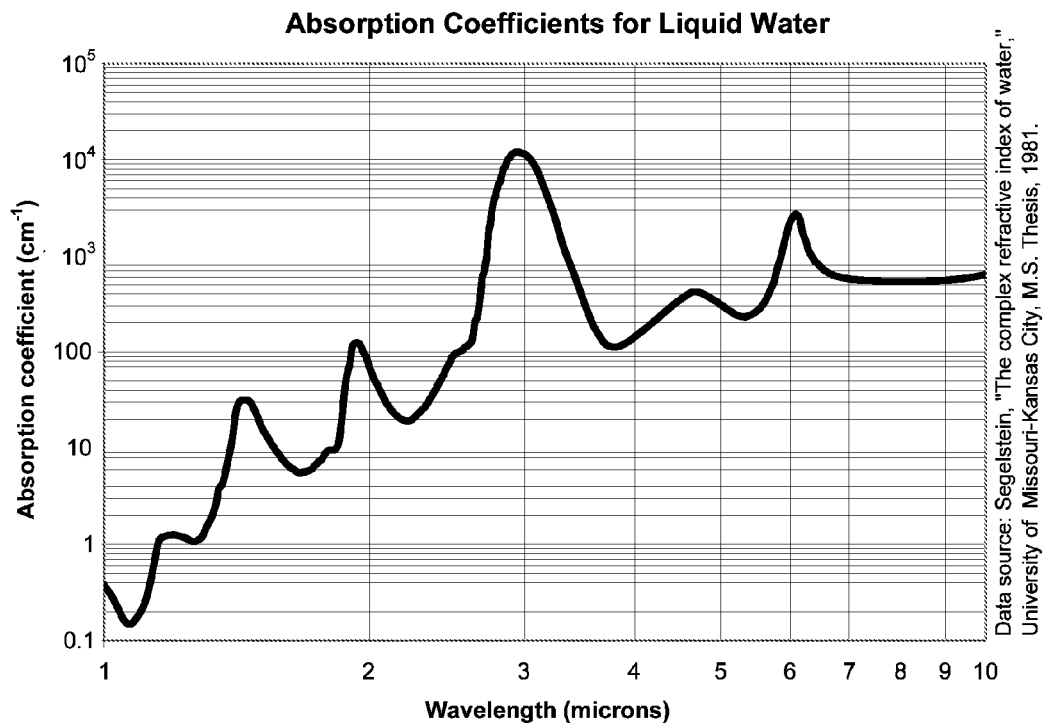

Absorption by intervening media must be considered as well. FIG. 52A is a graph of the absorption coefficients for liquid water as a function of wavelength. Although water is highly transparent in the visible region of the spectrum, water absorption increases significantly beginning at 1450 nm in the infrared region. FIG. 52B focuses on absorption coefficients for liquid water in the 1-10 micron range. Although still relatively high, water absorption is significantly less in the 3.5 to 5.5 micron range (where InSb detectors respond) as compared to the 8-9.2 micron range (where QWIP detectors respond). This implies that although a perfect black body radiating at 37 degrees Celsius emits more strongly in the 8-9.2 micron range than in the 3.5-5.5 micron range, after absorption by an intervening aqueous medium a stronger emission may be actually be perceived by a detector operating in the 3.5-5.5 micron range.

Referring back to an exemplary FIG. 24A, absorption is also an important consideration when a layer 95 forming an optical window 90 has to provide for transmission over diverse wavelengths. For example, quartz glass ($SiO_2$), though clear in the visible region, only provides optical transmission to about 3.7 microns in the infrared. Thus, an optical window made of quartz glass will not provide a clear path for a QWIP camera, because quartz glass is opaque in the whole range (8-9.2 microns) of a QWIP's sensitivity.

Optical windows with various transmission ranges are known in the art. When employing a material as an optical window for a microcradle, a number of considerations must be taken into account in addition to the transmission range itself. These include but are not limited to an ability to make the optical window thin (e.g., as a cover glass 170 microns thick), an ability to form lenses, an ability to accept a polish, solubility, scratch resistance, a need for anti-reflection coatings due to high index of refraction, biocompatibility, an ability to accept surface coatings to enable biocompatibility, modulus of rupture, and an ability to be modified to extend transmission range. Such considerations will be appreciated by those skilled in the art.

The ability of electromagnetic radiation to pass through a material at given wavelengths is known generally as transmission. Transmission is quantified by those skilled in the arts of optics and spectroscopy using a number of related measurement techniques, such that the material can be variously defined as having a low absorbance, low transmission loss, high transmittance, low absorption coefficient, low extinction coefficient, high penetration depth, or low optical density. External transmission takes into account reflection at the surface of the material as well as internal transmission. For materials with a high index of refraction, reflection losses can be high unless anti-reflection coatings are used. Internal transmission takes into account both absorption and scattering. Note that for emissions by a body submerged in a fluid only the internal transmission data for the fluid medium are pertinent, not the external transmission data for the fluid.

Referring to FIG. 52B, in the mid wavelength IR (MWIR) region (3-8 microns) water absorbs the least at 3.80 microns. Those skilled in the art of optics are able to engineer coatings to reduce reflection losses for a selected wavelength or wavelengths. For example, as infrared radiation emitted by a patient's body travels through an aqueous medium, it is desirable that wavelengths to which a radiometer is sensitive are not reflected back at the surface of an intervening material such as the cover glass bottom of a microcradle. By taking into account the emissive flux of the patient at given wavelengths, subtracting internal transmission losses in the aqueous medium, and subtracting internal transmission losses in the cover glass material, one determines the wavelengths that would potentially yield the most intense signal if there were no reflection losses associated with the cover glass material. Thus, in view of the wavelengths to which the radiometer is sensitive, those skilled in the art of anti-reflection coatings will be able to coat the cover glass material to minimize such reflection losses.

In a white paper titled, "Common Misconceptions Related to Infrared Inspection Ports," Martin Robinson, managing director at Global Maintenance Technologies (Chelmsford, United Kingdom), explains that higher transmission in an optical window is not necessarily of greater advantage to thermography if it comes at the expense of other desirable properties. This is because a radiometer can be calibrated to account for, say, a 75% transmission loss as easily as it can for a 50% transmission loss. This point is particularly important since some suppliers of optical materials specify a transmission range that is narrower than a range including relatively weak transmissions as transmittance falls off. In other words, to detect and measure temperature a radiometer only needs enough incident radiation to distinguish temperatures.

For example, referring to FIG. 4, placing a thermal imaging camera 21 above the patient P has the disadvantage that thermal radiation from the patient will be substantially absorbed by an intervening layer of aqueous medium M above the patient P. However, the camera 21 only requires enough radiation from the patient P to distinguish her or his temperature from the temperature of the surrounding medium M. The ability to make this distinction will be aided if the microcradle is opaque and reflection back to the camera is limited. In other words, in practice the camera only has to be able to distinguish between various radiation amounts.

To give another example, when used in thin layers many materials will transmit beyond what may typically be quoted as their useful range of spectral transmission. For example, a 170 micron layer of IR grade fused silica ($SiO_2$) will allow for appreciable transmission at 3.80 microns, a spectral region where MWIR water absorption is at a minimum. In other words, although the MWIR transmission of fused silica, for example, is inferior to that of a number of other optical window materials, as long as the material permits sufficient transmission so that a given radiometer can perform useful thermography, then the suitability of the material for other concerns (e.g., visible light transmission, biocompatibility, etc.) will dominate.

Figure 53:
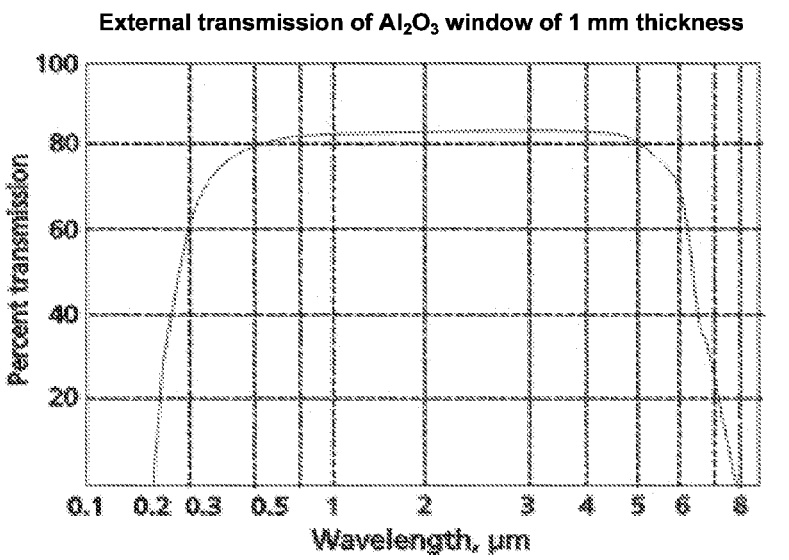
FIG. 53 is a graph of an external transmission report for sapphire.

Those skilled in the arts of optics and spectroscopy will appreciate that there are a large number of optical window materials available today, with new materials under development. Sapphire ($Al_2O_3$), calcium fluoride ($CaF_2$), zinc sulfide (ZnS), magnesium fluoride (MgF2), and zinc selenide (ZnSe) name but a few. Such materials can generally be provided with coatings to achieve improved biocompatibility, durability, or to minimize reflection losses. FIG. 53 shows an external transmission report for uncoated sapphire, which is relatively transparent in both the visible region and in the 3-5.5 micron infrared region of InSb sensitivity.

Figure 23:
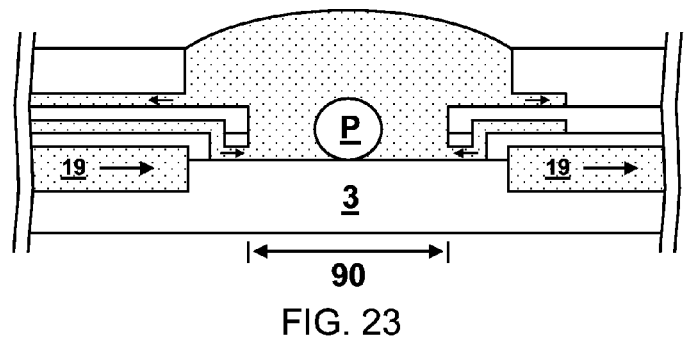
FIG. 23 is a side cross-sectional view of a side-vented microcradle.

With respect to the clear bottom 3 of a side-vented microcradle that serves as an optical window, the optical window can be pieced in (e.g., layer 95 of FIG. 24A), used continuously (e.g., layer 34 of FIG. 6B), or may include microfabrication (e.g., the clear bottom layer 3 of FIG. 23, which contains etched microchannels for a running fluid 19). Precision MicroFab, LLC is skilled in the art of laser milling microchannels in sapphire.

Figure 54A:
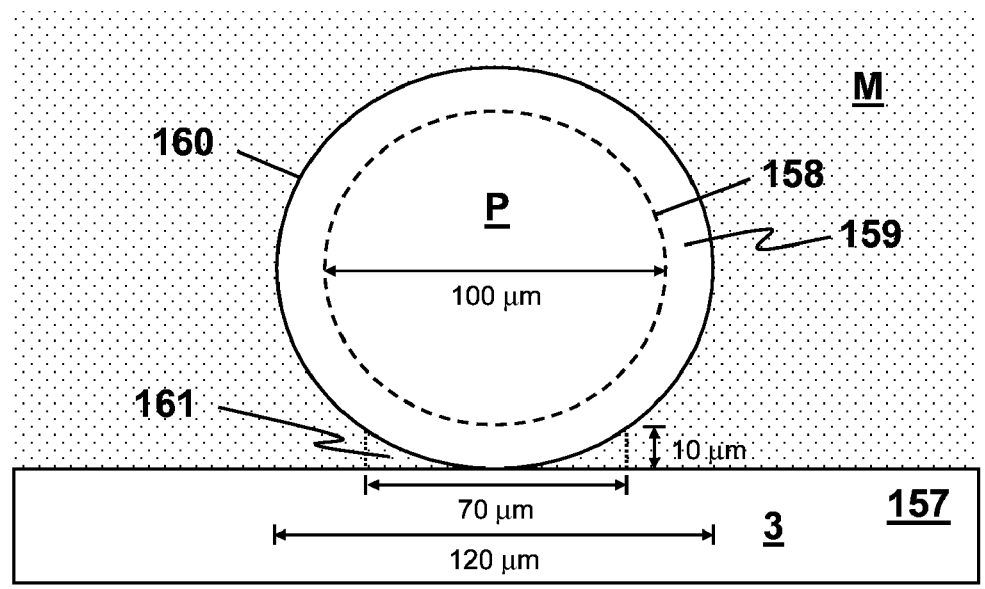
FIG. 54A is a side cross-sectional view of a prenid in an incubator who is resting on a flooring layer.
Figure 54B:
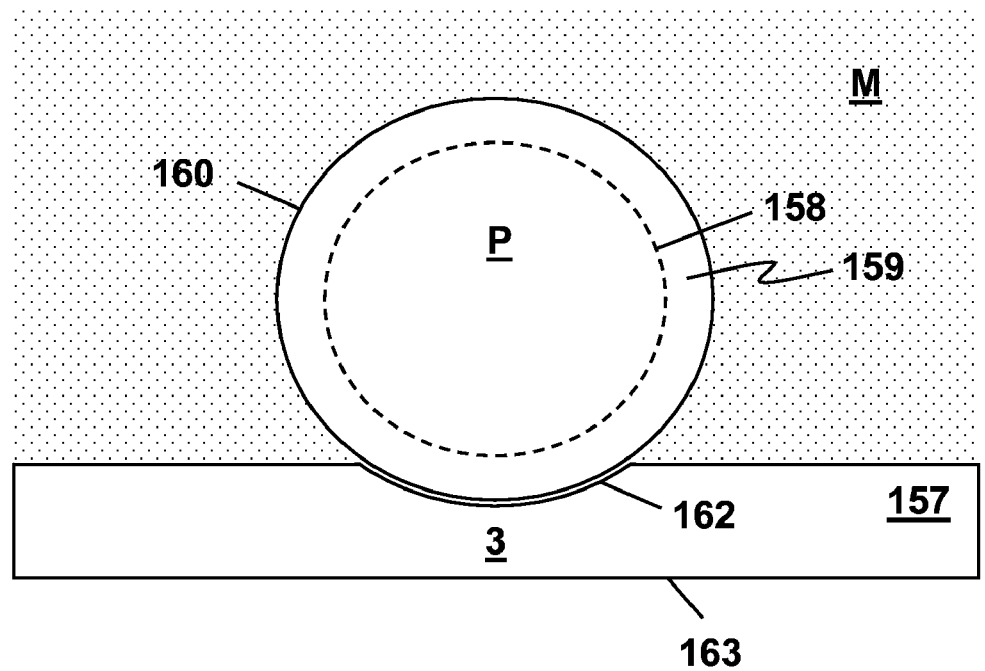
FIG. 54B is a side cross-sectional view of a prenidial patient in an incubator who is resting on a concave microlens flooring layer according to the invention.

Referring to FIGS. 54A-B, optical access to a patient P in spectral regions of strong water absorption (e.g., in infrared regions past the near infrared) is preferably accomplished via the clear bottom 3 of a side-vented vented microcradle. In this case, the clear bottom 3 is formed of a layer material 157 that transmits electromagnetic radiation at desirable wavelengths. Referring to FIG. 54A, during the embryonic stage of life the patient P is bounded by the inside boundary 158 of the shell 159 of the egg capsule 160. In this example, the baby's egg 160 is 120 microns in diameter and the shell 159 is 10 microns thick. Thus, the inner dimension comprising the tissues of the body of the patient P is 100 microns in diameter. As shown in FIG. 54A, due to the spherical geometry of the egg 160, nearly 70% or more of the patient's body inside the egg 160 will be observable via electromagnetic radiation that passes vertically through a thin layer 161 of aqueous incubation medium M no more than 10 microns thick.

Referring to FIG. 54B, an absorption of infrared radiation by the aqueous medium M can be significantly reduced by means of a concave microlens 162 that has been formed in the layer material 157 forming the clear bottom 3 of the vented microcradle. As shown in FIG. 54B, the concavity of the microlens 162 substantially fits the spherical shape of the egg 160 to the effect that there is little medium M left between the egg 160 and the layer 157 that serves as an optical window. In this way, absorption of electromagnetic radiation by an intervening aqueous layer is substantially avoided. Noted is that although the bottom side 163 of the layer 157 forming the optical window is shown to be flat in FIG. 54B, thus forming a plano-convex microlens, a biconcave or convex-concave (meniscus) microlens shape may also be practiced according to the art of optics. As shown in FIG. 54B, the concavity of the microlens 162 is slight enough that exposure of the patient P to ventilating fluid medium M is not substantially occluded; moreover, stagnation of a portion of the patient's body is not an issue in this respect inasmuch as the patient P exhibits a gradual turning inside the egg 160 (somersaulting behavior).

In this disclosure, emissivity (also known as emittance) is a measure of a body's emissive flux (or radiation amount) at a given temperature relative to the emissive flux (or radiation amount) of a perfect black body. Emissivity is a dimensionless ratio ranging from 0 (no emissive flux) to 1 (emissive flux of a perfect black body). In other words, a body with an emissivity of 0.75 emits 75% as much radiation as a perfect black body. Human skin has an emissivity of 0.98, which approaches very closely that of a perfect black body.

Unlike a perfect black body, ordinary bodies and substances do not exhibit a smoothly continuous distribution of radiation amount as a function of wavelength; instead they exhibit a "fingerprint" pattern that characterizes the substance. Such a pattern occurs because a substance tends to emit radiation at the same wavelengths it absorbs radiation. For this reason, the emissions spectrum of a substance tends to mimic the absorption spectrum. Looked at from the perspective of transmission, the substance will tend not to emit so strongly at wavelengths where it transmits. In contrast, according to definition a perfect black body absorbs and (hence) emits radiation at all wavelengths. Consequently, when bodies or substances are compared to a perfect black body it is understood that emissivity regards either an average comparison over a range of wavelengths or a comparison at a given wavelength.

"The emissive characteristics of a target can be quantified by evaluating its relative emittance at two known wavelengths or at two known temperatures," explains Pat Finney, Senior Applications Engineer at FLIR Systems, Inc. (Jacob, "Thermographic Imaging Essential to Avoid Thermal Calamities," Evaluation Engineering, August 1996.) To estimate emissivity for human embryos and hatchlings the two wavelength approach can be applied for a live determination and the two temperature approach can be applied for an autopsy determination. Similarly, the two wavelength approach can be applied to the estimate emissivity for unfertilized eggs, but unfertilized eggs subjected to temperature changes may be made unhealthy.

In the context of an incubator system for human embryos and hatchlings, U.S. Pat. No. 6,694,175 teaches the need to distinctly "measure an actual body temperature of the human embryo or hatchling" for the reason that "said body temperature can differ from an ambient temperature of a fluid incubation medium". (Claim 1) Prior to this teaching practitioners invariably confused ambient temperature readings as if they represented accurate indications of patient temperature. This error has been persistent even despite the patented teaching.

In the general case of non-contact temperature detection and measurement by means of a radiometer, there are many unknown variables to accommodate. For this reason, in general even a well calibrated radiometer will have difficulty in determining an actual temperature to an accuracy of 0.1 Celsius degrees. This is true even of a relatively specialized radiometer such as an ear thermometer, because variables such as ear shape, placement of the thermometer, and wax in the ear can affect readings.

From an engineering perspective, however, use of radiometry to measure the temperature of a human embryo or hatchling in a non-contact way presents an idealized scenario: Parameters of the care environment (e.g., temperature, composition of the fluid incubation medium, etc.) are highly controlled, the patient's body is largely spherical and is thus amenable to simplified calculations, the distance between the patient and the radiometer can be known with micron accuracy, and the emissivities of the patient and various constituents of the care environment can all be determined along with the absorbances of intervening media.

Further idealization is provided in that the care environment can accommodate references for calibration purposes, including thermistors and emissivity test patterns. In the usual case of the prior art of thermography, a radiometer is calibrated separately from a taking of temperature measurements, and then temperature measurements are taken afterwards in the field. However, in addition to performing this type of calibration procedure, a care environment according to the invention may maintain calibration references in the radiometer's field of view.

For example, a thermistor may be placed in the radiometer's field of view on the floor of the microcradle. The thermistor itself may be calibrated in advance by submerging the floor layer in a temperature bath prior to assembly. Hart Scientific, Inc. (American Fork, Utah) provides high accuracy temperature baths suitable for this purpose. Furthermore, a thermistor surface facing the radiometer may be conditioned (e.g., by coating) so that it exhibits a known emissivity (e.g., 0.98). In this way the temperature and emissivity of an area covered by the thermistor will be accurately known so as to serve as a reference. Note that if the temperature of the fluid incubation medium is accurately known, an area of known emissivity at the temperature of the fluid medium will suffice without the thermistor. Either way, when the radiometer focuses on the reference area, the radiometer's response to emissions from that area will be calibrated based on the presence of a known reference for temperature and emissivity.

Figure 55:
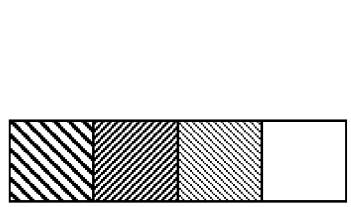
FIG. 55 is a top orthogonal view of an emissivity pattern.

Emissivity test patterns placed in the radiometer's field of view can also be employed. Referring to FIG. 55, an emissivity pattern containing a plurality of areas having known emissivities and transparencies may be deposited on a surface in the radiometer's field of view. Optical filters may also be used so that the patterns are restricted to certain wavelengths.

Figure 56:
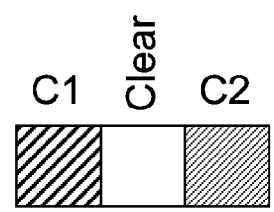
FIG. 56 is a top orthogonal view of an emissivity pattern according to the invention.
Figure 57A:
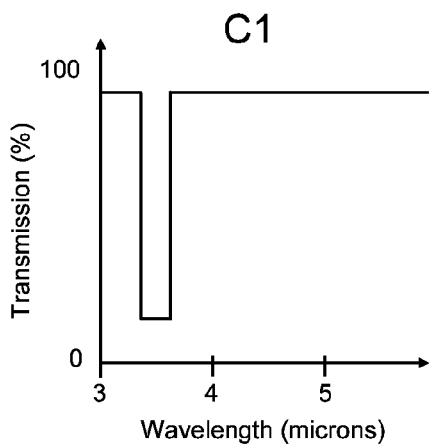
FIGS. 57A-B are graphs of transmission reports for coating substances associated with respective areas of the emissivity pattern shown in FIG. 56.
Figure 57B:
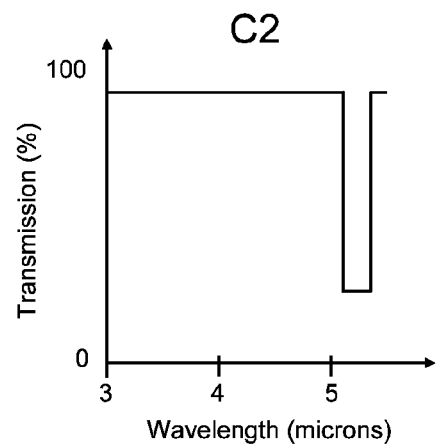
Figure 58A:
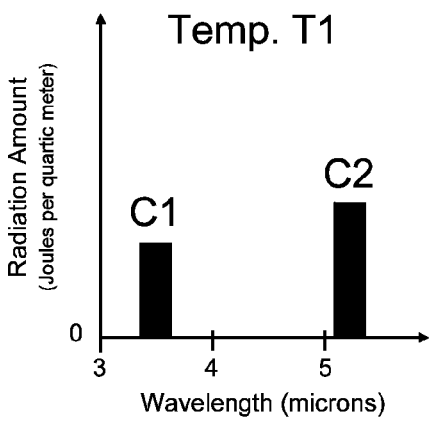
FIGS. 58A-B are graphs comparing radiation amount as a function of temperature for the coating substances associated with the emissivity pattern shown in FIG. 56.
Figure 58B:
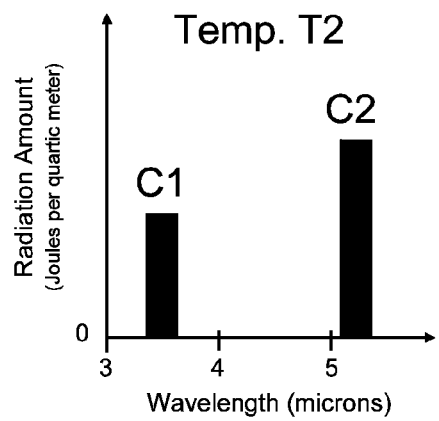

Referring to FIG. 56, a more specific example of an emissivity pattern takes advantage of selective emission by different substances C1 and C2. Consider a radiometer that is sensitive to radiation in the 3-5.5 micron range. Referring to FIGS. 57A-B, a coating substance C1 is relatively transparent in the 3-5.5 micron range, except at 3.5 microns where it strongly absorbs; similarly, a coating substance C2 is also relative transparent in the 3-5.5 micron range, except at 5.3 microns where it strongly absorbs. Referring to FIGS. 58A-B, because C1 and C2 absorb radiation at respective wavelengths they will also emit radiation at these wavelengths; the radiation amount associated with these emissions will vary according to temperature. Referring back to FIG. 51, because the slope of the distribution curve is changing at different rates for different wavelengths, the ratio of radiation amounts for C1 and C2 will change according to temperature. Importantly, a plot of this ratio as a function of temperature will serve as a calibration reference. In other words, by comparing radiometer readings for areas C1 and C2 and taking their ratio, a corresponding temperature can be looked up by referring to a plot of this ratio as a function of temperature. Greater resolution will be obtained by choosing C1 and C2 at given wavelengths such that the rate change in radiation amount per unit temperature is changing disparately between them, as can be seen from an examination of the distribution curve, because in this way the change in ratio per unit temperature will be greater than if the rate change in radiation amount were similar between the two. A clear area may be maintained as a reference for subtracting background emissions; filters for various wavelengths can also be employed to enhance resolution. Interpolation may also be employed. In theory, C1 and C2 could also be chosen such that they transmit in a specific region and absorb elsewhere, which is the opposite of the situation depicted in FIGS. 57A-B.

In the prior art of thermography, to access, for example, a high voltage electrical panel with a thermal imaging camera, an IR window is placed in the door that covers the panel so that the panel can be viewed without exposing the operator to high voltages. Then, in order to determine temperatures, the transmittance of the IR window must be entered as a parameter. In contrast, by employing an emissivity pattern according to the FIG. 56 embodiment of the invention, there is no need to know the transmittance of the IR window because the ratio of C1 and C2 will not be affected. Thus, whether affixed or patterned on an area of the floor of a microcradle, another area of an FCA, or on an area of an electrical panel, an emissivity pattern according to the FIG. 56 embodiment offers a uniquely flexible means of calibrating a radiometer such as a thermal imaging system for real temperature. For example, instead of having to worry about transmittance changes when intervening optics or materials are changed, the ratio of C1 to C2 can be relied upon for temperature calibration. (An exception occurs when an intervening material selectively transmits at the wavelengths of C1 and C2.)

In general, an emissivity pattern may have a clear backing, a reflective backing, or a backing of known emittance or emittances, in any combination.

Calibration test patterns may be endowed with machine-readable indicia so they can be recognized and interpreted by a computer.

In general, software may be used to aid in temperature calibration, determination, and interpretation. FLIR Systems, Inc. is a provider of software products to acquire, calibrate, process, analyze, and store data from digital infrared camera systems.

Because field-of-view calibration of a radiometer is possible, U.S. Pat. No. 6,694,175 teaches use of an infrared camera attached to a camera port of an inverted microscope to thermally image a patient. In such a case, however, it should be noted that the microscope's optics must support infrared wavelengths to which the camera is sensitive. Fluorite optics have the advantage of being fairly standard in the microscopy industry while at the same time being able to transmit both visible and infrared light. Accordingly, an inverted microscope equipped with dual camera ports can be used to thermally and visually image the patient, such that one camera port is used for a CCD or CMOS camera to capture high resolution visible images while the other is used to support an InSb, QWIP, or other infrared camera for thermal imaging.

Thermopile sensors are contemplated for use in non-contact temperature measurement in a prenidial care environment. Widely used for ear thermometers, thermopiles consist of a series of thermocouples, such that a reference side is exposed to a reference temperature and an object side is exposed to incident radiation emitted by a target. Since a precise temperature bath is used in regulating the care environment, the reference side can be controlled by the same bath. Unlike InSb and QWIP infrared cameras, thermopiles can detect a broad spectrum of radiation, although filters can be employed to restrict sensitivity to a desired range. Thermopile technology is highly cost competitive, running in the hundred dollar range as compared to InSb and QWIP technology running in the hundred thousand dollar plus range.

It may be noted that a sensitive enough radiometer will be able to detect temperature even with respect to wavelengths that regard very little emission at 37 degrees Celsius. A radiometer sensitive enough to detect temperature using wavelengths below 1450 microns, where strong water absorption begins, would offer extreme versatility in terms of an ability to position the radiometer with respect to the patient. In contrast, a radiometer functioning at wavelengths of strong water absorption will prefer optical access to the patient either from the bottom surface or from another surface in very close proximity to the patient.

In addition to providing optical access to a patient through the clear bottom 3 of a vented microcradle in a substantially vertical direction, optical access to the patient may also be gained through the flooring at an angle, including with the aid of mirrors, lenses, prisms, fiber optics, specialized optical windows, and so on. Optical access may be similarly gained from the sides or above, or through an alternately routed location in the flooring.

Inasmuch the clear bottom 3 of a side-vented microcradle provides a preferred route for optical access to a patient, competition by visible and infrared equipment will be somewhat constrained. Accordingly, a sharing of the optical route by means of prisms, beamsplitters, dichroic mirrors, dual camera ports, and so on may be necessary. To improve or share access, it may also be necessary to move equipment, or the FCA itself, by means of a motorized x-y stage or slider, for example.

Figure 59:
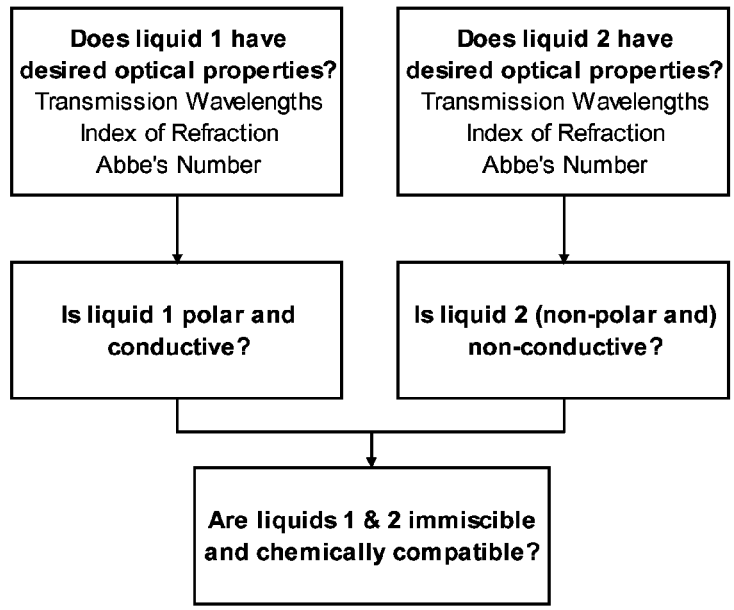
FIG. 59 is a flowchart representing search criteria for finding optical liquids to form a liquid lens.

Based on strong water absorption, a liquid lens employing water as a lens liquid would not be optimum for transmission in an infrared region above 1450 microns. However, those skilled in the arts of optics and spectroscopy will be able to select suitable optical liquids according to the following simple method. In general, by means of spectroscopy those skilled in the art can determine the transmission loss characteristics of a material at given wavelengths. Other optical parameters such as the index of refraction and Abbe's number can also be determined. Referring to FIG. 59, having found liquids with suitable optical properties, optical liquids 1 & 2 will be compatible for forming a liquid lens provided that liquids 1 & 2 are immiscible and chemically compatible, that liquid 1 is polar and conducting, and that liquid 2 is non-conducting, which essentially implies that liquid 2 is non-polar as well.

As those skilled in the art of chemistry will appreciate, some liquids that are unable to conduct electricity in their pure state will become conductive when relatively small amounts of appropriate substances are dissolved or mixed in as additives. For example, water and acetic acid are non-conductive in their pure state. But water becomes conductive when a small amount of salt is dissolved in and acetic acid becomes conductive when a small amount of water is mixed in. As those skilled in the art of spectroscopy will appreciate, the contribution of such additives to transmission losses will be proportional to their concentration.

U.S. Pat. No. 6,694,175 teaches a use of tiny heat lamps to warm a patient. In effect, any radiation absorbed by the body and translated into thermal energy will warm the patient. Similarly, electromagnetic radiation may be applied to the patient at various wavelengths and intensities in the form of phototherapy. However, electromagnetic radiation applied to the patient will be subject to a consideration of transmission losses (absorption by intervening media). The same is true of electromagnetic radiation used for other purposes such as illumination or for heating the fluid incubation medium. In each case, the optics of transmission must be considered. Otherwise absorption (or scattering) by intervening media may produce unsatisfactory results.

Figure 60:
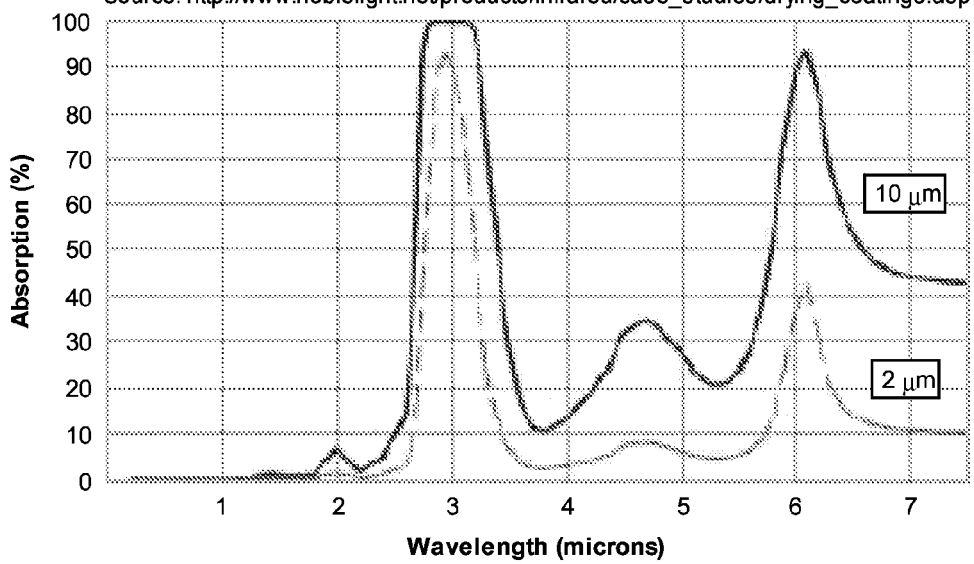
FIG. 60 is a graph of infrared absorption for thin water films.

Although not strictly necessary, using heat lamps to warm the patient adds flexibility to the thermodynamics and control of patient thermoregulation. However, a complication arises in that at some wavelengths water absorption is very strong. Referring to FIG. 60, at wavelengths near 2.95 microns, 100% absorption is observed through a layer of water only 10 microns thick. At a wavelength of 3 microns, referring to FIG. 4, infrared radiation from above (FIG. 4, infrared heat lamps 23) would heat the water of the fluid medium M rather than reaching the patient P; referring to FIG. 54A, at wavelengths near 2.95 microns even a thin layer of water 161 would be heated by infrared radiation from below before reaching the patient P; however, referring to FIG. 54B, by minimizing any intervening water, absorption by water will no longer be such an issue.

Those skilled in the art of spectroscopy will recognize that an emissions spectrum also indicates an absorption spectrum. Accordingly, an absorption spectrum (e.g., of the patient's body) can be collected by radiometry either by studying transmission losses or indirectly by studying emissions. Referring to FIGS. 48A-E, different features of the body may have different emissions spectra; in turn, this implies that some parts of the body absorb more strongly at certain wavelengths than at others. By having the relevant emissions spectra in hand, or equivalently the absorption spectra, it is a simple matter to select wavelengths absorbed by the body more so than by intervening media, so as to preferentially warm the body, or selected regions of the body, as opposed to intervening media or regions of the body not selected. This same principle applies to phototherapy in general. Also, an optical focus of heat lamps or phototherapy light sources may be employed to better direct electromagnetic radiation onto the patient. For example, an infrared wavelength below 1.4 microns (to minimize absorption by water) can be used to warm the patient with the aid of optical focus. In another example, an absorption band of the three-layered glycoprotein matrix that forms the shell of the human egg can be preferentially used to heat the shell of the egg.

Infrared radiation in a region of strong water absorption (e.g., 2.95 microns) can be used to heat the fluid incubation medium or other fluids in the FCA environment. Because of strong absorption the heating will be highly localized about the area being illuminated to a depth of about 10 microns or so. However, for relatively thick streams or bodies of fluid, wavelengths of moderate absorption may be preferred so that the radiation is able to penetrate deeper for more even heating. Heating may be further localized by applying a gold surface coating, for example, to reflect the infrared radiation away from areas not to be heated.

Roithner Lasertechnik GmbH (Vienna, Austria) supplies light emitting diodes having various wavelength ranges in the 255 nanometer to 7.0 micron spectral range. Other light sources, including in combination with optical filters, may be used to warm the patient or to provide phototherapy.

Absorption spectroscopy (transmission spectroscopy), emission spectroscopy, scattering spectroscopy, and reflectance spectroscopy can be used to investigate the optical, chemical, or physical properties of a patient, fluid, or material. In an application of emissions spectroscopy, Malchoff et al disclose a non-invasive glucose monitor for blood measurements based on thermal infrared emissions spectroscopy. Their technique employs a thermopile with a variable filter for detecting infrared radiation from 7.7 to 14.1 microns; because glucose absorbs (and, thus, emits) at characteristic wavelengths (e.g., a main band at 9.8 microns) and because the radiation amount varies with glucose concentration, glucose levels can be determined in reference to calibration. Although absorption and reflectance spectroscopy may lead to similar results, this technique has the advantage of being purely non-invasive. (Malchoff et al, "A Novel Noninvasive Blood Glucose Monitor," Diabetes Care, Vol. 25, No. 12, December 2002, pp. 2268-75) Consequently, this technique can be used to non-invasively monitor chemical levels (e.g., glucose) inside a prenidial infant's body. Similarly, spectroscopy techniques can be employed to monitor chemical levels in the fluid incubation medium or in other fluids of the FCA environment.

In view of human anatomy during prenidial life, it will oftentimes be desirable to image temperatures for different parts of the baby's body as a whole. For example, as the baby grows inside the egg it will be desirable to image temperatures for tissues of the formal body distinctly from those of the peripheral body; it will also be desirable to image a temperature distribution within the fluid of the baby's spacesuit. Similarly, a temperature gradient around the baby (due to heat dissipation) is of interest to microthermography. Because cell sizes for the early embryo are larger than the spatial resolution of high precision infrared cameras, thermal variations within and between cells are also of interest. Therefore, spatial homogeneity and temporal modulation of temperature in the tissues can also be monitored by means of radiometry.

In the prior art, Anbar (U.S. Pat. Nos. 5,961,466; 5,999,843) teaches the use of a thermal imaging system such as a QWIP camera to detect breast cancer by monitoring the spatial homogeneity and temporal modulation of skin temperature related to changes in blood perfusion. Neilson et al (U.S. Pat. Nos. 6,821,787; 6,835,574; 6,991,765) teach an apparatus and methods for infrared calorimetric measurements employing a thermal imaging system.

Although patient temperature detection is best suited to a non-contact thermal imaging means, e.g., as provided by an infrared camera, this is not necessarily the case regarding a number of devices that may be associated with an FCA. Thermistors and thermocouples may be used in thermal contact with an FCA device to monitor device temperatures. But an added feature of an FCA providing clear optical paths to devices is that nematic and thermochromic liquid crystals provide a means of microthermography. Thermochromic liquid crystals change color across the spectrum as they change temperature over a given range. Referring to FIG. 43, these changes in color may be monitored by an optical device (e.g., via objective lens OL2) associated with the FCA. To create a color-coded temperature map, the typically micro-encapsulated liquid crystals are applied to a surface of a device; with the power off, the device is subjected to temperature increments within a given range of temperature response for the liquid crystals. The resulting map relates liquid crystal colors to specific temperatures, with 1 micron spatial resolution being typical. When the device is in operation, liquid crystal colors are digitally compared to the color-coded map by computer to determine device temperatures.

Hart Scientific, Inc. is a provider of temperature calibration and measurement products, including incremental temperature baths. Incremental temperature steps may be taken as an aid to calibration of FCA devices prior to patient use.

Other desirable features of a liquid crystal microthermography system include uniform illumination of a region of interest, infrared-free (cool) lighting to eliminate measurement errors due to infrared absorption, highly polarized optics to enhance image viewing and measurement accuracy, and software for data acquisition and image processing. A number of companies, e.g., Advanced Thermal Solutions, Inc. (Norwood, Mass.), provide liquid crystal microthermography equipment and technology of this sort. As with optical systems in general, such technology may be directly incorporated into an FCA or used in a stand alone fashion.

Polarized light microscopy is used to image and measure birefringent structures such as the three-layered shell (zona pellucida) of the egg. Tunable liquid crystal filters are preferably employed for this purpose. Tunable liquid crystal filters are also employed for multispectral imaging (to select a particular wavelength of light) and similarly for visible color selection. Multispectral imaging is an important technique for visualizing tissues based on their differing responses to different wavelengths of light. Cambridge Research & Instrumentation (CRI), Inc. (Woburn, Mass.) is a provider of liquid crystal polarized light microscopy equipment and tunable liquid crystal filters.

An auto-focus feature is used to compensate for focus drift over time in the context of time-lapse video microscopy. High definition television (HDTV) screens and other high resolution monitors are particularly indicated for high resolution microscopy. Time-lapse video can be stored and displayed on a screen as accelerated footage to evidence very slowly occurring behaviors such as hatching or an embryo's turning (somersaulting) inside the egg. Confocal time-lapse video microscopy can be used to create three-dimensional snapshots of patient development that can be played back as video. This can be used, for example, to monitor changes in cell number, morphology, and differentiation. A computer can be used to assign a constant reference point so that a stationary view can be generated with software despite relative changes in bodily position over time, e.g., due to somersaulting. Other microscopy techniques may be similarly used in a time-lapse video format.

Those skilled in the arts of microfabrication and optical techniques will appreciate that a vented microcradle employing an FCA, and particularly a side-vented microcradle with an optical path provided by a clear bottom and an open top, is amenable to any number of important optical techniques, including but not limited to: bright field microscopy, oblique illumination, Hoffman's modulation contrast microscopy, dark field microscopy, phase contrast microscopy, differential interference contrast (DIC) microscopy, fluorescence microscopy, confocal microscopy, deconvolution microscopy, polarized light microscopy, stereomicroscopy, and optical coherence tomography; infrared spectrometry (e.g., for chemical analysis), and optical Doppler tomography (e.g., for fluid velocity measurement); thermal imaging via a thermal imaging system such as an InSb camera attached to a microscope objective, and thermal imaging via thermochromic liquid crystals viewed under a microscope; and, phototherapy.

It may be noted that preference for a clear bottom for a side-vented microcradle does not obviate the possibility of an opaque or reflective bottom. Dedication of the bottom to optical purposes is simply one possible use. Other uses can include support for a cell scaffold (e.g., to support a blanket of cumulus cells), sensor arrays (e.g., an array of electrophysiological sensors), biological coatings, or surface treatments.

The invention may be operated with the aid of an eyewear viewer (or other head-mounted display system) and a control console. The Microoptical Corporation (Westwood, Mass.) makes wired and wireless eyewear viewers for medical use. Control consoles are well known in the prior art of microsurgical systems. For example, Metzler (U.S. Pat. No. 6,022,088) teaches an ophthamalic microsurgical system. Because prenidial care is operated at the microscopic level, the present invention contributes to the field of microsurgery and microsurgical techniques and is compatible with microsurgical systems and methods.

Attention is now turned to the subject of additional microfluidic design considerations.

In computer science, a bus is a system of addressable interconnects used in the routing of electronic data between devices. The "bus" principle may be extended beyond electronics. For example, in optical computing optical data are routed. In the present case, there is a need to route fluid data or samples. In this disclosure, a fluidic bus routes fluid amounts between devices. Such amounts or quantities may be referred to as data or samples.

As a prenidial infant metabolizes resources in the fluid incubation medium, the chemical content of the fluid changes, and it will oftentimes be desirable to detect such changes by means of an analytic device associated with the FCA environment. Likewise, there will oftentimes be a need to deliver fluidic treatments to the patient. In general, there is a need to rapidly route fluidic data in an FCA environment to enable fast response times regarding such processes.

However, given a human embryo with an outer shell diameter of 120 microns, then even at a rate of flow as high as 1 micrometer per second, it would take a whole two minutes for a flowing fluid simply to travel the length of the patient's body. Thus, if a fluid sample is to be routed from the patient to an FCA device at the same rate of flow as the fluid ventilating the patient, then it will take a long time for the fluid sample to reach such a device located elsewhere on the FCA where it is to be analyzed. The same is true of fluid samples to be delivered as treatments to the patient from a device located elsewhere on the FCA. Consequently, in this type of scenario response times will be very slow.

One way of solving this problem is by exchanging parcels of fluid between slow and fast moving channels so as to speed fluid transit and delivery. Referring to FIGS. 61A-B, fluid from a slow flow rate channel 164 can be merged with fluid in a fast flow rate channel 165, and vice versa, to speed transit of the fluid to and from a patient and various FCA devices. Though not shown in these figures, it will be appreciated by one skilled in the art that valves, pumps, sensors, and various microfluidic features will assist in such exchanges.

Another approach to the problem is to employ digital microfluidics to bus fluid samples around in an FCA environment. Digital microfluidics offers advantages such as rapid transit rates of discrete fluid quantities coupled with digital control of routing. The prior art easily handles microliter droplets of fluid. But a microcradle 150 microns high and 500 microns square only holds about $\frac{1}{27}^{th}$ of a microliter, or 37.5 nanoliters. Thus, if the flow rate of fluid in the microcradle is as much as 1 micrometer per second, it would take about an hour to generate enough fluid to produce a one microliter sample of fluid. So, apart from a digital microfluidic system capable of busing nanoliter droplet samples, the analog fluidic busing method illustrated in FIGS. 61A-B must be relied upon to speed transit.

To make it easier to achieve nanoliter busing in a digital microfluidic system, a clarification of the theory of electrowetting appears needed. Specifically, I believe that a "capacitive spreading" of charges causes fluid movement. Referring to FIGS. 62A-B, charges in a polar, conducting liquid LIQ. 1 seek to spread out based on a capacitive relationship with opposite charges present in a sidewall electrode 120. As the charges in the conducting liquid LIQ. 1 move (see arrow) so as to spread out over a greater surface area, polar molecules "piggyback" the moving charges in the fluid via polar bonds 166, thus causing a liquid interface 167 to move as well.

This theory helps to clarify a distinction between ordinary capillarity and electrowetting. Referring to FIGS. 62A-B, it is evident that the hydrophobic coating 118 could be replaced by a hydrophilic coating and a capacitive spreading of conductive charges would still occur. But in such a case a spreading of polar molecules would also occur independently of the spreading of charges, based on their affinity for the hydrophilic coating. In contrast, by employing a hydrophobic coating 118, it enables the spreading event to be turned on or off based on the presence of charges in a capacitive relationship. Accordingly, it is theorized that electrowetting regards a spreading of charges (electrolytes) to which polar molecules are clinging in piggyback, whereas ordinary capillarity regards an independent spreading of polar molecules.

Figure 63:
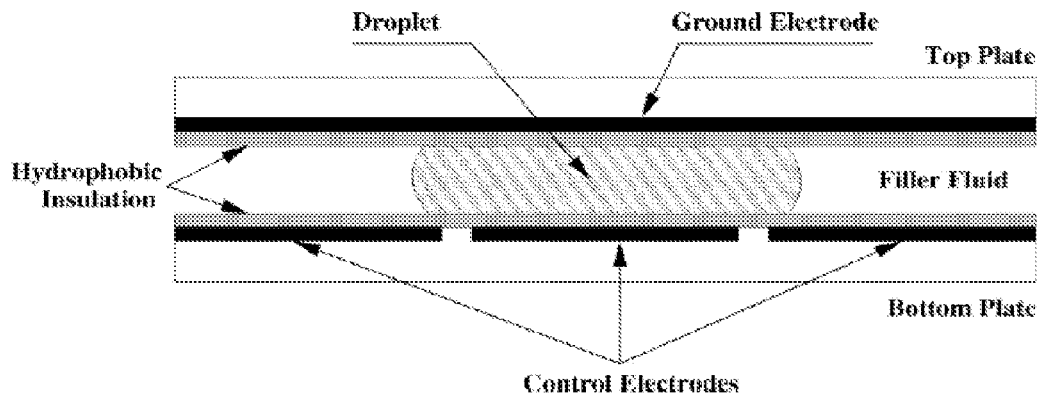
FIG. 63 is a side cross-sectional view of a prior art digital microfluidic system.

FIG. 63 shows a classic arrangement for digital microfluidics. A droplet of fluid is made to move by turning on a voltage between a ground electrode and a control electrode; the droplet moves in the direction of the leading control electrode. But a wiring problem is encountered as the droplet size gets smaller and smaller, because the number of control electrodes needed will increase. In other words, the classic arrangement routes an electrical connection for each control electrode to a remote switch.

Figure 64:
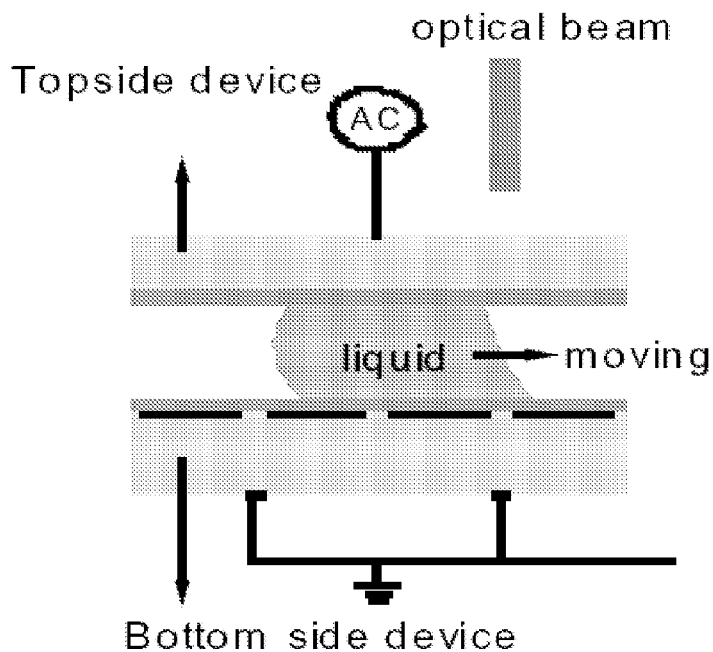
FIG. 64 is a side cross-sectional view of a prior art digital microfluidic system.

FIG. 64, on the other hand, shows a prior art arrangement for digital microfluidics in which the need for remote switching is eliminated. Although both arrangements employ electrowetting, this particular one is more specifically known as opto-electrowetting because an optical beam or stylus is used to turn control electrodes on and off. This arrangement eliminates the need to route electrical connections for each control electrode. Instead, the control electrodes are patterned in photoconductive silicon and an optical beam is used to switch a selected electrode on. To enable illumination by the optical stylus, an indium tin oxide coating is used as an electrode along with a hydrophobic coating of Teflon®, such that both coatings are thin enough to be transparent. An artifact of this arrangement is that an AC voltage is required unlike the classic electrowetting arrangement, which relies on DC voltage; however, it is contemplated that by biasing the control electrode circuitry DC voltages might also be used with opto-electrowetting.

At various frequencies, and especially at high voltages, AC electrical fields may have adverse implications for human health as well as for sensitive electrical or magnetic equipment. Another problem with the opto-electrowetting arrangement concerns the use of an optical stylus, which in turn must be subject to finer and finer optical controls as the size of the control electrodes decreases, which is needed to move smaller and smaller droplets. The costs and bulk of such optical equipment will be prohibitive at some point as fineness increases.

Figure 65A:
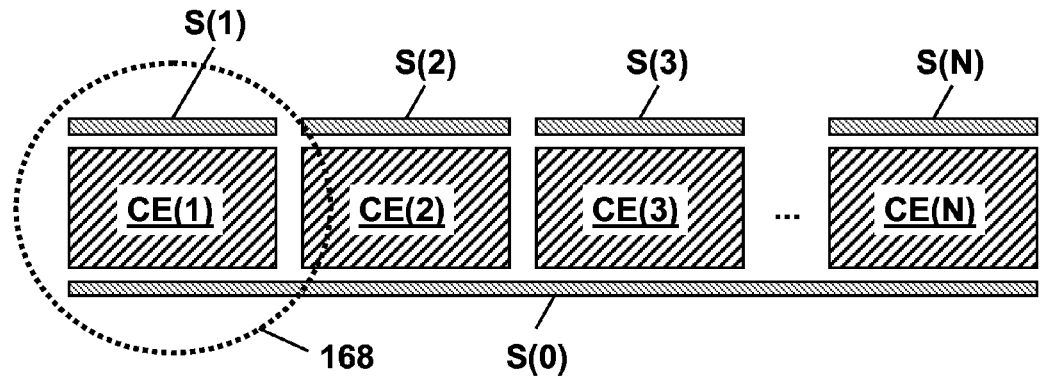
FIG. 65A is a top orthogonal view of an arrangement of electrodes for self-scooting circuitry according to the invention.
Figure 65B:
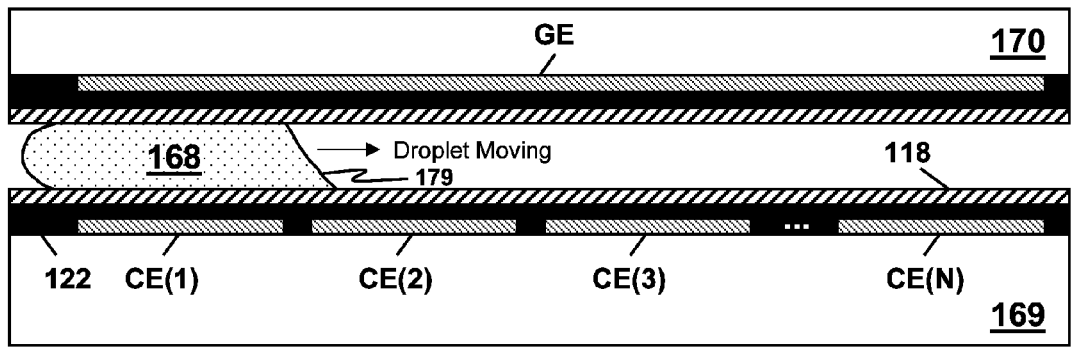
FIG. 65B is a side cross-sectional view of a digital microfluidic system employing the electrode arrangement shown in FIG. 65A.
Figure 66:
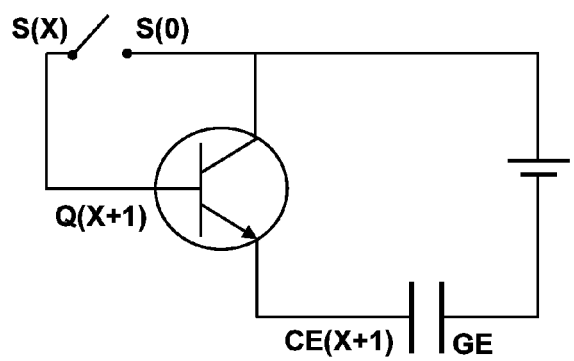
FIG. 66 is a schematic view of an electronic circuit for the self-scooting circuitry of the digital microfluidic system shown in FIGS. 65A-B.

The present invention prefers a distinct arrangement for digital microfluidics for droplets of extremely small size. This arrangement employs "self-scooting" circuitry according to the invention. FIGS. 65A-66 illustrate the self-scooting principle. Referring to FIG. 65A, which provides a simplified top view of a bottom layer 169 containing a series of control electrodes CE(1)-CE(N), a droplet of conducting fluid 168 (e.g., aqueous) is moved along by turning the control electrodes CE(1)-CE(N) on an off in succession. FIG. 65B provides a side view, which shows the droplet 168 moving horizontally while sandwiched between a top layer 170 containing a ground electrode GE and the bottom layer 169 containing the control electrodes CE(1)-CE(N). Referring to FIG. 65A, the series of control electrodes CE(1)-CE(N) forms a track for the droplet 168 to move on; a series of liquid contact switches is formed by conducting strips S(0)-S(N), where S(0) serves as a common pole for each of the switches and S(X) serves as the opposite pole for the Xth switch along the track. When the droplet 168 passes over the Xth position of the track, the Xth switch is thrown closed by the electrical conductivity of the droplet 168. FIG. 66 illustrates exemplary self-scooting circuitry in general, non-limiting terms; referring to FIG. 66, when the Xth switch is closed by the droplet 168, an electronic circuit is activated such that the control electrode at position X+1 is turned on. When the droplet 168 passes the Xth location along the track, the Xth switch will open and, using relevant circuitry, the electrode is turned off.

The circuitry shown in FIGS. 65A-66 is merely exemplary. The distinct principle of self-scooting circuitry for a digital microfluidic system is that a series of liquid contact switches are employed to detect a position of an electrically conducting droplet along a track formed by control electrodes, such that an opening and closing of such switches can be used to control a turning on and off of selected control electrodes, so that the droplet in effect "scoots" itself along the track. The droplet will move along the track until a break is encountered.

FIG. 67A shows an exemplary CMOS circuit employing NAND gates to control the Xth control electrode CE(X) such that droplet movement in the right or left direction may be selectively controlled. FIG. 67C shows an equivalent circuit employing AND and OR gates. FIG. 67D shows an equivalent circuit employing tri-state buffers. FIG. 67B shows an exemplary CMOS circuit to enable or disable signals from liquid droplet contact switches (switching electrodes) to a control electrode; for example, such a circuit can be used to stop droplet flow along a track; similarly, referring to FIG. 67E, such a circuit can be used to stop flow along one track and to route flow onto another track. FIG. 67E shows enabling conditions (0, disabled; 1, enabled) for control electrodes, such that a droplet's path is routed at a fork in the road. Referring to FIG. 67F, droplet switches can be used to enable encoding, control, or event circuitry; for example, the position of a droplet may be encoded, a device for sensing a condition of the droplet may be controlled so as to turn the device on, or an event may be commenced in response to a signal from a droplet switch.

Computer control of control electrode circuitry enables droplet movements to be digitally controlled in response to events, sensed conditions, or software. Computer control of circuitry also enables droplets to be sensed, monitored, and acted upon; it also enables droplet events to trigger or moderate other events. Note that each control electrode or droplet position does not need to have the same circuitry associated with it; instead, circuitry, including computer controls, is required only as needed to handle droplets at given points along a track.

Referring to FIG. 65B, simple transistor circuits, more complex CMOS circuits, and other circuitry may be directly integrated into a layer 169 containing the control electrodes. However, unlike the opto-electronic arrangement of FIG. 64, control electrode electronics may also be routed to remotely located circuitry according to the self-scooting arrangement. For example, though remote location is generally not preferred, in some cases it may be desirable in specific locations to enable a clear optical path through a droplet. This can be achieved by employing indium tin oxide coatings for electrodes and Teflon® for the hydrophilic coatings according to the art. In contrast, the optical path would be effectively blocked by circuitry placed immediately underneath the control electrodes, as semiconductors are opaque to visible light.

Referring to FIG. 68, under the action of electrowetting in an electrowetting region 171 a liquid 172 flows continuously from a reservoir 173; in this case a series of control electrodes is not required for flow. But when discrete quantities of liquid such as a droplet are used, control electrodes at the trailing end of the droplet must be turned off in order to create a preference for motion in a given direction; otherwise the droplet will not move. For this reason, a series of control electrodes is required to move droplets by electrowetting. Referring to FIG. 69A, one alternative is to turn a leading control electrode on and then off again as a droplet passes; this is consistent with the exemplary circuitry shown in FIGS. 67A, C-D. Referring to FIG. 69B, another alternative, called a one-shot approach, is to first turn all control electrodes on and to then turn trailing electrodes off to move the droplet; then at some point in time the control electrodes may be reset again to the on position. Referring to FIG. 69C, control electrodes are reset essentially as soon as the droplet has passed.

Figure 70A:
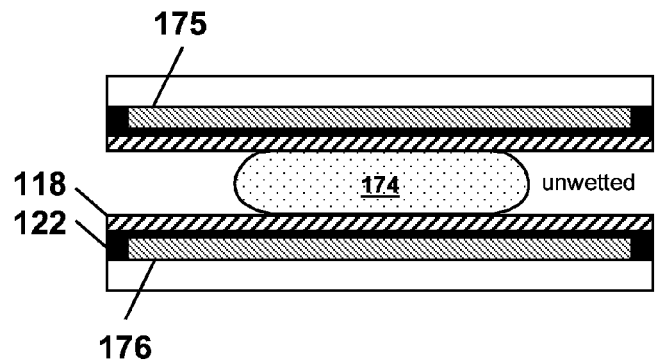
FIGS. 70A-B are side cross-sectional views of a droplet sandwiched between electrodes to illustrate a theory of dielectric electrowetting.
Figure 70B:
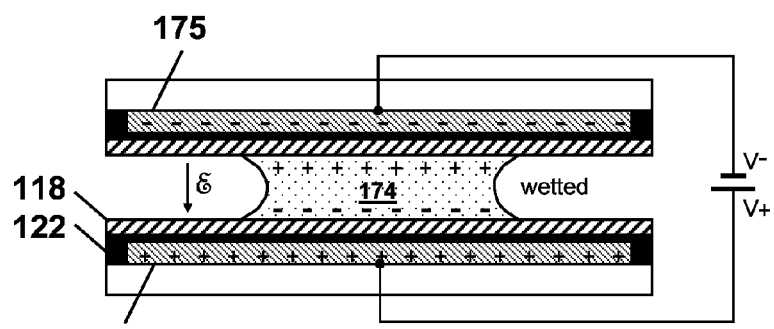

In this disclosure, two categories of electrowetting are distinguished. The electrowetting arrangement of FIGS. 29A-B relies on what is here is termed "charged" electrowetting. Referring to FIG. 29B, an electrode 119 placed in contact with a conducting liquid 116 charges the liquid 116, in this case with a net positive charge. Though the charge on the liquid 116 is balanced by an equal and opposite charge on an external sidewall electrode 120 in a capacitive relationship, so that the system as a whole is neutral in charge, nevertheless the liquid 116 itself carries a net charge. Hence, this is called charged electrowetting. In contrast, FIGS. 70A-B illustrate what is here termed "dielectric" electrowetting. A droplet 174 is sandwiched between top 175 and bottom 176 electrodes that are coated with insulative 122 and hydrophobic 118 coatings. Referring to FIG. 70A, the hydrophobic coating 118 is unwetted. However, referring to FIG. 70B, when an electric potential is applied between electrodes 175-176, an electric field e is set up between the electrodes 175-176. In this example, the droplet 174 contains ionic charges (electrolytes) that separate according to charge polarity in response to the electric field $\xi$ (note that there is no net charge on the droplet 174, unlike the case of charged electrowetting). Then, according to the principle of electrowetting, a capacitive spreading of the charges, coupled with piggybacking by polar molecules in the droplet 174, will cause the coating surface 118 to be wetted despite being hydrophobic.

Referring to FIGS. 70A-B, note that although a droplet containing mobile ionic species is preferred to enable better charge separation and migration to opposite electrodes, in theory even a non-conducting polar droplet will exhibit dielectric electrowetting if the electric field e is strong enough to cause polar molecules to orient and spread according to their dipole moments. Referring to FIGS. 70A-B, note that for a droplet containing mobile charges the ability to separate charges of opposite polarity is limited by the dielectric constant of the droplet and the strength of the applied electric field e. Note also an opposing relationship of electrodes is required for dielectric electrowetting in order to set up an electric field e. From a physical perspective, this is the same relationship as that of a parallel plate capacitor, such that the dielectric medium between the plates happens to be an electrolyte solution that is insulated from electrodes. In contrast, charged electrowetting derives its charge storing power from the principle of an electrolytic capacitor.

Referring to FIG. 29B, a net charge in a conducting liquid 116 is created by a voltage potential applied to the liquid 116 in the manner of an electrolytic capacitor. Because electrolytic capacitors can store more charge energy than parallel plate capacitors, in general it is contemplated that charged electrowetting will offer more power to move fluid in a microfluidic system than dielectric electrowetting.

Figure 71:
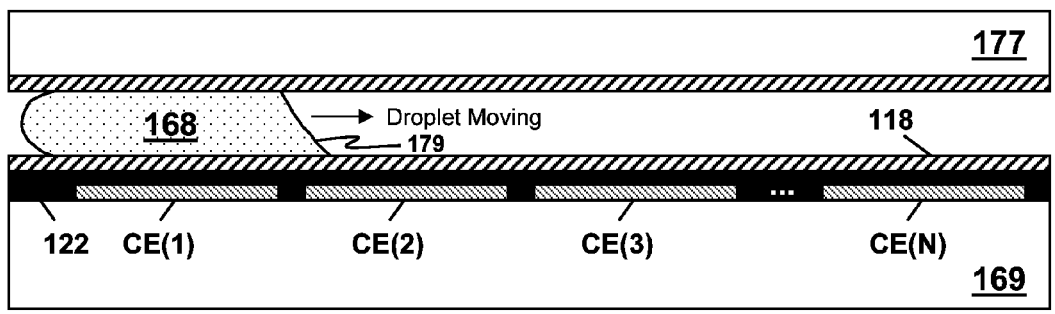
FIG. 71 is a side cross-sectional view of a digital microfluidic system employing charged electrowetting according to the invention.

Referring to FIG. 71, the dielectric electrowetting arrangement of FIG. 65B could be practiced as a charged electrowetting arrangement instead. For example, referring to FIG. 65A, electrode S(0) could be employed to charge the droplet 168 with a charge opposite to that placed on control electrodes CE(1)-CE(N). Note that no ground electrode (GE) is required on top, in contrast to the case of dielectric electrowetting. Instead, in this case a top plate 177 simply serves to flatten the droplet 168 to increase surface contact with the bottom plate 169 while the hydrophobic coating 118 helps to reduce friction. Notably, remote switching, optical switching, and self-scooting circuitry are all compatible with the FIG. 71 arrangement.

Referring to FIGS. 63-64 of the prior art, as well as FIG. 65B according to the present invention, note that the top plate (ground) electrode does not participate substantially in capacitive spreading, given that charge is distributed in the ground electrode more or less equally on both sides of the droplet, in contrast to the control electrodes, which lead the droplet in a given direction by turning leading control electrodes on and trailing ones off. In contrast, referring to FIG. 72, a series of ground electrodes GE(1)-GE(N) in a top layer 178 can be turned on and off at the same time as the control electrodes CE(1)-CE(N), which have opposite polarity. That this dielectric electrowetting arrangement is more powerful than the others is indicated by a singly-wetted meniscus 179 in the FIGS. 63-64 and FIG. 65B arrangements versus a doubly-wetted meniscus 180 in the FIG. 72 arrangement.

Figure 72:
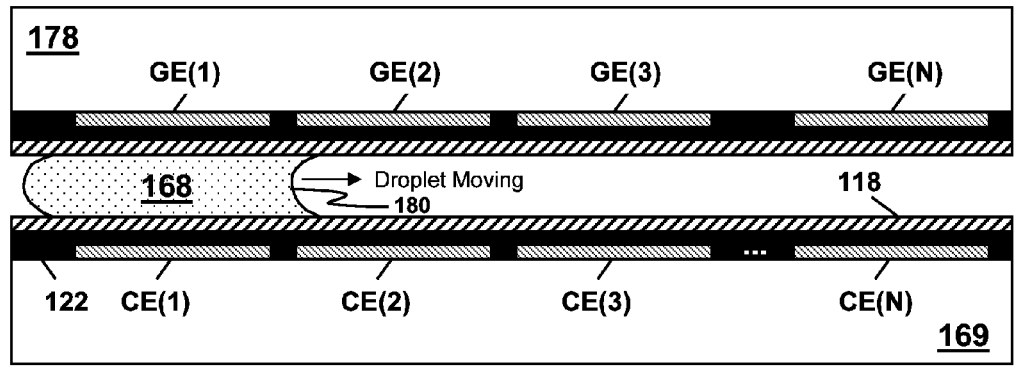
FIG. 72 is a side cross-sectional view of a digital microfluidic system employing dielectric electrowetting according to the invention.
Figure 73:
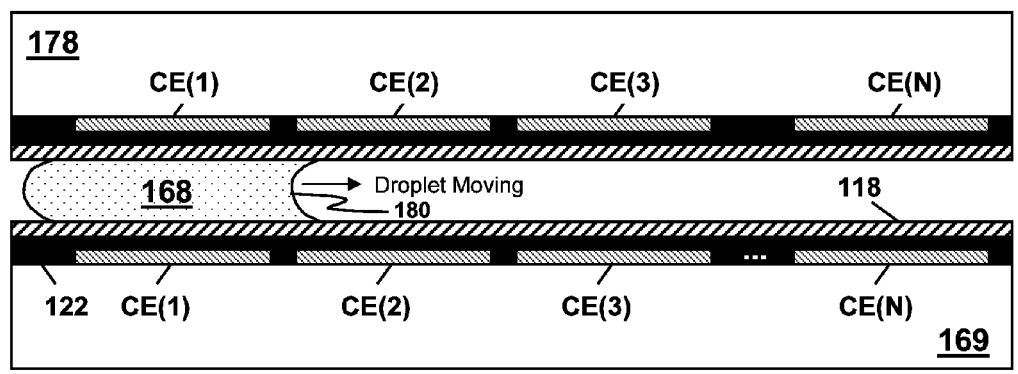
FIG. 73 is a side cross-sectional view of a digital microfluidic system employing charged electrowetting according to the invention.

FIG. 73 shows a double-sided, charged electrowetting arrangement. In this case, control electrodes CE(1)-CE(N) face each other in the top 178 and bottom 169 and an electrode in contact with the droplet 168 (e.g., electrode S(0) shown in FIG. 65A) is used to charge the droplet with an opposite charge. Although the FIG. 73 embodiment could conceivably be practiced in an annular embodiment, to manufacture it would be challenging for small sizes of the control electrodes. In contrast, embodiments with electrodes placed at, say, 90 degrees to each other, though more challenging than a top and bottom layer arrangement, would nevertheless appear to be more feasible by comparison. The electrowetting arrangements of FIGS. 72-73 can be practiced either as remote switching or self-scooting embodiments; however, in general, use of a semiconductor in both layers 169, 178 will render the layers opaque to visible light, and so optical control of electrodes (i.e., opto-electrowetting) will not be possible, unless, for example, photoconductivity can be established in a semiconductor layer by means of a wavelength of light to which the semiconductor is transparent, e.g., infrared light.

Figure 74:
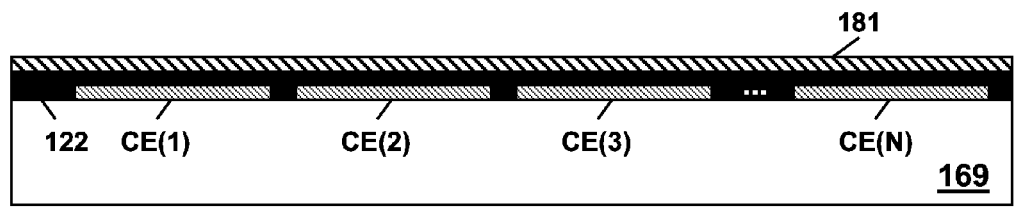
FIG. 74 is a side cross-sectional view of an open-top digital microfluidic system employing charged electrowetting according to the invention.
Figure 75:
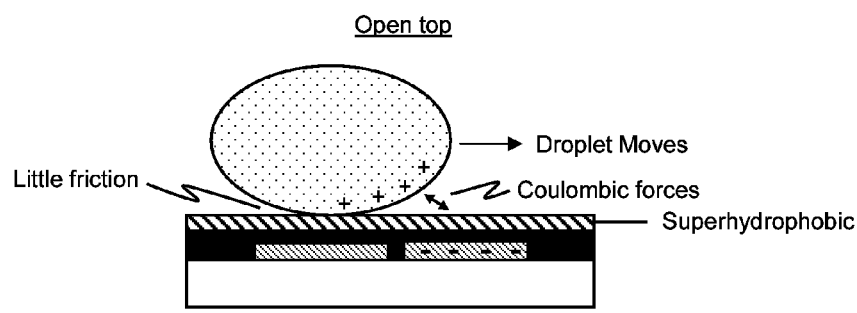
FIG. 75 is a side cross-sectional view of a droplet supported by a track of control electrodes, illustrating the effect of coulombic forces in an open top arrangement.

FIG. 74 shows an open-top charged electrowetting arrangement for digital microfluidics; an exposed electrode S(0) (not shown) maintains a charge in a moving droplet that is opposite to a charge in the control electrodes C1-C(N) when turned on. Remote switching, optical switching, or self-scooting circuitry can be employed with this arrangement. As with other arrangements, such an arrangement can be practiced using any desired pattern of electrodes (e.g., a two-dimensional planar array of control electrodes). However, consider a surface coating 181. If the surface coating is hydrophilic, the bottom edges of a droplet will be made to spread out on the floor; this places the leading edge of the droplet in contact near the control electrodes; but even though this contact improves the force exerted on the droplet by a control electrode, this force will be counteracted by frictional forces due to the hydrophilic nature of the coating; however, as droplet size gets smaller, these frictional forces will be proportionately less compared to the force exerted on the leading edge of the droplet. In contrast, a hydrophobic or superhydrophobic coating will make the droplet form a ball and so there will be less contact between the leading edge of the droplet and the surface where control electrodes are embedded underneath. However, coulombic forces will exert more influence as droplets get smaller (see FIG. 75).

In general, the switching electrodes carry some charge and so the polarity and voltage of the switching electrodes becomes an issue in reference to their location inasmuch as they may partially block coulombic interaction with control or ground electrodes. Also, the hydrophilic versus hydrophobic quality of an electrode such as a switching electrode or an electrode used to charge a droplet becomes an issue in reference to its contact with the droplet. Although a pattern of switching electrodes S(0)-S(N) in FIG. 65A is exemplary, electrodes may be placed and routed electronically in any desirable fashion. For example, referring to FIG. 71, electrode S(0) may be placed on the top layer 177 and S(1)-S(N) may be placed over and routed through control electrodes CE(1)-CE(N) on the bottom layer 169 using vias that connect to self-scooting circuitry in the bottom layer 169, which is formed of a semiconductor, and S(0) may be wired down to the circuitry in the bottom layer 169. In another example, electrode S(0) may be placed side-by-side with electrodes S(1)-S(N) on top of the control electrodes CE(1)-CE(N) and routed to circuitry underneath.

In general, control electrodes may take on any variety of shapes; for example, electrodes may be shaped to match the leading edge of a droplet. In cases where bi-directional droplet transit is desired and electrodes have an asymmetric shape, two layers of control electrodes, formed to serve respective transit directions, may be placed one on top of the other and separated by an insulating layer. Various stencil patterns may be used to guide droplets in layers. However, such patterns do not necessarily need to provide lateral support for a droplet, unlike the case of analog microfluidics. Borders may be used to guide droplets in open-top arrangements, including borders made of a contrast of hydrophilic and hydrophobic coatings.

Referring to FIG. 30B, a liquid lens according to the invention will move under the action of charged electrowetting in the manner of capillarity unless valves controlling either microfluidic channels 128 or 129 are closed to prevent fluid transit. With the valves closed, the lens will change shape rather than moving as a whole.

Figure 76A:
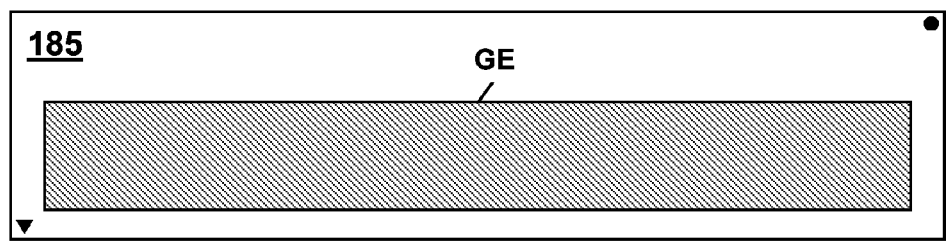
FIGS. 76A-77B are top (76B, 77B) and bottom (76A, 77A) orthogonal views of electrode arrangements for transistorless self-scooting circuitry according to the invention.
Figure 76B:
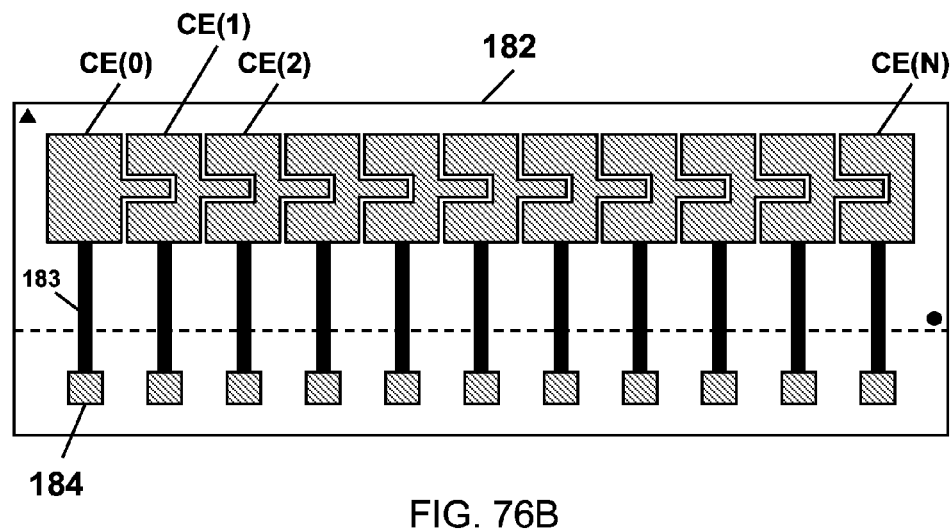
Figure 77A:
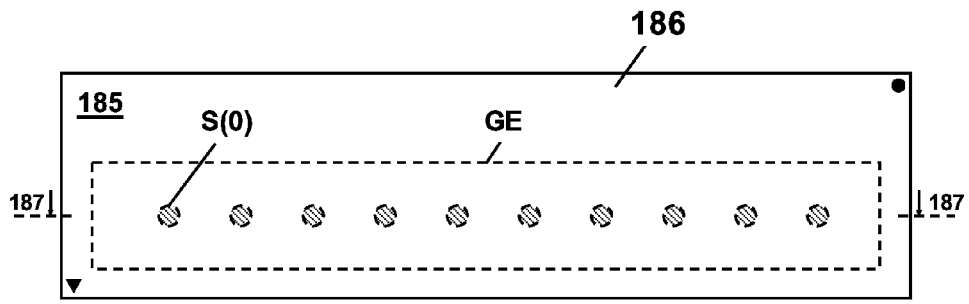
Figure 77B:
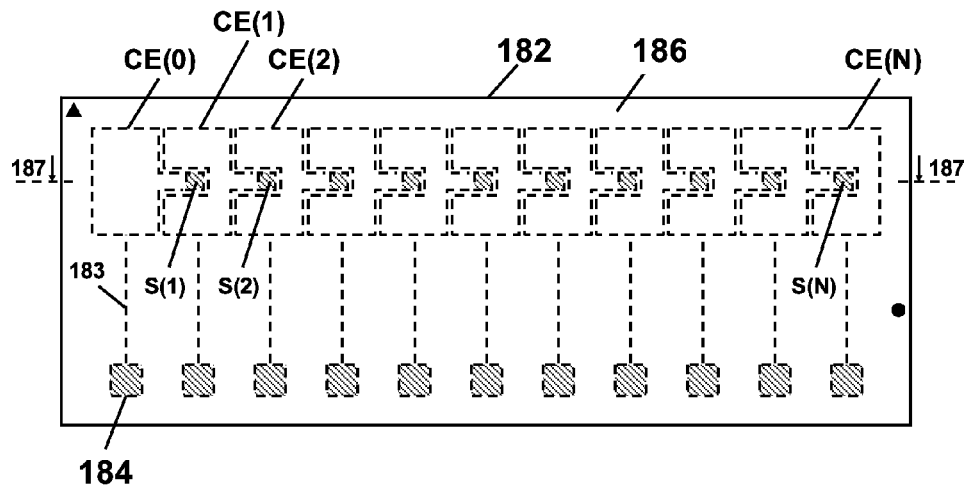

In general, self-scooting circuitry will require a semiconductor layer in which switching operations are performed by integrated circuitry. However, a special exception occurs. In this simple case, called transistorless self-scooting circuitry, the circuitry at minimum requires only conductive elements. Of main interest is a dielectric electrowetting arrangement. Referring to FIGS. 76A-B, control electrodes CE(0)-CE(N) are patterned on a bottom layer 182 and each control electrode CE(0)-CE(N) is separately connected to its own electrical contact pad 184 by a conductive trace 183. A top layer 185 contains a ground electrode GE. FIG. 76A shows the bottom face of the top layer 185 and FIG. 76B shows the top face of the bottom layer 182. The top layer 185 is aligned over the bottom layer 182 as indicated by an alignment marking ▲ such that the ground electrode GE goes over the control electrodes CE(0)-CE(N). Not shown is a middle layer to provide separation between the top 185 and bottom 182 layers. Referring to FIGS. 77A-B, the electrode surfaces of both layers 182, 185 are coated with a hydrophobic layer 186, which also needs to be electrically insulating on the bottom layer 182.

However, on the bottom layer 182 the contact pads 184 are left exposed and a switching contact region S(1)-S(N) is left exposed on respective control electrodes CE(0)-CE(N−1). The control electrodes CE(0)-CE(N) are interdigitated such that the switching contact region S(X) associated with control electrode CE(X−1) extends in the manner of a digit into an invaginated region of control electrode CE(X). If a hydrophobic or otherwise relatively frictionless electrode material is available, then the top layer 185 does not necessarily need to be coated. Otherwise, assuming a hydrophobic coating 186 that is also electrically insulating, a series of holes or a continuous line can be patterned in the coating 186 so that a switching electrode S(0) is exposed while at the same time minimizing droplet friction with the ground electrode GE.

Figure 78:
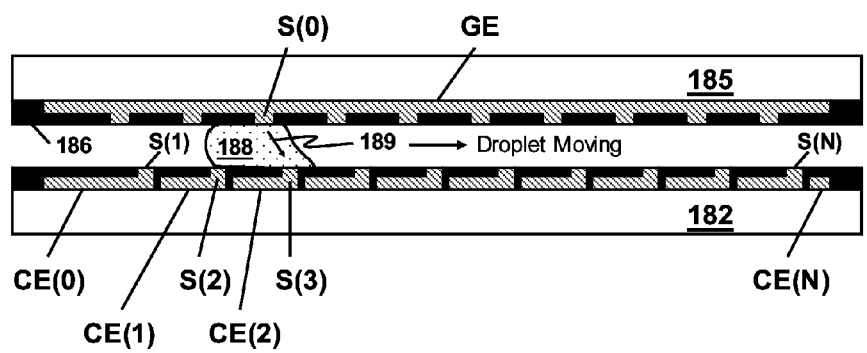
FIG. 78 is a side cross-sectional view of a digital microfluidic system employing the transistorless self-scooting circuitry shown in FIGS. 76A-77B.

FIG. 78 is a side cross-sectional view taken along a line 187 with respect to FIGS. 77A-B. According to operation, electrical contact (not shown) is made between the ground electrode GE and each of the contact pads 184 so as to charge the ground GE and control electrodes CE(0)-CE(N) in the manner of parallel plate capacitors. The charging can be accomplished, for example, by drawing a brush-type electrical contact across each of the contact pads 184 or by employing a clamp-type contact switch to contact each of the pads 184. Once the electrodes GE, CE(0)-CE(N) are charged, all of the control electrodes CE(0)-CE(N) are turned on, which is the time t0 condition shown in FIG. 69B for a one-shot arrangement.

Referring to FIG. 78, a droplet 188 formed of a conducting liquid is shown to move as a trailing control electrode CE(2) is turned off by electrical discharge 189 as an electrical contact is made by the droplet 188 between switching electrodes S(0) and S(3). In other words, the droplet 188 is made to move as trailing control electrodes are turned off via electrical discharge through the droplet 188 itself.

Figure 79A:
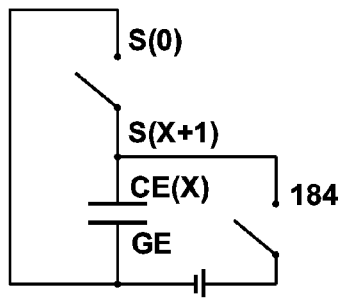
FIGS. 79A-B are schematic views of electronic circuits according to the invention for the transistorless self-scooting circuitry of the digital microfluidic system shown in FIGS. 76A-78.
Figure 79B:
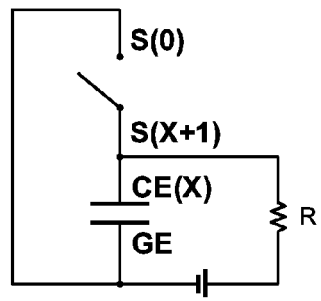

FIG. 79A shows a basic circuit diagram for transistorless self-scooting circuitry. This circuit corresponds to the one-shot operation shown in FIG. 69B, except that discharge does not occur as a square wave inasmuch as the droplet 188 has some electrical resistance. FIG. 79B shows a self-refreshing circuit diagram for transistorless self-scooting circuitry that follows the pattern shown in FIG. 69C, such that trailing electrodes are refreshed after they are turned off, except that the resetting does not occur as a square wave due to a resistor R; the resistor, which should have a resistance that is larger than the resistance of the droplet 188, enables a control electrode to be turned off momentarily as the droplet 188 passes, but the control electrode turns on again after the droplet 188 has passed.

To practice transistorless self-scooting circuitry in a charged electrowetting arrangement, a net static charge has to be placed on control electrodes. An opposite charge on the droplet is maintained by an electrode S(0) while discharge is enabled via switching electrodes S(1)-S(N) so as to turn trailing electrodes off. However, whether placed on droplets or on electrodes, net static charges will generally not be preferred.

Figure 80:
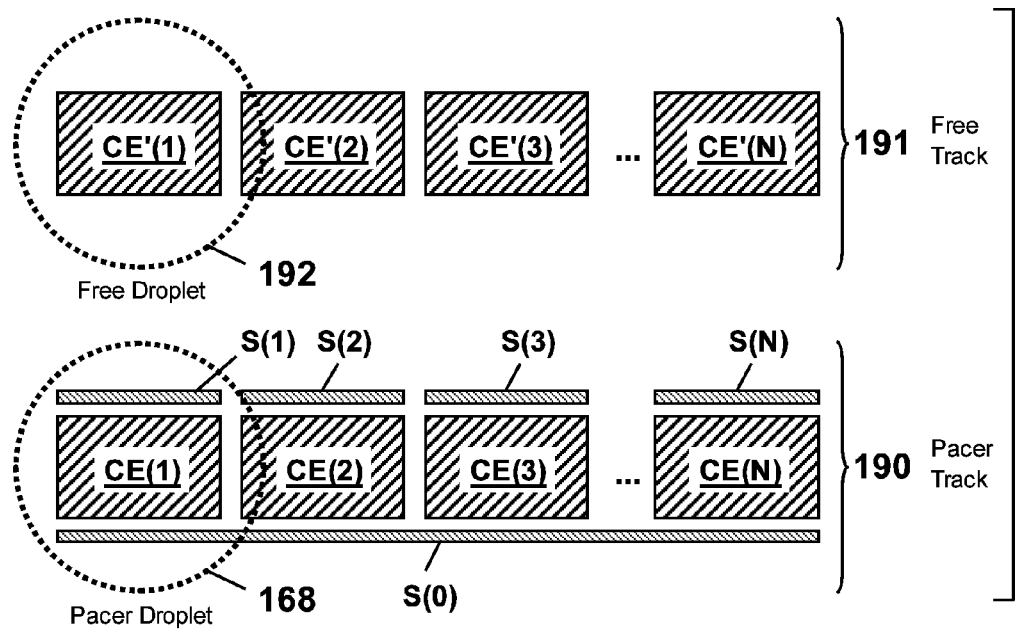
FIG. 80 is a top orthogonal view of an arrangement of electrodes for self-scooting circuitry employing a pacer track and a free track according to the invention.
Figure 81:
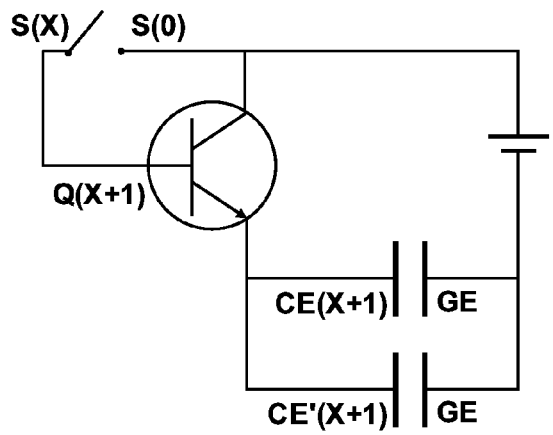
FIG. 81 is a schematic view of an electronic circuit for the self-scooting circuitry of the digital microfluidic system shown in FIG. 80.

Sometimes droplets or their contents will not be tolerant of an electric current passed through them in any way. For example, a droplet may contain chemicals that may react electrochemically, or the droplet may contain a cell or virus that is being manipulated by digital microfluidics. In such a case, referring to FIG. 80, a parallel or "pacer track" circuitry may be employed. In this case, a pacer track 190 controls movement of a pacer droplet 168. The movement of the pacer droplet 168 controls underlying circuitry associated with the turning on and off of control electrodes associated with the pacer track 190 as well as those associated with a "free track" 191 containing a free droplet 192. FIG. 81 shows an exemplary circuit diagram for a pacer track arrangement, which is related to the circuit diagram of FIG. 66. Note that the free droplet's 192 movement is controlled by the pacer droplet's 168 movement.

The free droplet 192 does not need to be subject to currents associated with the switching electrodes S(0)-S(N), since those currents are borne by the pacer droplet 168. However, in a charged electrowetting arrangement, the free track 191 will still need to maintain an electrode in continuous contact with the free droplet 192 so as to maintain a net charge in the manner of an electrolytic capacitor, as previously described. However, in an electrically well-insulated system, a net static charge might be maintained without such an electrode.

Referring to FIG. 78, surface features on surfaces where the droplet 188 travels become important, especially as electrode size gets smaller and smaller. In this example, the surface is figuratively shown to be somewhat planarized, with the switching electrodes S(0)-S(N) being somewhat raised to form slight nubs. The importance of surface features is evident in that the passing droplet 188 must be able to make electrical contact with the switching electrodes S(0)-S(N). At the same time, it is desirable to reduce friction.

Referring to FIG. 82, although an interdigitated arrangement of control and switching electrode contact regions has been shown in FIG. 76B, other arrangements are also possible, including by use of vias. Also, discharge currents may be used to drive other circuitry. Referring to FIG. 83A, in some cases two or more different tracks of control electrodes 193-194 may be separated from each other by insulation, so that, for example, droplet travel in respective directions can be controlled by respective tracks; the control electrodes of different layers may share circuitry to some extent (e.g., a ground electrode). Referring to FIG. 83B, at selected locations having two or more layers of separately controlled control electrodes 193-194 may help to prevent droplets from getting stuck at points. Referring to FIG. 84, interdigitated control electrodes are known in the prior art to permit close contact. However, as control electrodes become very small, it may be preferable to slightly overlap control electrodes in a given control electrode layer 195; although FIG. 84 shows overlapping in a staggered fashion, a fallen domino pattern, though challenging to manufacture, may also be considered.

Referring to FIGS. 29A-B, in the absence of a hydrophilic surface, a water droplet 116 wants to revert to a droplet shape, as shown in FIG. 29A, based on its own surface tension (mutual attraction of polar molecules). However, a shape of the water droplet 116 as shown in FIG. 29B will be obtained as the forces of surface tension are counterbalanced by the forces of capacitive spreading as shown in FIGS. 62A-B. Either polarity may be used since either way the charges will participate in capacitive spreading. Notably, since the charges are maintained by capacitance, the shape of the water droplet 116 will be maintained even when disconnected from a battery that established a voltage potential difference V. Stronger voltages will overcome a greater amount of surface tension, and so the shape of the water droplet 116 will change more. However, without an insulating layer of oil 117 charges will jump from the water droplet 116 and spread by themselves over an opposing sidewall electrode 120 if the voltage is high enough. In turn, this neutralizes the effect of the potential difference. Referring to FIG. 70B, the same sort of thing will happen even in the case of dielectric electrowetting. As droplet size gets smaller and smaller, and as microfluidic power is maximized by using an annular arrangement as shown in FIG. 30B or by using an arrangement such as shown in FIGS. 72 & 73 as compared to an arrangement with less power as shown in FIG. 65B, the amount of voltage required to move or manipulate a droplet will be lowered. If low enough, use of an insulating filler fluid will not be essential. However, for larger droplets or less efficient arrangements, or even for small droplets, it is contemplated that in the future nanotechnology will someday provide a means to switch a surface back and forth between hydrophobic and hydrophilic states. In such a case, control electrodes will be replaced by "control surfaces"; yet, the use of self-scooting circuitry to switch the control surfaces on and off will be equally pertinent. Of note, the paper by Rosario et al (Ibid.) provides a primitive example of turning a control surface on and off in response to light so as to move a droplet.

One skilled in the art of digital microfluidics will appreciate that self-scooting circuitry according to the invention will enable droplet events such as dispensing, merging, mixing, rotating, injecting, locating, sensing, conditioning, moving, routing, and so on to be choreographed with much greater control based on an ability to finely detect droplet position electronically. It will also be appreciated that self-scooting circuitry will enable a more intimate control of droplets and a control of finer droplets than has been previously realized.

Attention is now turned to the subject of additional design considerations concerning incubator environmental controls.

In the prior art, human embryos are kept in incubator ovens and are moved back and forth manually in laboratory dishes between the oven and a microscope stage for examination and treatment. This introduces numerous problems, such as poor control of temperature and handling errors such as spillage. Whether inside a humidity controlled oven or outside the oven on the microscope, evaporation of water from the fluid incubation medium means the concentrations of dissolved substances (osmolarity) will change over time due to water loss. Alternate approaches have included containing the embryo within a complete enclosure such as a tank-like chamber (Thompson et al, U.S. Pat. No. 6,673,008; Campbell et al, US published application 2002/0068358) or a microchannel (Beebe et al, U.S. Pat. No. 6,193,647); though these approaches serve to reduce evaporative losses, complications abound.

For one thing, unlike the open-top arrangement provided by the present invention, patient access is hindered. Also, ambient pressure is not independent of a pressure used to urge fluid to flow past the embryo in such devices; and, as anyone familiar with scuba diving knows, osmotic balance in the tissues is related to fluid pressure; thus, with some irony, in some cases due to pressure variations, osmotic balance might be upset more so than it would have if osmolarity had even been allowed to vary slightly.

However, these complications are unnecessary. For one thing, in a flowing system it is an easy matter to correct for evaporative losses as they occur. For example, referring to FIG. 6D, exemplary FCA device D1 might be an osmolarity compensator. The purpose of the osmolarity compensator (or regulator), then, is to correct for changes in water content in the fluid incubation medium M, as caused, for example, by evaporation.

For another thing, evaporative losses can be substantially controlled and prevented in the first place by means of a number of environmental controls. For example, a laminar and substantially lateral flow of air from an air system located intimately above a vented microcradle's open top can be combined with a substantially vertical flow in the form of a laminar flow hood. The function of the lateral flow is to maintain parameters of air temperature, humidity, and gaseous content (e.g., $CO_2$ content) in proximity to the vented microcradle, whereas the function of the vertical flow is to maintain temperature and to remove stray amounts of humidity and air at the given composition that are not desirable for operators.

Referring to FIG. 86, lateral 196 and vertical 197 airflow systems have respective inlets 198-199 and outlets 200-201 for the entry and exit of air. In other words, the flow systems function in the manner of air curtains, and not merely in the sense of a laminar flow system that provides only for air suction. As shown in FIG. 86, the lateral flow system 196 is intimately located above a vented microcradle 202 and may even be integrated with an FCA 203 containing the microcradle 202.

In practice the need for lateral airflow as shown in FIG. 86 will generally be limited to a subtle amount of flow, being that the fluid incubation medium bathing the patient will most likely be discarded after passing by over the patient for a short period of time, including in a recirculating or to-an-fro mode of fluidic ventilation. Thus, there will generally not be a great deal of time for evaporation to occur. The discarded fluid should be kept for scientific analysis in reference to patient outcomes and in reference to data collected for the patient during the time in which the given quantity of fluid was used.

Referring to FIG. 6D, exemplary FCA device D3 might be a device for discarding used fluid M and replacing it with fresh media M, including sequential media or media selected according to patient needs. Similarly, although various devices can be used to maintain the gaseous and other content parameters of the fluid incubation medium M, in general the medium M will simply be refreshed with new medium M as needed.

Figure 87:
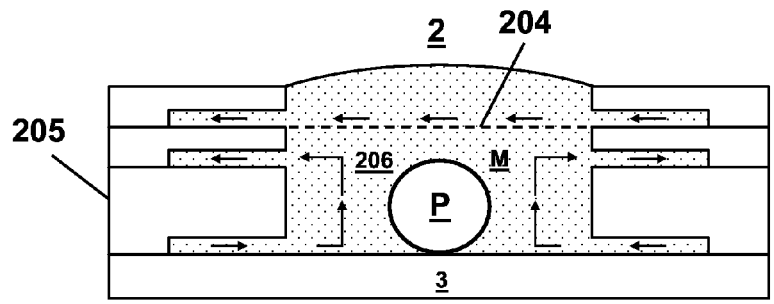
FIG. 87 is a side cross-sectional view of a side-vented microcradle.

As an alternative or complement to use of a lateral airflow system 196 as shown in FIG. 86, referring to FIG. 87 microfluidics can be employed to provide a horizontal laminar flow curtain 204 in an upper portion of a vented microcradle 205 to isolate a ventilation region 206 below from the environment above the open top 2 of the microcradle 205. The laminar flow curtain 204 contains substantially the same fluid content of the incubation medium M as is needed for patient health. Based on laminar flow, which is a characteristic of microfluidic systems, the curtain 204 provides isolation to protect the ventilation region 206 from exposure to the environment. In other words, the flow curtain 204 experiences the effects of exposure to the environment above, rather than the ventilation region 206 having to.

In special cases, an FCA may be provided with a bell jar type cover having air inlets and outlets to provide environmental isolation, for example, in a portable embodiment. In general, a MEMS-actuated cover may be provided on top of an FCA to cover the open top of a vented microcradle for whenever added protection or temporary isolation is needed. For example, an earthquake sensor might trigger the actuation of the cover to protect the patient from spillage during an earthquake. The MEMS-actuated cover is preferably made of a covering material that is transparent to light at suitable wavelengths. By MEMS-actuated is meant actuated according to micro-electro-mechanical systems technology (MEMS).

As a stationary incubator platform for the care of human infants, the invention is best operated in an industry standard clean room environment. Clean room technology is well known to the semiconductor industry to keep dust particles from falling on semiconductor chips during manufacture. In the prior art, practitioners of in vitro fertilization have generally relied on laminar flow hoods to keep dust particles from falling into a dish in which an embryo is kept. However, although a flow hood 207 as shown in FIG. 86 can be used to an extent in this fashion, exclusive reliance on a flow hood to keep particles away from the baby may be inadequate. In contrast, industry standard clean room practices may be confidently relied upon, as these are well established to ensure a particle free environment. Those entering the clean room environment should be free of volatile substances and particulates, and gowns and face coverings should be worn at all times. The design and construction of the clean room should be free of volatile substances and other contaminates (e.g., residues from construction adhesives) with special emphasis on teratogenic or other toxic substances. A separate fume hood or ventilated storage area should be provided for storage of volatile or potentially hazardous articles within the clean room. Sliding glass doors, preferably vertically sliding or laterally folding, and preferably double-walled, may be employed about the patient flow hood 207 to provide added isolation for the patient when operators do not require access.

Pressure, temperature, and humidity in the clean room environment are closely regulated. However, the temperature and humidity, along with air composition, are preferably set in a manner suitable for operator comforts. Clean room air pressure should be the same as ambient pressure for patients. Care should be taken so that ambient pressure is not disturbed when sliding glass doors are shut on the flow hood 207.

Figure 88:
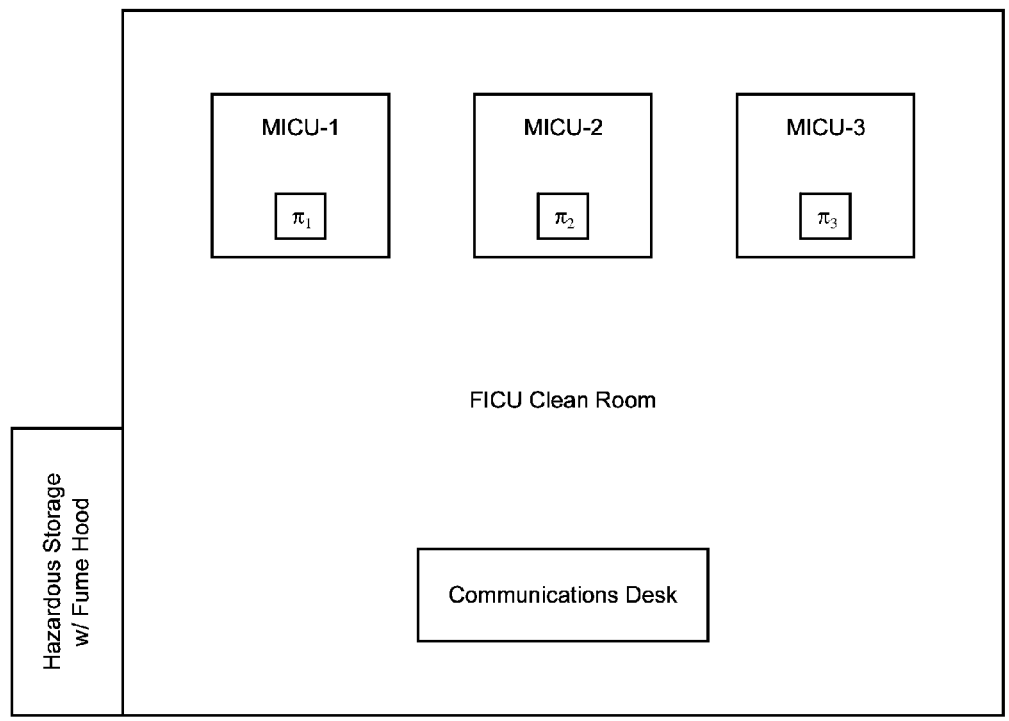
FIG. 88 is a floor plan for a "fertility intensive care unit" clean room according to the invention.

FIG. 88 shows an exemplary layout for a fertility intensive care unit (FICU) clean room containing three micro intensive care units (MICUs). Each MICU contains a prenidial incubator ($\pi$) on a table platform with a flow hood on top. The flow hoods are preferably supported from the ceiling so that when vertical sliding glass doors are lifted the entire table platform is left unobstructed by vertical supports. Accordingly, the sliding glass doors have interlocking corners that permit sliding against each other. Nurses' stations, patient transfer rooms, patient rooms, operating rooms, family rooms, and other usual medical facilities are provided outside the FICU clean room environment.

Prior to each use, prenidial incubators and their environments should be clean, sterile, and non-pyrogenic. They should also be free of endotoxins, teratogens, and other toxins.

The invention requires intensive care medical operation at the micro level. A number of existing medical disciplines may contribute to such operation. However, of the existing medical disciplines, microsurgery and intensive care nursing provide the most closely related medical fields to operate a prenidial incubator according to the invention. Obstetrics and obstetrical nursing also provide closely related medical fields in view of an ability to ease the transition between prenidial incubation and patient transfer. Gynecology, endocrinology, and a number of subspecialties of biology also provide relevant expertise.

Referring to FIG. 48E, human hatchlings are especially sensitive because, unlike embryos inside their protective egg capsules, the tissues of hatchlings are directly exposed. Also, because hatchlings are dedicated to implantation for survival, contact with an artificial (non-implanting) surface can be hazardous and unhealthy. For example, they may attempt implantation on an inappropriate surface of a prenidial incubator. Referring to an exemplary FIG. 8 of the parent application, fluid flow in the upward direction through the vented flooring can be used to lift the patient above the flooring. It is therefore possible to retain the patient in a fixed location within a column of fluid flow, based on the same principle of Bernoulli's equations in fluid mechanics that enables a ping pong ball to levitate over a column of air. In this way, the patient will not contact any surfaces during incubation. Using fluid pressure variations or relevant orientations of fluid streams, it is further possible to rotate the patient.

The use of water effects to provide a massaging action is well known. It is therefore also possible to provide a therapeutic water massage for hatchlings using streams or fluid pressure variations. Because prenidial infants are kinesthetically active, it is contemplated that water massage may offer a useful therapeutic benefit, particularly for hatchlings. In the maternal body, a massaging effect is likely to be provided by maternal movements, contractions, and the pulsing of the maternal heart and circulatory system.

Figure 89A:
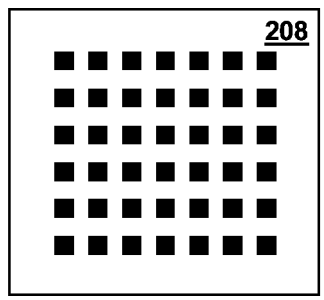
FIGS. 89A-D are top orthogonal views of patterns of openings for fluid in a vented flooring for a microcradle according the invention and its parent teaching.
Figure 89B:
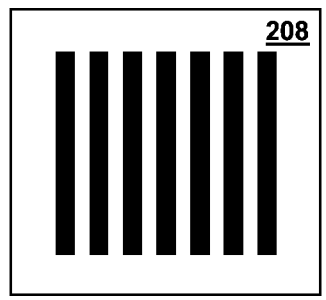
Figure 89C:
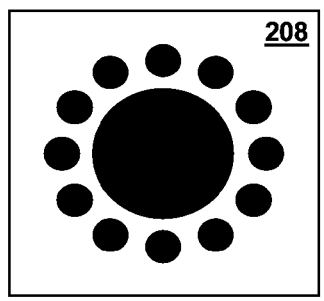
Figure 89D:
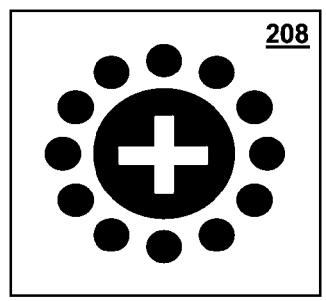

Referring to FIGS. 89A-D, the vented flooring 208 for a microcradle may include any desirable pattern of openings for fluid. In FIG. 89D, a raised feature from a layer below (here shown in the exemplary shape of a plus sign) is provided as a breach guard. To rely on a floor opening (as opposed to a side opening) to provide rotary fluid flow, openings for fluid may be etched at an angle to the vertical to provide rotary flow.

Figure 90:
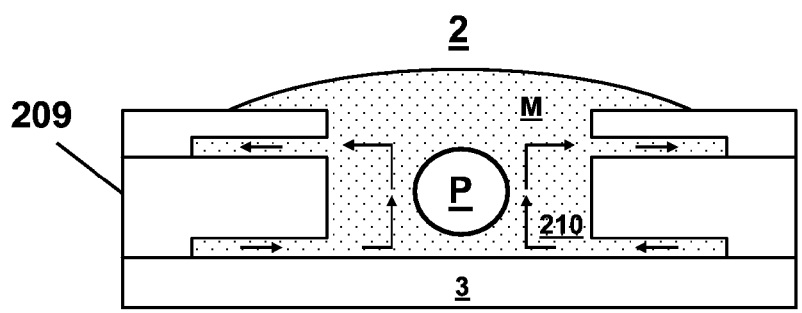
FIG. 90 is a side cross-sectional view of a side-vented microcradle illustrating a method according to the invention, whereby a patient is lifted by fluid flow.

Referring to FIG. 90, a side-vented microcradle 209 can be employed to lift a patient P off the bottom 3 by urging fluid to flow in an upward pattern 210 via side vents (ventilation ports) at a rate needed to lift the patient P, as illustrated. Additional ports for fluid flow (from the bottom, sides, or above the microcradle 209) may be used to produce various flow effects. To provide a lifting of the patient P, the pattern of fluid flow 210 may preferably be a vortex pattern caused by angling fluid streams in a vortex pattern.

The invention provides for a control of fluid flow and other parameters of the care environment based on feedback from patient temperature and other indicators of patient health status. Other indicia (e.g., chemical content of flow samples) also provide feedback.

Devices are contemplated to enable biofeedback between a mother and her externally incubated child, including by means of wireless communication. For example, a device placed inside or in fluidic communication with the mother may release an amount of human chorionic gonadotropin into her fallopian tube, uterus, or other part of her body in response to production of the same by an infant in a prenidial incubator. Biofeedback of this sort will enable mother and child to "synchronize" in preparation for implantation. In another example, a transfer catheter may be equilibrated with uterine temperature. In another example, fluid flow ventilating the patient in a prenidial incubator may be made to pulse in response to indications of the maternal heart rate. Careful examination of parameters and conditions of natural gestation will lead to a discovery of parameters and conditions (e.g., the infrared output of the maternal body inside the womb) that are suitable for engineered provisions as well. In general, parameters associated with the invention or its operation may be refined based on knowledge of the human body.

Prenidial incubators can be designed to accommodate different patient parameters. For example, human eggs are naturally covered with corona radiata cells. These cells, which are maternal cells surrounding the shell of the egg, have been traditionally removed prior to fertilization, leaving the surface of the egg bare. However, techniques to incubate patients with the corona radiata cells intact, or intact on a region or hemisphere of the egg, will generally require a larger size of the incubator due to a larger effective size of the egg. Similarly, if hatchlings are to be accommodated then the incubator's size will generally have to be larger than for embryos alone; also, the infant must be protected from attaching to or breaching a structure of the incubator (or transfer catheter). In general, it is contemplated that research into a use of structures with breachable apertures to enable a hatchling to repeat his or her hatching behavior for exercise, research into a use of hydrotherapy, and research into a patient's behavioral sensitivity and response to chemical, optical, surfacial, electrophyiological, biologicial, mechanical, and physical stimuli may be explored. In other words, a variety of therapeutic novelties may be considered in the context of the controlled care environment provided by a prenidial incubator.

Figure 91:
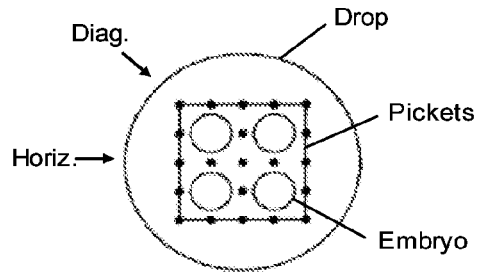
FIG. 91 is a top orthogonal view of a prior art compartmentalized structure for embryos covered by a microdrop that is stabilized by pickets.

Referring to FIG. 91, Cecchi et al employ a picket fence structure for the dual purpose of enclosing embryos and for stabilizing a microdrop of fluid incubation medium under which the embryos are submerged. However, as illustrated in FIG. 91, a problem arises in that the pickets are not arranged in the shape of the drop, leading to a difference in stabilizing resistance depending on whether the drop is accidentally accelerated (e.g., by tilting under gravity when dishes containing embryos are moved) in a horizontal versus diagonal direction. Another problem is that the pickets, as a stabilizing structure, are not arranged substantially near the circumference of the droplet. The problem with this is that the drop will be allowed to accelerate substantially before encountering any stabilizing resistance.

Figure 92A:
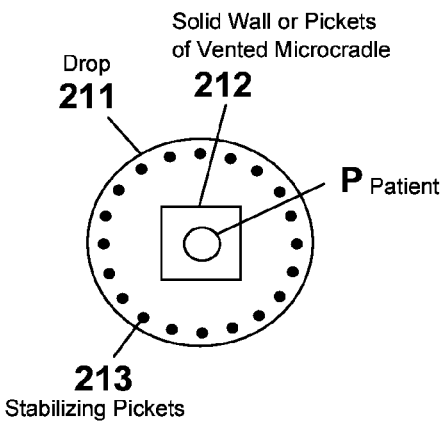
FIGS. 92A-C are top orthogonal views of stabilizing structures for a microdrop according to the invention; the microdrop covers a vented microcradle.
Figure 92B:
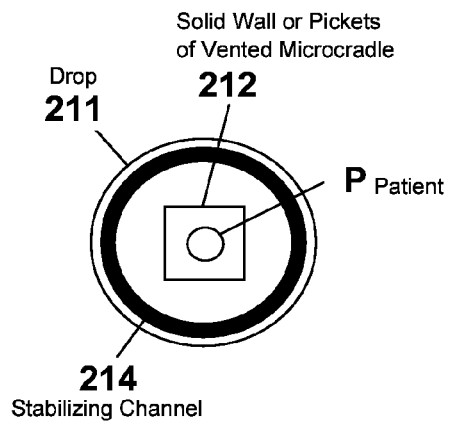
Figure 92C:
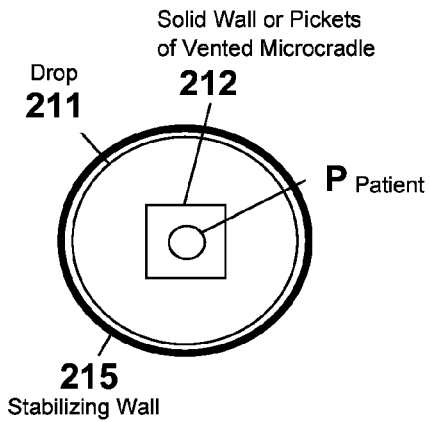

In general, when practiced as a stationary incubator platform a problem of tilting under gravity is not a major issue with respect to the present invention, because there is no need to move patients back and forth between incubator ovens and microscope stages as there is with the art of Cecchi et al. At any rate, referring to FIGS. 92A-C, the present invention prefers to use stabilizing structures for a droplet 211 that take the same shape as the circular circumference of the droplet 211 and are placed substantially next to the droplet's 211 circumference. Referring to FIG. 92A, to stabilize the droplet 211 in which a vented microcradle 212 is submerged, an independent set of pickets 213 forms a circumferential structure just inside the droplet's 211 circumference. Pickets may also be elongated to form standing plates along radial lines emanating from the droplet's 211 center. Shaping the outer vertical contours of the pickets to match the contours of the droplet 211 will maximize resistance. Stabilizing pickets or plates placed on the outside of the droplet 211 should be hydrophobic, whereas those placed on the inside may be hydrophilic or hydrophobic (since either way the droplet 211 will resist breaking its surface tension) but are preferably hydrophilic. Referring to FIG. 92B, alternatively, a hydrophilic channel 214 may be etched just inside the circumference of the droplet 211. If the surface on which the droplet 211 rests is hydrophobic, a hydrophilic strip may be used on the inside surface in place of a channel 214. Alternating concentric hydrophobic and hydrophilic strips (not shown) may also be used adjacent to the droplet's circumference. Also, if the inner surface on which the droplet 211 rests is hydrophilic a hydrophobic area may be placed around the droplet's 211 outer circumference. Referring to FIG. 92C, preferred is a stabilizing wall 215 on the outside of the droplet 211.

Generally speaking, although a vented microcradle is provided with relatively small ports for fluid entry and exit, one or more larger holes, or alternatively high velocity channels, may be provided for the sake of quick refilling or refreshing of the fluid in the microcradle. For example, patient health status, as indicated by monitors, may warrant an emergency treatment with an alternate fluid or medicine. Ports introducing medications or other fluidic treatments can be arranged to improve mixing in the microcradle to ensure proper patient exposure. Fluorescent dyes and other techniques can be used to assess microcradle hydrodynamics (e.g., mixing) when contemplating new configurations for a vented microcradle. In the drawing, a figure such as FIG. 7B shows a via 41 forming walls of a microcradle provided with a total of eight ventilation ports 4 at the bottom of the cradle arranged in a given spacing arrangement. But in general such ports may be provided in any number as needed, with nominal spacing or even under a continuous shelf.

Metals such as copper, if leached into the fluid of the patient's fluid incubation medium, would be highly toxic. For example, a structural failure, such as a leakage of fluid between FCA layers due to imperfect bonding, might enable metal-fluid interaction in places where such contact is normally impossible. In contrast, employing metals such as gold or platinum in such places would be safer. Safety coatings may also be applied to ensure the chemical and electrical inertness of underlying materials in relevant areas of potential hazard.

Figure 93:
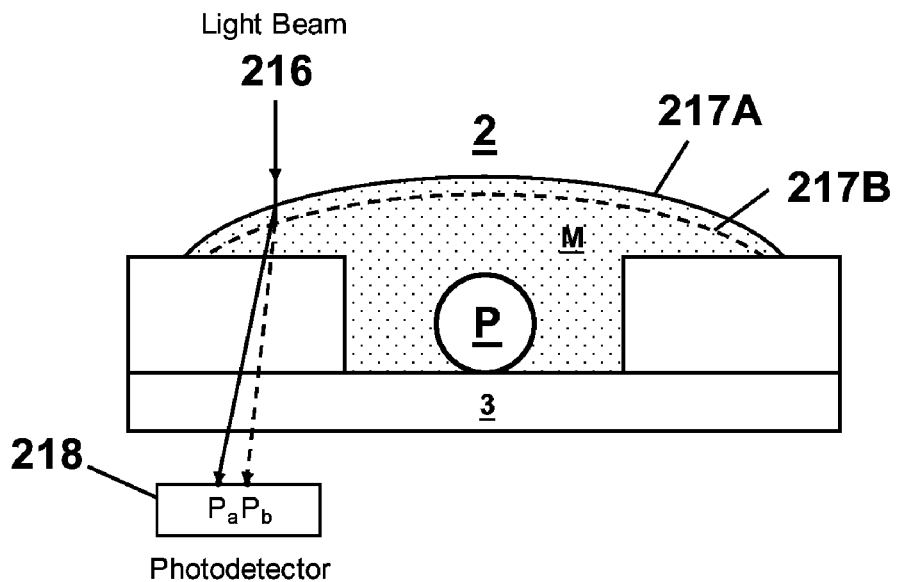
FIG. 93 is a side cross-sectional view of a side-vented microcradle employing an optical device according to the invention for sensing microdrop volume.

When a microdrop configuration is employed, problems with fluid flow into and out of the microcradle may result in an imbalance that causes significant changes in the volume of fluid bathing the patient. To avoid this potentially disastrous situation, an alarm should be provided to detect changes in the fluid volume of the microdrop. Such changes can also provide feedback for the control of fluid flow events. Referring to FIG. 93, an optical alarm or volume-sensing device employs a beam of light 216 from a light source directed through the meniscus 217A of the droplet in a lens-like fashion, which is then detected at a point $P_a$ on a photodetector array 218; changes in droplet volume are registered by the photodetector 218 based on corresponding changes in the shape of the meniscus 217B, which cause the light 216 to be focused on a different point $P_b$. In general, the beam of light may traverse the droplet in any number of configurations, including downward (as shown), upward, or sideways through the droplet to a photodetector, or the beam of light may be reflected back to a photodetector after passing through the meniscus. The light source should provide a beam of light at a wavelength or wavelengths that do not heat or otherwise affect the fluid of the droplet or FCA. An optical means of detecting volume changes has the advantage that no electricity is used in contact with the fluid of the droplet, unlike use of an electrical sensor. As an alternative or complementary technique, changes in droplet size can be monitored by means of recording a digital image of the droplet and processing it by a computer.

Specific heat capacity is a measure of the amount of heat needed to raise the temperature of an amount of substance by a given number of degrees. Low specific heat capacity means small changes in heat transfer will produce large changes in temperature. Generally, a fluid with high specific heat capacity, such as water, will be preferred for the running fluid of the temperature bath because large heat transfer is possible without changing the temperature much. However, in some cases it may also be desirable to heat or cool a branch of running fluid quickly to a certain temperature for the benefit of an auxiliary device, such as a micro chem lab, that requires a certain temperature for a brief period of operation, or a spectrum of temperatures over a given period of time. In such a case, a running fluid with a low specific heat capacity would be desirable. Separate baths may also be provided for this purpose.

In general, it is desirable to minimize electrical effects in a prenidial incubator because, for example, either the patient or sensitive electrophysiological equipment may be adversely affected. Faraday cages, including ones built into the FCA, may be provided to improve electrical isolation. Indium tin oxide may be used as a faraday cage material wherever optical transparency is needed. Reliance on pneumatic and mechanical components over electrical ones can also help to reduce electrical effects.

Although each FCA is generally dedicated for single use only, a number of FCA components can be recycled after each use to help lower costs.

Microfabrica, Inc. (Van Nuys, Calif.) has developed a microfabrication platform called EFAB™ for the fabrication of 3-dimensional microdevices. Presently, the technology only works with metals. However, if a similar method could be developed for use with biocompatible materials, the present invention could be manufactured using this alternate method, as opposed to the layer-based method described above. According to the EFAB™ micromanufacturing process, a patterned layer of sacrificial material is deposited on a substrate, a blanket layer of structural material is deposited on the patterned layer, and then the resulting layer is planarized; successive layers are formed in this fashion, and the sacrificial material is released. To include an embedded structure or device using EFAB™ technology such as optical fibers, some additional steps are needed in addition to the standard process. For example, after a base structure is formed and the sacrificial material is released, an optical fiber is embedded, the next patterned layer of sacrificial material is deposited on top, a blanket layer of structural material is deposited on the patterned layer, and then the resulting layer, with fiber optics underneath, is planarized. One skilled in the art of microfabrication will appreciate that although the use of laminated glass layers is preferred with present technology, the making of the invention is not limited to a single technology of manufacture. Indeed, any suitable technology for arriving at a relevant 3-dimensional structure may be used to fabricate the invention.

Those skilled in their respective arts will appreciate that the invention represents a highly interdisciplinary technology and is amenable to any number of design considerations.

8. Other Embodiments

Up to this point in the disclosure, embodiments of a side-vented microcradle have been described that translate a horizontal motion of fluid into a vertical motion past the patient, so that the patient is ventilated vertically. However, referring to FIG. 94A, rather than providing side ports for a fluid flow that translates into a vertical ventilation of the patient, side ports 219 can be used to ventilate the patient horizontally instead. Referring to FIGS. 94A-E, FIG. 94A shows an FCA 220 containing a side-vented microcradle 221 that is covered by a microdrop 222. An optional retaining structure 223, such as a picket fence structure, may be included to retain the patient P in a more localized area, while at the same time permitting a flow of fluid through the retaining structure 223. Ventilation may occur in the form of flow in a single direction, in alternating directions, to-and-fro, or using a back-and-forth rocking motion to rock the egg of the patient P back-and-forth. Note that an intake of fluidic ventilation must equal an output of fluidic ventilation in order to maintain a constant volume of the droplet 222.

Figure 94A:
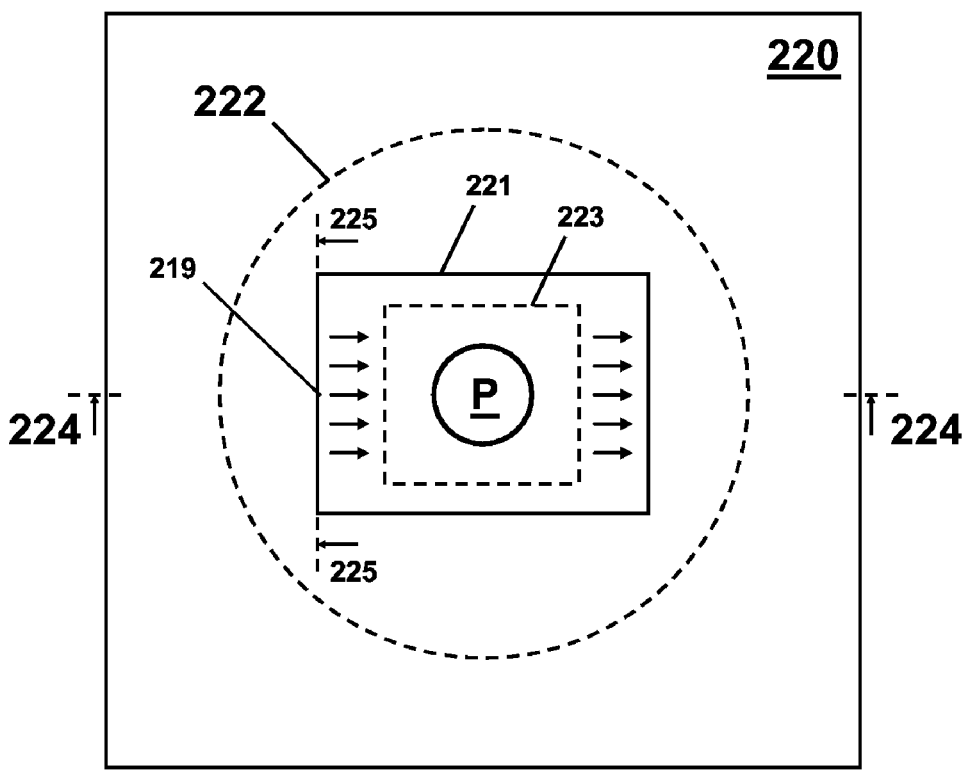
FIG. 94A is a top orthogonal view of a side-vented microcradle.
Figure 94B:
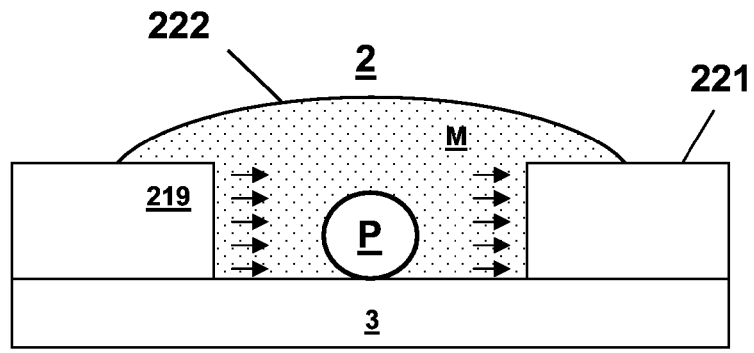
FIG. 94B is a side cross-sectional view of the side-vented microcradle shown in FIG. 94A, taken along a line 224.
Figure 94C:
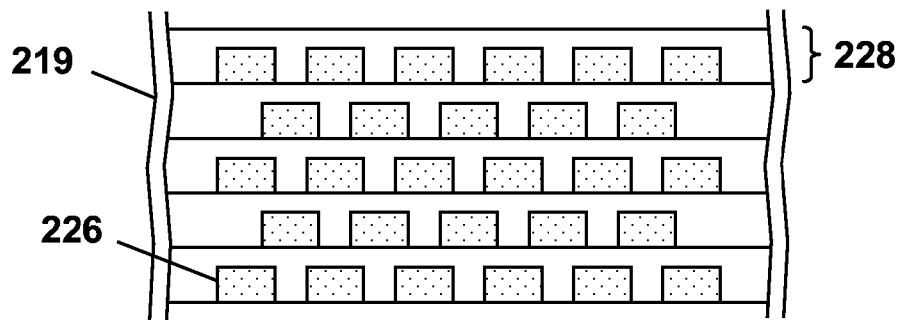
FIGS. 94C-E are side cross-sectional views of a sidewall section of the side-vented microcradle shown in FIG. 94A, taken along a line 225; each shows a different arrangement of ventilation ports in the sidewall.
Figure 94D:
Figure 94E:
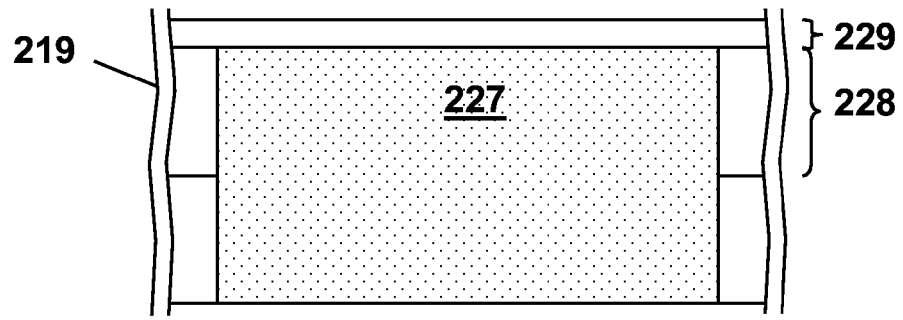

Referring to FIG. 94B, which is a side cross-sectional view taken along a line 224 with respect to FIG. 94A, the patient P is horizontally ventilated in the microcradle 221 via side ports 219. Note the open top 2 and clear bottom 3 of the present invention. Unlike the art of Beebe et al (U.S. Pat. No. 6,193, 647), which includes a covered well or covered channels in which to rock an embryo back and forth using a microfluidic flow, the open top 2 arrangement of the present invention enables easy access to the patient P while allowing him or her to remain continuously subject to an ambient pressure rather than to a pressure used to urge fluid to flow Referring to FIGS. 94C-E, which are side cross-sectional views taken along a line 225 (flooring layers omitted) with respect to FIG. 94A, side ventilation ports 219 may be formed by channels etched in (226) or through (227) layers 228. Referring to FIG. 94E, a top layer 229 caps off channels 227 etched through layers 228. Note that the patient P will experience the microfluidic benefits of laminar flow in this arrangement.

Beebe et al (U.S. Pat. No. 6,695,765) teach a network of covered channels in which to house an embryo for purposes including transport to analysis stations. However, a great liability of their teaching is that embryos are not available for easy access while traveling inside the covered channels and, moreover, they are subject to a pressure used to urge fluid to flow rather than an ambient pressure of the environment.

Figure 95A:
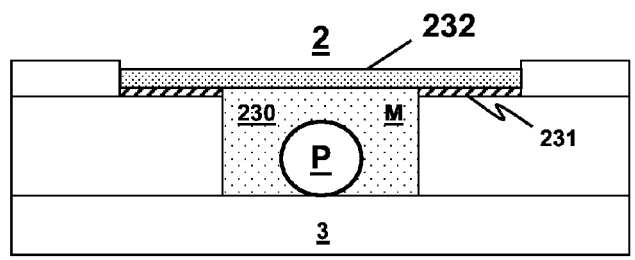
FIGS. 95A-B are side cross-sectional views of micro-canals according to the invention, which are embodiments of a side-vented microcradle.
Figure 95B:
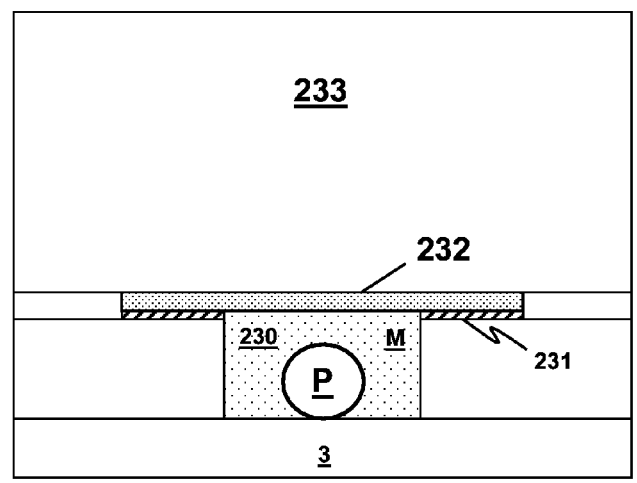
Figure 95C:
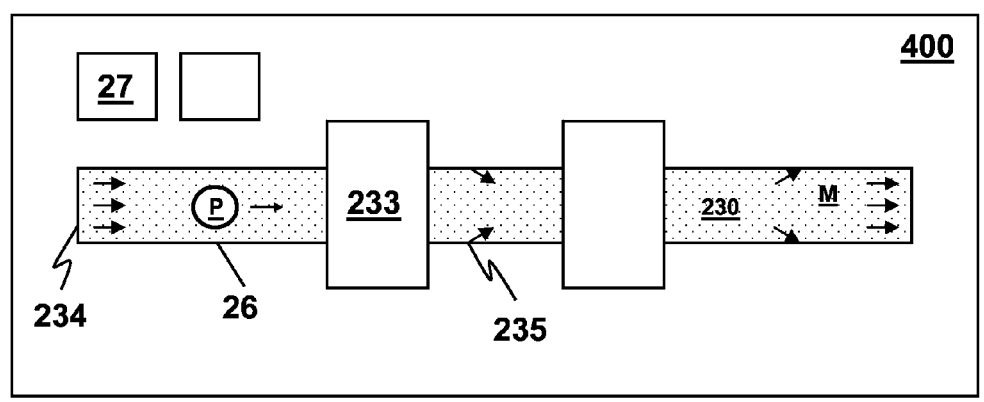
FIG. 95C is a top orthogonal view of a micro-canal according to the invention.

Referring to FIGS. 95A-C, the invention overcomes these liabilities with an embodiment of a side-vented microcradle known as a "micro-canal". Referring to FIG. 95A, the micro-canal is formed by a microchannel 230 with an open top 2 and clear bottom, which houses a patient P in a fluid incubation medium M. As shown in FIGS. 95A-B, a hydrophobic coating 231 may be optionally applied to a surface surrounding the micro-canal (microchannel) 230 and a layer of embryo tested mineral oil 232 or other hydrophobic and biocompatible liquid is placed as a cover over the incubation medium M.

Referring to FIG. 95B, an FCA device 233 or other equipment may be placed above the patient P in the micro-canal 230 as shown, or below or at the sides. Those skilled in the art will appreciate that such a device 233 will provide means to perform such exemplary functions as those of a gate, filter, microsurgical device, optical device, micromanipulator, sensor, transfer catheter docking station, treatment station, analysis station, and so on.

Referring to FIG. 95C, which is a particular example of the general embodiment of an FCA according to the invention shown in FIG. 5, an FCA 400 populated with any number of components 27 and micro-canal devices 233 cradles a patient P in a micro-canal 230, which serves as a greatly elongated version of a side-vented microcradle 26. In general, the patient P will be ventilated with fluid medium M by ventilation ports on the sides of the micro-canal 230, including by ventilation ports located at the ends 234 or along the sides 235 of the micro-canal 230. Ventilation may also be provided via a vented flooring or from above.

Such ports may be used to cause the patient P to transit in the canal by means of a fluid flow. Accordingly, the patient P may be moved from one micro-canal device 233 to another as desired. A circular micro-canal or network of micro-canals may also be employed. Flow in a network of micro-canals can be controlled by gates and fluid flow. A recirculating pump is preferred to maintain an equal inflow and outflow of fluid between ventilation ports exhibiting opposing fluid flow. Fluid flow and patient transit may occur in a micro-canal 230 in a desired manner, including to-and-fro, pulsating, bidirectional, unidirectional, and so on. The course or circuit traveled by the micro-canal 230 may imitate in some respects the course of the human fallopian tube. Spillways and spillway sensors may be employed to help ensure fluid balance is maintained in the micro-canals, including an optical sensor as shown in FIG. 93 (since overflow will cause a bulging meniscus).

An optical device may follow the patient P on a track (e.g., under the micro-canal) for visualization and thermography as the patient P travels the course of the micro-canal 230. Alternatively, an FCA 400 on a motorized x-y stage subject to computer controls may be made to scroll over optical or other equipment in response to patient P movement along the course of the micro-canal 230. A computer can be used to perform tracking functions digitally.

Oil 232 or other substance, if used to cover the fluid medium M in the micro-canal 230, should not interfere with optics. Although a micro-canal 230 with vertical sides has been shown, sloped or curved sides are also possible.

Importantly, an FCA containing a micro-canal enjoys the same benefits of a temperature bath according to the invention as do other side-vented microcradle embodiments.

Figure 96A:
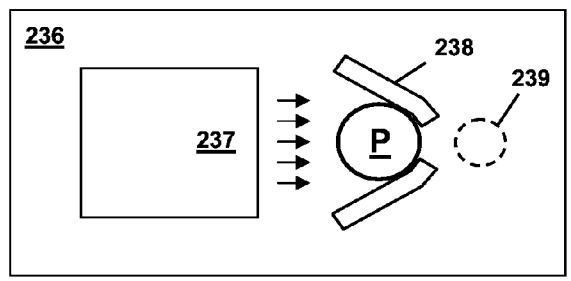
FIG. 96A is a top orthogonal view of a side-vented microcradle.
Figure 96B:
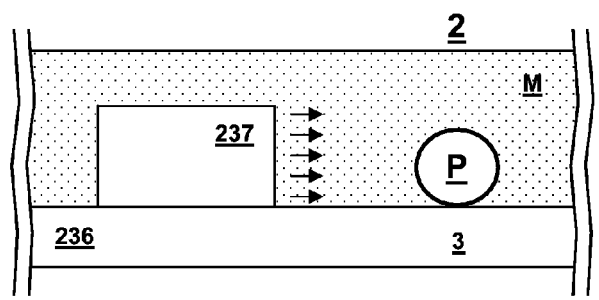
FIG. 96B is a side cross-sectional view of a side-vented microcradle.

Referring to FIGS. 96A-B, a minimalist embodiment of a side-vented microcradle 236 with an open top 2 and clear bottom 3 comprises a ventilation port 237 and a retaining structure 238 to localize the patient P. Referring to FIG. 96B, the ventilation port 237 provides ventilation from the sides. In FIG. 96B a retaining structure is not shown. However, it is understood that if the retaining structure provides bidirectional localization for the patient P, then a flow to-and-fro can be provided via the ventilation port 237. In contrast, FIG. 96A shows a retaining structure 238 providing unidirectional localization; note that a flooring port (drain) 239 may be employed to drain fluid away.

Figure 97:
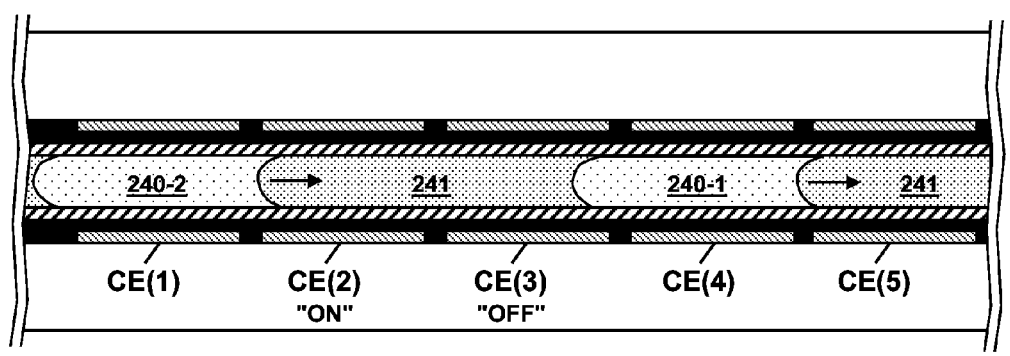
FIG. 97 is a side cross-sectional view of a digital microfluidic system employing self-scooting circuitry according to the invention.

Referring to FIG. 97, a digital microfluidic system employing self-scooting circuitry according to the invention can be made to urge a continuous train (or stream) of droplets (or fluid cells) separated and spaced apart by a filler medium. This provides a very powerful hydraulic arrangement capable of pumping fluid with great force. But there is a limitation as to how close together the droplets can be spaced.

To move a droplet by electrowetting a leading control electrode (or control surface) must be turned on and a trailing control electrode must be turned off. Accordingly, referring to FIG. 97, for a leading droplet 240-1 to move, a control electrode CE(3) at the trailing edge of the droplet 240-1 must be turned off. Similarly, in order for a trailing droplet 240-2 to move, a control electrode CE(2) at the leading edge of the droplet 240-2 must be turned on. Since an electrode cannot be on and off at the same time, the leading edge of one droplet 240-2 cannot share a control electrode in common with the trailing edge of another droplet 240-1. Consequently, enough filler medium 241 must be provided to separate droplets with enough spacing so that they do not share a control electrode in common between their respective leading and trailing edges.

Figure 98A:
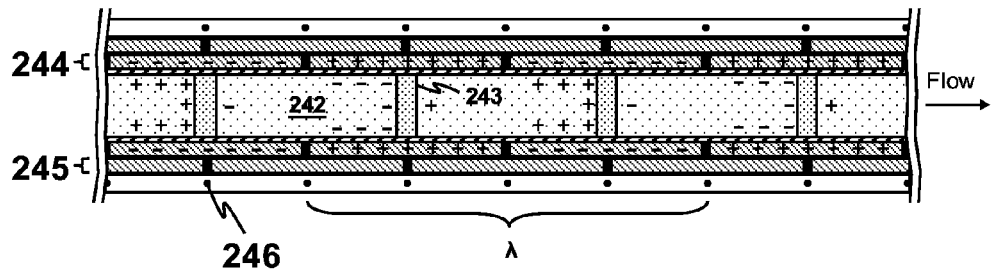
FIGS. 98A-B are side cross-sectional views of a digital microfluidic system employing self-scooting circuitry according to the invention.
Figure 98B:
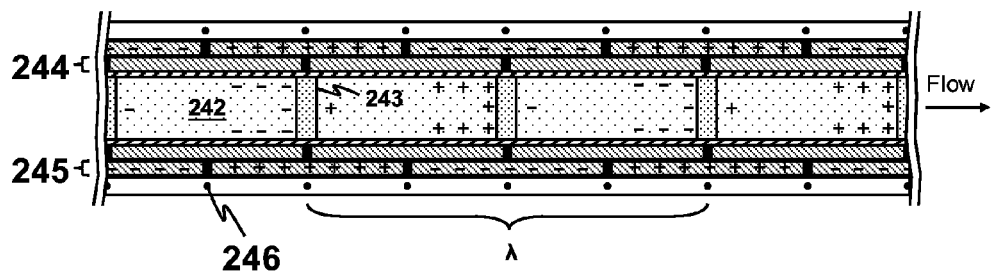

However, in some cases it may be desirable to space conductive fluid droplets (or fluid cells) even more closely. Referring to FIGS. 98A-B, a somewhat peculiar charged electrowetting arrangement employing self-scooting circuitry is provided to satisfy this goal according to the invention. Referring to FIG. 98A, a train of fluid cells composed of a polar, conducting liquid 242 (e.g., aqueous) are separated by an immiscible, non-conducting liquid 243 (e.g., oil) that serves as a filler medium. As shown, adjacent fluid cells 242 are maintained with opposite charge polarity. Referring to FIGS. 98A-B, inner 244 and outer 245 layers of control electrodes urge the train of fluid cells 242 in the manner of charged electrowetting, as shown. Note that adjacent control electrodes in a given layer have opposite polarity with respect to each other and with respect to the fluid cells 242 they are leading.

The length of two fluid cells 242 plus the filler medium 243 in between establishes what may be called the wavelength $\lambda$ of the arrangement. Charges in the control electrodes layers 244-245 propagate in the same direction with the same wavelength $\lambda$. Quarter-wavelength nodes 246 have been inscribed on the drawing of FIGS. 98A-99 for convenience. The polarity of a given fluid cell 242 remains constant as it travels. Inner and outer layers of control electrodes 244-245 alternate in being turned on and off as the fluid cells 242 travel one-quarter wavelength. Each time a given control electrode layer 244-245 is turned on and off, individual control electrodes alternate (advance) in polarity, so that charges in the control electrodes lead opposite charges in the fluid cells 242. Charges in the fluid cells 242 would come to rest with respect to charges in either control electrode layer 244-245 at a phase difference of $\frac{1}{2}\lambda$; so, to keep the fluid cells 242 flowing constantly the control electrodes propagate their charges with a leading phase difference of $\frac{3}{4}\lambda$ as they alternate back and forth between layers 244-245.

Figure 99:
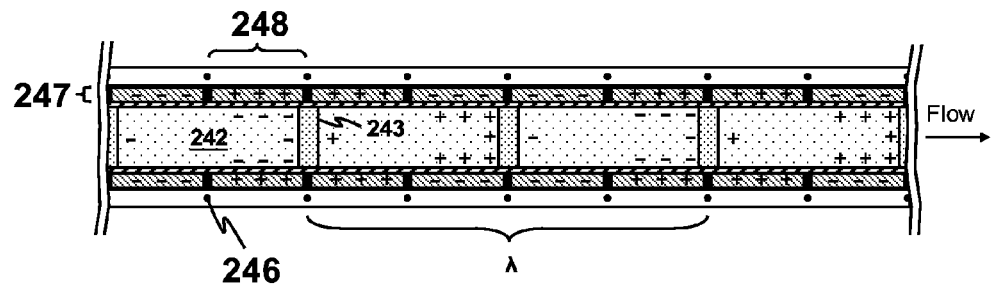
FIG. 99 is a side cross-sectional view of a digital microfluidic system employing self-scooting circuitry according to the invention.

Referring to FIG. 99, a slightly different arrangement employs only one layer of control electrodes 247. Trailing control electrodes 248 may be turned off when appropriate; control electrodes may be further divided as desired so that trailing control electrodes may be turned off more or less continuously.

FIGS. 98A-B and 99 show what are here called lamellae pumps since the filler medium 243 forms a lamella (thin plate) between fluid cells.

For comparison, consider the approximate size of one droplet (fluid cell) plus the size of a filler medium used between droplets in terms of a corresponding number of control electrodes needed to cover an associated amount of space. With respect to FIG. 97, approximately three control electrodes are needed; with respect to FIG. 99, two control electrodes are needed; and, with respect to FIGS. 98A-B, only one control electrode is needed. Accordingly, the arrangement of FIGS. 98A-B is found to be the most conservative in this respect.

Referring to FIGS. 98A-99, ideally the fluid cells 242 are endowed with a net charge that is preserved at least for some time by electrical isolation, and the self-scooting circuitry needed to control the control electrodes 244-245, 247 is controlled by an optical sensing of the passing of fluid cells 242 or filler medium 243. Magnetic or electrostatic sensing may replace optical sensing. An exemplary means of magnetic sensing may include an implementation of the giant magnetoresistive (GMR) effect. However, in many cases the passing of fluid cells 242 or filler medium 243 will have to be electronically sensed, and charges on fluid cells 242 will need to be constantly maintained by means of charging electrodes.

Note that although a net charge is placed on a fluid cell 242, the charge is nevertheless balanced by electrolytic capacitance with respect to the control electrodes, in contrast to a purely static net charge. Still, without good electrical isolation, charge may leak.

Figure 100:
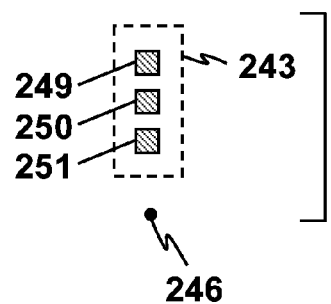
FIG. 100 is a top orthogonal view of an electrode arrangement for the digital microfluidic system shown in FIG. 99.

Referring to FIG. 100, at one or more nodes 246, in place of an optical means, a pair of switching electrodes 249-250 senses the passing of the conducting fluid medium 242 and the non-conducting filler medium 243 as the switching electrodes 249-250 form an open and closed liquid contact switch. At each node 246 a charging electrode 251 placed in contact with the passing fluid maintains an electrolytic charge on fluid cells 242 using nominal self-scooting circuitry, which in turn is controlled by an exemplary means of sensing the passing of the fluid cells 242, such as the above-stated electronic or optical means. The switching and charging electrodes 249-251 must be sized smaller than the width of the filler medium 243, as shown, so that electrical contact is not made between adjacent fluid cells 242.

In a microfluidic system, fluid cells are partitioned by injecting immiscible media in an alternating series. A computer-readable "bar code" series is formed by spacing the alternating media in long versus short amounts over a given region in a train of fluid cells. Media of different optical properties may also be employed (e.g., light vs. dark). The passage of the bar code region over a sensor may be used to provide information for the control and operation of a microfluidic system. For example, electrowetting voltages can be temporarily turned off in response to recognition of a given bar code sequence, so that certain fluid cells in a continuous train of fluid cells are not exposed to voltages or charges as they pass. Similarly, bar code regions written among leading fluid cells can be used to encode information about the contents of trailing fluid cells, e.g., for routing purposes. Alternatively, bar codes may be written in fluid cells on a pacer track, or on a separate bar code or reader track.

In general, any method of information science can be used in practice to write bar codes using a series of fluid cells. For example, fluid cells of equal length, but of low versus high electrical conductivity, can be used to code for 0 and 1 respectively. Clear versus opaque, high versus low pH, and other binary contrasts may also be employed.

In general, fluid cells manipulated by digital or analog microfluidics may contain various chemical contents. They may also contain cells, sperm, viruses, particles, and so on, which in turn may be subjected to various processes, such as transport, sorting, flow cytometry, treatment, handling, and so on.

It may be noted that a micro-canal serves in effect as an elongated fluid cell for housing a patient, which in turn may be subject to additional partitioning.

9. Examples of Human Medical Use

The purpose of a prenidial incubator according to the invention is to sustain the life of a premature infant during life before implantation. In other words, the invention enables us to extend our care for preterm infants to life before implantation.

The invention finds use whenever an infant requires incubation outside the maternal body during life before implantation.

Examples of medically acceptable uses include a monitoring and care of the infant after in vitro fertilization with transfer to the infant's biological mother, rescue of the infant after maternal demise with transfer to an adoptive mother, separation of mother and child with transfer to a surrogate mother in cases where conception has been detected yet where continued pregnancy is not possible with the biological mother, and temporary separation of mother and child with transfer back to the biological mother in cases where the mother requires treatments that cannot be safely performed with her infant present. It is contemplated that as technology advances it will someday be possible to detect a condition of the infant in the maternal body during life before implantation, such that rescue and temporary incubator involvement will then be indicated for the infant in cases where the condition merits it.

The invention enables an infant to sustain meaningful life outside the mother's womb from the time of creation until transfer becomes necessary for implantation.

10. Other Uses

Because the invention has the clear moral status of an infant incubator, it cannot be used, advertised, or exploited in any manner that is contrary to patient rights. However, based on the level of technology that has gone into the making of the invention, it cannot be denied that the invention is amenable to a variety of non-human uses as well. In fact, some of these uses may even serve to benefit the care of prenidial infants in the form of useful research.

Those skilled in the arts of veterinary medicine and microbiology will appreciate that obvious modifications of the invention are amenable to non-human use. Exemplary mammalian uses include murine, porcine, bovine, and equine use. An exemplary use in the field of developmental marine biology includes the study of echinoderm development. Those skilled in the art of electrophysiology will appreciate that modifications of the present invention, which include the advantages of microfluidics combined with an open top arrangement, are superior to the prior art of perfusion chambers and closed-top microfluidic arrangements.

For example, the invention may be modified to accommodate a Xenopus oocyte.

11. Principles of Prenidial Thermoregulation

Historically, an accurate taking of a patient's temperature proved to be the gateway to modern medicine. Today, it goes without saying that no clinical practice is more basic to modern medicine than the taking of a patient's temperature. It should also be understood that the key ingredient of an incubator system is found in its ability to thermoregulate the patient. However, modern medicine has been slow to catch onto the latter understanding.

The nature of the problem of thermoregulating a patient in an incubator is actually more complicated than may be initially appreciated. For example, pediatric historian Thomas E. Cone, Jr. recounts shortcomings in the history of neonatal incubation by teaching as follows: "Early chick incubators in this country failed because their users maintained a constant ambient temperature during the entire 21-day period of hatching. Eventually they learned the Egyptian secret; namely, that as the chicks' endogenous [internal, bodily] heat production increased [due to increased energy metabolism based on growth], the ambient temperature within the incubator needed to be reduced accordingly. The incubation of human infants also stumbled for many years because physicians did not appreciate that environmental temperatures should be reduced as endogenous heat production increased [with growth due to increased energy metabolism]." (Cone T. E. Jr. History of the Care and Feeding of the Premature Infant. Boston: Little, Brown, 1985. pp. 21-22) This important and substantially correct teaching is quoted in texts on neonatal incubation today.

Yet the nature of thermoregulation in an incubator system is complex enough that even Cone proves to be befuddled on the subject. For it turns out that modern chick incubators maintain a constant ambient temperature during the entire period from fertilization to hatching! Since Cone's teaching is correct in context, how can this contradiction be explained?

Human and animal organisms may be categorized either as thermoregulators (like birds, mammals, and humans) that rely on a given body temperature for healthy operation or as thermoconformers (like fish and reptiles) that allow body temperature to change with the temperature of the environment. What this implies, for example, is that a chick embryo growing in an egg actually prefers a certain body temperature.

Neglecting for the moment the additional topic of heat exchange due to radiant energy sources, as well as non-applicable topics such as cooling by evaporation of sweat, the body temperature will be determined by a contrast between bodily heat production, the ambient environmental temperature, and one other factor: dissipation. Notably, it is a difference in heat dissipation that explains the contradiction behind Cone's teaching.

Egyptian incubators kept poultry eggs in heap-like piles offering poor dissipation of heat. Consequently, as internal heat production increased, the ambient temperature of the environment needed to decrease. In contrast, a modern chick incubator spaces eggs apart on trays and the air is allowed to circulate. In this manner, heat dissipation is favorable enough that the ambient temperature does not need to be lowered to accommodate increases in the chicks' internal heat production. However, after hatching modern hatcheries lower the ambient temperature by about one degree Fahrenheit per day until ordinary temperatures are reached; otherwise the hatchlings will become overheated due to increasing endogenous heat production, given that the warmth of their bodies is now insulated by downy feathers, which limits heat dissipation. Note that incubation is no longer necessary once the chicks are able to produce enough heat to sustain the proper body temperature at ordinary temperatures of the environment.

Cone recounts an important observation regarding the Egyptian methodology, namely, they would place an egg against the sensitive skin of the eyelid in order to determine its temperature. In this way, they knew from experience whether the egg was too cold or too hot. Accordingly, they would change the temperature of the incubator environment. Importantly, their methodology was correct in that they changed the ambient temperature of their incubators in response to feedback from readings of body temperature. In contrast, early practitioners of neonatal care made the terrible blunder of monitoring only the temperature of the incubator, which they endeavored to keep constant. In this regard, Cone's teaching could be clarified somewhat in that the major blunder of early practitioners was found more specifically in a failure to monitor the patient's own temperature, as opposed to the temperature inside the incubator microenvironment. For, it is from a monitoring of the patient's personal body temperature that the need to alter the thermal parameters of the environment can be inferred.

Unfortunately, the mistakes of the past have been stubbornly repeated by practitioners of what has been called in vitro fertilization. In defiance of my teaching in U.S. Pat. No. 6,694,175, they continue to monitor only the temperatures of their incubators, and not patient temperature itself. For example, at Boston IVF (Brookline, Mass.), the only fertility clinic affiliated with Harvard Medical School, chief embryologist C. Brent Barrett responded to my teaching as follows: "The embryos that we incubate are microscopic in size and therefore, there is no difference in the temperature of the interior of the incubator and the embryo. We constantly monitor the temperature of our incubators and have conducted numerous studies to ensure that we maintain an optimal temperature for the embryos." (Personal communication. Jul. 12, 2004) Note his focus on the temperature inside the incubator combined with his unskilled assumption that there is no difference between that temperature and the temperatures of the embryos.

It is known from the science of thermodynamics that heat transfer by thermal contact implies a thermal gradient from higher to lower temperature. Put another way, heat flows downhill. Therefore, in terms of heat transfer by thermal contact, at steady-state equilibrium even the temperature of a thermoconformer must be at a higher temperature than the surrounding environment! In other words, because the organism produces heat, and the heat must be dissipated into the surrounding environment, a temperature gradient must exist. Put another way, if the body and the environment were at the same temperature, the body temperature would rise as heat is produced internally, and at that point a net thermal exchange from higher to lower temperature would occur. The rise in body temperature would then stop once a steady-state equilibrium is achieved in terms of heat dissipation. In this sense, although the temperature of a thermoconformer changes with the temperature of the surrounding environment, it does not match it exactly since the body produces heat and heat dissipation by thermal contact implies a thermal gradient from higher to lower temperature. Understandably, this teaching applies equally to microscopic human embryos, being based on sound thermodynamic principles.

Today, an understanding of these principles is generally a commonplace experience. For example, a nurse relies on a patient thermometer, rather than on room thermostat readings. A chef relies on a meat thermometer, rather than on thermostat readings of oven temperature. Unlike practices of old, in which incubator temperature readings were mistakenly relied upon, today neonatologists distinctly monitor a neonate's body temperature without confusion. Even Albert Einstein believed that the laws thermodynamics always apply, including in the outer space world of relativity!

It makes sense to believe that these laws also apply in the world of a petri dish.

Figure 101:
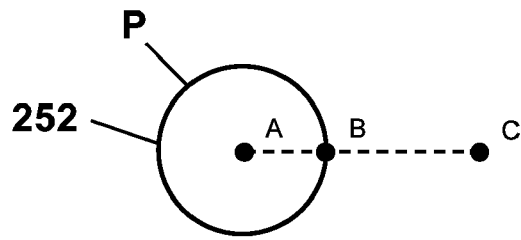
FIG. 101 is a side cross-sectional view of a prenidial infant depicted in reference to points A, B, and C, respectively located inside the patient's body, on the outer surface of the body, and at a distance of a few microns away from the outer surface of the body in the surrounding fluid of the incubation medium.

Referring to FIG. 101, a prenidial infant P is depicted in reference to points A, B, and C respectively located inside, on the outer surface, and at a distance of a few microns away from the outer surface of the body. FIGS. 102A-103B graph temperature as a function of distance from the body surface. For the purposes here, the temperature measured on the outer surface of the body is treated as patient temperature, $T_p$.

Figure 102A:
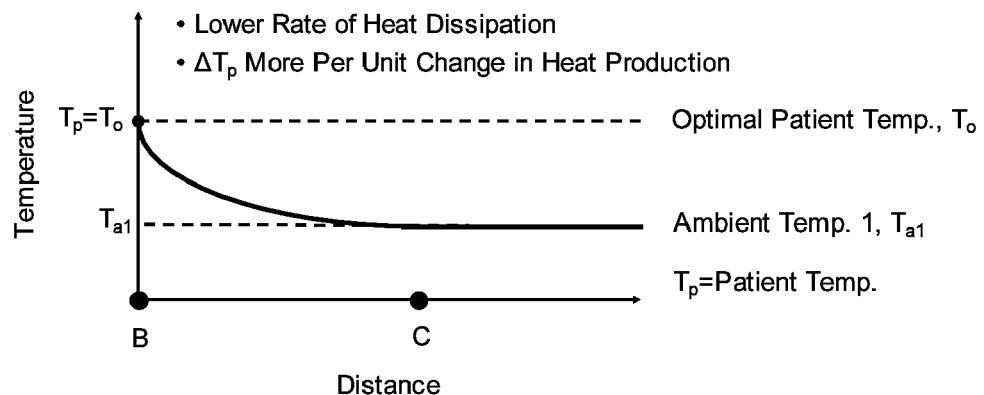
FIGS. 102A-103B are graphs of temperature as a function of distance from point B on the outer surface of the body to point C located a distance away in the surrounding fluid incubation medium, as designated in FIG. 101.

In the graphs of FIGS. 102A-103B, optimal body temperature $T_o$ for the patient P is the same in each case. FIGS. 102A-B illustrate a difference in heat dissipation regarding the rate at which heat produced by the baby's body P is carried away into the surrounding environment. FIG. 102A represents a case of lower heat dissipation than that of FIG. 102B. In both of these figures, however, the temperature of the baby P happens to be optimal; in other words, $T_p=T_o$. In the case of FIG. 102A heat is dissipated into the surrounding environment more slowly than it is in the case of FIG. 102B. For example, fluid ventilating the patient P may be flowing at a faster rate in the case of FIG. 102B than it is in the case of FIG. 102A, thus providing for a greater rate of heat dissipation. All else being equal, in order to establish the optimal patient temperature condition, $T_p=T_o$, the ambient temperature $T_{a1}$ associated with the case of lower heat dissipation (FIG. 102A) will have to be lower than the ambient temperature $T_{a2}$ associated with the case of higher heat dissipation (FIG. 102B).

All else being equal, the reason for the difference is that a case of poorer heat dissipation (e.g., a stagnant fluid medium) requires a lower pull-down temperature to allow for the same body temperature at steady-state equilibrium as does a case of improved heat dissipation. An appreciation of this difference is very important because it teaches us that an optimal ambient temperature does not regard an absolute setting; instead, it is a variable quantity that depends on factors such as heat dissipation.

Figure 102B:
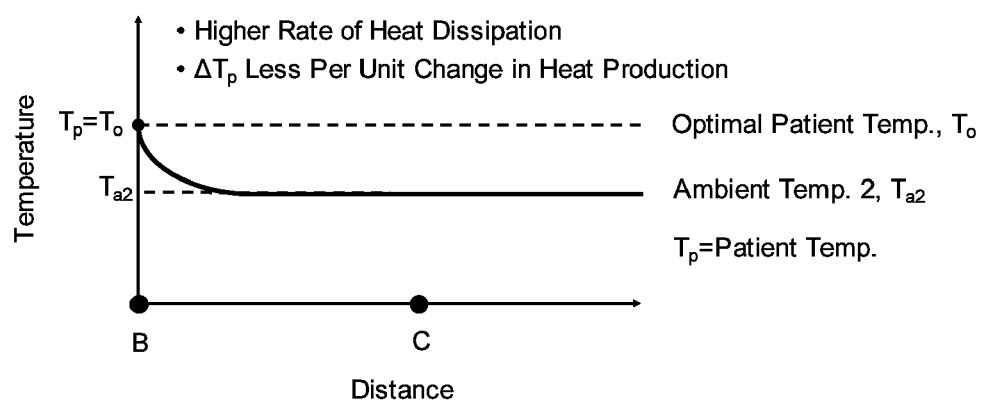

Looked at in another way, suppose the case of FIG. 102A regards a stagnant fluid medium and the case of FIG. 102B regards a fluid medium flowing over the patient P at a rate of X microns per second. This implies that when increasing the rate of flow from 0 to X, the ambient temperature of the fluid medium must be raised from $T_{a1}$ to $T_{a2}$ in order to maintain the optimal temperature $T_o$ for the patient P. Otherwise the patient P will be chilled, as in a draft, by the fluid flowing at the cooler temperature. In other words, unless the ambient temperature is raised in response to an increase in flow-related heat dissipation, patient temperature will fall below what is optimal for the patient P.

Conscious of this critical problem, the parent application teaches the need to monitor patient temperature in response to flow and other parameters, so that feedback controls can be obtained for the sake of proper thermoregulation.

Figure 103A:
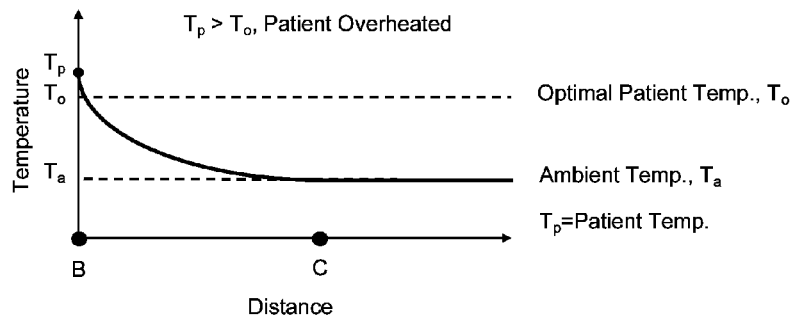
Figure 103B:
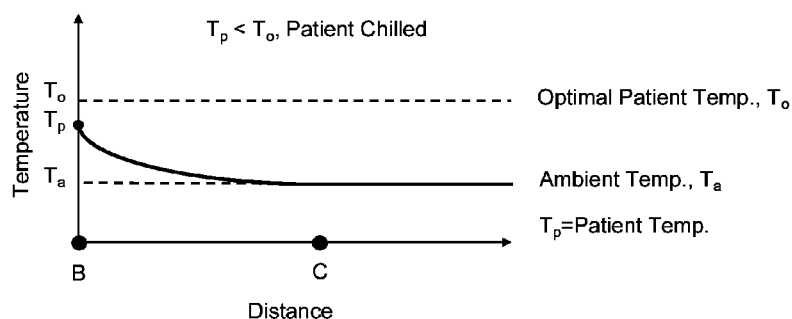
Figure 104:
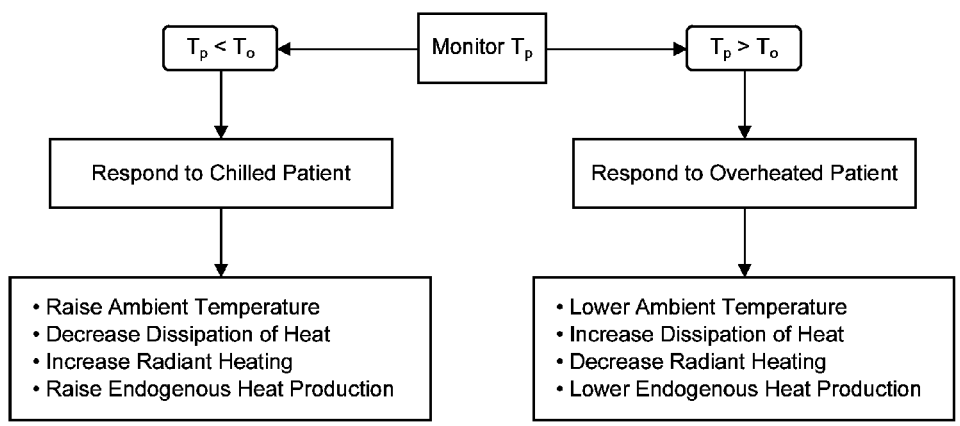
FIG. 104 is a flowchart representing responses to chilled and overheated patients according to the invention.
Figure 105:
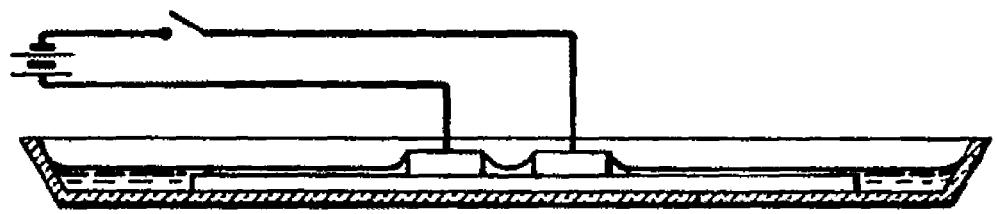
FIG. 105 is a side cross-sectional view of a prior art variable focus liquid lens.
Figure 106:
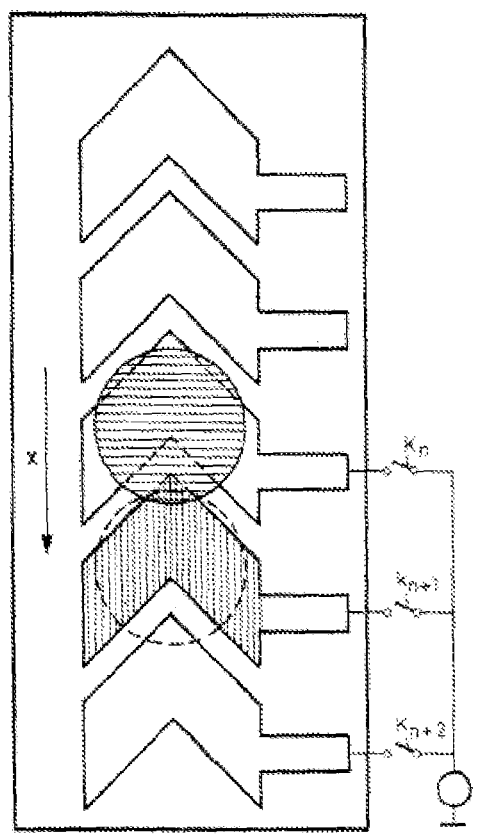

FIGS. 103A-B show graphs for cases in which patients are overheated (FIG. 103A) or chilled (FIG. 103B). In the case of an overheated patient, the patient's temperature is above the optimal body temperature; in other words, $T_p>T_o$. In the case of a chilled patient, the patient's temperature is below the optimal body temperature; in other words, $T_p<T_o$. FIG. 104 shows a flow chart outlining a variety of responses that can be taken to bring a patient's temperature to normal when he or she is overheated or chilled. Referring to FIG. 104, to cool an overheated patient we can lower the ambient temperature, increase the dissipation of heat (e.g., by increasing the rate of fluid flow past the patient), decrease radiant heating, or lower endogenous heat production. A decrease in radiant heating can include a decrease in heating from radiant heat sources (e.g., heat lamps) as well as allowing for an increase in radiant heat losses from the patient to the surroundings. Conversely, to warm a chilled patient we can raise the ambient temperature, decrease the dissipation of heat (e.g., by decreasing the rate of fluid flow past the patient), increase radiant heating, or raise endogenous heat production. An increase in radiant heating can include an increase in heating from radiant heat sources (e.g., heat lamps) as well as preventing radiant heat losses from the patient to the surroundings.

Consider a unit change in endogenous heat production, meaning, a change in the amount of heat produced by the patient per unit time. All else being equal, if the patient increases her or his heat production, body temperature will rise; conversely, if the patient decreases heat production, body temperature will fall. However, in going from one state of steady-state equilibrium to another, referring to FIGS. 102A-B, the net change in patient temperature $\Delta T_p$ per unit change in heat production will depend on the rate at which heat is dissipated into the surroundings; more specifically, the change in patient temperature $\Delta T_p$ observed per unit change in heat production will be lower in a case of greater heat dissipation (FIG. 102B) than it will in a case of less heat dissipation (FIG. 102A).

In this sense, increasing heat dissipation will indirectly have somewhat of a buffering effect on temperature stability. But unnecessary reliance on this effect threatens to lead to an unsophisticated result. For example, it is clear that setting the ambient temperature of the fluid medium equal to the optimal surface body temperature of the patient and flowing it past the patient at a high enough rate will have the effect of forcing the patient's surface temperature to the optimal temperature, by virtue of heat dissipation, regardless of variations in endogenous heat production. In fact, it might be tempting to think that this approach would obviate the need to monitor patient temperature at all. However, such thinking turns out to be non-subtle. First, independence of the flow rate variable is sacrificed; one problem with this is that beneficial substances produced endogenously might be whisked away too soon at a rate of flow needed to buffer temperature completely; although the rate of flow might be minimized in this respect, an element of loss of control over the variable will still be evident. Second, this approach only serves to buffer the patient's surface temperature; referring to FIG. 101, dissipation of heat internally from a point A inside the body of the patient P to a point on the surface B is also an issue; factors affecting the rate of interior heat dissipation in this respect can include insulation 252 surrounding the patient P, such as a shell, corona cells, or spacesuit; this can be a particular problem in that a rate of heat dissipation provided by fluid flow will not necessarily be evenly distributed over the patient's surface; for example, referring to FIGS. 48B-C & E, the patient's formal body may be facing away from the course of fluid flow; thus, flow and, hence, an effect of heat dissipation can be uneven; the unevenness in turn can be magnified by the rate of flow itself. Third, forcing a patient's temperature to a set value will mask important indicators of her or his health status.

The problem of masking indicators of patient health status by exercising total control over thermoregulation parameters is a well known problem regarding the care of neonates in incubators in the field of neonatology today. For this reason, it is necessary to allow the patient to exhibit detectable changes in temperature, since these changes can be a sign of changing health status. For this reason, generally speaking, some change in temperature $\Delta T_p$ should be allowed per unit change in patient heat production; in this way, the change may be noted and incubation protocols can be adapted to respond accordingly. In other words, even though the response may be, for example, to restore the patient to optimal temperature, noting the change itself can provide important information that would otherwise be masked.

For example, if the patient's surface temperature is forced to the same temperature as the fluid bathing the patient using a high rate of flow, then even if the surface body temperature is being monitored it will still not be possible to distinguish a healthy patient from a deceased patient on the basis of body temperature alone. In contrast, if the ambient temperature of the fluid medium is less than optimal body temperature, which implies a lower rate of heat dissipation, then deceased patients will exhibit the ambient temperature of the fluid whereas a healthy patient will exhibit a higher temperature due to her or his heat production.

An incubator for babies should provide a control of body temperature without masking patient health status and without subjecting the patient to inappropriate rates of flow. For example, to produce ventilation on par with what is experienced naturally in the human fallopian tube, it is evident from natural transit rates that flow rates past the patient's body will be extremely subtle. Thus, using high flow rates to maintain patient temperature will conflict with this subtlety.

According to the invention, basic control of patient temperature is provided in view of feedback from patient temperature readings based on an adaptable setting of the ambient temperature of the fluid bathing the patient in contrast to a rate of heat dissipation provided by fluid flow; consequently, there is no need to crudely force the patient to a given temperature since proper monitoring and control ensures the requisite adaptability. However, although this level of basic control may suffice, there are added advantages to employing radiant heat to provide a fine control of patient temperature in addition to the basic controls afforded by the invention. Most important is that radiant heat sources can be quickly adjusted or relaxed, in contrast to changes of ambient temperature or the fluid flow rate. Relaxation techniques, also known as perturbation techniques, enable information about a system to be gathered as the system proceeds to a new state of equilibrium, or new state of steady-state equilibrium, after a system variable (or parameter) is relaxed or perturbed.

For example, consider a patient whose body temperature is maintained by internal heat production, ambient temperature, and radiant heat. When the radiant heat source is turned off, the patient will proceed to a lower temperature. The time taken to reach the new temperature can be plotted as a function of temperature, and this curve can yield information about individual characteristics of the patient. A similar approach can be taken regarding other parameters of incubation. Relaxation techniques form an important part in the sciences, particular physical chemistry. Thus, it is contemplated that research in this area will help to elucidate indicators of patient health status as well as individualized determinations of optimal settings.

Because past practices were incompetent, it should be reflected that a number of changes will need to be made to incubation protocols in addition to refining the technology of incubator controls. For example, consider an incubator system in which patients are likely to become overheated due to increases in their own metabolic activity. In this unfortunate scenario, a formula for the baby's fluid incubation medium that suppresses metabolic activity may actually yield higher survival rates than an optimal formula! For this reason, the present invention is an enabling technology, along with U.S. Pat. No. 6,694,175 and the parent application, because together these teachings enable proper control of thermoregulation and ventilation.

In other words, because thermoregulation and ventilation establish the universal basis of a competent incubator system, having a competent means of thermoregulation and ventilation enables other parameters of incubation to be determined in a competent light. In contrast, the performance characteristics of an incompetent means will leave us guessing as to whether given protocols are truly advantageous or merely advantageous in an inferior light.

Prenids are to be regarded as being especially delicate compared to other babies insofar as their thermal sensitivities and requirements are concerned. For example, they appear to be especially susceptible to cytogenetic abnormalities induced by improper thermoregulation, often leading to lethal mosaicism. Accordingly, it is all too easy to understand why prior art practices have been disastrous and why tremendous medical and scientific reform is needed.

In conclusion, taking care of babies from the moment God has created them is a deeply religious form of endeavor. It therefore commands our honor and seriousness. The advent of prenidial care not only represents a great milestone for medicine, but, like neonatal care before it, also an immeasurable gift for the human family. Accordingly, those skilled in the art of health care will appreciate that an incubator for babies during prenidial development demands subtlety, sophistication, and technological elegance, as taught by the present invention.

What is claimed is:

1. An incubator for babies before implantation, comprising: a layer-based microfluidic enclosure designed to maintain a human embryo or hatchling as a patient in a controlled environment for medical care,
   the enclosure, having a flooring and a surrounding wall structure with an open top, forming a cradle support for the patient, and having a microfluidic ventilation system to provide a flow of incubation liquid media in and out of the enclosure, wherein the enclosure is further characterized as being assembled from a plurality of layers bonded together and populated with at least one patient care device;
   the layers, including at least one layer forming the flooring, at least one other layer forming the wall structure by means of a hole disposed completely therethrough, and a ventilation network of microfluidic channels or vias disposed in one or more layers in fluidic communication with the enclosure;
   the at least one patient care device, including a microfluidic device for urging fluid in the ventilation network; and,
   the microfluidic ventilation system, including the microfluidic device and the associated ventilation network to provide the patient in the cradle support with gentle, fluidic ventilation.

2. The incubator of claim 1 further including means of a temperature bath to maintain predetermined incubator temperatures, including a predetermined temperature of the incubation liquid media ventilating the patient in the cradle support, the bath, comprising a running fluid urged at a preset bath temperature through a bath network of housings formed by channels, vias, coils, a double-walled vessel, a jacketing system, or a bed in thermal contact with the incubator, wherein the bath network is separate from the ventilation network and which bath network communicates thermally but not fluidically with the incubation liquid media ventilating the patient in the cradle support.

3. The incubator of claim 2, wherein the flooring comprises an optical glass layer 170 microns thick with a refractive index of 1.515 to enable conformity with high resolution microscopy techniques employing an inverted microscope to monitor the patient in the cradle support via a vertical path for optics.

4. The incubator of claim 3 further including a MEMS-actuated cover for the enclosure to provide a means of closure for the open top in case of a need for closure.

5. The incubator of claim 1 further including a volume-sensing device to detect volume changes in the incubation liquid media covering the patient in the enclosure, wherein the microfluidic device is responsive to the volume-sensing device to adjust the flow in and out of the enclosure to maintain predetermined volumes of the incubation liquid media in the enclosure.

6. The incubator of claim 1, wherein the flooring comprises a material which permits the passage of infrared radiation.

7. The incubator of claim 2, wherein the layers are made of glass.

8. The incubator of claim 7, wherein the glass layers are bonded together adhesivelessly.

9. The incubator of claim 8, wherein the hole forming the enclosure walls is 500 microns in diameter or 500 microns square and the wall structure has a layer height of 100 or 150 microns.

10. The incubator of claim 1, wherein the microfluidic ventilation system is adapted to adjusting a rate of flow of the incubation liquid media over the patient to maintain an optimal rate of flow-related heat dissipation for an endogenous heat of the patient in reference to a reading of patient temperature acquired by means of patient thermometry.

11. The incubator of claim 2, wherein the temperature bath means is adapted to adjusting the temperature of the incubation liquid media to maintain an optimal ambient temperature for the patient in reference to a reading of patient temperature acquired by means of patient thermometry.

12. The incubator of claim 2, wherein the flooring, being formed of clear layers, provides an optical path into the incubator for viewing, measuring, or illuminating the patient or other incubator interest by means of an optical technique.

13. An incubator for a baby before implantation, comprising: a flooring to support the baby, liquid media to cover and incubate the baby, a microfluidic system to circulate the liquid media at a predetermined temperature and flow rate to provide the baby with fluidic ventilation and thermoregulatory support, and a volume-sensing device to detect a volume of the liquid media, wherein the microfluidic system is adapted to maintaining the volume of the liquid media covering the baby within a predetermined range of volumes based on feedback from the volume-sensing device.

14. The incubator of claim 13, wherein the liquid media covering the baby is a microdrop.

15. The incubator of claim 14, wherein the volume-sensing device comprises a beam of light from a light source and a photodetector array, the beam of light being directed through a meniscus of the microdrop in a lens fashion and detected by the photodetector array, whereby changes in a lens shape of the meniscus cause the light beam to be focused on corresponding points on the photodetector array as an indicator of microdrop volume.

16. An incubator for a baby before implantation, comprising: an enclosure having a flooring to support the baby, an open top and at least one sidewall, liquid media to cover and incubate the baby, and a microfluidic system to circulate the liquid media to provide the baby with fluidic ventilation in the enclosure, the sidewall having at least one ventilation port disposed therein through which the liquid media are urged by the microfluidic system to fluidically ventilate the baby in the enclosure, wherein the sidewall is formed by at least one layer bonded to the flooring by means of layer-based microfabrication and includes microfluidic channels or vias disposed therein, the ventilation port of the sidewall being formed by at least one of the microfluidic channels to provide horizontal flow or at least one of the microfluidic vias to provide vertical flow in or out of the enclosure.

17. The incubator of claim 16, wherein at least one sidewall provides flow into the enclosure and at least one sidewall provides flow out of the enclosure.

18. The incubator of claim 16, wherein the flooring contains at least one ventilation port in fluidic communication with the ventilation port of the sidewall to circulate the liquid media in and out of the enclosure by means of the microfluidic system.

19. The incubator of claim 7 further including thermal barriers or voids disposed in the flooring or walls of the enclosure as thermal insulation to thermally isolate the patient in the cradle support in a manner of double-walled incubator construction.

20. The incubator of claim 12 further including a microlens formed in the flooring or attached thereto.

* * * * *